(12) United States Patent  (10) Patent No.: US 8,076,487 B2
Takabe et al.  (45) Date of Patent: Dec. 13, 2011

(54) PYRIDONE DERIVATIVE AND HERBICIDE

(75) Inventors: Fumiaki Takabe, Iwata (JP);
Shunichirou Fukumoto, Iwata (JP);
Ryu Kajiki, Iwata (JP); Sohei Asakura, Tokyo (JP); Ryohei Ueno, Westchester, NY (US); Masami Kobayashi, Tokyo (JP); Satoru Takahashi, Tokyo (JP); Norihisa Yonekura, Tokyo (JP); Ryo Hanai, Tokyo (JP); Takashi Mitsunari, Tokyo (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 694 days.

(21) Appl. No.: 12/087,892

(22) PCT Filed: Jan. 31, 2007

(86) PCT No.: PCT/JP2007/051566
§ 371 (c)(1),
(2), (4) Date: Jul. 17, 2008

(87) PCT Pub. No.: WO2007/088876
PCT Pub. Date: Aug. 9, 2007

(65) Prior Publication Data
US 2010/0222592 A1  Sep. 2, 2010

(30) Foreign Application Priority Data
Feb. 2, 2006  (JP) ................................. 2006-025322

(51) Int. Cl.
*C07D 401/00* (2006.01)
(52) U.S. Cl. ...................... 546/276.1; 546/290; 546/298
(58) Field of Classification Search ............... 546/576.1, 546/298, 290
See application file for complete search history.

(56) References Cited

U.S. PATENT DOCUMENTS

| | | | |
|---|---|---|---|
| 5,098,464 A | 3/1992 | Barton et al. | 71/92 |
| 5,250,501 A | 10/1993 | Barton et al. | 504/266 |
| 5,426,091 A | 6/1995 | Barton et al. | 504/729 |
| 5,563,115 A | 10/1996 | Barton et al. | 504/288 |
| 5,744,610 A | 4/1998 | Barton et al. | 548/217 |
| 5,958,839 A | 9/1999 | Barton et al. | 504/289 |
| 6,048,823 A | 4/2000 | Yamaguchi et al. | 504/130 |
| 6,265,349 B1 | 7/2001 | Yamaguchi et al. | 504/235 |
| 6,291,400 B1 | 9/2001 | Barton et al. | 504/348 |
| 6,472,348 B1 | 10/2002 | Yamaguchi et al. | 504/130 |
| 6,498,125 B2 * | 12/2002 | Edmunds et al. | 504/130 |
| 2002/0016345 A1 | 2/2002 | Edmunds et al. | 514/344 |

OTHER PUBLICATIONS

Helvetica Chimica Acta, 1988, vol. 71, p. 596.

* cited by examiner

*Primary Examiner* — Yong Chu
*Assistant Examiner* — Valerie Rodriguez-Garcia
(74) *Attorney, Agent, or Firm* — Bacon & Thomas, PLLC

(57) ABSTRACT

A pyridone derivative represented by Formula [1] or an agriculturally acceptable salt thereof:

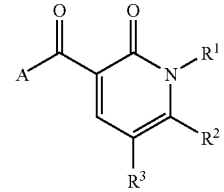

[1]

wherein $R^1$ is a $C_{1-6}$ alkyl group, a $C_{2-6}$ alkenyl group, a $C_{2-6}$ alkynyl group, or the like; $R^2$ and $R^3$ are each independently a hydrogen atom, a nitro group, a cyano group, or the like; and A is a group represented by Formula A-1, Formula A-2, Formula A-3, Formula A-4, or Formula A-5:

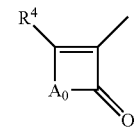

A-1

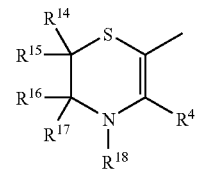

A-2

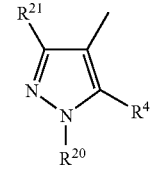

A-3

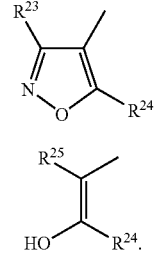

A-4

A-5

The compounds represented by general formula [1] control various weeds growing in upland fields, orchards, paddy fields, and non-crop lands while showing high safety to useful plants and crops.

6 Claims, No Drawings

PYRIDONE DERIVATIVE AND HERBICIDE

TECHNICAL FIELD

The present invention relates to a pyridone derivative or an agriculturally acceptable salt thereof, and a herbicide containing the same as the active ingredient. More specifically, the invention relates to a specific pyridone derivative and a method of using the same.

BACKGROUND ART

There are descriptions about pyridone derivatives in, for example, Patent Document 1 and Non-Patent Document 1, but there are no descriptions on a herbicidal activity of the compounds described in those documents. Also, there has been reported in, for example, Patent Document 2 that a substituted cyclic dione compound has a herbicidal activity. However, a pyridone derivative of the present invention is not disclosed in those documents. Consequently, it can be said from the above that a pyridone derivative represented by Formula [1] has a herbicidal activity is not known upon the face of documents.

Patent Document 1: WO 2004/043924
Patent Document 2: EP No. 283261
Non-Patent Document 1: Helvetica Chimica Acta, 1988, Vol. 71, p. 596

DISCLOSURE OF THE INVENTION

Problems to be Solved by the Invention

A herbicide that can be used for useful crops is desirably an agent to be applied to soil or foliage, which exhibits a sufficient herbicidal effect at a low dose. In addition, demand for safety of chemical substances and effects on the environment is increasing, and thus a development of a safer plant control agent for agricultural and horticultural use has been demanded. The present invention is made to deal with such problems.

Means for Solving the Problems

In order to achieve the above-mentioned objects, the present inventors have synthesized a pyridone derivative which has not been known to have a herbicidal activity until now, and its herbicidal activity and usefulness have been keenly investigated. As a result, they have found that, by applying the pyridone derivative of the invention directly to plants, or to soils on which plants are grown, or to a water surface of paddy field, an excellent herbicidal effect is exhibited against wide variety of weeds over a long period of time, and a high selectivity between useful crops and various weeds is shown. Thus, they have completed the invention.

That is, the invention provides the following (1) to (4):
(1) a pyridone derivative represented by Formula [1]:

[Chemical Formula 1]

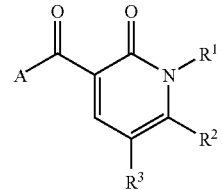

[1]

[wherein
$R^1$ is a $C_{1-6}$ alkyl group, a $C_{2-6}$ alkenyl group, a $C_{2-6}$ alkynyl group, a $C_{3-8}$ cycloalkyl group, a $C_{3-8}$ cycloalkyl $C_{1-6}$ alkyl group, a $C_{1-6}$ haloalkyl group, a $C_{2-6}$ haloalkenyl group, a $C_{2-6}$ haloalkynyl group, a $C_{1-6}$ alkylamino $C_{1-6}$ alkyl group, a di($C_{1-6}$ alkyl)amino $C_{1-6}$ alkyl group, a $C_{1-6}$ alkylthio $C_{1-6}$ alkyl group, a $C_{1-6}$ alkylsulfinyl $C_{1-6}$ alkyl group, a $C_{1-6}$ alkylsulfonyl $C_{1-6}$ alkyl group, a $C_{3-8}$ cycloalkylthio $C_{1-6}$ alkyl group, a $C_{3-8}$ cycloalkylsulfinyl $C_{1-6}$ alkyl group, a $C_{3-8}$ cycloalkylsulfonyl $C_{1-6}$ alkyl group, a $C_{3-8}$ cycloalkyl $C_{1-6}$ alkylthio $C_{1-6}$ alkyl group, a $C_{3-8}$ cycloalkyl $C_{1-6}$ alkylsulfinyl $C_{1-6}$ alkyl group, a $C_{3-8}$ cycloalkyl $C_{1-6}$ alkylsulfonyl $C_{1-6}$ alkyl group, a $C_{2-6}$ alkenylthio $C_{1-6}$ alkyl group, a $C_{2-6}$ alkenylsulfinyl $C_{1-6}$ alkyl group, a $C_{2-6}$ alkenylsulfonyl $C_{1-6}$ alkyl group, a $C_{2-6}$ alkynylthio $C_{1-6}$ alkyl group, a $C_{2-6}$ alkynylsulfinyl $C_{1-6}$ alkyl group, a $C_{2-6}$ alkynylsulfonyl $C_{1-6}$ alkyl group, a $C_{1-6}$ haloalkylthio $C_{1-6}$ alkyl group, a $C_{1-6}$ haloalkylsulfinyl $C_{1-6}$ alkyl group, a $C_{1-6}$ haloalkylsulfonyl $C_{1-6}$ alkyl group, a $C_{1-6}$ alkoxy $C_{1-6}$ alkyl group, a $C_{1-6}$ alkoxy $C_{1-6}$ alkoxy $C_{1-6}$ alkyl group, a $C_{3-8}$ cycloalkyloxy $C_{1-6}$ alkyl group, a benzyloxy $C_{1-6}$ alkyl group which may be substituted with one or more substituents selected from Substituent Group α, a cyano $C_{1-6}$ alkyl group, a $C_{1-6}$ haloalkoxy $C_{1-6}$ alkyl group, a phenyl group which may be substituted with one or more substituents selected from Substituent Group α, a benzyl group which may be substituted with one or more substituents selected from Substituent Group α, a phenyl $C_{1-6}$ alkyl group which may be substituted with one or more substituents selected from Substituent Group α, a phenyl $C_{2-6}$ alkenyl group which may be substituted with one or more substituents selected from Substituent Group α, a phenyl $C_{2-6}$ alkynyl group which may be substituted with one or more substituents selected from Substituent Group α, a $C_{1-6}$ alkoxyimino $C_{1-6}$ alkyl group, a phenoxyimino $C_{1-6}$ alkyl group which may be substituted with one or more substituents selected from Substituent Group α, a di($C_{1-6}$ alkoxy)$C_{1-6}$ alkyl group, a formyl $C_{1-6}$ alkyl group, a $C_{2-6}$ alkylideneamino group, a di($C_{1-10}$ alkyl)amino $C_{1-6}$ alkylideneamino group, a $NR^{31}R^{32}$ group, a $C_{1-6}$ alkoxy group, a $C_{2-6}$ alkenyloxy group, a $C_{2-6}$ alkynyloxy group, a $C_{3-8}$ cycloalkyloxy group, a $C_{3-8}$ cycloalkyl $C_{1-3}$ alkyloxy group, a $C_{1-6}$ haloalkoxy group, a $C_{2-10}$ heterocyclic group having one or more of the same or different hetero atoms selected from the group consisting of an oxygen atom, a sulfur atom and a nitrogen atom (the group may also be substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups), a $C_{1-6}$ alkyl group substituted with a $C_{2-10}$ heterocyclic ring having one or more of the same or different hetero atoms selected from the group consisting of an oxygen atom, a sulfur atom and a nitrogen atom (the heterocyclic ring of the group may also be substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups), a $C_{1-6}$ alkylamino group substituted with a $C_{2-10}$ heterocyclic ring having one or more of the same or different hetero atoms selected from the group consisting of an oxygen atom, a sulfur atom and a nitrogen atom (the heterocyclic ring of the group may also be substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups) or a $C_{1-6}$ alkoxy $C_{1-6}$ alkyl group substituted with a $C_{2-10}$ heterocyclic ring having one or more of the same or different hetero atoms selected from the group consisting of an oxygen atom, a sulfur atom and a nitrogen atom (the heterocyclic ring of the group may also be substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups);

$R^2$ and $R^3$ are each independently a hydrogen atom, a nitro group, a cyano group, a $C_{1-6}$ alkyl group, a $C_{2-6}$ alkenyl group, a $C_{2-6}$ alkynyl group, a $C_{3-8}$ cycloalkyl group, a $C_{1-6}$ haloalkyl group, a $C_{2-6}$ haloalkenyl group, a $C_{2-6}$ haloalkynyl group, a $C_{1-6}$ alkoxy group, a $C_{1-6}$ haloalkoxy group, a $C_{1-6}$ alkylthio group, a $C_{1-6}$ alkylsulfinyl group, a $C_{1-6}$ alkylsulfonyl group, a $C_{1-6}$ alkylsulfonyl $C_{1-6}$ alkyl group, a $C_{1-6}$ haloalkylthio group, a $C_{1-6}$ haloalkylsulfinyl group, a $C_{1-6}$ haloalkylsulfonyl group, a $C_{1-6}$ alkoxy $C_{1-6}$ alkyl group, a $C_{3-8}$ cycloalkyloxy $C_{1-4}$ alkyl group, a di($C_{1-6}$ alkoxy) $C_{1-6}$ alkyl group, a phenyl group which may be substituted with one or more substituents selected from Substituent Group α, a benzyl group which may be substituted with one or more substituents selected from Substituent Group α, a phenyl $C_{1-6}$ alkyl group which may be substituted with one or more substituents selected from Substituent Group α, a phenyl $C_{2-6}$ alkenyl group which may be substituted with one or more substituents selected from Substituent Group α, a phenyl $C_{2-6}$ alkynyl group which may be substituted with one or more substituents selected from Substituent Group α, or a halogen atom; and A is a group represented by any of Formula A-1, Formula A-2, Formula A-3, Formula A-4, and Formula A-5:

[Chemical Formula 2]

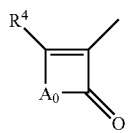

A-1

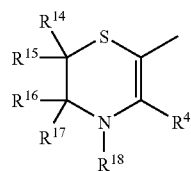

A-2

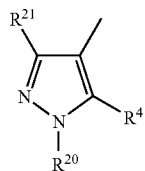

A-3

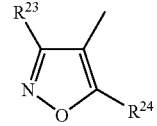

A-4

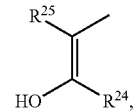

A-5 where $R^4$ is a hydroxyl group, $O^-M^+$ (where $M^+$ represents an alkali metal cation or an ammonium cation), a halogen atom, a cyano group, an isothiocyanate group, an isocyanate group, a hydroxycarbonyloxy group, a $C_{1-6}$ alkoxycarbonyloxy group, a benzyloxy carbonyloxy group which may be substituted with one or more substituents selected from Substituent Group α, a $C_{1-12}$ alkoxy group, a $C_{2-6}$ alkenyloxy group, a $C_{2-6}$ alknyloxy group, a $C_{3-6}$ cycloalkyloxy group, a cyanomethyleneoxy group, a $C_{3-8}$ cycloalkyl $C_{1-3}$ alkyloxy group, a $C_{1-6}$ alkylcarbonyloxy group, a $C_{1-6}$ haloalkylcarbonyloxy group, a $C_{2-6}$ alkenylcarbonyloxy group, a $C_{2-6}$ haloalkenylcarbonyloxy group, a $C_{2-6}$ alkynylcarbonyloxy group, a $C_{2-6}$ haloalkynylcarbonyloxy group, a $C_{1-6}$ alkoxycarbonyl $C_{1-6}$ alkoxy group, a phenyloxy group which may be substituted with one or more substituents selected from Substituent Group α, a benzyloxy group which may be substituted with one or more substituents selected from Substituent Group α, a phenylcarbonyloxy group which may be substituted with one or more substituents selected from Substituent Group α, a benzylcarbonyloxy group which may be substituted with one or more substituents selected from Substituent Group α, a phenylcarbonyl $C_{1-6}$ alkyloxy group which may be substituted with one or more substituents selected from Substituent Group α, a $C_{1-3}$ alkylsulfonyloxy group, a phenylsulfonyloxy group which may be substituted with one or more substituents selected from Substituent Group α, a benzylsulfonyloxy group which may be substituted with one or more substituents selected from Substituent Group α, a $C_{1-10}$ alkylthio group, a $C_{1-10}$ alkylsulfinyl group, a $C_{1-10}$ alkylsulfonyl group, a phenylthio group which may be substituted with one or more substituents selected from Substituent Group α, a benzylthio group which may be substituted with one or more substituents selected from Substituent Group α, a phenylsulfinyl group which may be substituted with one or more substituents selected from Substituent Group α, a benzylsulfinyl group which may be substituted with one or more substituents selected from Substituent Group α, a phenylsulfonyl group which may be substituted with one or more substituents selected from Substituent Group α, a benzylsulfonyl group which may be substituted with one or more substituents selected from Substituent Group α, a $C_{1-10}$ alkylamino group, a di($C_{1-10}$ alkyl)amino group, a $C_{1-6}$ alkoxycarbonylamino group, a $C_{1-6}$ alkyloxy group substituted with a $C_{2-10}$ heterocyclic ring having one or more of the same or different hetero atoms selected from the group consisting of an oxygen atom, a sulfur atom and a nitrogen atom (the heterocyclic ring of the group may also be substituted with 1 to 5 halogen atoms, oxo groups, $C_{1-6}$ alkyl groups, $C_{1-6}$ haloalkyl groups, $C_{1-6}$ alkoxy groups or cyano groups) or a $C_{2-10}$ heterocyclic group having one or more of the same or different hetero atoms selected from the group consisting of an oxygen atom, a sulfur atom and a nitrogen atom (the group may also be substituted with 1 to 5 halogen atoms, oxo groups, $C_{1-6}$ alkyl groups, $C_{1-6}$ haloalkyl groups, $C_{1-6}$ alkoxy groups or cyano groups);

$A_0$ is a group represented by Formula $X_{10}$ or Formula $X_{11}$:

[Chemical Formula 3]

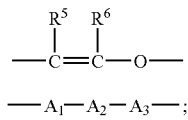

$$—C=C—O— \quad [X_{10}]$$
$$—A_1—A_2—A_3— \quad [X_{11}]$$

$A_1$ is a group represented by Formula $X_1$ or Formula $X_2$:

[Chemical Formula 4]

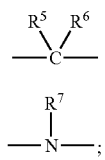

$A_2$ is a group represented by any of Formula $X_3$, Formula $X_4$, Formula $X_5$, Formula $X_6$, and Formula $X_7$:

[Chemical Formula 5]

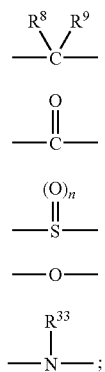

$A_3$ is a group represented by Formula $X_8$ or Formula $X_9$:

[Chemical Formula 6]

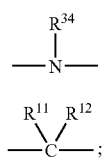

n is 0, 1 or 2;

$R^5$, $R^6$, $R^8$, $R^9$, $R^{11}$ and $R^{12}$ are each independently a hydrogen atom or a $C_{1-6}$ alkyl group, herein, $R^5$ and $R^8$ may form a ring by bonding with a $C_{1-5}$ alkylene chain or a $C_{2-5}$ alkenylene chain, or $R^5$ and $R^{11}$ may form a ring by bonding with a $C_{2-5}$ alkylene chain or a $C_{2-5}$ alkenylene chain;

$R^7$, $R^{33}$, and $R^{34}$ are each independently a hydrogen atom, a $C_{1-6}$ alkyl group, a $C_{1-6}$ haloalkyl group, a $C_{2-6}$ alkenyl group, a $C_{2-6}$ alkynyl group or a $C_{1-6}$ alkoxy group;

$R^{14}$, $R^{15}$, $R^{16}$, and $R^{17}$ are each independently a hydrogen atom, a $C_{1-6}$ alkyl group, a $C_{1-6}$ alkoxy group or a benzyl group which may be substituted with one or more substituents selected from Substituent Group α;

$R^{18}$ is a hydrogen atom, a $C_{1-6}$ alkyl group, a $C_{2-6}$ alkenyl group, a $C_{2-6}$ alkynyl group, a cyanomethyl group or a benzyl group which may be substituted with one or more substituents selected from Substituent Group α;

$R^{20}$ is a $C_{1-6}$ alkyl group, a $C_{2-6}$ alkenyl group, a $C_{2-6}$ alkynyl group, a $C_{3-8}$ cycloalkyl group or a $C_{3-8}$ cycloalkyl $C_{1-6}$ alkyl group;

$R^{21}$ is a hydrogen atom, a $C_{1-6}$ alkyl group or a halogen atom;

$R^{23}$ is a $C_{1-6}$ alkyl group, a $C_{1-6}$ haloalkyl group, a $C_{3-8}$ cycloalkyl group, a $C_{1-10}$ alkylthio group, a $C_{1-10}$ alkylsulfinyl group, a $C_{1-10}$ alkylsulfonyl group, a phenylthio group which may be substituted with one or more substituents selected from Substituent Group α, a benzylthio group which may be substituted with one or more substituents selected from Substituent Group α, a phenylsulfinyl group which may be substituted with one or more substituents selected from Substituent Group α, a benzylsulfinyl group which may be substituted with one or more substituents selected from Substituent Group α, a phenylsulfonyl group which may be substituted with one or more substituents selected from Substituent Group α or a benzylsulfonyl group which may be substituted with one or more substituents selected from Substituent Group α;

$R^{24}$ is a hydrogen atom, a halogen atom, a cyano group, a $C_{1-6}$ alkyl group, a $C_{3-8}$ cycloalkyl group, or a $C_{1-6}$ alkoxycarbonylamino group; and $R^{25}$ is a $C_{1-6}$ alkoxycarbonyl group, a cyano group or a nitro group, and $R^{31}$ and $R^{32}$ are each independently a hydrogen atom, a $C_{1-6}$ alkyl group, a phenyl group which may be substituted with one or more substituents selected from Substituent Group α, a benzyl group which may be substituted with one or more substituents selected from Substituent Group α, a $C_{1-6}$ alkoxy $C_{1-6}$ alkyl group, a $C_{1-6}$ alkylcarbonyl group, a $C_{1-6}$ alkoxycarbonyl group, a benzyloxycarbonyl group which may be substituted with one or more substituents selected from Substituent Group α, a $C_{1-6}$ haloalkyl group, a $C_{3-8}$ cycloalkyl group, a $C_{3-8}$ cycloalkyl $C_{1-6}$ alkyl group, a $C_{1-6}$ alkylsulfonyl group, a phenylsulfonyl group which may be substituted with one or more substituents selected from Substituent Group α, a benzylsulfonyl group which may be substituted with one or more substituents selected from Substituent Group α, a $C_{2-10}$ heterocyclic group having one or more of the same or different hetero atoms selected from the group consisting of an oxygen atom, a sulfur atom and a nitrogen atom (the group may also be substituted with 1 to 5 halogen atoms, oxo groups, $C_{1-6}$ alkyl groups, $C_{1-6}$ haloalkyl groups, $C_{1-6}$ alkoxy groups or cyano groups) or a $C_{1-6}$ alkyl group substituted with a $C_{2-10}$ heterocyclic ring having one or more of the same or different hetero atoms selected from the group consisting of an oxygen atom, a sulfur atom and a nitrogen atom (the heterocyclic ring of the group may also be substituted with 1 to 5 halogen atoms, oxo groups, $C_{1-6}$ alkyl groups, $C_{1-6}$ haloalkyl groups, $C_{1-6}$ alkoxy groups or cyano groups), while Substituent Group α being defined as follows:

"Substituent Group α":

a halogen atom, a $C_{1-6}$ alkyl group, a $C_{1-6}$ haloalkyl group, a $C_{1-6}$ alkoxy group, a $C_{1-6}$ haloalkoxy group, a $C_{1-4}$ alkylenedioxy group, a nitro group, a cyano group, a $C_{1-6}$ alkylthio group, a $C_{1-6}$ alkylsulfinyl group, a $C_{1-6}$ alkylsulfonyl group, a $C_{1-6}$ alkoxy $C_{1-6}$ alkyl group and a $C_{1-6}$ haloalkylsulfonylamino group], or an agriculturally acceptable salt thereof;

(2) The pyridone derivative or an agriculturally acceptable salt thereof as described in (1),
wherein, A is a group represented by any of above-mentioned Formula A-1, Formula A-2, Formula A-3, Formula A-4 and Formula A-5; and $A_0$ in A-1 is a group represented by any of Formula $X_{10}$, Formulae $X_{11}$-a and $X_{11}$-b:

[Chemical Formula 7]

$$—\overset{R^5}{\underset{|}{C}}=\overset{R^6}{\underset{|}{C}}—O— \quad [X_{10}]$$

$$—\overset{}{\underset{R^6}{\underset{|}{C}}}\overset{T}{\underset{A_2}{\diagup\diagdown}}\overset{}{\underset{R^{12}}{\underset{|}{C}}}— \quad [X_{11}\text{-a}]$$

$$—\overset{R^7}{\underset{|}{N}}—A_2—A_3— \quad [X_{11}\text{-b}]$$

where $A_2$ is a group represented by any of Formula $X_3$, Formula $X_4$, Formula $X_5$, Formula $X_6$, and Formula $X_7$:

[Chemical Formula 8]

$$—\overset{R^8}{\underset{}{\diagdown}}\overset{R^9}{\underset{}{\diagup}}— \quad [X_3]$$
$$\phantom{---}\overset{|}{C}\phantom{---}$$

$$—\overset{O}{\underset{\|}{C}}— \quad [X_4]$$

$$—\overset{(O)_n}{\underset{\|}{S}}— \quad [X_5]$$

$$—O— \quad [X_6]$$

$$—\overset{R^{33}}{\underset{|}{N}}—; \quad [X_7]$$

$A_3$ is a group represented by Formula $X_8$ or Formula $X_9$:

[Chemical Formula 9]

$$—\overset{R^{34}}{\underset{|}{N}}— \quad [X_8]$$

$$—\overset{R^{11}}{\underset{|}{C}}\overset{R^{12}}{\phantom{|}}—; \quad [X_9]$$

n is 0, 1 or 2;

$R^5$, $R^6$, $R^8$, $R^9$, $R^{11}$ and $R^{12}$ are each independently a hydrogen atom or a $C_{1-6}$ alkyl group;

$R^7$, $R^{33}$, and $R^{34}$ are each independently a hydrogen atom, a $C_{1-6}$ alkyl group, a $C_{1-6}$ haloalkyl group, a $C_{2-6}$ alkenyl group, a $C_{2-6}$ alkynyl group or a $C_{1-6}$ alkoxy group; and T is a $C_{2-5}$ alkylene chain or a $C_{2-5}$ alkenylene chain;

(3) The pyridone derivative or an agriculturally acceptable salt thereof as described in (1),
wherein, $R^1$ in Formula [1] is a $C_{3-8}$ cycloalkyl $C_{1-6}$ alkyl group, a $C_{2-6}$ haloalkenyl group, a $C_{2-6}$ haloalkynyl group, a $C_{1-6}$ alkylamino $C_{1-6}$ alkyl group, a di($C_{1-6}$ alkyl)amino $C_{1-6}$ alkyl group, a $C_{1-6}$ alkylthio $C_{1-6}$ alkyl group, a $C_{1-6}$ alkylsulfinyl $C_{1-6}$ alkyl group, a $C_{1-6}$ alkylsulfonyl $C_{1-6}$ alkyl group, a $C_{3-8}$ cycloalkylthio $C_{1-6}$ alkyl group, a $C_{3-8}$ cycloalkylsulfinyl $C_{1-6}$ alkyl group, a $C_{3-8}$ cycloalkylsulfonyl $C_{1-6}$ alkyl group, a $C_{3-8}$ cycloalkyl $C_{1-6}$ alkylthio $C_{1-6}$ alkyl group, a $C_{3-8}$ cycloalkyl $C_{1-6}$ alkylsulfinyl $C_{1-6}$ alkyl group, a $C_{3-8}$ cycloalkyl $C_{1-6}$ alkylsulfonyl $C_{1-6}$ alkyl group, a $C_{2-6}$ alkenylthio $C_{1-6}$ alkyl group, a $C_{2-6}$ alkenylsulfinyl $C_{1-6}$ alkyl group, a $C_{2-6}$ alkenylsulfonyl $C_{1-6}$ alkyl group, a $C_{2-6}$ alkynylthio $C_{1-6}$ alkyl group, a $C_{2-6}$ alkynylsulfinyl $C_{1-6}$ alkyl group, a $C_{2-6}$ alkynylsulfonyl $C_{1-6}$ alkyl group, a $C_{1-6}$ haloalkylthio $C_{1-6}$ alkyl group, a $C_{1-6}$ haloalkylsulfinyl $C_{1-6}$ alkyl group, a $C_{1-6}$ haloalkylsulfonyl $C_{1-6}$ alkyl group, a $C_{1-6}$ alkoxy $C_{1-6}$ alkyl group, a $C_{1-6}$ alkoxy $C_{1-6}$ alkoxy $C_{1-6}$ alkyl group, a $C_{3-8}$ cycloalkyloxy $C_{1-6}$ alkyl group, a benzyloxy $C_{1-6}$ alkyl group which may be substituted with one or more substituents selected from Substituent Group α, a cyano $C_{1-6}$ alkyl group, a $C_{1-6}$ haloalkoxy $C_{1-6}$ alkyl group, a phenyl group which is substituted with one or more substituents selected from Substituent Group α', a benzyl group which may be substituted with one or more substituents selected from the Substituent Group α, a phenyl $C_{1-6}$ alkyl group which may be substituted with one or more substituents selected from the Substituent Group α, a phenyl $C_{2-6}$ alkenyl group which may be substituted with one or more substituents selected from the Substituent Group α, a phenyl $C_{2-6}$ alkynyl group which may be substituted with one or more substituents selected from the Substituent Group α, a $C_{1-6}$ alkoxyimino $C_{1-6}$ alkyl group, a phenoxyimino $C_{1-6}$ alkyl group which may be substituted with one or more substituents selected from the Substituent Group α, a di($C_{1-6}$ alkoxy)$C_{1-6}$ alkyl group, a formyl $C_{1-6}$ alkyl group, a $C_{2-6}$ alkylideneamino group, a di($C_{1-10}$ alkyl)amino $C_{1-6}$ alkylideneamino group, a $NR^{31}R^{32}$ group, a $C_{2-6}$ alkenyloxy group, a $C_{2-6}$ alkynyloxy group, a $C_{3-6}$ cycloalkyloxy group, a $C_{3-8}$ cycloalkyl $C_{1-3}$ alkyloxy group, a $C_{2-10}$ heterocyclic group having one or more of the same or different hetero atoms selected from the group consisting of an oxygen atom, a sulfur atom and a nitrogen atom (the group is substituted with one or more substituents selected from a halogen atom, an oxo group, a $C_{1-6}$ alkyl group, a $C_{1-6}$ haloalkyl group, a $C_{1-6}$ alkoxy group, a $C_{1-6}$ haloalkoxy group and a cyano group), a $C_{1-6}$ alkyl group substituted with a $C_{2-10}$ heterocyclic ring having one or more of the same or different hetero atoms selected from the group consisting of an oxygen atom, a sulfur atom and a nitrogen atom (the heterocyclic ring of the group may also be substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups), a $C_{1-6}$ alkylamino group substituted with a $C_{2-10}$ heterocyclic ring having one or more of the same or different hetero atoms selected from the group consisting of an oxygen atom, a sulfur atom and a nitrogen atom (the heterocyclic ring of the group may also be substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups) or a $C_{1-6}$ alkoxy $C_{1-6}$ alkyl group substituted with a $C_{2-10}$ heterocyclic ring having one or more of the same or different hetero atoms selected from the group consisting of an oxygen atom, a sulfur atom and a nitrogen atom (the heterocyclic ring of the group may also be substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups), where $R^{31}$ is a hydrogen atom, a $C_{1-6}$ alkyl group, a phenyl group which may be substituted with one or more substituents selected from the Substituent Group α, a benzyl group which may be substituted with one or more substituents selected from the Substituent Group α, a $C_{1-6}$ alkoxy $C_{1-6}$ alkyl group, a $C_{1-6}$ alkoxycarbonyl group, a benzyloxycarbonyl group which may be substituted with one or more substituents selected from Substituent Group α, a $C_{1-6}$ haloalkyl group, a $C_{3-8}$ cycloalkyl group, a $C_{3-8}$ cycloalkyl $C_{1-6}$ alkyl group, a $C_{1-6}$ alkylsulfonyl group, a phenylsulfonyl group which may be substituted with one or more substituents selected from the Substituent Group α, a benzylsulfonyl group which may be substituted with one or more substituents selected from the Substituent Group α, a $C_{2-10}$ heterocyclic group having one or more of the same or different hetero atoms selected from the group consisting of an oxygen atom, a sulfur atom and a nitrogen atom (the group may also be substituted with 1 to 5 halogen atoms, oxo groups, $C_{1-6}$ alkyl groups, $C_{1-6}$ haloalkyl groups, $C_{1-6}$ alkoxy groups or cyano groups), or a $C_{1-6}$ alkyl group substituted with a $C_{2-10}$ heterocyclic ring having one or more of the same or different hetero atoms selected from the group consisting of an oxygen atom, a sulfur atom and a nitrogen atom (the heterocyclic ring of the group may also be substituted with 1 to 5 halogen atoms, oxo groups, $C_{1-6}$ alkyl groups, $C_{1-6}$ haloalkyl groups, $C_{1-6}$ alkoxy groups or cyano groups); and $R^{32}$ is a phenyl group which may be substituted with one or more substituents selected from the Substituent Group α, a benzyl group which may be substituted with one or more substituents selected from the Substituent Group α, a $C_{1-6}$ alkoxy $C_{1-6}$ alkyl group, a $C_{1-6}$ alkoxycarbonyl group, a benzyloxycarbonyl group which may be substituted with one or more substituents selected from Substituent Group α, a $C_{1-6}$ haloalkyl group, a $C_{3-8}$ cycloalkyl group, a $C_{3-6}$ cycloalkyl $C_{1-6}$ alkyl group, a $C_{1-6}$ alkylsulfonyl group, a phenylsulfonyl group which may be substituted with one or more substituents selected from the Substituent Group α, a benzylsulfonyl group which may be substituted with one or more substituents selected from the Substituent Group α, a $C_{2-10}$ heterocyclic group having one or more of the same or different hetero atoms selected from the group consisting of an oxygen atom, a sulfur atom and a nitrogen atom (the group may also be substituted with 1 to 5 halogen atoms, oxo groups, $C_{1-6}$ alkyl groups, $C_{1-6}$ haloalkyl groups, $C_{1-6}$ alkoxy groups or cyano groups) or a $C_{1-6}$ alkyl group substituted with a $C_{2-10}$ heterocyclic ring having one or more of the same or different hetero atoms selected from the group consisting of an oxygen atom, a sulfur atom and a nitrogen atom (the heterocyclic ring of the group may also be substituted with 1 to 5 halogen atoms, oxo groups, $C_{1-6}$ alkyl groups, $C_{1-6}$ haloalkyl groups, $C_{1-6}$ alkoxy groups or cyano groups), while Substituent Group α' being defined as follows:
"Substituent Group α'":

a $C_{1-6}$ haloalkyl group, a $C_{1-6}$ haloalkoxy group, a methylenedioxy group, a nitro group, a cyano group, a $C_{1-6}$ alkylthio group, a $C_{1-6}$ alkylsulfinyl group, a $C_{1-6}$ alkylsulfonyl group, a $C_{1-6}$ alkoxy $C_{1-6}$ alkyl group and a $C_{1-6}$ haloalkylsulfonylamino group;

(4) A herbicide containing the pyridone derivative or an agriculturally acceptable salt thereof as described in any one of (1) to (3), as the active ingredient.

ADVANTAGE OF THE INVENTION

The compound of the invention represented by a general formula [1] or an agriculturally acceptable salt thereof enables to control various weeds growing in upland fields, orchards, paddy fields, and non-crop lands, and further provides high safety to useful plants, useful crops, or the like.

BEST MODE FOR CARRYING OUT THE INVENTION

Symbols and terms mentioned in the present specification will be explained.

The halogen atom is a fluorine atom, a chlorine atom, a bromine atom or an iodine atom.

A notation such as $C_{1-6}$ refers to a number of carbon atoms of the following substituent, which is from 1 to 6 in this case.

The $C_{1-6}$ alkyl group represents, unless otherwise particularly defined, a linear or branched chain alkyl group having 1 to 6 carbon atoms. Examples thereof may include groups such as methyl, ethyl, n-propyl, isopropyl, n-butyl, sec-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl and 1-ethyl-2-methylpropyl.

The $C_{3-8}$ cycloalkyl group represents, unless otherwise particularly defined, a cycloalkyl group having 3 to 8 carbon atoms. Examples thereof may include groups such as cyclopropyl, cyclobutyl, cyclopentyl, and cyclohexyl.

The $C_{1-6}$ haloalkyl group represents, unless otherwise particularly defined, a linear or branched chain alkyl group having 1 to 6 carbon atoms while the group is substituted with 1 to 13 halogen atoms that may be the same with or different from each other. Examples thereof may include groups such as fluoromethyl, chloromethyl, bromomethyl, difluoromethyl, dichloromethyl, trifluoromethyl, trichloromethyl, chlorodifluoromethyl, bromodifluoromethyl, 2-fluoroethyl, 1-chloroethyl, 2-chloroethyl, 1-bromoethyl, 2-bromoethyl, 2,2-difluoroethyl, 1,2-dichloroethyl, 2,2-dichloroethyl, 2,2,2-trifluoroethyl, 2,2,2-trichloroethyl, 1,1,2,2-tetrafluoroethyl, pentafluoroethyl, 2-bromo-2-chloroethyl, 2-chloro-1,1,2,2-tetrafluoroethyl, 1-chloro-1,2,2,2-tetrafluoroethyl, 1-chloropropyl, 2-chloropropyl, 3-chloropropyl, 2-bromopropyl, 3-bromopropyl, 2-bromo-1-methylethyl, 3-iodopropyl, 2,3-dichloropropyl, 2,3-dibromopropyl, 3,3,3-trifluoropropyl, 3,3,3-trichloropropyl, 3-bromo-3,3-difluoropropyl, 3,3-dichloro-3-fluoropropyl, 2,2,3,3-tetrafluoropropyl, 1-bromo-3,3,3-trifluoropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 2,3-dichloro-1,1,2,3,3-pentafluoropropyl, 2-chlorobutyl, 3-chlorobutyl, 4-chlorobutyl, 2-chloro-1,1-dimethylethyl, 4-bromobutyl, 3-bromo-2-methylpropyl, 2-bromo-1,1-dimethylethyl, 2,2-dichloro-1,1-dimethylethyl, 2-chloro- 1-chloromethyl-2-methylethyl, 4,4,4-trifluorobutyl, 3,3,3-trifluoro-1-methylpropyl, 3,3,3-trifluoro-2-methylpropyl, 2,3,4-trichlorobutyl, 2,2,2-trichloro-1,1-dimethylethyl, 4-chloro-4,4-difluorobutyl, 4,4-dichloro-4-fluorobutyl, 4-bromo-4,4-difluorobutyl, 2,4-dibromo-4,4-difluorobutyl, 3,4-dichloro-3,4,4-trifluorobutyl, 3,3-dichloro-4,4,4-trifluorobutyl, 4-bromo-3,3,4,4-tetrafluorobutyl, 4-bromo-3-chloro-3,4,4-trifluorobutyl, 2,2,3,3,4,4-hexafluorobutyl, 2,2,3,4,4,4-hexafluorobutyl, 2,2,2-trifluoro-1-methyl-1-trifluoromethylethyl, 3,3,3-trifluoro-2-trifluoromethylpropyl, 2,2,3,3,4,4,4-heptafluorobutyl, 2,3,3,3-tetrafluor-2-trifluoromethylpropyl, 1,1,2,2,3,3,4,4-octafluorobutyl, nonafluorobutyl, 4-chloro-1,1,2,2,3,3,4,4-octafluorobutyl, 5-fluoropentyl, 5-chloropentyl, 5,5-difluoropentyl, 5,5-dichloropentyl, 5,5,5-trifluoropentyl, 6,6,6-trifluorohexyl and 5,5,6,6,6-pentafluorohexyl.

The $C_{2-6}$ alkenyl group represents, unless otherwise particularly defined, a linear or branched chain alkenyl group having 2 to 6 carbon atoms. Examples thereof may include groups such as vinyl, 1-propenyl, isopropenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadienyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2-dimethyl-1-propenyl, 2-methyl-3-butenyl, 3-methyl-3-butenyl, 1,3-pentadienyl, 1-vinyl-2-propenyl, 1-hexenyl, 1-propyl-2-propenyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 1-(isobutyl)vinyl, 1-ethyl-1-methyl-2-propenyl, 1-ethyl-2-methyl-2-propenyl, 1-(isopropyl)-2-propenyl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-propenyl, 1,5-hexadienyl, 1-vinyl-3-butenyl and 2,4-hexadienyl.

The $C_{2-6}$ alkynyl group represents, unless otherwise particularly defined, a linear or branched chain alkynyl group having 2 to 6 carbon atoms. Examples thereof may include groups such as ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 1-(n-propyl)-2-propynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, 1-ethyl-3-butynyl, 1-ethyl-1-methyl-2-propynyl, 1-(isopropyl)-2-propynyl, 1,1-dimethyl-2-butynyl and 2,2-dimethyl-3-butynyl.

The $C_{2-6}$ haloalkenyl group represents, unless otherwise particularly defined, a linear or branched chain alkenyl group having 2 to 6 carbon atoms while the group is substituted with 1 to 11 halogen atoms that may be the same with or different from each other. Examples thereof may include groups such as 2-chlorovinyl, 2-bromovinyl, 2-iodovinyl, 3-chloro-2-propenyl, 3-bromo-2-propenyl, 1-chloromethylvinyl, 2-bromo-1-methylvinyl, 1-trifluoromethylvinyl, 3,3,3-trichloro-1-propenyl, 3-bromo-3,3-difluoro-1-propenyl, 2,3,3,3-tetrachloro-1-propenyl, 1-trifluoromethyl-2,2-difluorovinyl, 2-chloro-2-propenyl, 3,3-difluoro-2-propenyl, 2,3,3-trichloro-2-propenyl, 4-bromo-3-chloro-3,4,4-trifluoro-1-butenyl, 1-bromomethyl-2-propenyl, 3-chloro-2-butenyl, 4,4,4-trifluoro-2-butenyl, 4-bromo-4,4-difluoro-2-butenyl, 3-bromo-3-butenyl, 3,4,4-trifluoro-3-butenyl, 3,4,4-tribromo-3-butenyl, 3-bromo-2-methyl-2-propenyl, 3,3-difluoro-2-methyl-2-propenyl, 3,3,3-trifluoro-2-methylpropenyl, 3-chloro-4,4,4-trifluoro-2-butenyl, 3,3,3-trifluoro-1-methyl-1-propenyl, 3,4,4-trifluoro-1,3-butadienyl, 3,4-dibromo-1-pentenyl, 4,4-difluoro-3-methyl-3-butenyl, 3,3,4,4,5,5,5-heptafluoro-1-pentenyl, 5,5-difluoro-4-pentenyl, 4,5,5-trifluoro-4-pentenyl, 3,4,4,4-tetrafluoro-3-trifluoromethyl-1-butenyl, 4,4,4-trifluoromethyl-3-methyl-2-butenyl, 3,5,5-trifluoro-2,4-pentadienyl, 4,4,5,5,6,6,6-heptafluoro-2-hexenyl, 3,4,4,5,5,5-hexafluoro-3-trifluoromethyl-1-pentenyl, tetrafluoro-4-trifluoromethyl-2-pentenyl and 5-bromo-4,5,5-trifluoro-4-trifluoromethyl-2-pentenyl.

The $C_{2-6}$ haloalkynyl group represents, unless otherwise particularly defined, a linear or branched chain alkynyl group having 2 to 6 carbon atoms while the group is substituted with 1 to 9 halogen atoms that may be the same with or different from each other. Examples thereof may include 3-chloro-2-propynyl, 3-bromo-2-propynyl, 3-iodo-2-propynyl, 3-chloro-1-propynyl and 5-chloro-4-pentynyl.

The $C_{1-6}$ alkoxy group represents, unless otherwise particularly defined, an (alkyl)-O— group having 1 to 6 carbon atoms in the alkyl moiety. Examples thereof may include groups such as methoxy, ethoxy, propoxy, isopropoxy, butoxy, isobutoxy, pentyloxy and hexyloxy.

The $C_{1-12}$ alkoxy group represents, unless otherwise particularly defined, an (alkyl)-O— group having 1 to 12 carbon atoms in the alkyl moiety. Examples thereof may include groups such as methoxy, ethoxy, propoxy, isopropoxy, butoxy, isobutoxy, pentyloxy, hexyloxy, heptyloxy, octyloxy and nonyloxy.

The $C_{1-6}$ haloalkoxy group represents, unless otherwise particularly defined, a linear or branched chain alkyl-O— group having 1 to 6 carbon atoms while the group is substituted with 1 to 13 halogen atoms that may be the same with or different from each other, and the haloalkyl moiety thereof has the same meaning as defined above. Examples may include groups such as chloromethoxy, difluoromethoxy, chlorodifluoromethoxy, trifluoromethoxy and 2,2,2-trifluoroethoxy.

The $C_{1-6}$ alkoxy $C_{1-6}$ alkyl group represents, unless otherwise particularly defined, an alkyl group having 1 to 6 carbon atoms while the group is substituted with an alkoxy group having 1 to 6 carbon atoms, where the alkyl moiety and the alkoxy moiety have the same meanings as defined above. Examples may include groups such as methoxymethyl, ethoxymethyl, isopropoxymethyl, pentyloxymethyl, methoxyethyl and butoxyethyl.

The $C_{1-6}$ alkoxy $C_{1-6}$ alkoxy $C_{1-6}$ alkyl group represents, unless otherwise particularly defined, an alkyl group having 1 to 6 carbon atoms while the group is substituted with a $C_{1-6}$ alkoxy group-substituted alkoxy group having 1 to 6 carbon atoms, where the alkyl moiety and the alkoxy moiety have the same meanings as defined above. Examples may include groups such as 2-(2-methoxyethoxy)ethyl and 2-(2-ethoxyethoxy)ethyl.

The $C_{1-6}$ haloalkoxy $C_{1-6}$ alkyl group represents, unless otherwise particularly defined, an alkyl group having 1 to 6 carbon atoms while the group is substituted with a haloalkoxy group having 1 to 6 carbon atoms, where the haloalkoxy moiety and the alkyl moiety have the same meanings as defined above. Examples may include groups such as chloromethoxymethoxy, difluoromethoxymethoxy, chlorodifluoromethoxymethoxy, trifluoromethoxymethoxy and 2,2,2-trifluoroethoxymethoxy.

The $C_{3-8}$ cycloalkyloxy group represents, unless otherwise particularly defined, a (cycloalkyl)-O— group having 3 to 8 carbon atoms, where the cycloalkyl moiety has the same meaning as defined above. Examples may include groups such as cyclopropyloxy, cyclobutyloxy, cyclopentyloxy and cyclohexyloxy.

The $C_{3-8}$ cycloalkyloxy $C_{1-4}$ alkyl group represents, unless otherwise particularly defined, an alkyl group having 1 to 4 carbon atoms while the group is substituted with a (cycloalkyl)-O— group having 3 to 8 carbon atoms, where the alkyl moiety and the cycloalkyl moiety have the same meanings as defined above. Examples may include groups such as cyclopropyloxymethyl, cyclobutyloxymethyl, cyclopentyloxymethyl and cyclohexyloxymethyl.

The $C_{3-8}$ cycloalkyloxy $C_{1-6}$ alkyl group represents, unless otherwise particularly defined, an alkyl group having 1 to 6 carbon atoms while the group is substituted with a (cycloalkyl)-O— group having 3 to 8 carbon atoms, where the alkyl moiety and the cycloalkyl moiety have the same meanings as defined above. Examples may include groups such as cyclopropyloxymethyl, cyclobutyloxymethyl, cyclopentyloxymethyl and cyclohexyloxymethyl.

The $C_{3-6}$ cycloalkyl $C_{1-6}$ alkyl group represents, unless otherwise particularly defined, an alkyl group having 1 to 6 carbon atoms while the group is substituted with cycloalkyl having 3 to 8 carbon atoms, where the cycloalkyl moiety and the alkyl moiety have the same meanings as defined above. Examples may include groups such as cyclopropylmethyl, 1-cyclopropylethyl, 2-cyclopropylethyl, 1-cyclopropylpropyl, 2-cyclopropylpropyl, 3-cyclopropylpropyl, cyclobutylmethyl, cyclopentylmethyl and cyclohexylmethyl.

The $C_{3-8}$ cycloalkyl $C_{1-3}$ alkyloxy group represents, unless otherwise particularly defined, an (alkyl)-O— group having 1 to 3 carbon atoms while the group is substituted with cycloalkyl having 3 to 8 carbon atoms, where the cycloalkyl moiety and the alkyl moiety have the same meanings as defined above. Examples may include groups such as cyclopropylmethoxy, 1-cyclopropylethoxy, 2-cyclopropylethoxy, 1-cyclopropylpropoxy, 2-cyclopropylpropoxy, 3-cyclopropylpropoxy, cyclobutylmethoxy, cyclopentylmethoxy and cyclohexylmethoxy.

The $C_{2-6}$ alkenyloxy group represents, unless otherwise particularly defined, an (alkenyl)-O— group having 2 to 6 carbon atoms, where the alkenyl moiety has the same meaning as defined above. Examples may include groups such as 2-propenyloxy.

The $C_{2-6}$ alkynyloxy group represents, unless otherwise particularly defined, an (alkynyl)-O— group having 2 to 6 carbon atoms, where the alkynyl moiety has the same meaning as defined above. Examples may include groups such as 2-propynyloxy.

The $C_{1-6}$ alkoxyimino $C_{1-6}$ alkyl group represents, unless otherwise particularly defined, an alkyl group having 1 to 6 carbon atoms while the group is substituted with ($C_{1-6}$ alkoxy)-N=CH—, where the alkoxy moiety and the alkyl moiety have the same meanings as defined above. Examples may include groups such as methoxyiminomethyl and ethoxyiminomethyl.

The phenoxyimino $C_{1-6}$ alkyl group represents, unless otherwise particularly defined, an alkyl group having 1 to 6 carbon atoms while the group is substituted with a phenoxy-N=CH— group, where the phenoxy moiety and the alkyl moiety have the same meanings as defined above. Examples may include groups such as phenoxyiminomethyl.

The di($C_{1-6}$ alkoxy) $C_{1-6}$ alkyl group represents, unless otherwise particularly defined, an alkyl group having 1 to 6 carbon atoms di-substituted with an alkoxy group having 1 to 6 carbon atoms. Examples thereof may include groups such as (2,2-dimethoxy)ethyl, (3,3-dimethoxy)propyl, (2,2-diethoxy)ethyl group and (3,3-diethoxy)propyl.

The $C_{1-6}$ alkylthio group represents, unless otherwise particularly defined, an (alkyl)-S— group having 1 to 6 carbon atoms, where the alkyl moiety has the same meaning as defined above. Examples thereof may include groups such as methylthio, ethylthio, n-propylthio and isopropylthio.

The $C_{1-6}$ alkylsulfinyl group represents, unless otherwise particularly defined, an (alkyl)-SO— group having 1 to 6 carbon atoms, where the alkyl moiety has the same meaning as defined above. Examples thereof may include groups such as methylsulfinyl, ethylsulfinyl, n-propylsulfinyl and isopropylsulfinyl.

The $C_{1-6}$ alkylsulfonyl group represents, unless otherwise particularly defined, an (alkyl)-$SO_2$— group having 1 to 6 carbon atoms, where the alkyl moiety has the same meaning as defined above. Examples thereof may include groups such as methylsulfonyl, ethylsulfonyl, n-propylsulfonyl and isopropylsulfonyl.

The $C_{1-10}$ alkylthio group represents, unless otherwise particularly defined, an (alkyl)-S— group having 1 to 10 carbon atoms, where the alkyl moiety has the same meaning as defined above. Examples thereof may include groups such as methylthio, ethylthio, n-propylthio and isopropylthio.

The $C_{1-10}$ alkylsulfinyl group represents, unless otherwise particularly defined, an (alkyl)-SO— group having 1 to 10 carbon atoms, where the alkyl moiety has the same meaning as defined above. Examples thereof may include groups such as methylsulfinyl, ethylsulfinyl, n-propylsulfinyl and isopropylsulfinyl.

The $C_{1-10}$ alkylsulfonyl group represents, unless otherwise particularly defined, an (alkyl)-$SO_2$— group having 1 to 10 carbon atoms, where the alkyl moiety has the same meaning as defined above. Examples thereof may include groups such as methylsulfonyl, ethylsulfonyl, n-propylsulfonyl and isopropylsulfonyl.

The $C_{1-3}$ alkylsulfonyloxy group represents, unless otherwise particularly defined, an (alkyl)-$SO_2$—O— group having 1 to 3 carbon atoms, where the alkyl moiety has the same meaning as defined above. Examples thereof may include groups such as methylsulfonyloxy and ethylsulfonyloxy.

The $C_{1-6}$ alkylthio $C_{1-6}$ alkyl group represents, unless otherwise particularly defined, an alkyl group having 1 to 6 carbon atoms while the group is substituted with an alkylthio group having 1 to 6 carbon atoms, where the alkyl moiety and the alkylthio moiety have the same meanings as defined above. Examples thereof may include groups such as methylthiomethyl and ethylthiomethyl.

The $C_{1-6}$ alkylsulfinyl $C_{1-6}$ alkyl group represents, unless otherwise particularly defined, an alkyl group having 1 to 6 carbon atoms while the group is substituted with an alkylsulfinyl group having 1 to 6 carbon atoms, where the alkyl moiety and the alkylsulfinyl moiety have the same meanings as defined above. Examples thereof may include groups such as methylsulfinylmethyl and ethylsulfinylmethyl.

The $C_{1-6}$ alkylsulfonyl $C_{1-6}$ alkyl group represents, unless otherwise particularly defined, an alkyl group having 1 to 6 carbon atoms while the group is substituted with an alkylsulfonyl group having 1 to 6 carbon atoms, where the alkyl moiety and the alkylsulfonyl moiety have the same meanings as defined above. Examples thereof may include groups such as methylsulfonylmethyl and ethylsulfonylmethyl.

The $C_{1-6}$ alkylcarbonyl group represents, unless otherwise particularly defined, an ($C_{1-6}$ alkyl)-C(=O)— group where the alkyl moiety has the same meaning as defined above. Examples thereof may include groups such as acetyl and propionyl.

The $C_{1-8}$ alkylcarbonyloxy group represents, unless otherwise particularly defined, a ($C_{1-8}$ alkyl)-C(=O)—O— group where the alkyl moiety has the same meaning as defined above. Examples thereof may include groups such as methylcarbonyloxy group and ethylcarbonyloxy group.

The $C_{1-6}$ haloalkylcarbonyloxy group represents, unless otherwise particularly defined, a $(C_{1-6}$ haloalkyl)-C(=O)—O— group where the haloalkyl moiety has the same meaning as defined above. Examples thereof may include groups such as chloromethylcarbonyloxy, difluoromethylcarbonyloxy, chlorodifluoromethylcarbonyloxy, trifluoromethylcarbonyloxy and 2,2,2-trifluoroethylcarbonyloxy.

The $C_{2-6}$ alkenylcarbonyloxy group represents, unless otherwise particularly defined, a $(C_{2-6}$ alkenyl)-C(=O)—O— group where the alkenyl moiety has the same meaning as defined above. Examples thereof may include groups such as 1-propenylcarbonyloxy, 2-propenylcarbonyloxy, 1-butenylcarbonyloxy and 1-methyl-1-propenylcarbonyloxy.

The $C_{2-6}$ haloalkenylcarbonyloxy group represents, unless otherwise particularly defined, a $(C_{2-6}$ haloalkenyl)-C(=O)—O— group where the haloalkenyl moiety has the same meaning as defined above. Examples thereof may include groups such as 3-chloro-2-propenylcarbonyloxy and 3-bromo-2-propenylcarbonyloxy.

The $C_{2-6}$ alkynylcarbonyloxy group represents, unless otherwise particularly defined, a $(C_{2-6}$ alkynyl)-C(=O)—O— group where the alkynyl moiety has the same meaning as defined above. Examples thereof may include groups such as 1-propynylcarbonyloxy and 2-propynylcarbonyloxy.

The $C_{2-6}$ haloalkynylcarbonyloxy group represents, unless otherwise particularly defined, a $(C_{2-6}$ haloalkynyl)-C(=O)—O— group where the haloalkynyl moiety has the same meaning as defined above. Examples thereof may include groups such as 3-chloro-1-propynylcarbonyloxy and 3,3,3-trifluoro-1-propynylcarbonyloxy.

The $C_{2-6}$ alkylideneamino group represents, unless otherwise particularly defined, an amino group substituted with alkylidene having 2 to 6 carbon atoms. Examples thereof may include groups such as ethylideneamino and propylideneamino.

The di($C_{1-10}$alkyl)amino $C_{1-6}$ alkylideneamino group represents, unless otherwise particularly defined, the amino group substituted with a $C_{1-6}$ alkylidene group where the alkylidene group is further substituted with a $C_{1-10}$ alkyl group-di-substituted amino group, while the alkyl moiety has the same meaning as defined above. Examples thereof may include groups such as a dimethylaminomethylideneamino group and a diethylaminomethylideneamino group.

The $C_{1-10}$ alkylamino group represents, unless otherwise particularly defined, an (alkyl)-NH— group having 1 to 10 carbon atoms, where the alkyl moiety has the same meaning as defined above. Examples thereof may include groups such as methylamino and ethylamino.

The di($C_{1-10}$ alkyl)amino group represents, unless otherwise particularly defined, an (alkyl)$_2$N— group where the alkyl moiety has the same meaning as defined above. Examples thereof may include groups such as dimethylamino, diethylamino, methylethylamino, dipropylamino and dibutylamino.

The $C_{1-6}$ alkylamino $C_{1-6}$ alkyl group represents, unless otherwise particularly defined, an alkyl group having 1 to 6 carbon atoms while the group is substituted with an alkylamino group having 1 to 6 carbon atoms, where the alkyl moiety has the same meaning as defined above. Examples thereof may include groups such as N-methylaminomethyl and N-methylaminoethyl.

The di($C_{1-6}$ alkyl)amino $C_{1-6}$ alkyl group represents, unless otherwise particularly defined, an alkyl group having 1 to 6 carbon atoms while the group is substituted with a ($C_{1-6}$ alkyl)$_2$N— group where the alkyl moiety has the same meaning as defined above. Examples thereof may include groups such as N,N-dimethylaminomethyl and N,N-dimethylaminoethyl.

The $C_{1-6}$ alkoxycarbonylamino group represents, unless otherwise particularly defined, an amino group substituted with a ($C_{1-6}$ alkoxy)-C(=O)— group where the alkoxy moiety has the same meaning as defined above. Examples thereof may include groups such as methoxycarbonylamino and ethoxycarbonylamino.

The $C_{1-6}$ alkoxycarbonyl group represents, unless otherwise particularly defined, a ($C_{1-6}$ alkyl)-O—C(=O)— group where the alkyl moiety has the same meaning as defined above. Examples thereof may include groups such as methoxycarbonyl, ethoxycarbonyl, n-propoxycarbonyl and isopropoxycarbonyl.

The $C_{1-6}$ alkoxycarbonyl $C_{1-6}$ alkoxy group represents, unless otherwise particularly defined, an (alkyl)-O— group having 1 to 6 carbon atoms while the group is substituted with a ($C_{1-6}$ alkyl)-O—C(=O)— group where the alkyl moiety has the same meaning as defined above. Examples thereof may include groups such as methoxycarbonylmethoxy, ethoxycarbonylethoxy, n-propoxycarbonylpropyloxy and isopropoxycarbonylpropoxy.

The $C_{1-6}$ alkoxycarbonyloxy group represents, unless otherwise particularly defined, a ($C_{1-6}$ alkoxy)-C(=O)—O— group where the alkoxycarbonyl moiety has the same meaning as defined above. Examples thereof may include groups such as methoxycarbonyloxy and ethoxycarbonyloxy.

The $C_{1-6}$ haloalkylthio group represents, unless otherwise particularly defined, a (haloalkyl)-S— group having 1 to 6 carbon atoms, where the haloalkyl moiety has the same meaning as defined above. Examples thereof may include groups such as difluoromethylthio and trifluoromethylthio.

The $C_{1-6}$ haloalkylsulfinyl group represents, unless otherwise particularly defined, a (haloalkyl)-SO— group having 1 to 6 carbon atoms, where the haloalkyl moiety has the same meaning as defined above. Examples thereof may include groups such as trifluoromethylsulfinyl and difluoromethylsulfinyl.

The $C_{1-6}$ haloalkylsulfonyl group represents, unless otherwise particularly defined, a (haloalkyl)-SO$_2$— group having 1 to 6 carbon atoms, where the haloalkyl moiety has the same meaning as defined above. Examples thereof may include groups such as chloromethylsulfonyl, difluoromethylsulfonyl and trifluoromethylsulfonyl.

The $C_{1-6}$ haloalkylsulfonylamino group represents, unless otherwise particularly defined, a (haloalkyl)-SO$_2$-amino group having 1 to 6 carbon atoms, where the haloalkyl moiety has the same meaning as defined above. Examples thereof may include groups such as chloromethylsulfonylamino, difluoromethylsulfonylamino and trifluoromethylsulfonylamino.

The $C_{3-8}$ cycloalkylthio $C_{1-6}$ alkyl group represents, unless otherwise particularly defined, an alkyl group having 1 to 6 carbon atoms while the group is substituted with a (cycloalkyl)-S— group having 3 to 8 carbon atoms, where the alkyl moiety and the cycloalkyl moiety have the same meanings as defined above. Examples thereof may include groups such as cyclopropylthiomethyl, cyclobutylthiomethyl, cyclopentylthiomethyl and cyclohexylthiomethyl.

The $C_{3-8}$ cycloalkylsulfinyl $C_{1-6}$ alkyl group represents, unless otherwise particularly defined, an alkyl group having 1 to 6 carbon atoms while the group is substituted with a (cycloalkyl)-SO— group having 3 to 8 carbon atoms, where the alkyl moiety and the cycloalkyl moiety have the same meanings as defined above. Examples thereof may include groups such as cyclopropylsulfinylmethyl, cyclobutylsulfinylmethyl, cyclopentylsulfinylmethyl and cyclohexylsulfinylmethyl.

The $C_{3-8}$ cycloalkylsulfonyl $C_{1-6}$ alkyl group represents, unless otherwise particularly defined, an alkyl group having 1 to 6 carbon atoms while the group is substituted with a (cycloalkyl)-$SO_2$— group having 3 to 8 carbon atoms, where the alkyl moiety and the cycloalkyl moiety have the same meanings as defined above. Examples thereof may include groups such as cyclopropylsulfonylmethyl, cyclobutylsulfonylmethyl, cyclopentylsulfonylmethyl and cyclohexylsulfonylmethyl.

The $C_{3-8}$ cycloalkyl $C_{1-8}$ alkylthio $C_{1-8}$ alkyl group represents, unless otherwise particularly defined, an alkyl group having 1 to 6 carbon atoms while the group is substituted with a $C_{3-8}$ cycloalkyl group-substituted alkyl-S— group having 1 to 6 carbon atoms, where the alkyl and cycloalkyl moieties have the same meanings as defined above. Examples thereof may include groups such as cyclopropylmethylthiomethyl, cyclobutylethylthiomethyl, cyclopentylethylthiomethyl and cyclohexylmethylthioethyl.

The $C_{3-8}$ cycloalkyl $C_{1-6}$ alkylsulfinyl $C_{1-6}$ alkyl group represents, unless otherwise particularly defined, an alkyl group having 1 to 6 carbon atoms while the group is substituted with a $C_{3-8}$ cycloalkyl group-substituted $C_{1-6}$ alkyl group-SO—, where the alkyl and cycloalkyl moieties have the same meanings as defined above. Examples thereof may include groups such as cyclopropylmethylsulfinylmethyl, cyclobutylethylsulfinylmethyl, cyclopentylethylsulfinylmethyl and cyclohexylmethylsulfinylethyl.

The $C_{3-8}$ cycloalkyl $C_{1-6}$ alkylsulfonyl $C_{1-6}$ alkyl group represents, unless otherwise particularly defined, an alkyl group having 1 to 6 carbon atoms while the group is substituted with a $C_{3-8}$ cycloalkyl group-substituted $C_{1-6}$ alkyl group-$SO_2$—, where the alkyl and cycloalkyl moieties have the same meanings as defined above. Examples thereof may include groups such as cyclopropylmethylsulfonylmethyl, cyclobutylethylsulfonylmethyl, cyclopentylethylsulfonylmethyl and cyclohexylmethylsulfonylethyl.

The $C_{2-6}$ alkenylthio $C_{1-6}$ alkyl group represents, unless otherwise particularly defined, an alkyl group having 1 to 6 carbon atoms while the group is substituted with an (alkenyl)-S— group having 2 to 6 carbon atoms, where the alkyl moiety and the alkenyl moiety have the same meanings as defined above. Examples thereof may include groups such as propenylthiomethyl and butenylthiomethyl.

The $C_{2-6}$ alkenylsulfinyl $C_{1-6}$ alkyl group represents, unless otherwise particularly defined, an alkyl group having 1 to 6 carbon atoms while the group is substituted with an (alkenyl)-SO— group having 2 to 6 carbon atoms, where the alkyl moiety and the alkenyl moiety have the same meanings as defined above. Examples thereof may include groups such as ethenylsulfinylmethyl, propenylsulfinylmethyl and butenylsulfinylmethyl.

The $C_{2-6}$ alkenylsulfonyl $C_{1-6}$ alkyl group represents, unless otherwise particularly defined, an alkyl group having 1 to 6 carbon atoms while the group is substituted with an (alkenyl)-$SO_2$— group having 2 to 6 carbon atoms, where the alkyl moiety and the alkenyl moiety have the same meanings as defined above. Examples thereof may include groups such as ethenylsulfonylmethyl, propenylsulfonylmethyl and butenylsulfonylmethyl.

The $C_{2-6}$ alkynylthio $C_{1-6}$ alkyl group represents, unless otherwise particularly defined, an alkyl group having 1 to 6 carbon atoms while the group is substituted with an (alkynyl)-S— group having 2 to 6 carbon atoms, where the alkyl moiety and the alkynyl moiety have the same meanings as defined above. Examples thereof may include groups such as propynylthiomethyl and butynylthiomethyl.

The $C_{2-6}$ alkynylsulfinyl $C_{1-6}$ alkyl group represents, unless otherwise particularly defined, an alkyl group having 1 to 6 carbon atoms while the group is substituted with an (alkynyl)-SO— group having 2 to 6 carbon atoms, where the alkyl moiety and the alkynyl moiety have the same meanings as defined above. Examples thereof may include groups such as propynylsulfinylmethyl and butynylsulfinylmethyl.

The $C_{2-6}$ alkynylsulfonyl $C_{1-6}$ alkyl group represents, unless otherwise particularly defined, an alkyl group having 1 to 6 carbon atoms while the group is substituted with an (alkynyl)-$SO_2$— group having 2 to 6 carbon atoms, where the alkyl moiety and the alkynyl moiety have the same meanings as defined above. Examples thereof may include groups such as propynylsulfonylmethyl and butynylsulfonylmethyl.

The $C_{1-6}$ haloalkylthio $C_{1-6}$ alkyl group represents, unless otherwise particularly defined, an alkyl group having 1 to 6 carbon atoms while the group is substituted with a (haloalkyl)-S— group having 1 to 6 carbon atoms, where the alkyl moiety and the haloalkyl moiety have the same meanings as defined above. Examples thereof may include groups such as difluoromethylthiomethyl and trifluoromethylthioethyl.

The $C_{1-6}$ haloalkylsulfinyl $C_{1-6}$ alkyl group represents, unless otherwise particularly defined, an alkyl group having 1 to 6 carbon atoms while the group is substituted with a (haloalkyl)-SO— group having 1 to 6 carbon atoms, where the alkyl moiety and the haloalkyl moiety have the same meanings as defined above. Examples thereof may include groups such as difluoromethylsulfinylmethyl and trifluoromethylsulfinylmethyl.

The $C_{1-6}$ haloalkylsulfonyl $C_{1-6}$ alkyl group represents, unless otherwise particularly defined, an alkyl group having 1 to 6 carbon atoms while the group is substituted with a (haloalkyl)-$SO_2$— group having 1 to 6 carbon atoms, where the alkyl moiety and the haloalkyl moiety have the same meanings as defined above. Examples thereof may include groups such as difluoromethylsulfonylmethyl and trifluoromethylsulfonylmethyl.

The cyano $C_{1-6}$ alkyl group represents, unless otherwise particularly defined, an alkyl group having 1 to 6 carbon atoms while the group is substituted with a cyano group, where the alkyl moiety has the same meaning as defined above. Examples thereof may include groups such as cyanomethyl and cyanoethyl.

The phenyl $C_{1-6}$ alkyl group represents, unless otherwise particularly defined, an alkyl group having 1 to 6 carbon atoms while the group is substituted with a phenyl group, where the alkyl moiety has the same meaning as defined above. Examples thereof may include groups such as phenethyl and phenylpropyl.

The phenyl $C_{2-6}$ alkenyl group represents, unless otherwise particularly defined, an alkenyl group having 2 to 6 carbon atoms while the group is substituted with a phenyl group, where the alkenyl moiety has the same meaning as defined above. Examples thereof may include styryl and cinnamyl.

The phenyl $C_{2-6}$ alkynyl group represents, unless otherwise particularly defined, an alkynyl group having 2 to 6 carbon atoms while the group is substituted with a phenyl group, where the alkynyl moiety has the same meaning as defined above. Examples thereof may include groups such as phenylethynyl and 4-phenyl-1-butynyl.

The benzyloxy $C_{1-6}$ alkyl group represents, unless otherwise particularly defined, an alkyl group having 1 to 6 carbon atoms the group is substituted with a phenyl-$CH_2$—O— group, where the alkyl moiety has the same meaning as defined above. Examples thereof may include groups such as benzyloxymethyl and benzyloxyethyl.

The phenylcarbonyl $C_{1-6}$ alkyloxy group represents, unless otherwise particularly defined, a (phenyl)-C(=O)—$C_{1-6}$ (alkyl)-O— group. Examples thereof may include groups such as phenylcarbonylmethyloxy.

Examples of the $C_{2-10}$ heterocyclic group having one or more of the same or different hetero atoms selected from the group consisting of an oxygen atom, a sulfur atom and a nitrogen atom, may include, unless otherwise particularly defined, groups such as oxirane, furan, thiophene, pyrrole, pyrazole, imidazole, triazole, pyridine, pyrimidine, pyrazine, pyridazine, pyrrolidine, piperidine, piperazine, morpholine, benzofuran, benzothiophene, indole, benzoxazole, benzothiazole, benzimidazole, isoxazole, isoxazoline, oxazole, oxazoline, isothiazole, isothiazoline, thiazole, tetrahydrofuran, thiomorpholine and thiazoline.

The $C_{1-6}$ alkyl group substituted with a $C_{2-10}$ heterocyclic ring having one or more of the same or different hetero atoms selected from the group consisting of an oxygen atom, a sulfur atom and a nitrogen atom represents, unless otherwise particularly defined, an alkyl group having 1 to 6 carbon atoms while the group is substituted with a heterocyclic ring, where the alkyl moiety and the heterocyclic ring moiety have the same meanings as defined above. Examples thereof may include groups such as (2-furyl)methyl, (3-furyl)methyl, (2-thienyl)methyl, and (3-thienyl)methyl.

The $C_{1-6}$ alkylamino group substituted with a $C_{2-10}$ heterocyclic ring having one or more of the same or different hetero atoms selected from the group consisting of an oxygen atom, a sulfur atom and a nitrogen atom represents, unless otherwise particularly defined, an alkyl-N— group having 1 to 6 carbon atoms while the group is substituted with a heterocyclic ring, where the alkyl moiety and the heterocyclic ring moiety have the same meanings as defined above. Examples thereof may include groups such as (2-furyl)methylamino, (3-furyl)methylamino, (2-thienyl)methylamino, and (3-thienyl)methylamino.

The $C_{1-6}$ alkoxy $C_{1-6}$ alkyl group substituted with a $C_{2-10}$ heterocyclic ring having one or more of the same or different hetero atoms selected from the group consisting of an oxygen atom, a sulfur atom and a nitrogen atom represents, unless otherwise particularly defined, an alkyl group having 1 to 6 carbon atoms while the group is substituted with a heterocyclic ring-substituted $C_{1-6}$ alkoxy group, where the alkyl moiety, the alkoxy moiety, and the heterocyclic ring moiety have the same meanings as defined above. Examples thereof may include groups such as tetrahydrofurfryloxyethyl and tetrahydrofurfryloxymethyl.

The $C_{1-6}$ alkyloxy group substituted with a $C_{2-10}$ heterocyclic ring having one or more of the same or different hetero atoms selected from the group consisting of an oxygen atom, a sulfur atom and a nitrogen atom represents, unless otherwise particularly defined, an (alkyl)-O— group having 1 to 6 carbon atoms while the group is substituted with a heterocyclic ring, where the heterocyclic ring moiety has the same meaning as defined above. Examples thereof may include groups such as a 6-methyl-2-pyridinemethoxy group and a tetrahydrofurfryloxy group.

Examples of the alkali metal may include sodium, potassium and the like.

Examples of the $C_{1-5}$ alkylene chain may include methylene, ethylene, propylene, pentamethylene and the like.

Examples of the $C_{2-5}$ alkylene chain may include ethylene, propylene, pentamethylene and the like.

Examples of the $C_{1-4}$ alkylenedioxy group may include a methylenedioxy group, an ethylenedioxy group, a propylenedioxy group and the like.

Examples of the $C_{2-5}$ alkenylene group may include vinylene, propenylene and the like.

Next, specific examples of the compound of the invention represented by Formula [1] will be shown in Tables 1 to 21. However, the compound of the invention is not limited to those compounds.

The following abbreviations in Tables in the present specification represent groups as shown below, respectively.

Me: methyl group
Et: ethyl group
Pr-n: n-propyl group
Pr-i: isopropyl group
Pr-c: cyclopropyl group
Bu-n: n-butyl group
Bu-s: secondary butyl group
Bu-i: isobutyl group
Bu-t: tertiary butyl group
Bu-c: cyclobutyl group
Pen-n: n-pentyl group
Pen-c: cyclopentyl group
Hex-n: n-hexyl group
Hex-c: cyclohexyl group
Ac: acetyl
Ph: phenyl group
Bn: benzyl group
Ts: toluenesulfonyl group
pyridyl: pyridyl group
pyrimidinyl: pyrimidinyl group
Ph(2-OMe): 2-methoxyphenyl group
$CH_2$Ph(2-OMe): 2-methoxybenzyl group
Ph(3,4-di-Cl): 3,4-dichlorphenyl group

TABLE 1

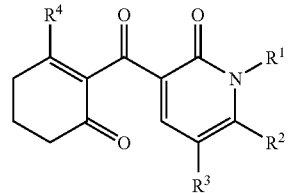

| Compound No | $R^1$ | $R^2$ | $R^3$ | $R^4$ |
|---|---|---|---|---|
| I-1 | Me | $C_3$ | H | OH |
| I-2 | Et | $CF_3$ | H | OH |
| I-3 | Pr-n | $CF_3$ | H | OH |
| I-4 | Pr-i | $CF_3$ | H | OH |
| I-5 | Bu-n | $CF_3$ | H | OH |
| I-6 | Bu-i | $CF_3$ | H | OH |
| I-7 | Bu-s | $CF_3$ | H | OH |
| I-8 | Bu-t | $CF_3$ | H | OH |
| I-9 | Hex-n | $CF_3$ | H | OH |
| I-10 | $CH_2CF_3$ | $CF_3$ | H | OH |
| I-11 | $CH_2CH=CH_2$ | $CF_3$ | H | OH |
| I-12 | $CH_2C(Me)=CH_2$ | $CF_3$ | H | OH |
| I-13 | $CH_2CH_2CH=CMe_2$ | $CF_3$ | H | OH |
| I-14 | $CH_2C\equiv CH$ | $CF_3$ | H | OH |
| I-15 | $CH_2C\equiv CCH_3$ | $CF_3$ | H | OH |
| I-16 | Pr-c | $CF_3$ | H | OH |
| I-17 | Bu-c | $CF_3$ | H | OH |
| I-18 | Pen-c | $CF_3$ | H | OH |
| I-19 | Hex-c | $CF_3$ | H | OH |
| I-20 | $CH_2$Pr-c | $CF_3$ | H | OH |
| I-21 | $CH_2$Bun-c | $CF_3$ | H | OH |
| I-22 | $CH_2$Pen-c | $CF_3$ | H | OH |
| I-23 | $CH_2$Hex-c | $CF_3$ | H | OH |
| I-24 | $CH_2CH=CCl_2$ | $CF_3$ | H | OH |

TABLE 1-continued

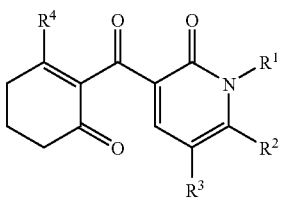

| Compound No | R¹ | R² | R³ | R⁴ |
|---|---|---|---|---|
| I-25 | CH$_2$CCl=CHCl | CF$_3$ | H | OH |
| I-26 | CH$_2$CH$_2$CH=CCl$_2$ | CF$_3$ | H | OH |
| I-27 | CH$_2$CH$_2$C(Me)=CF$_2$ | CF$_3$ | H | OH |
| I-28 | CH$_2$CH$_2$CH$_2$C(Me)=CF$_2$ | CF$_3$ | H | OH |
| I-29 | CH$_2$CH=CF$_2$ | CF$_3$ | H | OH |
| I-30 | CH$_2$OMe | CF$_3$ | H | OH |
| I-31 | CH$_2$CH$_2$OMe | CF$_3$ | H | OH |
| I-32 | CH$_2$CH$_2$OEt | CF$_3$ | H | OH |
| I-33 | CH(Me)CH$_2$OMe | CF$_3$ | H | OH |
| I-34 | CH$_2$CH$_2$OCH$_2$OMe | CF$_3$ | H | OH |
| I-35 | CH$_2$CH$_2$OPr-n | CF$_3$ | H | OH |
| I-36 | CH$_2$CH$_2$OPr-i | CF$_3$ | H | OH |
| I-37 | CH$_2$CH$_2$OPr-c | CF$_3$ | H | OH |

TABLE 2

| Compound No | R¹ | R² | R³ | R⁴ |
|---|---|---|---|---|
| I-38 | CH$_2$CH$_2$OBu-c | CF$_3$ | H | OH |
| I-39 | CH$_2$CH$_2$OPen-c | CF$_3$ | H | OH |
| I-40 | CH$_2$CH$_2$OHex-c | CF$_3$ | H | OH |
| I-41 | CH$_2$CH$_2$OCH$_2$CF$_3$ | CF$_3$ | H | OH |
| I-42 | CH$_2$CH$_2$CH$_2$OMe | CF$_3$ | H | OH |
| I-43 | CH$_2$CH(Me)OCH$_2$Ph | CF$_3$ | H | OH |
| I-44 | CH$_2$CH$_2$CN | CF$_3$ | H | OH |
| I-45 | CH$_2$CH$_2$NMe$_2$ | CF$_3$ | H | OH |
| I-46 | CH$_2$SMe | CF$_3$ | H | OH |
| I-47 | CH$_2$SO$_2$Me | CF$_3$ | H | OH |
| I-48 | CH$_2$SEt | CF$_3$ | H | OH |
| I-49 | CH$_2$SO$_2$Et | CF$_3$ | H | OH |
| I-50 | CH$_2$SPr-n | CF$_3$ | H | OH |
| I-51 | CH$_2$SO$_2$Pr-n | CF$_3$ | H | OH |
| I-52 | CH$_2$SPr-c | CF$_3$ | H | OH |
| I-53 | CH$_2$SO$_2$Pr-c | CF$_3$ | H | OH |
| I-54 | CH$_2$SO$_2$Pr-i | CF$_3$ | H | OH |
| I-55 | CH$_2$SBu-t | CF$_3$ | H | OH |
| I-56 | CH$_2$SO$_2$Bu-t | CF$_3$ | H | OH |
| I-57 | CH$_2$SCH$_2$Pr-c | CF$_3$ | H | OH |
| I-58 | CH$_2$SO$_2$CH$_2$Pr-c | CF$_3$ | H | OH |
| I-59 | CH$_2$SPen-c | CF$_3$ | H | OH |
| I-60 | CH$_2$SO$_2$Pen-c | CF$_3$ | H | OH |
| I-61 | CH$_2$SHex-c | CF$_3$ | H | OH |
| I-62 | CH$_2$SO$_2$Hex-c | CF$_3$ | H | OH |
| I-63 | CH$_2$SCH$_2$CH=CH$_2$ | CF$_3$ | H | OH |
| I-64 | CH$_2$SO$_2$CH$_2$CF$_3$ | CF$_3$ | H | OH |
| I-65 | CH$_2$CH$_2$SMe | CF$_3$ | H | OH |
| I-66 | CH$_2$CH$_2$SOMe | CF$_3$ | H | OH |
| I-67 | CH$_2$CH$_2$SO$_2$Me | CF$_3$ | H | OH |
| I-68 | CH$_2$CH(Me)SO$_2$Me | CF$_3$ | H | OH |
| I-69 | CH$_2$CH$_2$CH$_2$SMe | CF$_3$ | H | OH |
| I-70 | CH$_2$CH$_2$CH$_2$SOMe | CF$_3$ | H | OH |
| I-71 | CH$_2$CH$_2$CH$_2$SO$_2$Me | CF$_3$ | H | OH |
| I-72 | Ph | CF$_3$ | H | OH |
| I-73 | Ph(2-Cl) | CF$_3$ | H | OH |
| I-74 | Ph(3-Cl) | CF$_3$ | H | OH |
| I-75 | Ph(4-Cl) | CF$_3$ | H | OH |
| I-76 | Ph(2-OMe) | CF$_3$ | H | OH |
| I-77 | Ph(3-OMe) | CF$_3$ | H | OH |
| I-78 | Ph(4-OMe) | CF$_3$ | H | OH |

TABLE 3

| Compound No | R¹ | R² | R³ | R⁴ |
|---|---|---|---|---|
| I-79 | Ph(4-OCF3) | CF$_3$ | H | OH |
| I-80 | Ph(3-SMe) | CF$_3$ | H | OH |
| I-81 | Ph(3-SOMe) | CF$_3$ | H | OH |
| I-82 | Ph(3-SO$_2$Me) | CF$_3$ | H | OH |
| I-83 | Ph(4-SO$_2$Me) | CF$_3$ | H | OH |
| I-84 | Ph(2-CF$_3$) | CF$_3$ | H | OH |
| I-85 | Ph(3-CF$_3$) | CF$_3$ | H | OH |
| I-86 | Ph(4-CF$_3$) | CF$_3$ | H | OH |
| I-87 | Ph(3-NO$_2$) | CF$_3$ | H | OH |
| I-88 | Ph(4-NO$_2$) | CF$_3$ | H | OH |
| I-89 | Ph(4-Me) | CF$_3$ | H | OH |
| I-90 | Ph(4-Br) | CF$_3$ | H | OH |
| I-91 | Ph(2-F) | CF$_3$ | H | OH |
| I-92 | Ph(3-F) | CF$_3$ | H | OH |
| I-93 | Ph(4-F) | CF$_3$ | H | OH |
| I-94 | Ph(3-CN) | CF$_3$ | H | OH |
| I-95 | Ph(4-CN) | CF$_3$ | H | OH |
| I-96 | Ph(4-Bu-t) | CF$_3$ | H | OH |
| I-97 | Ph(4-NHSO$_2$CF$_3$) | CF$_3$ | H | OH |
| I-98 | Ph(3,4-di-Cl) | CF$_3$ | H | OH |
| I-99 | Ph(2,4-di-OMe) | CF$_3$ | H | OH |
| I-100 | Ph(3,4-di-OMe) | CF$_3$ | H | OH |
| I-101 | Ph(3,5-di-OMe) | CF$_3$ | H | OH |
| I-102 | Ph(2,4-di-F) | CF$_3$ | H | OH |
| I-103 | Ph(2,5-di-F) | CF$_3$ | H | OH |
| I-104 | Ph(2,6-di-F) | CF$_3$ | H | OH |
| I-105 | Ph(3,4-di-F) | CF$_3$ | H | OH |
| I-106 | Ph(3,5-di-F) | CF$_3$ | H | OH |
| I-107 | Ph(2-F,5-NO$_2$) | CF$_3$ | H | OH |
| I-108 | Ph(3-OMe-4-Cl) | CF$_3$ | H | OH |
| I-109 | Ph(3-F-4-OMe) | CF$_3$ | H | OH |
| I-110 | Ph(3-Cl-4-OMe) | CF$_3$ | H | OH |
| I-111 | 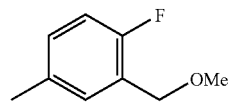 | CF$_3$ | H | OH |
| I-112 | 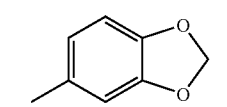 | CF$_3$ | H | OH |
| I-113 | 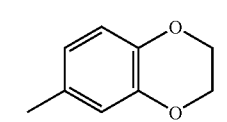 | CF$_3$ | H | OH |
| I-114 | CH$_2$Ph | CF$_3$ | H | OH |
| I-115 | CH$_2$Ph(2-NO$_2$) | CF$_3$ | H | OH |
| I-116 | CH$_2$Ph(3-NO$_2$) | CF$_3$ | H | OH |

TABLE 4

| Compound No | R¹ | R² | R³ | R⁴ |
|---|---|---|---|---|
| I-117 | CH$_2$Ph(4-NO$_2$) | CF$_3$ | H | OH |
| I-118 | CH$_2$Ph(3-CN) | CF$_3$ | H | OH |
| I-119 | CH$_2$Ph(4-CN) | CF$_3$ | H | OH |
| I-120 | CH$_2$Ph(2-OMe) | CF$_3$ | H | OH |
| I-121 | CH$_2$Ph(3-OMe) | CF$_3$ | H | OH |
| I-122 | CH$_2$Ph(4-OMe) | CF$_3$ | H | OH |
| I-123 | CH$_2$Ph(4-SO$_2$Me) | CF$_3$ | H | OH |
| I-124 | 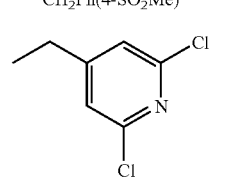 | CF$_3$ | H | OH |

TABLE 4-continued

| Compound No | R¹ | R² | R³ | R⁴ |
|---|---|---|---|---|
| I-125 | 5-ethyl-4,5-dihydroisoxazol-5-yl (ethyl-isoxazoline) | $CF_3$ | H | OH |
| I-126 | 5-ethyl-3-methyl-4,5-dihydroisoxazolyl | $CF_3$ | H | OH |
| I-127 | 4-ethyl-5-(OCHCF₂)-1-methyl-3-(CF₃)-pyrazolyl | $CF_3$ | H | OH |
| I-128 | 5-ethyl-3-methylisoxazolyl | $CF_3$ | H | OH |
| I-129 | $CH_2CH_2Ph$ | $CF_3$ | H | OH |
| I-130 | $CH_2CH_2CH_2Ph$ | $CF_3$ | H | OH |
| I-131 | $CH_2CH{=}CHPh$ | $CF_3$ | H | OH |
| I-132 | $CH_2C{\equiv}CPh$ | $CF_3$ | H | OH |
| I-133 | $CH_2CH{=}NOMe$ | $CF_3$ | H | OH |
| I-134 | $CH_2CH{=}NOEt$ | $CF_3$ | H | OH |
| I-135 | $CH_2CH{=}NOPr\text{-}n$ | $CF_3$ | H | OH |
| I-136 | $CH_2CH{=}NOPh$ | $CF_3$ | H | OH |
| I-137 | $CH_2CH(OMe)_2$ | $CF_3$ | H | OH |
| I-138 | 2-ethyl-1,3-dioxolanyl | $CF_3$ | H | OH |
| I-139 | $CH_2CHO$ | $CF_3$ | H | OH |
| I-140 | 3-methyl-4,5-dihydroisoxazolyl | $CF_3$ | H | OH |
| I-141 | 2-methyloxazolyl | $CF_3$ | H | OH |
| I-142 | 3-methyl-5-methylisoxazolyl | $CF_3$ | H | OH |
| I-143 | 3-methyltetrahydrothiophenyl | $CF_3$ | H | OH |
| I-144 | 2-methylthiazolyl | $CF_3$ | H | OH |
| I-145 | 2-methyl-4-methylthiazolyl | $CF_3$ | H | OH |

TABLE 5

| Compound No. | R¹ | R² | R³ | R⁴ |
|---|---|---|---|---|
| I-146 | 2-methyl-4,5-dihydrooxazolyl | $CF_3$ | H | OH |
| I-147 | 2-methylthienyl | $CF_3$ | H | OH |
| I-148 | 3-methylthienyl | $CF_3$ | H | OH |
| I-149 | 2,3-dimethylthienyl | $CF_3$ | H | OH |
| I-150 | 2-methylpyridyl | $CF_3$ | H | OH |
| I-151 | 3-methoxy-5-methylpyridyl | $CF_3$ | H | OH |
| I-152 | 2-ethyloxiranyl | $CF_3$ | H | OH |
| I-153 | 2-ethyltetrahydrofuranyl | $CF_3$ | H | OH |
| I-154 | 3-ethyltetrahydrofuranyl | $CF_3$ | H | OH |
| I-155 | 4-ethylmorpholinyl | $CF_3$ | H | OH |
| I-156 | $NH_2$ | $CF_3$ | H | OH |
| I-157 | $NHMe$ | $CF_3$ | H | OH |
| I-158 | $NHEt$ | $CF_3$ | H | OH |
| I-159 | $NHPr\text{-}n$ | $CF_3$ | H | OH |
| I-160 | $NHPr\text{-}i$ | CP3 | H | OH |
| I-161 | $NHBu\text{-}n$ | $CF_3$ | H | OH |
| I-162 | $NHBu\text{-}i$ | $CF_3$ | H | OH |
| I-163 | $NHBu\text{-}s$ | $CF_3$ | H | OH |
| I-164 | $NHCH_2Pr\text{-}c$ | $CF_3$ | H | OH |
| I-165 | $NHPen\text{-}n$ | $CF_3$ | H | OH |
| I-166 | $NHHex\text{-}n$ | $CF_3$ | H | OH |
| I-167 | $NHCH_2CH_2CH_2Cl$ | $CF_3$ | H | OH |
| I-168 | $NHCH_2CH_2CH_2F$ | $CF_3$ | H | OH |
| I-169 | $NHCH_2CH_2OMe$ | $CF_3$ | H | OH |
| I-170 | N-methyl-(tetrahydrofuran-2-ylmethyl)amino | $CF_3$ | H | OH |
| I-171 | $NMe_2$ | $CF_3$ | H | OH |
| I-172 | $NEt_2$ | $CF_3$ | H | OH |
| I-173 | $N(Pr\text{-}n)_2$ | $CF_3$ | H | OH |
| I-174 | $N(Bu\text{-}n)_2$ | $CF_3$ | H | OH |

TABLE 5-continued

| Compound No. | R¹ | R² | R³ | R⁴ |
|---|---|---|---|---|
| I-175 | N(Me)Et | $CF_3$ | H | OH |
| I-176 | N(Me)CH₂CH₂OMe | $CF_3$ | H | OH |

TABLE 6

| Compound No | R¹ | R² | R³ | R⁴ |
|---|---|---|---|---|
| I-177 | 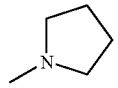 | $CF_3$ | H | OH |
| I-178 | 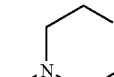 | $CF_3$ | H | OH |
| I-179 | 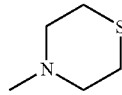 | $CF_3$ | H | OH |
| I-180 | 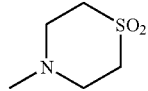 | $CF_3$ | H | OH |
| I-181 | NHPh | $CF_3$ | H | OH |
| I-182 | N(Me)Ph | $CF_3$ | H | OH |
| I-183 | NHCH₂Ph | $CF_3$ | H | OH |
| I-184 | N=CMe₂ | $CF_3$ | H | OH |
| I-185 | N=CEt₂ | $CF_3$ | H | OH |
| I-186 | N=CHNMe₂ | $CF_3$ | H | OH |
| I-187 | NHC(=O)Me | $CF_3$ | H | OH |
| I-188 | N[C(=O)Me]₂ | $CF_3$ | H | OH |
| I-189 | NHC(=O)OMe | $CF_3$ | H | OH |
| I-190 | N(Me)C(=O)OMe | $CF_3$ | H | OH |
| I-191 | N(Et)C(=O)OMe | $CF_3$ | H | OH |
| I-192 | NHC(=O)OEt | $CF_3$ | H | OH |
| I-193 | NHC(=O)OBu-t | $CF_3$ | H | OH |
| I-194 | N(Me)C(=O)OBu-t | $CF_3$ | H | OH |
| I-195 | N(Et)C(=O)OBu-t | $CF_3$ | H | OH |
| I-196 | NHC(=O)OBn | $CF_3$ | H | OH |
| I-197 | N(Me)C(=O)OBn | $CF_3$ | H | OH |
| I-198 | N[C(=O)OMe]₂ | $CF_3$ | H | OH |
| I-199 | NHSO₂Me | $CF_3$ | H | OH |
| I-200 | NHSO₂Ph | $CF_3$ | H | OH |
| I-201 | NHSO₂CH₂Ph | $CF_3$ | H | OH |
| I-202 | OMe | $CF_3$ | H | OH |
| I-203 | OEt | $CF_3$ | H | OH |
| I-204 | OPr-n | $CF_3$ | H | OH |
| I-205 | OPr-i | $CF_3$ | H | OH |
| I-206 | OCH₂Pr-c | $CF_3$ | H | OH |
| I-207 | OCH₂Cl | $CF_3$ | H | OH |
| I-208 | OCHCl₂ | $CF_3$ | H | OH |
| I-209 | OCCl₃ | $CF_3$ | H | OH |
| I-210 | OCH₂F | $CF_3$ | H | OH |
| I-211 | OCHF₂ | $CF_3$ | H | OH |
| I-212 | OCF₃ | $CF_3$ | H | OH |
| I-213 | Me | $CF_3$ | Me | OH |

TABLE 7

| Compound No | R¹ | R² | R³ | R⁴ |
|---|---|---|---|---|
| I-214 | Et | $CF_3$ | Me | OH |
| I-215 | Pr-n | $CF_3$ | Me | OH |
| I-216 | Pr-i | $CF_3$ | Me | OH |
| I-217 | Bu-n | $CF_3$ | Me | OH |
| I-218 | Bu-i | $CF_3$ | Me | OH |
| I-219 | Bu-s | $CF_3$ | Me | OH |
| I-220 | Bu-t | $CF_3$ | Me | OH |
| I-221 | Me | $CHF_2$ | H | OH |
| I-222 | Et | $CHF_2$ | H | OH |
| I-223 | Ph | $CHF_2$ | H | OH |
| I-224 | Ph | $CHF_2$ | Br | OH |
| I-225 | Me | $CClF_2$ | H | OH |
| I-226 | Et | $CClF_2$ | H | OH |
| I-227 | Me | $CF_2CF_3$ | H | OH |
| I-228 | Et | $CF_2CF_3$ | H | OH |
| I-229 | Ph | Me | H | OH |
| I-230 | Ph | Et | H | OH |
| I-231 | Ph | Pr-n | H | OH |
| I-232 | Ph | Pr-i | H | OH |
| I-233 | Ph(4-Cl) | Me | H | OH |
| I-234 | Ph(2-CF₃) | Me | H | OH |
| I-235 | Ph(3-CF₃) | Me | H | OH |
| I-236 | Ph(4-CF₃) | Me | H | OH |
| I-237 | Ph | CH₂SO₂Pr-n | Br | OH |
| I-238 | Ph(3-Me) | H | H | OH |
| I-239 | Me | Cl | H | OH |
| I-240 | Me | SMe | H | OH |
| I-241 | Me | SOMe | H | OH |
| I-242 | Me | SO₂Me | H | OH |
| I-243 | Ph | CN | H | OH |
| I-244 | Me | Ph | H | OH |

TABLE 8

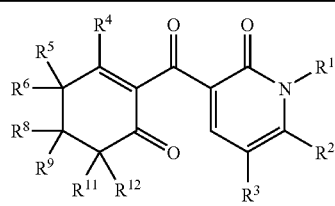

| Compound No | R¹ | R² | R³ | R⁴ | R⁵ | R⁶ | R⁸ | R⁹ | R¹¹ | R¹² |
|---|---|---|---|---|---|---|---|---|---|---|
| II-1 | Me | $CF_3$ | H | OH | Me | H | H | H | H | H |
| II-2 | Me | $CF_3$ | H | OH | Me | Me | H | H | H | H |
| II-3 | Me | $CF_3$ | H | OH | H | H | Me | Me | H | H |
| II-4 | Me | $CF_3$ | H | OH | H | H | H | H | Me | Me |
| II-5 | Me | $CF_3$ | H | OH | Me | H | H | H | Me | H |
| II-6 | Me | $CF_3$ | H | OH | Me | Me | H | H | Me | Me |
| II-7 | Me | $CF_3$ | H | OH | Me | H | H | H | Me | H |
| II-8 | Me | $CF_3$ | H | SPh | H | H | H | H | H | H |

TABLE 8-continued

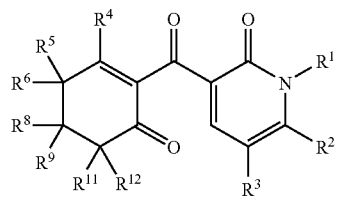

| Compound No | R¹ | R² | R³ | R⁴ | R⁵ | R⁶ | R⁸ | R⁹ | R¹¹ | R¹² |
|---|---|---|---|---|---|---|---|---|---|---|
| II-9 | Me | CF₃ | H | SPh(4-Me) | H | H | H | H | H | H |
| II-10 | Me | CF₃ | H | SPh(2,6-di-Me) | H | H | H | H | H | H |
| II-11 | Me | CF₃ | H | SPh(2-Cl) | H | H | H | H | H | H |
| II-12 | Me | CF₃ | H | SPh(3-Cl) | H | H | H | H | H | H |
| II-13 | Me | CF₃ | H | SPh(4-Cl) | H | H | H | H | H | H |
| II-14 | Me | CF₃ | H | SPh(2,4-di-Cl) | H | H | H | H | H | H |
| II-15 | Me | CF₃ | H | SPh(2,6-di-Cl) | H | H | H | H | H | H |
| II-16 | Me | CF₃ | H | SPh(2,3,4,5,6-penta-Cl) | H | H | H | H | H | H |
| II-17 | Me | CF₃ | H | pyrazol-1-yl | H | H | H | H | H | H |
| II-18 | Me | CF₃ | H | SPh | Me | Me | H | H | H | H |
| II-19 | Me | CF₃ | H | SPh | H | H | Me | Me | H | H |
| II-20 | Me | CF₃ | H | SPh | H | H | H | H | Me | Me |
| II-21 | Me | CF₃ | H | SPh | Me | Me | H | H | Me | Me |
| II-22 | Me | CF₃ | H | OMe | H | H | H | H | H | H |
| II-23 | Et | CF₃ | H | OMe | H | H | H | H | H | H |
| II-24 | Pr-n | CF₃ | H | OMe | H | H | H | H | H | H |
| II-25 | CH₂CH=CH₂ | CF₃ | H | OMe | H | H | H | H | H | H |
| II-26 | CH₂C(Me)=CH₂ | CF₃ | H | OMe | H | H | H | H | H | H |
| II-27 | CH₂CH₂C(Me)=CF₂ | CF₃ | H | OH | Me | H | H | H | Me | H |
| II-28 | CH₂C≡CH | CF₃ | H | OMe | H | H | H | H | H | H |
| II-29 | CH₂CH₂OMe | CF₃ | H | OH | Me | Me | H | H | H | H |
| II-30 | CH₂CH₂CH₂OMe | CF₃ | H | SPh | H | H | H | H | H | H |
| II-31 | CH₂CH₂OCH₂CH₂OMe | CF₃ | H | OH | Me | Me | H | H | H | H |

TABLE 9

| Compound No | R¹ | R² | R³ | R⁴ | R⁵ | R⁶ | R⁸ | R⁹ | R¹¹ | R¹² |
|---|---|---|---|---|---|---|---|---|---|---|
| II-32 | (2-ethyltetrahydrofuran) | CF₃ | H | OH | Me | H | H | H | H | H |
| II-33 | (2-ethyltetrahydrofuran) | CF₃ | H | OH | Me | Me | H | H | H | H |
| II-34 | (2-ethyltetrahydrofuran) | CF₃ | H | OH | Me | H | H | H | Me | H |
| II-35 | Me | CF₃ | H | OMe | Me | H | H | H | H | H |
| II-36 | Me | CF₃ | H | OMe | Me | Me | H | H | H | H |
| II-37 | Me | CF₃ | H | OMe | H | H | Me | Me | H | H |
| II-38 | Me | CF₃ | H | OMe | H | H | H | H | Me | Me |
| II-39 | Me | CF₃ | H | OMe | Me | Me | H | H | Me | Me |
| II-40 | Ph(3,5-di-F) | CF₃ | H | OH | H | H | H | H | Me | Me |
| II-41 | Ph | CF₃ | H | OH | Me | Me | =O | | Me | Me |
| II-42 | CH₂CH=CH₂ | CF₃ | H | OH | Me | Me | =O | | Me | Me |
| II-43 | (5-ethyl-3-methyl-4,5-dihydroisoxazol-3-yl) | CF₃ | H | OH | Me | Me | =O | | Me | Me |
| II-44 | (6-methyl-1,3-benzodioxol-5-yl) | CF₃ | H | OH | H | H | Me | H | H | H |

TABLE 10

| Compound No | R¹ | R² | R³ | R⁴ | Z |
|---|---|---|---|---|---|
| III-1 | Me | $CF_3$ | H | OH | —$CH_2CH_2$— |
| III-2 | Et | $CF_3$ | H | OH | —$CH_2CH_2$— |
| III-3 | Pr-n | $CF_3$ | H | OH | —$CH_2CH_2$— |
| III-4 | Pr-i | $CF_3$ | H | OH | —$CH_2CH_2$— |
| III-5 | Pr-c | $CF_3$ | H | OH | —$CH_2CH_2$— |
| III-6 | Bu-n | $CF_3$ | H | OH | —$CH_2CH_2$— |
| III-7 | Bu-i | $CF_3$ | H | OH | —$CH_2CH_2$— |
| III-8 | Bu-s | $CF_3$ | H | OH | —$CH_2CH_2$— |
| III-9 | Bu-t | $CF_3$ | H | OH | —$CH_2CH_2$— |
| III-10 | Hex-n | $CF_3$ | H | OH | —$CH_2CH_2$— |
| III-11 | Pen-c | $CF_3$ | H | OH | —$CH_2CH_2$— |
| III-12 | Me | $CF_3$ | H | OMe | —$CH_2CH_2$— |
| III-13 | Et | $CF_3$ | H | OMe | —$CH_2CH_2$— |
| III-14 | Me | $CF_3$ | H | SPh | —$CH_2CH_2$— |
| III-15 | Et | $CF_3$ | H | SPh | —$CH_2CH_2$— |
| III-16 | Me | $CF_3$ | Me | OH | —$CH_2CH_2$— |
| III-17 | Et | $CF_3$ | Me | OH | —$CH_2CH_2$— |
| III-18 | Pr-n | $CF_3$ | Me | OH | —$CH_2CH_2$— |
| III-19 | $CH_2CH_2OMe$ | $CF_3$ | H | OH | —$CH_2CH_2$— |
| III-20 | $CH_2CH_2OEt$ | $CF_3$ | H | OH | —$CH_2CH_2$— |
| III-21 | $CH(Me)CH_2OMe$ | $CF_3$ | H | OH | —$CH_2CH_2$— |
| III-22 | $CH_2CH_2CH_2OMe$ | $CF_3$ | H | OH | —$CH_2CH_2$— |
| III-23 | $CH_2CH_2OCH_2CH_2OMe$ | $CF_3$ | H | OH | —$CH_2CH_2$— |
| III-24 | $CH_2CH(Me)OMe$ | $CF_3$ | H | OH | —$CH_2CH_2$— |
| III-25 | $CH_2CH(OMe)_2$ | $CF_3$ | H | OH | —$CH_2CH_2$— |

TABLE 11

| Compound No | R¹ | R² | R³ | R⁴ | Z |
|---|---|---|---|---|---|
| III-26 | $CH_2SEt$ | $CF_3$ | H | OH | —$CH_2CH_2$— |
| III-27 | $CH_2SOEt$ | $CF_3$ | H | OH | —$CH_2CH_2$— |
| III-28 | $CH_2CH_2SMe$ | $CF_3$ | H | OH | —$CH_2CH_2$— |
| III-29 | $CH_2CH_2SOMe$ | $CF_3$ | H | OH | —$CH_2CH_2$— |
| III-30 | $CH_2CH_2SO_2Me$ | $CF_3$ | H | OH | —$CH_2CH_2$— |
| III-31 | $CH_2CH_2CH_2SMe$ | $CF_3$ | H | OH | —$CH_2CH_2$— |
| III-32 | $CH_2CH_2CH_2SOMe$ | $CF_3$ | H | OH | —$CH_2CH_2$— |
| III-33 | $CH_2CH_2CH_2SO_2Me$ | $CF_3$ | H | OH | —$CH_2CH_2$— |
| III-34 | Ph | $CF_3$ | H | OH | —$CH_2CH_2$— |
| III-35 | Ph(4-Me) | $CF_3$ | H | OH | —$CH_2CH_2$— |
| III-36 | Ph(4-$NHSO_2CF_3$) | $CF_3$ | H | OH | —$CH_2CH_2$— |
| III-37 | Ph(2,6-di-F) | $CF_3$ | H | OH | —$CH_2CH_2$— |
| III-38 | 2-ethyltetrahydrofuranyl | $CF_3$ | H | OH | —$CH_2CH_2$— |
| III-39 | N-methylmorpholinyl | $CF_3$ | H | OH | —$CH_2CH_2$— |
| III-40 | N-methylthiomorpholinyl | $CF_3$ | H | OH | —$CH_2CH_2$— |
| III-41 | N-methylthiomorpholinyl-1,1-dioxide | $CF_3$ | H | OH | —$CH_2CH_2$— |
| III-42 | Me | $CF_3$ | H | OH | —CH=CH— |
| III-43 | 2-ethyltetrahydrofuranyl | $CF_3$ | H | OH | —CH=CH— |
| III-44 | $CH(Me)CH_2OMe$ | $CF_3$ | H | OH | —CH=CH— |
| III-45 | $CH_2SPr-n$ | $CF_3$ | H | OH | —$CH_2CH_2$— |
| III-46 | $CH_2SOPr-n$ | $CF_3$ | H | OH | —$CH_2CH_2$— |
| III-47 | $CH_2SO_2Pr-n$ | $CF_3$ | H | OH | —$CH_2CH_2$— |

TABLE 12

| Compound No | R¹ | R² | R³ | R⁴ | R²⁰ | R²¹ |
|---|---|---|---|---|---|---|
| IV-1 | Me | $CF_3$ | H | OH | Me | H |
| IV-2 | Et | $CF_3$ | H | OH | Me | H |
| IV-3 | Pr-n | $CF_3$ | H | OH | Me | H |
| IV-4 | Pr-n | $CF_3$ | H | OCOPh | Me | H |
| IV-5 | Pr-i | $CF_3$ | H | OH | Me | H |
| IV-6 | Bu-n | $CF_3$ | H | OH | Me | H |
| IV-7 | Bu-i | $CF_3$ | H | OH | Me | H |
| IV-8 | Bu-s | $CF_3$ | H | OH | Me | H |
| IV-9 | Bu-t | $CF_3$ | H | OH | Me | H |
| IV-10 | $CH_2CF_3$ | $CF_3$ | H | $OSO_2Pr-n$ | Me | H |
| IV-11 | $CH_2CH=CH_2$ | $CF_3$ | H | OH | Me | H |
| IV-12 | $CH_2CH=CH_2$ | $CF_3$ | H | $OSO_2Pr-n$ | Et | H |
| IV-13 | $CH_2C(Me)=CH_2$ | $CF_3$ | H | OH | Me | H |
| IV-14 | $CH_2CH_2C(Me)=CH_2$ | $CF_3$ | H | OH | Me | H |
| IV-15 | $CH_2CH_2CH=CMe_2$ | $CF_3$ | H | OH | Me | H |
| IV-16 | $CH_2C\equiv CH$ | $CF_3$ | H | OH | Me | H |
| IV-17 | $CH_2C\equiv CCH_3$ | $CF_3$ | H | OH | Me | H |
| IV-18 | Pr-c | $CF_3$ | H | OH | Me | H |
| IV-19 | Pr-c | $CF_3$ | H | $OSO_2Pr-n$ | Me | H |
| IV-20 | Bu-c | $CF_3$ | H | OH | Me | H |
| IV-21 | Pen-c | $CF_3$ | H | OH | Me | H |
| IV-22 | Hex-c | $CF_3$ | H | OH | Me | H |
| IV-23 | $CH_2Pr-c$ | $CF_3$ | H | OH | Me | H |
| IV-24 | $CH_2Bu-c$ | $CF_3$ | H | OH | Me | H |
| IV-25 | $CH_2Pen-c$ | $CF_3$ | H | OH | Me | H |
| IV-26 | $CH_2Hex-c$ | $CF_3$ | H | OH | Me | H |
| IV-27 | $CH_2CH=CCl_2$ | $CF_3$ | H | OH | Me | H |
| IV-28 | $CH_2CCl=CHCl$ | $CF_3$ | H | OH | Me | H |
| IV-29 | $CH_2CH=CF_2$ | $CF_3$ | H | OH | Me | H |
| IV-30 | $CH_2CH_2CH=CCl_2$ | $CF_3$ | H | OH | Me | H |
| IV-31 | $CH_2CH_2CH=CCl_2$ | $CF_3$ | H | $OSO_2Pr-n$ | Me | H |

TABLE 13

| Compound No | R¹ | R² | R³ | R⁴ | R²⁰ | R²¹ |
|---|---|---|---|---|---|---|
| IV-32 | CH$_2$CH$_2$C(Me)=CF$_2$ | CF$_3$ | H | OH | Me | H |
| IV-33 | CH$_2$CH$_2$OMe | CF$_3$ | H | OH | Me | H |
| IV-34 | CH$_2$CH$_2$OEt | CF$_3$ | H | OH | Me | H |
| IV-35 | CH$_2$CH$_2$OEt | CF$_3$ | H | OCOPh | Me | H |
| IV-36 | CH(Me)CH$_2$OMe | CF$_3$ | H | OH | Me | H |
| IV-37 | CH(Me)CH$_2$OMe | CF$_3$ | H | OSO$_2$Pr-n | Me | H |
| IV-38 | CH$_2$CH(Me)OMe | CF$_3$ | H | OH | Me | H |
| IV-39 | CH$_2$CH(Me)OMe | CF$_3$ | H | OSO$_2$Pr-n | Me | H |
| IV-40 | CH$_2$CH$_2$OPr-n | CF$_3$ | H | OH | Me | H |
| IV-41 | CH$_2$CH$_2$OPr-i | CF$_3$ | H | OH | Me | H |
| IV-42 | CH$_2$CH$_2$OPr-c | CF$_3$ | H | OH | Me | H |
| IV-43 | CH$_2$CH$_2$OBu-c | CF$_3$ | H | OH | Me | H |
| IV-44 | CH$_2$CH$_2$OPen-c | CF$_3$ | H | OH | Me | H |
| IV-45 | CH$_2$CH$_2$OHex-c | CF$_3$ | H | OH | Me | H |
| IV-46 | CH$_2$CH$_2$OCH$_2$CF$_3$ | CF$_3$ | H | OH | Me | H |
| IV-47 | CH$_2$CH$_2$CH$_2$OMe | CF$_3$ | H | OH | Me | H |
| IV-48 | CH$_2$CH$_2$CH$_2$OMe | CF$_3$ | H | OCOCH$_3$ | Me | H |
| IV-49 | CH$_2$CH(Me)OCH$_2$Ph | CF$_3$ | H | OSO$_2$Pr-n | Me | H |
| IV-50 | CH$_2$CH$_2$NMe$_2$ | CF$_3$ | H | OH | Me | H |
| IV-51 | CH$_2$CH$_2$SMe | CF$_3$ | H | OH | Me | H |
| IV-52 | CH$_2$CH$_2$SOMe | CF$_3$ | H | OH | Me | H |
| IV-53 | CH$_2$CH$_2$SOMe | CF$_3$ | H | OSO$_2$Pr-n | Me | H |
| IV-54 | CH$_2$CH$_2$SO$_2$Me | CF$_3$ | H | OH | Me | H |
| IV-55 | CH$_2$CH$_2$SO$_2$Me | CF$_3$ | H | OSO$_2$Pr-n | Me | H |
| IV-56 | CH$_2$CH$_2$CH$_2$SMe | CF$_3$ | H | OH | Me | H |
| IV-57 | CH$_2$CH$_2$CH$_2$SMe | CF$_3$ | H | OSO$_2$Pr-n | Me | H |
| IV-58 | CH$_2$CH$_2$CH$_2$SOMe | CF$_3$ | H | OH | Me | H |
| IV-59 | CH$_2$CH$_2$CH$_2$SOMe | CF$_3$ | H | OSO$_2$Pr-n | Me | H |
| IV-60 | CH$_2$CH$_2$CH$_2$SO$_2$Me | CF$_3$ | H | OH | Me | H |
| IV-61 | CH$_2$CH$_2$CH$_2$SO$_2$Me | CF$_3$ | H | OSO$_2$Pr-n | Me | H |
| IV-62 | Ph | CF$_3$ | H | OH | Me | H |
| IV-63 | Ph(4-Cl) | CF$_3$ | H | OH | Me | H |
| IV-64 | Ph(2-OMe) | CF$_3$ | H | OH | Me | H |
| IV-65 | Ph(3-OMe) | CF$_3$ | H | OH | Me | H |
| IV-66 | Ph(4-OMe) | CF$_3$ | H | OH | Me | H |
| IV-67 | Ph(4-OCF3) | CF$_3$ | H | OH | Me | H |

TABLE 14

| Compound No | R¹ | R² | R³ | R⁴ | R²⁰ | R²¹ |
|---|---|---|---|---|---|---|
| IV-68 | Ph(4-NO$_2$) | CF$_3$ | H | OSO$_2$Pr-n | Me | H |
| IV-69 | Ph(2-CF$_3$) | CF$_3$ | H | OH | Me | H |
| IV-70 | Ph(3-CF$_3$) | CF$_3$ | H | OH | Me | H |
| IV-71 | Ph(4-CF$_3$) | CF$_3$ | H | OH | Me | H |
| IV-72 | Ph(3-SMe) | CF$_3$ | H | OH | Me | H |
| IV-73 | Ph(3-SOMe) | CF$_3$ | H | OSO$_2$Pr-n | Me | H |
| IV-74 | Ph(3-SO$_2$Me) | CF$_3$ | H | OH | Me | H |
| IV-75 | Ph(3-SO$_2$Me) | CF$_3$ | H | OSO$_2$Pr-n | Me | H |
| IV-76 | Ph(2,4-di-OMe) | CF$_3$ | H | OH | Me | H |
| IV-77 | Ph(3,4-di-OMe) | CF$_3$ | H | OH | Me | H |
| IV-78 | Ph(2,6-di-F) | CF$_3$ | H | OH | Me | H |
| IV-79 | Ph(2,6-di-F) | CF$_3$ | H | OSO$_2$Pr-n | Me | H |
| IV-80 | Ph(3,5-di-F) | CF$_3$ | H | OH | Me | H |
| IV-81 | Ph(3,5-di-F) | CF$_3$ | H | OH | Me | Me |
| IV-82 | Ph(3,5-di-F) | CF$_3$ | H | OSO$_2$Pr-n | Me | Me |
| IV-83 | Ph(2,5-di-F) | CF$_3$ | H | OH | Me | H |
| IV-84 | Ph(2,5-di-F) | CF$_3$ | H | OSO$_2$Pr-n | Me | H |
| IV-85 | Ph(3,4-di-F) | CF$_3$ | H | OH | Me | H |
| IV-86 | Ph(3,4-di-F) | CF$_3$ | H | OH | Me | Me |
| IV-87 | Ph(3,4-di-F) | CF$_3$ | H | OSO$_2$Pr-n | Me | H |
| IV-88 | Ph(3,4-di-F) | CF$_3$ | H | OSO$_2$Pr-n | Me | Me |
| IV-89 | Ph(2-F,5-NO$_2$) | CF$_3$ | H | OCOCH$_3$ | Me | H |
| IV-90 | Ph(3-OMe-4-Cl) | CF$_3$ | H | OH | Me | H |
| IV-91 | Ph(3-OMe-4-Cl) | CF$_3$ | H | OSO$_2$Pr-n | Me | H |
| IV-92 | Ph(3-F-4-OMe) | CF$_3$ | H | OH | Me | H |
| IV-93 | Ph(3-F-4-OMe) | CF$_3$ | H | OSO$_2$Pr-n | M | H |

TABLE 14-continued

| Compound No | R¹ | R² | R³ | R⁴ | R²⁰ | R²¹ |
|---|---|---|---|---|---|---|
| IV-94 | 2-F-5-Me-benzyl-OMe (see structure) | CF$_3$ | H | OSO$_2$Pr-n | Me | H |
| IV-95 | 2-F-5-Me-benzyl-OMe | CF$_3$ | H | OH | Me | H |
| IV-96 | 2-F-5-Me-benzyl-OMe | CF$_3$ | H | OSO$_2$Pr-n | Pr-i | H |
| IV-97 | methylenedioxyphenyl-Me | CF$_3$ | H | OH | Me | H |
| IV-98 | methylenedioxyphenyl-Me | CF$_3$ | H | OSO$_2$Pr-n | Me | H |

TABLE 15

| Compound No | R¹ | R² | R³ | R⁴ | R²⁰ | R²¹ |
|---|---|---|---|---|---|---|
| IV-99 | methylenedioxyphenyl-Me | CF$_3$ | H | OSO$_2$Pr-n | Et | H |
| IV-100 | methylenedioxyphenyl-Me | CF$_3$ | H | OSO$_2$Pr-n | Pr-i | H |
| IV-101 | benzodioxane-Me | CF$_3$ | H | OH | Me | H |
| IV-102 | CH$_2$Ph | CF$_3$ | H | OH | Me | H |
| IV-103 | CH$_2$Ph(3-OMe) | CF$_3$ | H | OH | Me | H |
| IV-104 | CH$_2$Ph(3-OMe) | CF$_3$ | H | OSO$_2$Pr-n | Me | H |
| IV-105 | Et-isoxazoline-Me | CF$_3$ | H | OH | Me | H |
| IV-106 | Et-isoxazoline-Me | CF$_3$ | H | OSO$_2$Pr-n | Et | H |
| IV-107 | Et-isoxazoline-Me | CF$_3$ | H | OH | Et | H |

TABLE 15-continued

| Compound No | R¹ | R² | R³ | R⁴ | R²⁰ | R²¹ |
|---|---|---|---|---|---|---|
| IV-108 | 4-ethyl-5-(OCHF₂)-1-methyl-3-(CF₃)-pyrazole | CF₃ | H | OH | Me | H |
| IV-109 | CH₂CH₂Ph | CF₃ | H | OH | Me | H |
| IV-110 | CH₂CH₂CH₂Ph | CF₃ | H | OH | Me | H |
| IV-111 | CH₂CH=CHPh | CF₃ | H | OH | Me | H |
| IV-112 | CH₂C≡CPh | CF₃ | H | OH | Me | H |
| IV-113 | CH₂CH=NOMe | CF₃ | H | OH | Me | H |
| IV-114 | CH₂CH=NOEt | CF₃ | H | OH | Me | H |
| IV-115 | CH₂CH=NOPr-n | CF₃ | H | OH | Me | H |
| IV-116 | CH₂CH=NOPh | CF₃ | H | OH | Me | H |
| IV-117 | CH₂CH(OMe)₂ | CF₃ | H | OH | Me | H |
| IV-118 | CH₂CH(OMe)₂ | CF₃ | H | OSO₂Pr-n | Me | H |
| IV-119 | 2-ethyl-1,3-dioxolane | | | OH | Me | H |
| IV-120 | CH₂CHO | CF₃ | H | OH | Me | H |
| IV-121 | 3-methyl-4,5-dihydroisoxazole | | | OH | Me | H |
| IV-122 | 2-methyloxazole | | | OH | Me | H |

TABLE 16

| Compound No | R¹ | R² | R³ | R⁴ | R²⁰ | R²¹ |
|---|---|---|---|---|---|---|
| IV-123 | 2-methylthiazol-yl | CF₃ | H | OH | Me | H |
| IV-124 | 2-methyl-4-Me-thiazolyl | CF₃ | H | OH | Me | H |
| IV-125 | 2-methyloxazoline | CF₃ | H | OH | Me | H |
| IV-126 | 2-methylthienyl | CF₃ | H | OH | Me | H |
| IV-127 | 3-methylthienyl | CF₃ | H | OH | Me | H |
| IV-128 | ethyloxiranyl | CF₃ | H | OH | Me | H |
| IV-129 | 2-ethyltetrahydrofuranyl | CF₃ | H | OH | Me | H |
| IV-130 | 2-ethyltetrahydrofuranyl | CF₃ | H | OCOC₇H₁₅-n | Me | H |
| IV-131 | 2-ethyltetrahydrofuranyl | CF₃ | H | OCOPh | Me | H |
| IV-132 | 2-ethyltetrahydrofuranyl | CF₃ | H | OCOPh(4-Bu-t) | Me | H |
| IV-133 | 2-ethyltetrahydrofuranyl | CF₃ | H | OCOPh(2,4,6-tri-Cl) | Me | H |
| IV-134 | 2-ethyltetrahydrofuranyl | CF₃ | H | OCOPh(2,4,6-tri-F) | Me | H |
| IV-135 | 2-ethyltetrahydrofuranyl | CF₃ | H | OCOPh(2,4,6-tri-Me) | Me | H |
| IV-136 | 2-ethyltetrahydrofuranyl | CF₃ | H | OCH₂Ph(2,6-di-F) | Me | H |
| IV-137 | 2-ethyltetrahydrofuranyl | CF₃ | H | OCH₂Ph(4-CF₃) | Me | H |
| IV-138 | 2-ethyltetrahydrofuranyl | CF₃ | H | OCH₂-(6-Me-pyridin-2-yl) | Me | H |
| IV-139 | 2-ethyltetrahydrofuranyl | CF₃ | H | OCH₂COPh(4-Me) | Me | H |

TABLE 17

| Compound No | R¹ | R² | R³ | R⁴ | R²⁰ | R²¹ |
|---|---|---|---|---|---|---|
| IV-140 | 2-ethyltetrahydrofuranyl | CF₃ | H | OSO₂Pr-n | Me | H |
| IV-141 | 2-ethyltetrahydrofuranyl | CF₃ | H | OSO₂Ph(4-Me) | Me | H |
| IV-142 | 2-ethyltetrahydrofuranyl | CF₃ | H | OSO₂Ph(4-NO₂) | Me | H |
| IV-143 | 3-ethyltetrahydrofuranyl | CF₃ | H | OH | Me | H |
| IV-144 | 4-ethylmorpholinyl | CF₃ | H | OH | Me | H |
| IV-145 | NH₂ | CF₃ | H | OH | Me | H |
| IV-146 | NHMe | CF₃ | H | OH | Me | H |

TABLE 17-continued

| Compound No | R¹ | R² | R³ | R⁴ | R²⁰ | R²¹ |
|---|---|---|---|---|---|---|
| IV-147 | NHEt | $CF_3$ | H | OH | Me | H |
| IV-148 | NHPr-n | $CF_3$ | H | OH | Me | H |
| IV-149 | $NMe_2$ | $CF_3$ | H | OH | Me | H |
| IV-150 | $NEt_2$ | $CF_3$ | H | OH | Me | H |
| IV-151 | $N(Pr-n)_2$ | $CF_3$ | H | OH | Me | H |
| IV-152 | NHPh | $CF_3$ | H | OH | Me | H |
| IV-153 | $NHCH_2Ph$ | $CF_3$ | H | OH | Me | H |
| IV-154 | $N=CMe_2$ | $CF_3$ | H | OH | Me | H |
| IV-155 | $N=CEt_2$ | $CF_3$ | H | OH | Me | H |
| IV-156 | NHC(=O)Me | $CF_3$ | H | OH | Me | H |
| IV-157 | $N[C(=O)Me]_2$ | $CF_3$ | H | OH | Me | H |
| IV-158 | NHC(=O)OMe | $CF_3$ | H | OH | Me | H |
| IV-159 | $N[C(=O)OMe]_2$ | $CF_3$ | H | OH | Me | H |
| IV-160 | $NHSO_2Me$ | $CF_3$ | H | OH | Me | H |
| IV-161 | $NHSO_2PH$ | $CF_3$ | H | OH | Me | H |
| IV-162 | $NHSO_2CH_2Ph$ | $CF_3$ | H | OH | Me | H |
| IV-163 | OMe | $CF_3$ | H | OH | Me | H |
| IV-164 | OEt | $CF_3$ | H | OH | Me | H |
| IV-165 | OPr-n | $CF_3$ | H | OH | Me | H |
| IV-166 | OPr-i | $CF_3$ | H | OH | Me | H |
| IV-167 | $OCH_2Pr$-c | $CF_3$ | H | OH | Me | H |
| IV-168 | $OCH_2Cl$ | $CF_3$ | H | OH | Me | H |
| IV-169 | $OCHCl_2$ | $CF_3$ | H | OH | Me | H |
| IV-170 | $OCCl_3$ | $CF_3$ | H | OH | Me | H |
| IV-171 | $OCH_2F$ | $CF_3$ | H | OH | Me | H |

TABLE 18

| Compound No | R¹ | R² | R³ | R⁴ | R²⁰ | R²¹ |
|---|---|---|---|---|---|---|
| IV-172 | $OCHF_2$ | $CF_3$ | H | OH | Me | H |
| IV-173 | $OCF_3$ | $CF_3$ | H | OH | Me | H |
| IV-174 | Me | $CF_3$ | H | $OCOCH_3$ | Me | H |
| IV-175 | Et | $CF_3$ | H | $OCOCH_3$ | Me | H |
| IV-176 | Pr-n | $CF_3$ | H | $OCOCH_3$ | Me | H |
| IV-177 | Pr-i | $CF_3$ | H | $OCOCH_3$ | Me | H |
| IV-178 | Pr-c | $CF_3$ | H | $OCOCH_3$ | Me | H |
| IV-179 | $CH_2CH=CH_2$ | $CF_3$ | H | $OCOCH_3$ | Me | H |
| IV-180 | $CH_2C(Me)=CH_2$ | $CF_3$ | H | $OCOCH_3$ | Me | H |
| IV-181 | $CH_2C\equiv CH$ | $CF_3$ | H | $OCOCH_3$ | Me | H |
| IV-182 | Bu-n | $CF_3$ | H | $OCOCH_3$ | Me | H |
| IV-183 | Bu-i | $CF_3$ | H | $OCOCH_3$ | Me | H |
| IV-184 | Bu-s | $CF_3$ | H | $OCOCH_3$ | Me | H |
| IV-185 | Bu-t | $CF_3$ | H | $OCOCH_3$ | Me | H |
| IV-186 | $CH_2CH_2OMe$ | $CF_3$ | H | $OCOCH_3$ | Me | H |
| IV-187 | Ph | $CF_3$ | H | $OCOCH_3$ | Me | H |
| IV-188 | Me | $CF_3$ | H | OMe | Me | H |
| IV-189 | Me | $CF_3$ | H | $OCH_2C\equiv CH$ | Me | H |
| IV-190 | Me | $CF_3$ | H | $OCH_2Ph$ | Me | H |
| IV-191 | Me | $CF_3$ | H | $OCH_2Ph$(4-Cl) | Me | H |
| IV-192 | Me | $CF_3$ | H | $OCH_2Ph$(4-Bu-t) | Me | H |
| IV-193 | Me | $CF_3$ | H | $OCH_2Ph$(2-OMe) | Me | H |
| IV-194 | Me | $CF_3$ | H | $OSO_2Ph$(4-Me) | Me | H |
| IV-195 | Me | $CF_3$ | H | $OCH_2CO_2Me$ | Me | H |
| IV-196 | Me | $CF_3$ | H | $OSO_2Pr$-n | Me | H |
| IV-197 | Me | $CF_3$ | H | OCOPh | Me | H |
| IV-198 | Me | $CF_3$ | H | OCOPh(4-Bu-t) | Me | H |
| IV-199 | Me | $CF_3$ | H | $OCO_2CH_2Ph$ | Me | H |
| IV-200 | Me | $CF_3$ | H | $OCO_2CH_2Ph$(4-Cl) | Me | H |
| IV-201 | Me | $CF_3$ | H | OH | Et | H |
| IV-202 | Pr-n | $CF_3$ | H | $OSO_2Pr$-n | Et | H |
| IV-203 | $CH_2CH_2OCH_2CH_2OMe$ | $CF_3$ | H | OH | Et | H |
| IV-204 | $CH_2CH_2OCH_2CH_2OMe$ | $CF_3$ | H | $OSO_2Pr$-n | Et | H |
| IV-205 | 2-ethyltetrahydrofuran | $CF_3$ | H | OH | Et | H |

TABLE 19

| Compound No | R¹ | R² | R³ | R⁴ | R²⁰ | R²¹ |
|---|---|---|---|---|---|---|
| IV-206 | 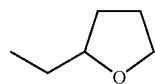 | $CF_3$ | H | OCOPh(2,4,6-tri-Cl) | Et | H |
| IV-207 | 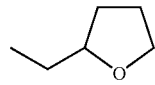 | $CF_3$ | H | $OSO_2Pr$-n | Et | H |
| IV-208 | Me | $CF_3$ | H | $OCOCH_3$ | Et | H |
| IV-209 | Me | $CF_3$ | H | OMe | Et | H |
| IV-210 | Me | $CF_3$ | H | $OCH_2Ph$ | Et | H |
| IV-211 | Me | $CF_3$ | H | $OCH_2Ph$(2-OMe) | Et | H |
| IV-212 | Me | $CF_3$ | H | $OSO_2Ph$(4-Me) | Et | H |
| IV-213 | Me | $CF_3$ | H | OH | Pr-n | H |
| IV-214 | Me | $CF_3$ | H | $OCOCH_3$ | Pr-n | H |
| IV-215 | Me | $CF_3$ | H | OMe | Pr-n | H |
| IV-216 | Me | $CF_3$ | H | $OCH_2Ph$ | Pr-n | H |
| IV-217 | Me | $CF_3$ | H | $OCH_2Ph$(2-OMe) | Pr-n | H |
| IV-218 | Me | $CF_3$ | H | $OSO_2Ph$(4-Me) | Pr-n | H |
| IV-219 | Me | $CF_3$ | H | OH | Pr-i | H |
| IV-220 | Me | $CF_3$ | H | $OCOCH_3$ | Pr-i | H |
| IV-221 | Me | $CF_3$ | H | OMe | Pr-i | H |
| IV-222 | Me | $CF_3$ | H | $OCH_2Ph$ | Pr-i | H |
| IV-223 | Me | $CF_3$ | H | $OCH_2Ph$(2-OMe) | Pr-i | H |
| IV-224 | Me | $CF_3$ | H | OSO2Ph(4-Me) | Pr-i | H |
| IV-225 | Me | $CF_3$ | H | OH | $CH_2CH=CH_2$ | H |
| IV-226 | Me | $CF_3$ | H | $OCOCH_3$ | $CH_2CH=CH_2$ | H |
| IV-227 | Me | $CF_3$ | H | OMe | $CH_2CH=CH_2$ | H |
| IV-228 | Me | $CF_3$ | H | $OCH_2Ph$ | $CH_2CH=CH_2$ | H |
| IV-229 | Me | $CF_3$ | H | $OCH_2Ph$(2-OMe) | $CH_2CH=CH_2$ | H |
| IV-230 | Me | $CF_3$ | H | $OSO_2Ph$(4-Me) | $CH_2CH=CH_2$ | H |
| IV-231 | Me | $CF_3$ | H | OH | Me | Me |
| IV-232 | Me | $CF_3$ | H | $OCOCH_3$ | Me | Me |
| IV-233 | Me | $CF_3$ | H | OMe | Me | Me |
| IV-234 | Me | $CF_3$ | H | $OCH_2Ph$ | Me | Me |
| IV-235 | Me | $CF_3$ | H | $OCH_2Ph$(2-OMe) | Me | Me |
| IV-236 | Me | $CF_3$ | H | $OSO_2Ph$(4-Me) | Me | Me |
| IV-237 | Ph | $CF_3$ | H | $OSO_2Pr$-n | Me | Me |
| IV-238 | 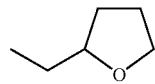 | $CF_3$ | H | OH | Me | Me |

TABLE 20

| Compound No | R¹ | R² | R³ | R⁴ | R²⁰ | R²¹ |
|---|---|---|---|---|---|---|
| IV-239 | 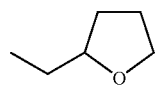 | $CF_3$ | H | $OSO_2Pr$-n | Me | Me |
| IV-240 | 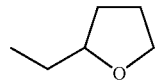 | $CF_3$ | H | $OSO_2Ph$(4-Me) | Me | Me |
| IV-241 | Pr-n | $CF_3$ | Me | OH | Me | H |
| IV-242 | Me | Cl | H | $OSO_2Pr$-n | Me | H |
| IV-243 | Me | Cl | H | OH | Me | H |
| IV-244 | $CH_2SPr$-n | $CF_3$ | H | OH | Me | H |
| IV-245 | $CH_2SOPr$-n | $CF_3$ | H | OH | Me | H |
| IV-246 | $CH_2SO_2Pr$-N | $CF_3$ | H | OH | Me | H |
| IV-247 | 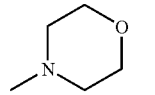 | $CF_3$ | H | OH | Me | H |
| IV-248 | 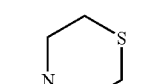 | $CF_3$ | H | OH | Me | H |

TABLE 20-continued

| Compound No | R¹ | R² | R³ | R⁴ | R²⁰ | R²¹ |
|---|---|---|---|---|---|---|
| IV-249 | (4-methylpiperazin-1-yl)sulfonyl | $CF_3$ | H | OH | Me | H |
| IV-250 | $C_2H_4OCH_3$ | $CHF_2$ | H | $OSO_2Pr$-n | Me | H |
| IV-251 | $C_2H_4OCH_3$ | $CHF_2$ | H | $OSO_2Pr$-n | Me | H |
| IV-252 | $CH_2CH=CH_2$ | $CF_3$ | H | $OSO_2Ph$(4-Me) | Me | H |
| IV-253 | $CH_2SC_2H_5$ | $CF_3$ | H | $OSO_2Pr$-n | Me | H |
| IV-254 | $CH_2SC_2H_5$ | $CF_3$ | H | OH | Me | H |
| IV-255 | (4-methylpiperazin-1-yl)sulfonyl | $CF_3$ | H | $OSO_2Pr$-n | Me | H |
| IV-256 | 4-methylthiomorpholin-yl | $CF_3$ | H | $OSO_2Pr$-n | Me | H |
| IV-257 | 4-methylmorpholin-yl | $CF_3$ | H | $OSO_2Pr$-n | Me | H |
| IV-258 | 3-chloro-4-methoxyphenyl-methyl | $CF_3$ | H | OH | Me | H |
| IV-259 | 3-chloro-4-methoxyphenyl-methyl | $CF_3$ | H | $OSO_2Pr$-n | Me | H |
| IV-260 | 4-(trifluoromethoxy)phenyl-methyl | $CF_3$ | H | OH | Et | H |

TABLE 21

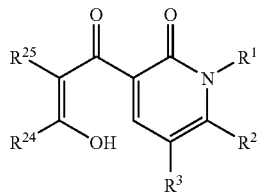
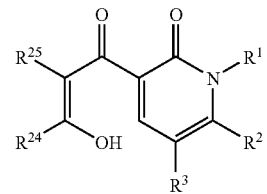

| Compound No | R¹ | R² | R³ | R²⁴ | R²⁵ | Compound No | R¹ | R² | R³ | R²⁴ | R²⁵ |
|---|---|---|---|---|---|---|---|---|---|---|---|
| V-1 | Me | $CF_3$ | H | Me | CN | V-13 | Me | $CF_3$ | H | Pr-n | $NO_2$ |
| V-2 | Me | $CF_3$ | H | Et | CN | V-14 | Me | $CF_3$ | H | Pr-i | $NO_2$ |
| V-3 | Me | $CF_3$ | H | Pr-n | CN | V-15 | Me | $CF_3$ | H | Bu-n | $NO_2$ |
| V-4 | Me | $CF_3$ | H | Pr-i | CN | V-16 | Me | $CF_3$ | H | Bu-i | $NO_2$ |
| V-5 | Me | $CF_3$ | H | Bu-n | CN | V-17 | Me | $CF_3$ | H | Bu-s | $NO_2$ |
| V-6 | Me | $CF_3$ | H | Bu-i | CN | V-18 | Me | $CF_3$ | H | Bu-t | $NO_2$ |
| V-7 | Me | $CF_3$ | H | Bu-s | CN | V-19 | Me | $CF_3$ | H | Pr-c | $NO_2$ |
| V-8 | Me | $CF_3$ | H | Bu-t | CN | V-20 | Me | $CF_3$ | H | Bu-c | $NO_2$ |
| V-9 | Me | $CF_3$ | H | Pr-c | CN | V-21 | Pr-n | $CF_3$ | H | Pr-c | CN |
| V-10 | Me | $CF_3$ | H | Bu-c | CN | V-22 | $CH_2CF_3$ | $CF_3$ | H | Pr-c | CN |
| V-11 | Me | $CF_3$ | H | Me | $NO_2$ | V-23 | Ph | $CF_3$ | H | Pr-c | CN |
| V-12 | Me | $CF_3$ | H | Et | $NO_2$ | V-24 | Pr-n | $CF_3$ | Me | Pr-c | CN |

TABLE 21-continued

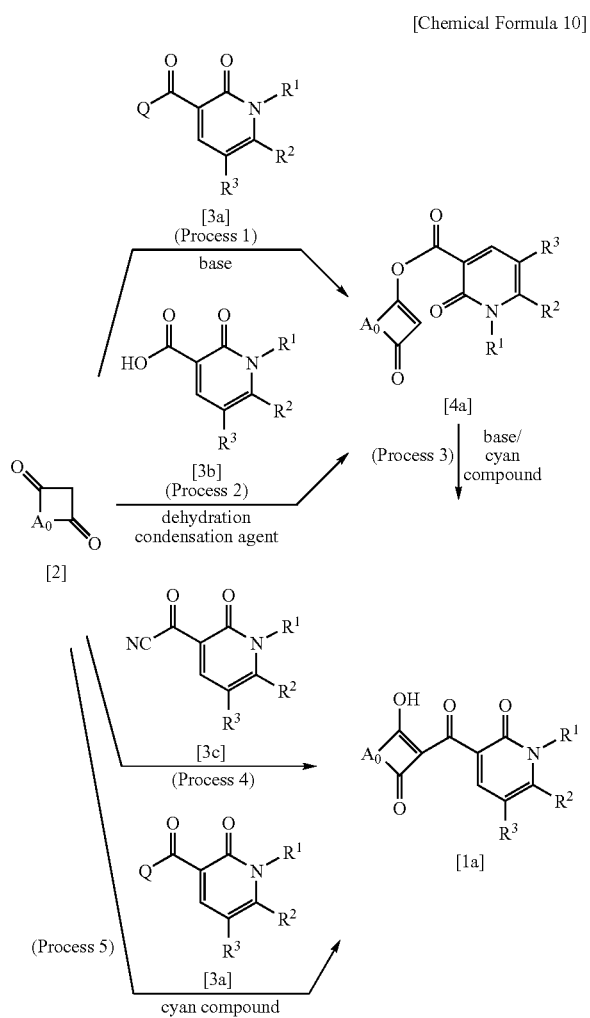

| Compound No | $R^1$ | $R^2$ | $R^3$ | $R^{24}$ | $R^{25}$ |
|---|---|---|---|---|---|
| V-25 | $CH_2CH_2O$ | $CF_3$ | H | Pr-c | CN |
| V-26 | (tetrahydrofuranyl-ethyl) | $CF_3$ | H | Pr-c | CN |

<Production Method 1>

The compound of Formula [1a] which is the compound of the invention can be produced according to a method comprising a reaction scheme exemplified below. The compound of Formula [1a] is the compound of Formula [1] in which A is a group represented by Formula A-1 and $R^4$ is a hydroxy group.

[Chemical Formula 10]

(wherein $R^1$, $R^2$, $R^3$ and $A_0$ are each the same as defined above, and Q is a leaving group such as a halogen atom, an alkylcarbonyloxy group, an alkoxycarbonyloxy group, a haloalkylcarbonyloxy group, a haloalkoxycarbonyloxy group, a benzoyloxy group, a pyridyl group or an imidazolyl group.)

(Process 1)

The enolester compound of Formula [4a] can be produced by allowing the compound of Formula [2] to react with the compound of Formula [3a] in a solvent in the presence of a base.

Herein, an amount of the compound of Formula [3a] to be used may be suitably selected from the range between 0.5 and 10 mol with respect to 1 mol of the compound of Formula [2], while the preferred amount is from 1.0 to 1.2 mol.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0.5 and 10 mol with respect to 1 mol of the compound of Formula [2], while the preferred amount is from 1.0 to 1.2 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

The reaction temperature can be selected from the range between –20° C. and boiling point region of an inert solvent to be used, and the reaction is preferably carried out at a temperature in the range of from 0 to 100° C. In addition, the reaction can also be carried out in a two-layer system with the use of a phase-transfer catalyst such as a quaternary ammonium salt. The reaction time varies according to a reaction temperature, a reactant, a reaction amount or the like, but is usually between 10 minutes and 48 hours.

The compound of Formula [4a] which is the desired product of the reaction is collected from the reaction system by the usual method after the reaction, and if necessary, can be purified by a manipulation such as column chromatography or recrystallization.

(Process 2)

The compound of Formula [4a] can be produced by allowing the compounds of Formula [2] and Formula [3b] to react with a dehydration condensation agent, in a solvent in the presence/absence of a base.

An amount of the compound of Formula [3b] to be used in the present process may be suitably selected from the range between 0.5 and 10 mol with respect to 1 mol of the compound of Formula [2], while the preferred amount is from 1.0 to 1.2 mol.

As the dehydration condensation agent, dicyclohexylcarbodiimide (DCC), N-(3-dimethylaminopropyl)-N'-ethylcarbodiimide (EDC or WSC), N,N-carbonyldiimidazole, 2-chloro-1,3-dimethylimidazoliumchloride, 2-chloro-1-pyridinium iodide or the like, can be used.

As the solvent that can be used in the present process, the same solvent mentioned in Process 1 can be exemplified. In addition, in the case of using a base in the present process, the same base mentioned in Process 1 can also be used.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount, or the like, but is usually between 10 minutes and 48 hours.

(Process 3)

The compound of Formula [1a] can be produced by allowing the compound of Formula [4a] produced according to Process 1 or 2, to react with a cyan compound in the presence of a base.

As the base that can be used in the present process, the same base mentioned in Process 1 can be exemplified. An amount of the base to be used in the present process may be suitably selected from the range between 0.5 and 10 mol with respect to 1 mol of the compound of Formula [4a], while the preferred amount is from 1.0 to 1.2 mol.

As the cyan compound that can be used in the present process, potassium cyanide, sodium cyanide, acetonecyanhydrin, hydrogen cyanide, a polymer holding hydrogen cyanide or the like can be exemplified. An amount of the cyan compound to be used may be suitably selected from the range between 0.01 and 1.0 mol with respect to 1 mol of the compound of Formula [4a], while the preferred amount is from 0.05 to 0.2 mol.

Further, in the present process, a small amount of phase-transfer catalyst such as crown ether may be used.

As the solvent that can be used in the present process, the same solvent mentioned in Process 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The compound of Formula [1a] can be produced by using, without being isolated, the compound of Formula [4a] produced via Process 1 or Process 2 according to the present process.

(Process 4)

The compound of Formula [1a] can also be produced by allowing the compound of Formula [2] to react with the compound of Formula [3c] in the presence of a base or Lewis acid.

An amount of the compound of Formula [3c] to be used in the present process may be suitably selected from the range between 0.5 and 10 mol with respect to 1 mol of the compound of Formula [2], while the preferred amount is from 1.0 to 1.2 mol.

As Lewis acid, zinc chloride, aluminum chloride or the like can be used.

As the base that can be used in the present process, the same base mentioned in Process 1 can be exemplified. An amount of the base to be used may be suitably selected from the range between 0.5 and 10 mol with respect to 1 mol of the compound of Formula [2], while the preferred amount is from 1.0 to 1.2 mol.

As the solvent that can be used in the present reaction, the same solvent mentioned in Process 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

(Process 5)

The compound of Formula [1a] can also be produced by allowing the compound of Formula [2] to react with the compound of Formula [3a] in the presence of a cyan compound.

An amount of the compound of Formula [3a] to be used in the present process may be suitably selected from the range between 0.5 and 10 mol with respect to 1 mol of the compound of Formula [2], while the preferred amount is from 1.0 to 1.2 mol.

As the cyan compound that can be used in the present process, potassium cyanide, sodium cyanide, acetonecyanhydrin, hydrogen cyanide, a polymer holding hydrogen cyanide or the like can be exemplified. An amount of the cyan compound to be used may be suitably selected from the range between 1 and 5.0 mol with respect to 1 mol of the compound of Formula [2], while the preferred amount is from 1.0 to 3.0 mol.

Further, in the present process, a small amount of phase-transfer catalyst such as crown ether may be used.

As the solvent that can be used in the present process, the same solvent mentioned in Process 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount, or the like, but is usually between 10 minutes and 48 hours.

<Production Method 2>

Compounds represented by Formulae [1b] and [1c-1] of the invention can be produced from the compound represented by Formula [1a] of the invention, according to the following production method.

[Chemical Formula 11]

$$\text{[1a]} \xrightarrow{\text{halogenating agent}}$$

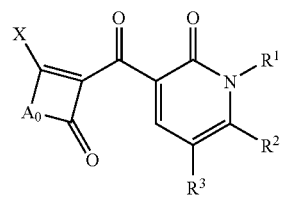

[1b]

nucleophilic agent ↓

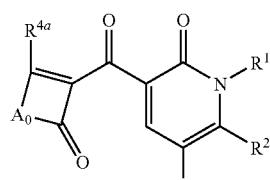

[1c-1]

(wherein $R^1$, $R^2$, $R^3$ and $A_0$ are each the same as defined above; $R^{4a}$ is the same as the group obtained when a halogen atom is removed from the $R^4$; and X is a halogen atom.)

In specific, the compound of Formula [1a] is reacted with a halogenating agent to produce the compound of Formula [1b], and the compound of Formula [1b] is further reacted with a nucleophilic agent in the presence of a base to produce the compound of Formula [1c-1].

As the halogenating agent that can be used in the process from Formula [1a] to Formula [1b], thionyl chloride, thionyl bromide, phosphorus oxychloride, phosphorus oxybromide, phenyl trimethyl ammonium tribromide, Meldrum's acid tribromide or the like can be exemplified. An amount of the halogenating agent to be used may be suitably selected from the range between 0.5 and 10 mol with respect to 1 mol of the compound of Formula [1a], while the preferred amount is from 1.0 to 1.2 mol.

As the solvent that can be used, the same solvent mentioned in Process 1 of Production Method 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

As the nucleophilic agent that can be used in the process from Formula [1b] to Formula [1c-1], alcohols such as methanol, ethanol and benzyl alcohol; mercaptans such as methyl mercaptan and ethyl mercaptan; amines such as ammonia, methylamine and ethylamine; or the like can be exemplified. An amount of the nucleophilic agent to be used may be suitably selected from the range between 0.5 and 10 mol with respect to 1 mol of the compound of Formula [1a], while the preferred amount is from 1.0 to 1.2 mol.

As the base that can be used, the same base mentioned in Process 1 of Production Method 1 can be exemplified. As the solvent that can be used, the same solvent mentioned in Process 1 of Production Method 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

<Production Method 3>

The compound of Formula [1c-2] can be produced according to a method comprising the following reaction scheme.

[Chemical Formula 12]

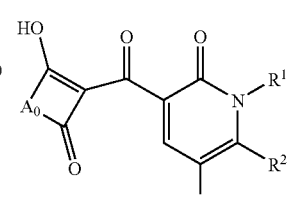

[1a]

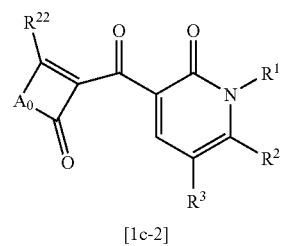

[1c-2]

(wherein $R^1$, $R^2$, $R^3$ and $A_0$ are each the same as defined above, and $R^{22}$ is a $C_{1-6}$ alkoxycarbonyloxy group, a benzyloxy carbonyloxy group which may be substituted with one or more substituents selected from Substituent Group α, a $C_{1-12}$ alkoxy group, a $C_{2-6}$ alkenyloxy group, a $C_{2-6}$ alkynyloxy group, a $C_{3-8}$ cycloalkyloxy group, a cyanomethyloxy group, a $C_{3-8}$ cycloalkyl alkyloxy group, a $C_{1-8}$ alkylcarbonyloxy group, a $C_{1-6}$ haloalkylcarbonyloxy group, a $C_{2-6}$ alkenylcarbonyloxy group, a $C_{2-6}$ haloalkenylcarbonyloxy group, a $C_{2-6}$ alkynylcarbonyloxy group, a $C_{2-6}$ haloalkynylcarbonyloxy group, a $C_{1-6}$ alkoxycarbonyl $C_{1-6}$ alkoxy group, a phenyloxy group which may be substituted with one or more substituents selected from Substituent Group α, a benzyloxy group which may be substituted with one or more substituents selected from Substituent Group α, a phenylcarbonyloxy group which may be substituted with one or more substituents selected from Substituent Group α, a benzylcarbonyloxy group which may be substituted with one or more substituents selected from Substituent Group α, a phenylcarbonyl $C_{1-6}$ alkyloxy group which may be substituted with one or more substituents selected from Substituent Group α, a $C_{1-3}$ alkylsulfonyloxy group, a phenylsulfonyloxy group which may be substituted with one or more substituents selected from Substituent Group α or a benzylsulfonyloxy group which may be substituted with one or more substituents selected from Substituent Group α.)

In specific, the compound of Formula [1c-2] can be produced by allowing the compound of Formula [1a] to react with an electrophilic agent in a solvent in the presence/absence of a base.

As the electrophilic agent that can be used, for example, halides such as iodomethane and benzyl bromide; acid chlorides such as acetyl chloride and benzoyl chloride; sulfonyl chlorides such as methanesulfonyl chloride and p-toluenesulfonyl chloride; sulfate esters such as dimethyl sulfate and diethyl sulfate; or the like can be exemplified.

An amount of the electrophilic agent to be used may be suitably selected from the range between 0.1 and 10 mol with respect to 1 mol of the compound of Formula [1a], while the preferred amount is from 1.0 to 1.2 mol.

As the base that can be used, the same base mentioned in Process 1 of Production Method 1 can be exemplified. An amount of the base to be used may be suitably selected from the range between 0 and 10 mol with respect to 1 mol of the compound of Formula [1a], while the preferred amount is from 1.0 to 1.2 mol.

As the solvent that can be used, the same solvent mentioned in Process 1 of Production Method 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount, or the like, but is usually between 10 minutes and 48 hours.

With regard to the compound of Formula [1a] of the invention, there are many tautomers as shown below, and the compound of the invention includes all of them.

[Chemical Formula 13]

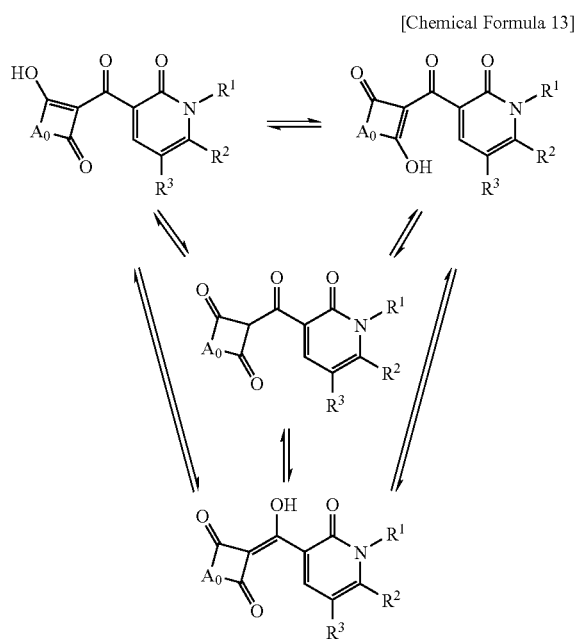

<Production Method 4>

The compound of Formula [1d] can be produced according to a method comprising the following reaction scheme. The compound of Formula [1d] is the compound of Formula [1] in which A is a group represented by Formula A-2 and $R^4$ is a hydroxy group.

[Chemical Formula 14]

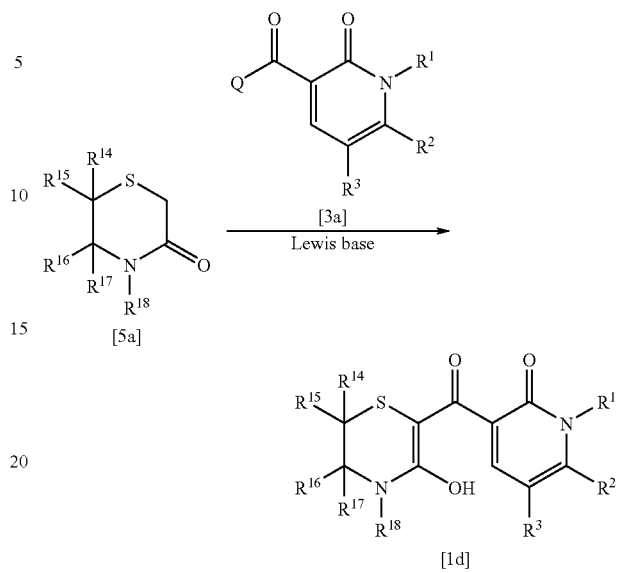

(wherein $R^1$, $R^2$, $R^3$, $R^{14}$, $R^{15}$, $R^{16}$, $R^{17}$, $R^{18}$ and Q are each the same as defined above.)

In specific, the compound of Formula [1d] can be produced by allowing the compound of Formula [5a] to react with the compound of Formula [3a] in a solvent in the presence of a Lewis base.

An amount of the compound of Formula [3a] to be used may be suitably selected from the range between 0.5 and 10 mol with respect to 1 mol of the compound of Formula [5a], while the preferred amount is from 1.0 to 1.2 mol.

As the Lewis base that can be used, organic lithium compounds such as methyllithium, ethyllithium, n-butyllithium, sec-butyllithium, tert-butyllithium and benzyllithium; Grignard reagents such as methylmagnesium iodide and ethylmagnesium bromide; metal compounds such as lithium, potassium and sodium; organic copper compounds prepared from a salt of monovalent copper salt and either a Grignard reagent or an organometallic compound; alkali metal amides such as lithium diisopropyl amide (LDA); organic amines such as triethylamine, pyridine, 4-dimethylaminopyridine, N,N-dimethylaniline and 1,8-diazabicyclo[5.4.0]undec-7-ene; or the like can be exemplified. Particularly preferred are n-butyllithium and lithium diisopropyl amide (LDA). An amount of the Lewis base to be used may be suitably selected from the range between 0.5 and 10 mol with respect to 1 mol of the compound of Formula [5a], while the preferred amount is from 1.0 to 1.2 mol.

As the solvent that can be used, the same solvent mentioned in Process 1 of Production Method 1 can be exemplified.

Particularly preferred are ethers such as diethylether and tetrahydrofuran.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

With regard to the compound of Formula [1d] of the invention, there are many tautomers as shown below, and the compound of the invention includes all of them.

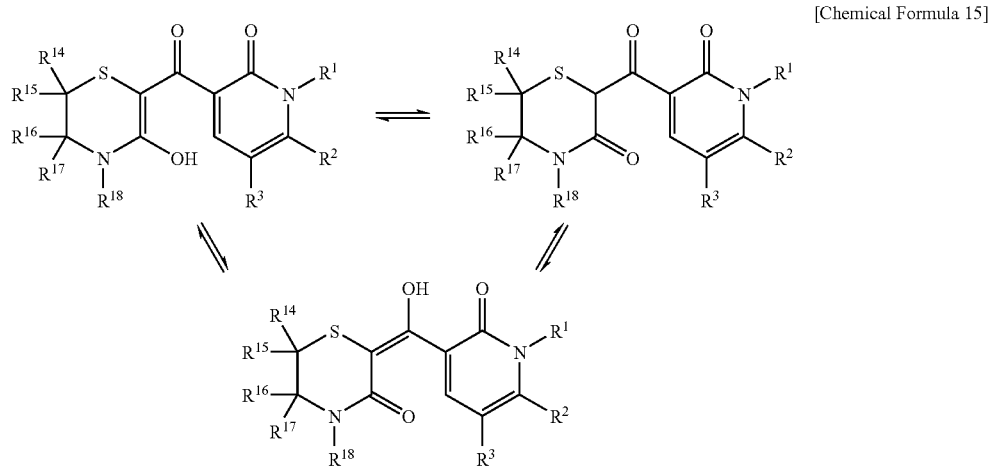

<Production Method 5>

The compound of Formula [1e] can be produced according to a method comprising the following reaction scheme. The compound of Formula [1e] is the compound of Formula [1] in which A is a group represented by Formula A-3 and $R^4$ is a hydroxy group.

[Chemical Formula 16]

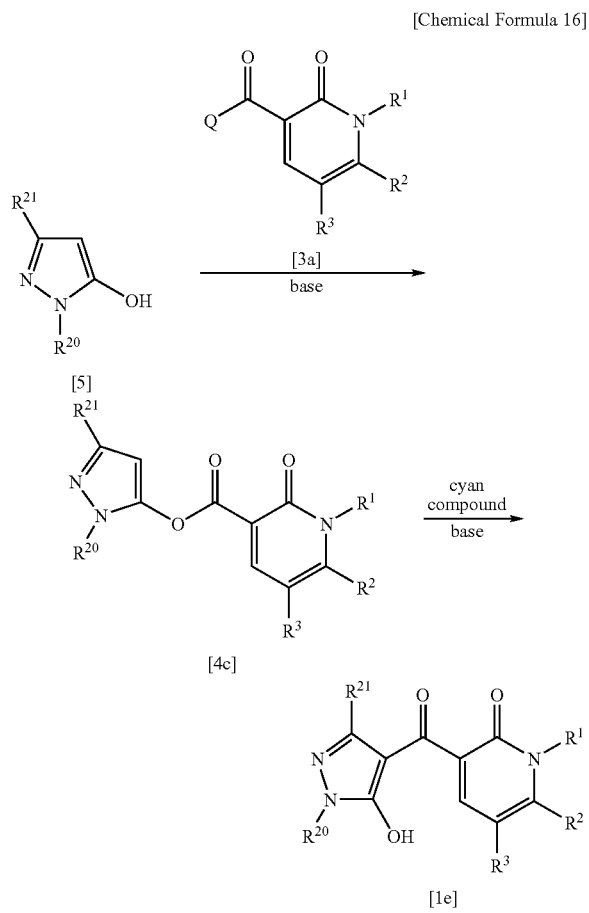

(wherein $R^1$, $R^2$, $R^3$, $R^{20}$, $R^{21}$ and Q are each the same as defined above.)

In specific, the compound of Formula [5] is reacted with the compound of Formula [3a] in a solvent in the presence of a base to produce the compound of Formula [4c], and the compound of Formula [4c] is further reacted with a cyan compound in the presence of a base to produce the compound of Formula [1e].

For the above-mentioned reaction, an amount of the compound of Formula [3a] to be used in the process from Formula [5] to Formula [4c] may be suitably selected from the range between 0.1 and 10 mol with respect to 1 mol of the compound of Formula [5], while the preferred amount is from 1.0 to 1.2 mol.

As the base and the solvent that can be used, the same ones mentioned in Process 1 of above-mentioned Production Method 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

For the above-mentioned reaction, the cyan compound that can be used in the process from Formula [4c] to Formula [1e] can be exemplified by potassium cyanide, sodium cyanide, acetonecyanhydrin, hydrogen cyanide, a polymer holding hydrogen cyanide or the like. An amount of the cyan compound to be used may be suitably selected from the range between 0.01 and 1.0 mol with respect to 1 mol of the compound of Formula [5], while the preferred amount is from 0.05 to 0.2 mol.

As the base that can be used, the same base mentioned in Process 1 of above-mentioned Production Method 1 can be exemplified. An amount of the base to be used may be suitably selected from the range between 0.1 and 10 mol with respect to 1 mol of the compound of Formula [5], while the preferred amount is from 1.0 to 1.2 mol.

As the solvent that can be used in the present process, the same solvent mentioned in Process 1 of above-mentioned Production Method 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount, or the like, but is usually between 10 minutes and 48 hours.

With regard to the compound of Formula [1e] of the invention, there are many tautomers as shown below, and the compound of the invention includes all of them.

[Chemical Formula 17]

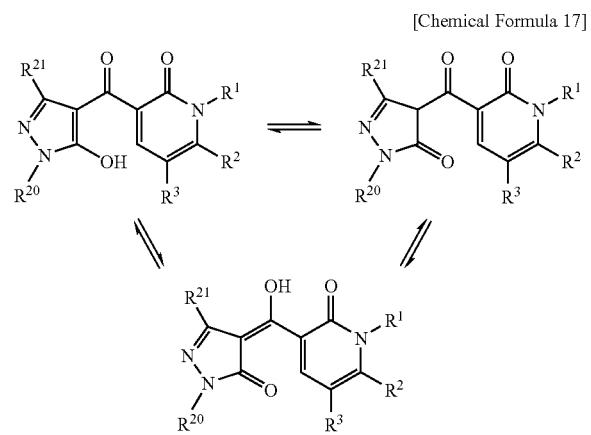

<Production Method 6>

The compound of Formula [1f] for which a substituent of the pyrazole ring is replaced with halogen, and, the compound of Formula [1g-1] for which the substituent is replaced with $R^{4a}$ can be produced using the compound of Formula [1e] synthesized in above-mentioned Production Method 5 according to a method comprising the following reaction scheme.

[Chemical Formula 18]

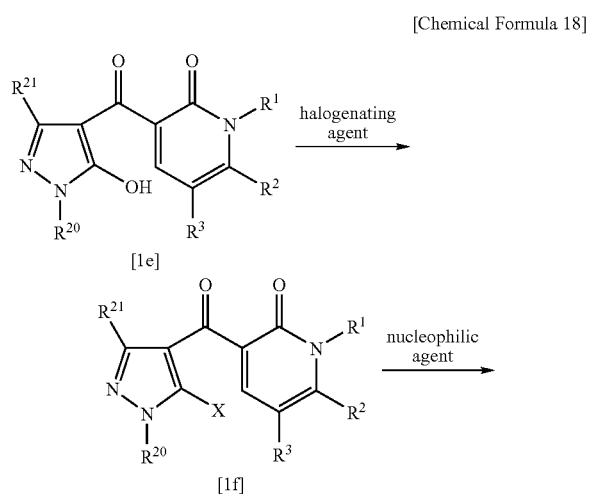

(wherein $R^1$, $R^2$, $R^3$, $R^{20}$, $R^{21}$, $R^{4a}$ and X are each the same as defined above.)

In specific, the compound of Formula [1e] is reacted with a halogenating agent to produce the compound of Formula [1f], and the compound of Formula [1f] is further reacted with a nucleophilic agent to produce the compound of Formula [1g-1].

For the above-mentioned reaction, the halogenating agent that can be used in the process from the compound of Formula [1e] to the compound of Formula [1f] can be exemplified by thionyl chloride, thionyl bromide, phosphorus oxychloride, phosphorus oxybromide, phenyl trimethyl ammonium tribromide, Meldrum's acid tribromide or the like. An amount of the halogenating agent to be used may be suitably selected from the range between 0.1 and 10 mol with respect to 1 mol of Formula [1e], while the preferred amount is from 1.0 to 1.2 mol.

As the solvent that can be used, the same solvent mentioned in Process 1 of above-mentioned Production Method 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount, or the like but is usually between 10 minutes and 48 hours.

As the nucleophilic agent that can be used in the process from the compound of Formula [1f] to the compound of Formula [1g-1], alcohols such as methanol, ethanol and benzyl alcohol; mercaptans such as methyl mercaptan and ethyl mercaptan; amines such as ammonia, methylamine and ethylamine; or the like can be exemplified. An amount of the nucleophilic agent to be used may be suitably selected from the range between 0.1 and 10 mol with respect to 1 mol of the compound of Formula [1f], while the preferred amount is from 1.0 to 1.2 mol.

As the solvent that can be used, the same solvent mentioned in Process 1 of above-mentioned Production Method 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

<Production Method 7>

The compound of Formula [1g-2] can be produced according to a method comprising the following reaction scheme.

[Chemical Formula 19]

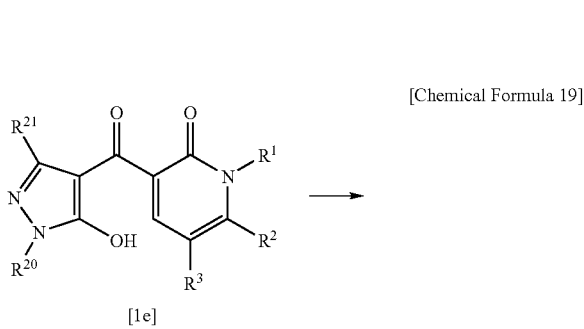

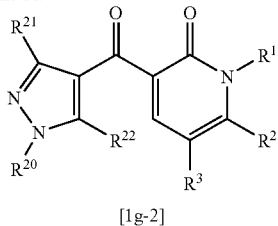

[1g-2]

(wherein $R^1$, $R^2$, $R^3$, $R^{20}$, $R^{21}$ and $R^{22}$ are each the same as defined above.)

In specific, the compound of Formula [1g-2] can be produced by allowing the compound of Formula [1e] to react with an electrophilic agent in a solvent in the presence/absence of a base.

As the electrophilic agent that can be used, halides such as iodomethane and benzyl bromide; acid chlorides such as acetyl chloride and benzoyl chloride; sulfonyl chlorides such as methanesulfonyl chloride and p-toluenesulfonyl chloride; sulfate esters such as dimethyl sulfate and diethyl sulfate; or the like can be exemplified. An amount of the electrophilic agent to be used may be suitably selected from the range between 0.1 and 10 mol with respect to 1 mol of the compound of Formula [1e], while the preferred amount is from 1.0 to 1.2 mol.

As the solvent that can be used in the present reaction, the same solvent mentioned in Process 1 of above-mentioned Production Method 1 can be exemplified.

In the case of using a base in the present reaction, the same base mentioned in Process 1 of above-mentioned Production Method 1 can also be used. An amount of the base to be used may be suitably selected from the range between 0 and 10 mol with respect to 1 mol of the compound of Formula [1e], while the preferred amount is from 1.0 to 1.2 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

<Production Method 8>

The compound of Formula [1 h] can be produced according to a method comprising the following reaction scheme. The compound of Formula [1 h] is the compound of Formula [1] in which A is a group represented by Formula A-5.

[Chemical Formula 20]

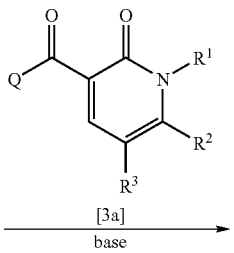

[7]

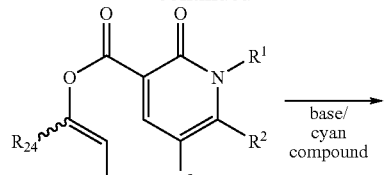

[4d]

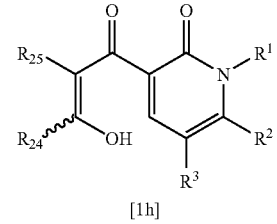

[1h]

(wherein $R^1$, $R^2$, $R^3$, $R^{24}$, $R^{25}$ and Q are each the same as defined above.)

In specific, the compound of Formula [7] is reacted with the compound of Formula [3a] in a solvent in the presence of a base to produce the compound of Formula [4d], and thereafter the compound of Formula [4d] can be reacted with a cyan compound in the presence of a base to produce the compound of Formula [1 h].

An amount of the compound of Formula [3a] to be used in the process from Formula [7] to Formula [4d] may be suitably selected from the range between 0.1 and 10 mol with respect to 1 mol of the compound of Formula [7], while the preferred amount is from 1.0 to 1.2 mol.

As the base that can be used, the same base mentioned in Process 1 of above-mentioned Production Method 1 can be exemplified. An amount of the base to be used may be suitably selected from the range between 0.1 and 10 mol with respect to 1 mol of the compound of Formula [7], while the preferred amount is from 1.0 to 1.2 mol.

As the solvent that can be used, the same solvent mentioned in Process 1 of above-mentioned Production Method 1 can be exemplified.

As the cyan compound that can be used in the process from Formula [4d] to Formula [1 h], potassium cyanide, sodium cyanide, acetonecyanhydrin, hydrogen cyanide, a polymer holding hydrogen cyanide or the like can be exemplified. An amount of the cyan compound to be used may be suitably selected from the range between 0.01 and 1.0 mol with respect to 1 mol of the compound of Formula [4d], while the preferred amount is from 0.05 to 0.2 mol.

As the base that can be used, the same base mentioned in Process 1 of above-mentioned Production Method 1 can be exemplified. An amount of the base to be used may be suitably selected from the range between 0.1 and 10 mol with respect to 1 mol of the compound of Formula [4d], while the preferred amount is from 1.0 to 1.2 mol.

As the solvent that can be used, the same solvent mentioned in Process 1 of above-mentioned Production Method 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount, or the like but is usually between 10 minutes and 48 hours.

With regard to the compound of Formula [1 h] of the invention, there are many tautomers as shown below, and the compound of the invention includes all of them.

[Chemical Formula 21]

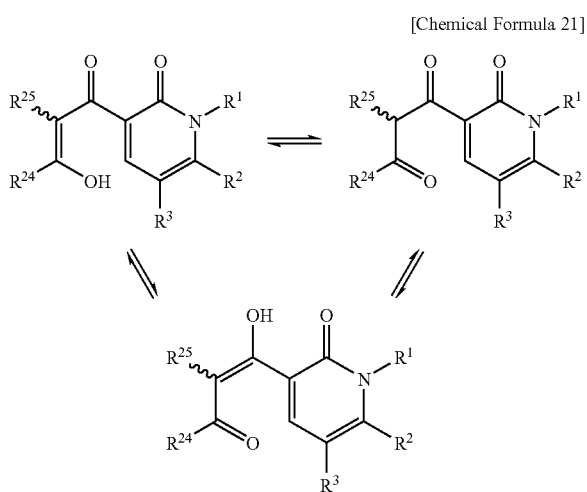

<Production Method 9>

The compound of Formula [1i] can be produced according to a method comprising the following reaction scheme. The compound of Formula [1i] is the compound of Formula [1] in which A is a group represented by Formula A-4.

amount of the acid to be used may be suitably selected from the range between 0.1 and 10 mol with respect to 1 mol of the compound of Formula [1 h], while the preferred amount is from 1.0 to 1.2 mol.

In the case of using a solvent in the present process, a solvent that can be used can be the same solvent mentioned in Process 1 of above-mentioned Production Method 1.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

(Process 2)

The compound of Formula [8b] can be obtained by allowing the compound Formula [8a] to react either with an N,N-dimethylacetamide dimethylacetal compound or an ortho-formate ester compound in anhydrous acetic acid.

An amount of each of N,N-dimethylacetamide dimethylacetal and ortho-formate ester to be used may be suitably selected from the range between 0.1 and 10 mol with respect to 1 mol of the compound of Formula [8a], while the preferred amount is from 1.0 to 3.0 mol.

The reaction temperature can be selected from the range between −20° C. and boiling point region of an inert solvent to be used, and the reaction is preferably carried out at a temperature in the range of from 0 to 150° C. The reaction time varies according to a reaction temperature, a reactant, a reaction amount, or the like, but is usually between 10 minutes and 48 hours.

[Chemical Formula 22]

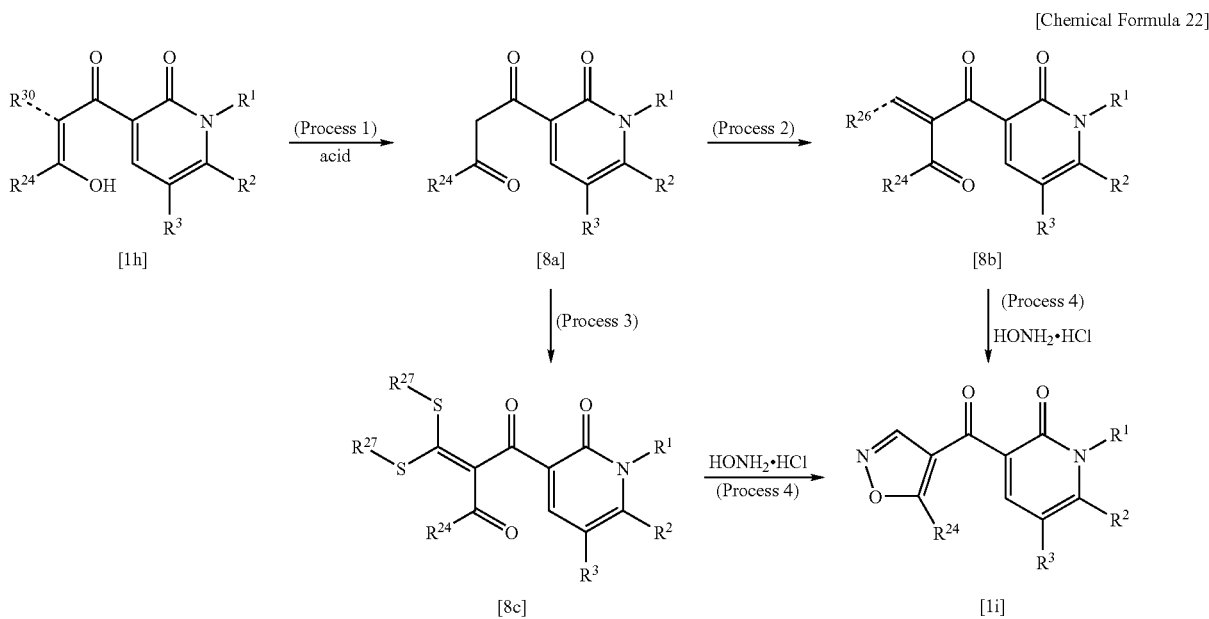

(wherein $R^1$, $R^2$, $R^3$ and $R^{24}$ are each the same as defined above, $R^{30}$ is carboxylic acid ester, $R^{26}$ is an alkoxy group, a haloalkoxy group, a cycloalkoxy group or a dimethylamino group, and $R^{27}$ is an alkyl group or a benzyl group.)

(Process 1)

According to the present process, the compound of Formula [8a] can be produced by allowing the compound of Formula [1 h] to react with acid either in an inert solvent or without using a solvent.

As the acid that can be used in the present process, sulfonic acids such as p-toluenesulfonic acid can be exemplified. An (Process 3)

The compound of Formula [8c] can be obtained by allowing the compound of Formula [8a] to react with carbon disulfide, and without subjecting isolation, adding a halogenating agent thereto.

An amount of the carbon disulfide to be used may be suitably selected from the range between 0.1 and 10 mol with respect to 1 mol of the compound of Formula [8a], while the preferred amount is from 1.0 to 1.2 mol. An amount of the halogenating agent to be used may be suitably selected from the range between 0.1 and 10 mol with respect to 1 mol of the compound of Formula [8a], while the preferred amount is from 2.0 to 2.4 mol.

As the halogenating agent, methyl iodide, methyl bromide, methyl chloride, ethyl iodide, ethyl bromide, ethyl chloride, benzyl bromide, benzyl chloride or the like can be exemplified.

As the solvent that can be used in the present process, the same solvent mentioned in Process 1 of above-mentioned Production Method 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

(Process 4)

The compound of Formula [1i] can be produced by allowing the compound of Formula [8b] or [8c] produced in Process 2 or Process 3, respectively, to react with hydroxylamine hydrochloride in a solvent.

An amount of hydroxylamine to be used may be suitably selected from the range between 0.1 and 10 mol with respect to 1 mol of the compound of Formula [8b] or [8c], while the preferred amount is from 1.0 to 1.2 mol.

As the solvent that can be used in the present process, the same solvent mentioned in Process 1 of above-mentioned Production Method 1 can be exemplified.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

<Production Method 10>

The compound of Formula [1l] can be produced according to a method comprising the following reaction scheme. The compounds of Formulae [1j], [1k], and [1l] are each the compound of Formula [1] in which A is a group represented by Formula A-1 and $R^2$s of each compound are a $C_{1-6}$ alkylthio group or $C_{1-6}$ haloalkylthio group, a $C_{1-6}$ alkylsulfinyl group or $C_{1-6}$ haloalkylsulfinyl group, and a $C_{1-6}$ alkylsulfonyl group or $C_{1-6}$ haloalkylsulfonyl group, respectively.

[Chemical Formula 23]

(wherein $R^1$, $R^3$ and $A_0$ are each the same as defined above, and $R^{44}$ is a $C_{1-6}$ alkyl group or a $C_{1-6}$ haloalkyl group.)

(Process 1)

The sulfoxide derivative represented by Formula [1k] can be produced by allowing the sulfide derivative represented by Formula [1j] to react with an oxidizing agent in a suitable solvent.

The reaction is carried out at an arbitrarily temperature between 0° C. and reflux temperature in the reaction system, and a preferred temperature range is from 0 to 60° C. Although it varies according to the compound, the reaction is completed in 1 to 72 hours.

For the amount of an agent to be provided in the reaction, an oxidizing agent is used in an amount of 1 to 3 mol with respect to 1 mol of the compound represented by Formula [1j].

Examples of the solvent may include halogenated hydrocarbons such as dichloromethane, chloroform, dichloroethane, carbon tetrachloride, chlorobenzene and dichlorobenzene; ethers such as dioxane, tetrahydrofuran (THF), dimethoxyethane and diethylether; amides such as N,N-dimethylacetamide, N,N-dimethylformamide and N-methyl-2-pyrrolidinone; alcohols such as methanol, ethanol, propanol, isopropanol, butanol and tert-butanol; ketones such as acetone and 2-butanone; nitriles such as acetonitrile; acetic acid; water; and mixtures thereof.

Examples of the oxidizing agent may include organic peroxides such as m-chloroperbenzoic acid, peroxyformic acid and peracetic acid; and inorganic peroxides such as hydrogen peroxide, potassium permanganate and sodium periodate.

(Process 2)

The sulfone derivative represented by Formula [1l] can be produced by allowing the sulfoxide derivative represented by Formula [1k] to react with an oxidizing agent in a suitable solvent.

The reaction is carried out at an arbitrarily temperature between 0° C. and reflux temperature in the reaction system, and a preferred temperature range is from 0 to 60° C. Although it varies according to the compound, the reaction is completed in 1 to 72 hours.

For the amount of a reagent to be provided in the reaction, an oxidizing agent is used in an amount of 1 to 3 mol with respect to 1 mol of the compound represented by Formula [1k].

As the solvent and the oxidizing agent, the same ones mentioned in Process 1 of Production Method 10 can be exemplified.

Next, methods of producing synthetic intermediates of the compound of the invention will be shown.

<Intermediate Production Method 1>

The compound of Formula [3b] to be used in Production Method 1 can be produced according to a method comprising the following reaction scheme.

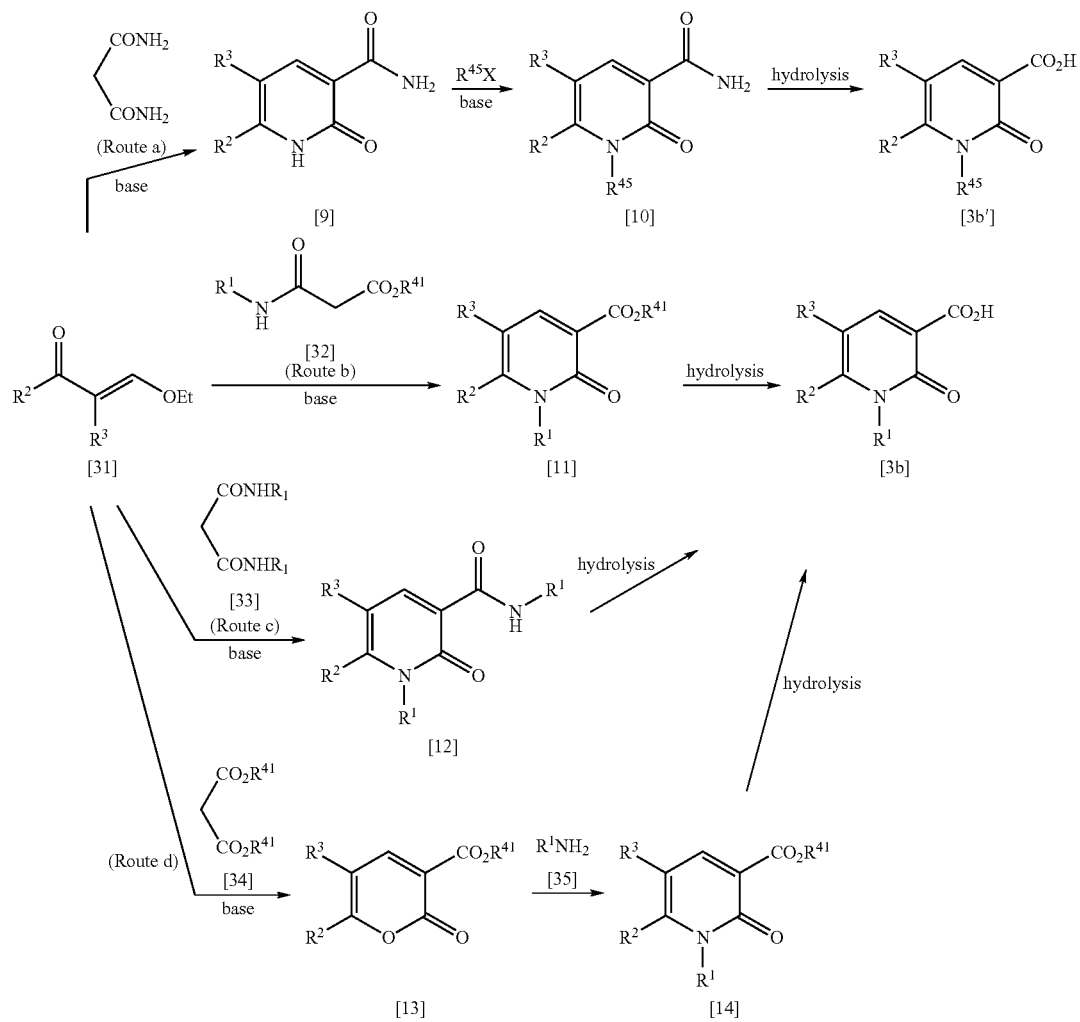

[Chemical Formula 24]

(wherein, $R^1$, $R^2$ and $R^3$ are each the same as defined above, $R^{41}$ is an alkyl group, $R^{45}$ is a $C_{1-6}$ alkyl group, a $C_{2-6}$ alkenyl group, a $C_{2-6}$ alkynyl group, a $C_{3-8}$ cycloalkyl group, a $C_{3-8}$ cycloalkyl $C_{1-6}$ alkyl group, a $C_{1-6}$ haloalkyl group, a $C_{2-6}$ haloalkenyl group, a $C_{2-6}$ haloalkynyl group, a $C_{1-6}$ alkylamino $C_{1-6}$ alkyl group, a di($C_{1-6}$ alkyl)amino $C_{1-6}$ alkyl group, a $C_{1-6}$ alkylthio $C_{1-6}$ alkyl group, a $C_{1-6}$ alkylsulfinyl $C_{1-6}$ alkyl group, a $C_{1-6}$ alkylsulfonyl $C_{1-6}$ alkyl group, a $C_{1-6}$ alkoxy $C_{1-6}$ alkyl group, a $C_{1-6}$ alkoxy $C_{1-6}$ alkoxy $C_{1-6}$ alkyl group, a $C_{3-6}$ cycloalkoxy alkyloxy $C_{1-6}$ alkyl group, a $C_{1-6}$ haloalkoxy $C_{1-6}$ alkyl group, a benzyl group which may be substituted with one or more substituents selected from Substituent Group α, a phenyl $C_{2-6}$ alkyl group which may be substituted with one or more substituents selected from Substituent Group α, a phenyl $C_{2-6}$ alkenyl group which may be substituted with one or more substituents selected from Substituent Group α, a phenyl $C_{2-6}$ alkynyl group which may be substituted with one or more substituents selected from Substituent Group α, a $C_{1-6}$ alkoxyimino $C_{1-6}$ alkyl group, a phenoxyimino $C_{1-6}$ alkyl group which may be substituted with one or more substituents selected from Substituent Group α, a di($C_{1-6}$ alkoxy)$C_{1-6}$ alkyl group or a formyl $C_{2-6}$ alkyl group.)

(Route a)
The compound of Formula [9] can be produced according to a method described in Helvetica Chimica Acta, Vol. 71, 596 (1988). In specific, the compound can be produced by allowing the compound of Formula [31] to react with malonodiamide in a solvent in the presence of a base.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like.

An amount of the base to be used may be suitably selected from the range between 0.5 and 10 mol with respect to 1 mol of the compound of Formula [31], while the preferred amount is from 1.0 to 1.2 mol.

An amount of the malonodiamide to be used may be suitably selected from the range between 1.0 and 3.0 mol with respect to 1 mol of the compound of Formula [31], while the preferred amount is from 1.0 to 1.5 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

The compound of Formula [10] can be produced by allowing the compound of Formula [9] to react with an alkylating agent in a solvent in the presence of a base according to a method described in *Tetrahedron Letters*, Vol. 36, No. 49, 8917 (1995).

As the alkylating agent, methyl iodide, methyl bromide, methyl chloride, ethyl iodide, ethyl bromide, ethyl chloride, dimethyl sulfate, diethyl sulfate or the like can be exemplified. An amount of the alkylating agent to be used may be suitably selected from the range between 1.0 and 5.0 mol with respect to 1 mol of the compound of Formula [9], while the preferred amount is from 1.0 to 1.2 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0.5 and 10 mol with respect to 1 mol of the compound of Formula [9], while the preferred amount is from 1.0 to 1.2 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

The compound of Formula [3b'] can be produced by hydrolyzing the compound of Formula [10] in a solvent under an acidic or basic condition.

Examples of the base that can be used in the present process may include metal hydroxides such as sodium hydroxide, potassium hydroxide, calcium hydroxide and magnesium hydroxyide, and the like. An amount of the base to be used may be suitably selected from the range between 1.0 and 10 mol with respect to 1 mol of the compound of Formula [10], while the preferred amount is from 1.0 to 3.0 mol.

As the acid that can be used in the present process, hydrochloric acid, sulfuric acid, hydrobromic acid or the like can be exemplified. An amount of the acid to be used may be suitably selected from the range between 0.1 and 10 mol with respect to 1 mol of the compound of Formula [10], while the preferred amount is from 1.0 to 3.0 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The solvent for use in the present process may be any solvent as long as it is the one not inhibiting the process of the present reaction. For example, water; alcohols such as methyl alcohol and ethyl alcohol; amides such as N,N-dimethylformamide and N,N-dimethylacetoamide; or a mixed solvent thereof can be used.

(Route b)

The compound of Formula [11] can be produced by allowing the compound of Formula [31] to react with the compound of Formula [32] in a solvent in the presence of a base.

An amount of the compound of Formula [32] to be used herein may be suitably selected from the range between 0.5 and 2.0 mol with respect to 1 mol of the compound of Formula [31], while the preferred amount is from 0.8 to 1.5 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0.5 and 10 mol with respect to 1 mol of the compound of Formula [31], while the preferred amount is from 1.0 to 1.2 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Further, a mixed solvent thereof can be used.

The compound of Formula [3b] can be produced by hydrolyzing the compound of Formula [11] in a solvent under an acidic or basic condition.

Examples of the base that can be used in the present process may include metal hydroxides such as sodium hydroxide, potassium hydroxide, calcium hydroxide and magnesium hydroxyide, and the like. An amount of the base to be used may be suitably selected from the range between 1.0 and 10 mol with respect to 1 mol of the compound of Formula [11], while the preferred amount is from 1.0 to 3.0 mol.

As the acid that can be used in the present process, hydrochloric acid, sulfuric acid, hydrobromic acid or the like can be exemplified. An amount of the acid to be used may be suitably selected from the range between 0.1 and 10 mol with respect to 1 mol of the compound of Formula [11], while the preferred amount is from 1.0 to 3.0 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The solvent for use in the present process may be any solvent as long as it is the one not inhibiting the process of the present reaction. For example, water; alcohols such as methyl alcohol and ethyl alcohol; amides such as N,N-dimethylformamide and N,N-dimethylacetoamide; or a mixed solvent thereof can be used.

(Route c)

The compound of Formula [12] can be produced by allowing the compound of Formula [31] to react with the compound of Formula [33] in a solvent in the presence of a base.

An amount of the compound of Formula [33] to be used herein may be suitably selected from the range between 0.5 and 2.0 mol with respect to 1 mol of the compound of Formula [31], while the preferred amount is from 0.8 to 1.5 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0.5 and 10 mol with respect to 1 mol of the compound of Formula [31], while the preferred amount is from 1.0 to 1.2 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Further, a mixed solvent thereof can be used.

The compound of Formula [3b] can be produced by hydrolyzing the compound of Formula [12] in a solvent under an acidic or basic condition.

Examples of the base that can be used in the present process may include metal hydroxides such as sodium hydroxide, potassium hydroxide, calcium hydroxide and magnesium hydroxyide, and the like. An amount of the base to be used may be suitably selected from the range between 1.0 and 10 mol with respect to 1 mol of the compound of Formula [12], while the preferred amount is from 1.0 to 3.0 mol.

As the acid that can be used in the present process, hydrochloric acid, sulfuric acid, hydrobromic acid or the like can be exemplified. An amount of the acid to be used may be suitably selected from the range between 0.1 and 10 mol with respect to 1 mol of the compound of Formula [12], while the preferred amount is from 1.0 to 3.0 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The solvent for use in the present process may be any solvent as long as it is the one not inhibiting the process of the present reaction. For example, water; alcohols such as methyl alcohol and ethyl alcohol; amides such as N,N-dimethylformamide and N,N-dimethylacetoamide; or a mixed solvent thereof can be used.

(Route d)

The compound of Formula [13] can be produced by allowing the compound of Formula [31] to react with the compound of Formula [34] in a solvent in the presence of a base.

An amount of the compound of Formula [34] to be used herein may be suitably selected from the range between 0.5 and 2.0 mol with respect to 1 mol of the compound of Formula [31], while the preferred amount is from 0.8 to 1.5 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0.5 and 10 mol with respect to 1 mol of the compound of Formula [31], while the preferred amount is from 1.0 to 1.2 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide (DMF) and N,N-dimethylacetamide; imidazolinones such as 1,3-dimethyl-2-imidazolinone; sulfur compounds such as dimethylsulfoxide; or the like can be used. Further, a mixed solvent thereof can be used.

The compound of Formula [14] can be produced by allowing the compound of Formula [13] to react with the compound of Formula [35] in a solvent or absence of a solvent, in the presence or absence of an acid.

An amount of the compound of Formula [35] to be used herein may be suitably selected from the range between 0.5 and 2.0 mol with respect to 1 mol of the compound of Formula [13], while the preferred amount is from 0.8 to 1.5 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

In the case of using an acid in the present process, an acid that be used can be exemplified by Lewis acid such as acetic acid, p-toluenesulfonic acid, aluminum chloride or titanium tetrachloride, or the like. A use amount thereof may be suitably selected from the range between 0.001 and an amount as the solvent with respect to 1 mol of the compound of Formula [13].

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Further, a mixed solvent thereof can be used.

The compound of Formula [3b] can be produced by hydrolyzing the compound of Formula [14] in a solvent under an acidic or basic condition.

Examples of the base that can be used in the present process may include metal hydroxides such as sodium hydroxide, potassium hydroxide, calcium hydroxide and magnesium hydroxide, and the like. An amount of the base to be used may be suitably selected from the range between 1.0 and 10 mol with respect to 1 mol of the compound of Formula [14], while the preferred amount is from 1.0 to 3.0 mol.

As the acid that can be used in the present process, hydrochloric acid, sulfuric acid, hydrobromic acid or the like can be exemplified. An amount of the acid to be used may be suitably selected from the range between 0.1 and 10 mol with respect to 1 mol of the compound of Formula [14], while the preferred amount is from 1.0 to 3.0 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The solvent for use in the present process may be any solvent as long as it is the one not inhibiting the process of the present reaction. For example, water; alcohols such as methyl alcohol and ethyl alcohol; amides such as N,N-dimethylformamide and N,N-dimethylacetoamide; or a mixed solvent thereof can be used.

<Intermediate Production Method 2>

The compound of Formula [3d] can be produced by applying the compound of Formula [15] to a rearrangement reaction in the presence of a catalyst, and then hydrolysis, according to a method described in *Tetrahedron Letters*, Vol. 37, No. 16, 2829 (1996).

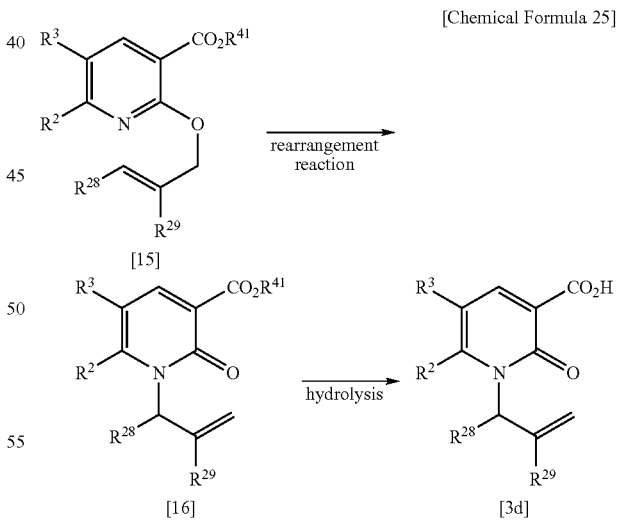

[Chemical Formula 25]

(wherein $R^2$, $R^3$ and $R^{41}$ are each the same as defined above, and $R^{28}$ and $R^{29}$ are each independently a hydrogen atom or an alkyl group.)

<Intermediate Production Method 3>

The thiazine compound of Formula [5a] for use in Production Method 4, which is an intermediate of the compound of the invention, can be produced according to a method described in *SYNLETT*, 915 (1997).

<Intermediate Production Method 4>

The compounds of Formula [19], Formula [20] and Formula [21] which are intermediates of the compound of the invention can be produced according to a method comprising the following reaction scheme.

[Chemical Formula 26]

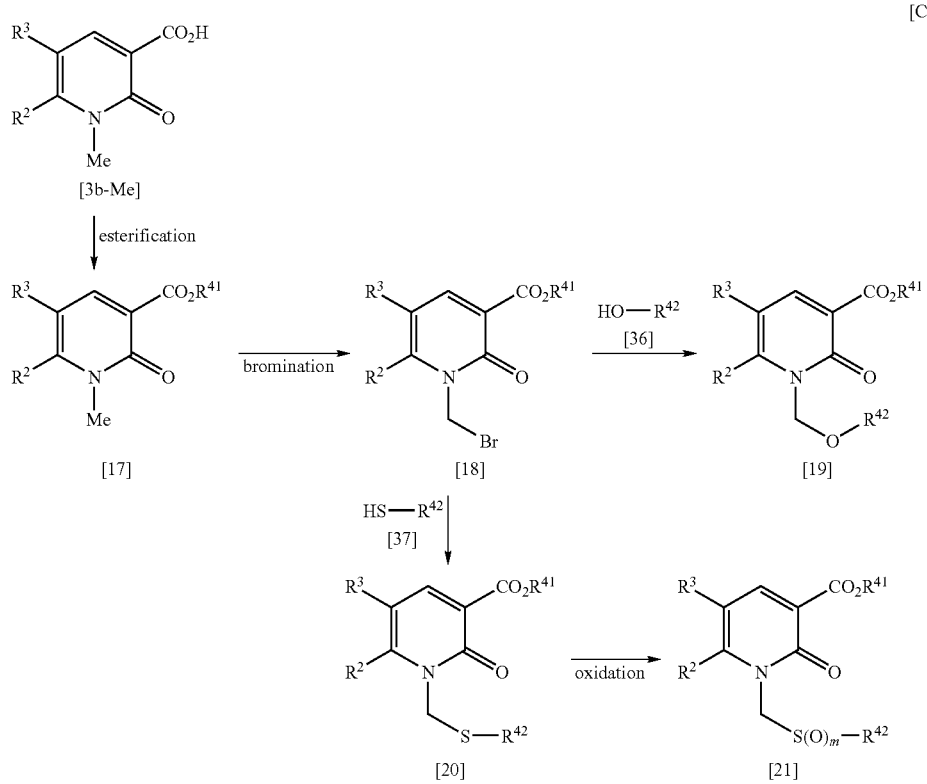

(wherein $R^2$, $R^3$ and $R^{41}$ are each the same as defined above, $R^{42}$ is a $C_{1-6}$ alkyl group, a $C_{2-6}$ alkenyl group, a $C_{2-6}$ alkynyl group, a $C_{3-8}$ cycloalkyl group, a $C_{3-8}$ cycloalkyl $C_{1-6}$ alkyl group, a $C_{1-6}$ haloalkyl group, a phenyl group which may be substituted with one or more substituents selected from Substituent Group α, a benzyl group which may be substituted with one or more substituents selected from Substituent Group α, a phenyl $C_{2-6}$ alkyl group which may be substituted with one or more substituents selected from Substituent Group α, and m is 1 or 2.)

In specific, the compound of Formula [17] can be produced by allowing the compound of Formula [3b-Me] to react with alcohol in the presence of an acid.

As the acid that can be used in the present process, for example, sulfonic acids such as p-toluenesulfonic acid; or sulfuric acid can be exemplified. An amount of the acid to be used may be suitably selected from the range between 0.0001 and 1 mol with respect to 1 mol of the compound of Formula [3b-Me], while the preferred amount is from 0.001 to 0.1 mol.

As the alcohol that can be used in the present process, for example, methanol, ethanol, propanol or the like can be exemplified. An amount of the alcohol to be used may be suitably selected from the range between 1.0 and 50 L with respect to 1 mol of the compound of Formula [3b-Me], while the preferred amount is from 1.0 to 20 L.

The reaction temperature can be selected from the range between −20° C. and boiling point region of a solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The compound of Formula [18] can be produced by allowing the compound of Formula [17] to react with a brominating agent in a solvent in the presence of a radical initiator, with or without the use of a photoreactor.

As the radical initiator that can be used in the present process, benzoyl peroxide or 2,2'-azobis(isobutylonitrile) can be exemplified. An amount of the radical initiator to be used may be suitably selected from the range between 0.0001 and 1 mol with respect to 1 mol of the compound of Formula [17], while the preferred amount is from 0.001 to 0.1 mol.

As the brominating agent that can be used in the present process, for example, bromine, N-bromosuccinimide or the like can be exemplified. An amount of the brominating agent to be used may be suitably selected from the range between 0.5 and 10 mol with respect to 1 mol of the compound of Formula [17], while the preferred amount is from 1.0 to 3.0 mol.

As the solvent that can be used in the present process, carbon tetrachloride, chlorobenzene or the like can be used, and also a mixed solvent thereof can be used as well.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The compound of Formula [19] can be produced by allowing the compound of Formula [18] to react with the compound of Formula [36] in a solvent in the presence or absence of a base.

An amount of the compound of Formula [36] to be used herein may be suitably selected from the range between 1.0 and 20.0 mol with respect to 1 mol of the compound of Formula [18], while the preferred amount is from 1.0 to 5.0 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0 and 10 mol with respect to 1 mol of the compound of Formula [18], while the preferred amount is from 1.0 to 1.2 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

The compound of Formula [20] can be produced by allowing the compound of Formula [18] to react with the compound of Formula [37] in a solvent in the presence or absence of a base.

An amount of the compound of Formula [37] to be used herein may be suitably selected from the range between 1.0 and 20.0 mol with respect to 1 mol of the compound of Formula [18], while the preferred amount is from 1.0 to 5.0 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

In the case of using a base in the present process, the base that can be used can be exemplified by organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; or the like. An amount of the base to be used may be suitably selected from the range between 0 and 10 mol with respect to 1 mol of the compound of Formula [18], while the preferred amount is from 1.0 to 1.2 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

Further, the compound of Formula [21] can be produced by allowing the compound of Formula [20] to react with an oxidizing agent in a solvent.

Examples of the oxidizing agent may include organic peroxides such as m-chloroperbenzoic acid, peroxyformic acid and peracetic acid; and inorganic peroxides such as hydrogen peroxide, potassium permanganate and sodium periodate.

An amount of the oxidizing agent to be used herein may be suitably selected from the range between 0.5 and 5.0 mol with respect to 1 mol of the compound of Formula [20], while the preferred amount is from 0.8 to 3.0 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

<Intermediate Production Method 5>

The compound of Formula [24] which is an intermediate of the compound of the invention can be produced according to a method comprising the following reaction scheme.

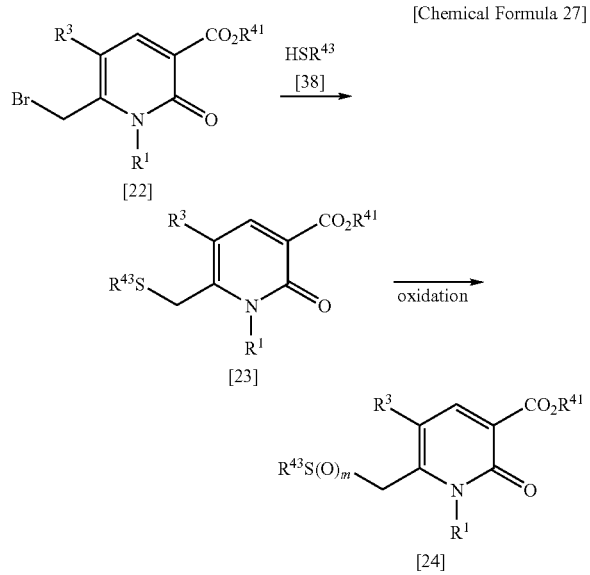

(wherein $R^1$, $R^3$ and $R^{41}$ are each the same as defined above, and $R^{43}$ is an alkyl group.)

In specific, the compound of Formula [23] can be produced by allowing the compound of Formula [22] to react with the compound of Formula [38] in a solvent in the presence of a base.

An amount of the compound of Formula [38] to be used herein may be suitably selected from the range between 1.0 and 5.0 mol with respect to 1 mol of the compound of Formula [22], while the preferred amount is from 1.0 to 3.0 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0.5 and 10 mol with respect to 1 mol of the compound of Formula [22], while the preferred amount is from 1.0 to 1.2 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

The compound of Formula [24] can be produced by allowing the compound of Formula [23] to react with an oxidizing agent in a solvent.

Examples of the oxidizing agent may include organic peroxides such as m-chloroperbenzoic acid, peroxyformic acid and peracetic acid; and inorganic peroxides such as hydrogen peroxide, potassium permanganate and sodium periodate.

An amount of the oxidizing agent to be used herein may be suitably selected from the range between 0.5 and 5.0 mol with respect to 1 mol of the compound of Formula [23], while the preferred amount is from 0.8 to 3.0 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

<Intermediate Production Method 6>

The compound of Formula [27] which is an intermediate of the compound of the invention can be produced according to a method comprising the following reaction scheme.

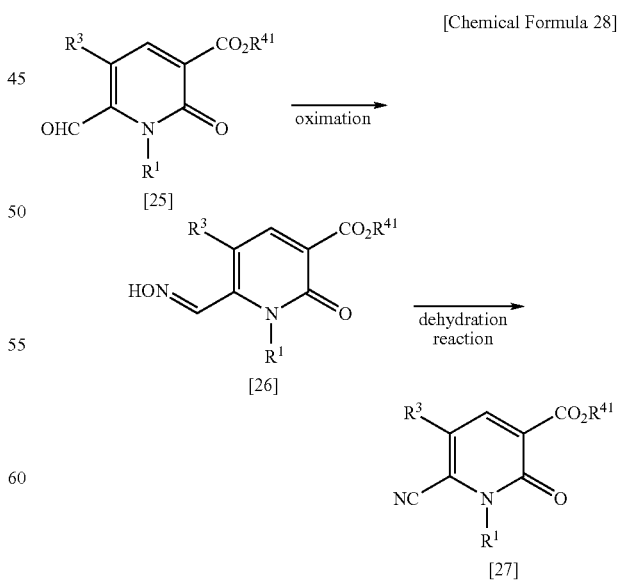

(wherein $R^1$, $R^3$ and $R^{41}$ are each the same as defined above.)

In specific, the compound of Formula [26] can be produced by allowing the compound of Formula [25] to react with hydroxylamine hydrochloride in a solvent in the presence of a base.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0.5 and 10 mol with respect to 1 mol of the compound of Formula [25], while the preferred amount is from 1.0 to 1.2 mol.

An amount of the hydroxylamine hydrochloride to be used may be suitably selected from the range between 0.8 and 5.0 mol with respect to 1 mol of the compound of Formula [25], while the preferred amount is from 1.0 to 3.0 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

The compound of Formula [27] can be produced by allowing the compound of Formula [26] to react with a dehydrating agent in a solvent.

Examples of the dehydrating agent may include WSC(N-(3-dimethylaminopropyl)-N'-ethylcarbodiimide), acetic anhydride, thionyl chloride, phosgene, phosphorus oxychloride and the like.

An amount of the dehydrating agent to be used may be suitably selected from the range between 1.0 and 20.0 mol with respect to 1 mol of the compound of Formula [26], while the preferred amount is from 1.0 to 10 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

<Intermediate Production Method 7>

The compound of Formula [30] which is an intermediate of the compound of the invention can be produced according to a method comprising the following reaction scheme.

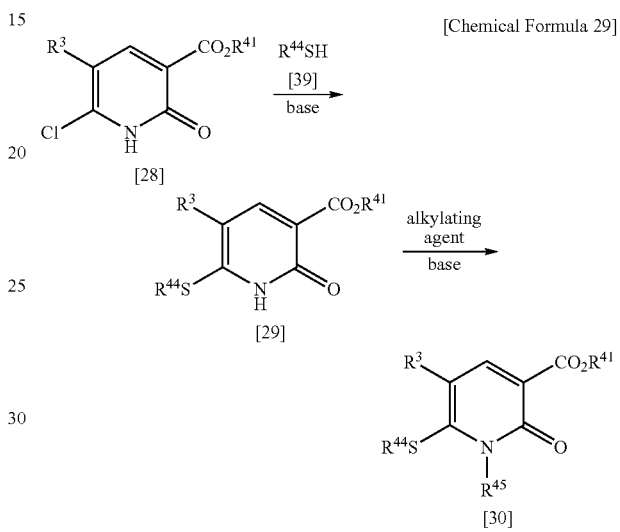

[Chemical Formula 29]

(wherein $R^3$, $R^{41}$, $R^{44}$ and $R^{45}$ are each the same as defined above.)

In specific, the compound of Formula [29] can be produced by allowing the compound of Formula [28] to react with the compound of Formula [39] in a solvent in the presence of a base.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0.5 and 10 mol with respect to 1 mol of the compound of Formula [28], while the preferred amount is from 1.0 to 1.2 mol.

Examples of the compound of Formula [39] to be used in the present process may include methyl mercaptan, ethyl mercaptan and the like. An amount of the compound of Formula [39] to be used may be suitably selected from the range between 1 and 10 mol with respect to 1 mol of the compound of Formula [28], while the preferred amount is from 1.0 to 2.0 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

The compound of Formula [30] can be produced by allowing the compound of Formula [29] to react with an alkylating agent in a solvent in the presence of a base.

As the alkylating agent, methyl iodide, methyl bromide, methyl chloride, ethyl iodide, ethyl bromide, ethyl chloride, dimethyl sulfate, diethyl sulfate or the like can be exemplified. An amount of the alkylating agent to be used may be suitably selected from the range between 1.0 and 5.0 mol with respect to 1 mol of the compound of Formula [29], while the preferred amount is from 1.0 to 3.0 mol.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0.5 and 10 mol with respect to 1 mol of the compound of Formula [29], while the preferred amount is from 1.0 to 1.2 mol.

The reaction temperature can be selected from the range between −20° C. and boiling point region of an inert solvent to be used, and the reaction is preferably carried out at a temperature in the range of from 0 to 100° C. The reaction time varies according to a reaction temperature, a reactant, a reaction amount or the like, but is usually between 10 minutes and 48 hours.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

<Intermediate Production Method 8>

The compound of Formula [3a] which is an intermediate of the compound of the invention can be produced according to a method comprising the following reaction scheme.

[Chemical Formula 30]

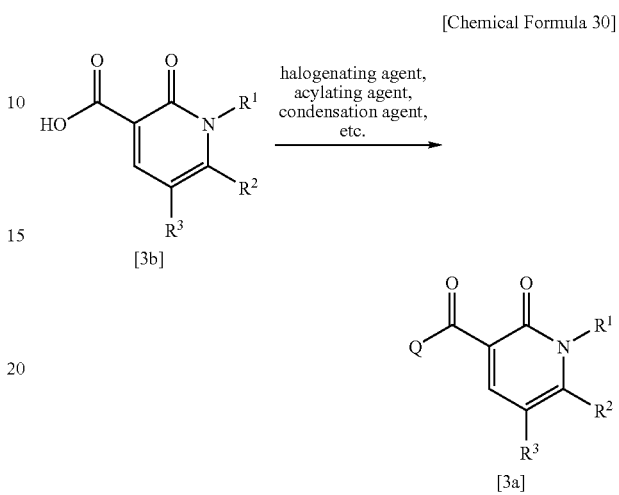

(wherein $R^1$, $R^2$, $R^3$ and Q are each the same as defined above.)

The compound of Formula [3a] can be produced by allowing the compound of Formula [3b] to react with a halogenating agent, an acylating agent and a condensation agent, in the presence of a base as necessary.

As the halogenating agent, thionyl chloride, thionyl bromide, oxalyl chloride or the like can be used.

As the acylating agent, acetyl chloride, methyl chlorocarbonate, ethyl chlorocarbonate, trifluoroacetic anhydride, benzoyl chloride or the like can be used.

As the condensation agent, 2-chloro-1-methylpyridinium iodide, N,N-carbonyldiimidazole or the like can be used.

Examples of the base that can be used in the present process include organic amines such as triethylamine, pyridine, 4-dimethylaminopyridine, N,N-dimethylaniline and 1,8-diazabicyclo[5.4.0]undec-7-ene; metal carbonates such as sodium carbonate, potassium carbonate, magnesium carbonate and calcium carbonate; metal bicarbonates such as sodium bicarbonate and potassium bicarbonate; metal carboxylates typified by metal acetates such as sodium acetate, potassium acetate, calcium acetate and magnesium acetate; metal alkoxides such as sodium methoxide, sodium ethoxide, sodium tert-butoxide, potassium methoxide and potassium tert-butoxide; metal hydroxides such as sodium hydroxide, potassium hydroxide, calcium hydroxide and magnesium hydroxide; metal hydrides such as lithium hydride, sodium hydride, potassium hydride and calcium hydride; and the like. An amount of the base to be used may be suitably selected from the range between 0.5 and 10 mol with respect to 1 mol of the compound of Formula [2], while the preferred amount is from 1.0 to 1.2 mol.

The solvent for use in the present process may be any solvent as long as it is the one not inhibiting the process of the present reaction. For example, nitriles such as acetonitrile; ethers such as diethylether, diisopropylether, tetrahydrofuran, dioxane, monoglyme and diglyme; halogenated hydrocarbons such as dichloroethane, chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide; or the like can be used. Also, a mixed solvent thereof can be used as well.

The reaction temperature can be selected from the range between −20° C. and boiling point region of an inert solvent to be used, and the reaction is preferably carried out at a temperature in the range of from 0 to 120° C. In addition, the reaction can also be carried out in a two-layer system with the use of a phase-transfer catalyst such as a quaternary ammonium salt. The reaction time varies according to a reaction temperature, a reactant, a reaction amount or the like, but is usually between 10 minutes and 48 hours.

The herbicide of the invention is characterized by containing the pyridone derivative as described above or an agriculturally acceptable salt thereof, as the active ingredient.

The herbicide of the present invention may contain additive components that may be normally employed for pesticide formulations, as needed.

Examples of the additive components may include carriers such as solid carrier and liquid carrier, surfactant, binder, tackifier, thickener, coloring agent, spreader, sticker, antifreezing agent, anticaking agent, collapsing agent, decomposition inhibitor and the like. If necessary, an anticeptic agent, a piece of plant and the like may also be employed as additive components.

These additive components may be used alone or in combination of two or more kinds.

The above additive components will be described.

Examples of the solid carrier may include natural minerals such as quartz, clay, kaolinite, pyrophyllite, sericite, talc, bentonite, acid clay, attapulgite, zeolite and diatomite; inorganic salts such as calcium carbonate, ammonium sulfate, sodium sulfate and potassium chloride; organic solid carriers such as synthetic silicic acid, synthetic silicate, starch, cellulose and plant powder; plastic carriers such as polyethylene, polypropylene and polyvinylidene chloride; and the like. These may be used alone or in combination of two or more kinds.

Examples of the liquid carrier may include alcohols classified broadly into monohydric alcohols such as methanol, ethanol, propanol, isopropanol and butanol, and polyhydric alcohols such as ethylene glycol, diethylene glycol, propylene glycol, hexylene glycol, polyethylene glycol, polypropylene glycol and glycerin; polyhydric alcohol derivatives such as propylene based glycol ether; ketones such as acetone, methylethylketone, methylisobutylketone, diisobutylketone, cyclohexanone and isophorone; ethers such as ethylether, dioxane, cellosolve, dipropylether and tetrahydrofuran; aliphatic hydrocarbons such as n-paraffin, naphthene, isoparaffin, kerosene and mineral oil; aromatic hydrocarbons such as benzene, toluene, xylene, solvent naphtha and alkylnaphthalene; halogenated hydrocarbons such as dichloroethane, chloroform and carbon tetrachloride; esters such as ethyl acetate, diisopropyl phthalate, dibutyl phthalate, dioctyl phthalate and dimethyl adipate; lactones such as γ-butyrolactone; amides such as dimethylformamide, diethylformamide, dimethylacetamide and N-alkyl pyrrolidinone; nitriles such as acetonitrile; sulfur compounds such as dimethylsulfoxide; vegetable oils such as soybean oil, canola oil, cottonseed oil and castor oil; water; and the like. These may be use alone or in combination of two or more kinds.

The surfactant is not particularly limited, but preferred are those either turning into a gel in water or exhibiting swelling property. Examples thereof may include non-ionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkylether, polyoxyethylene alkylphenylether, polyoxyethylene dialkylphenylether, polyoxyethylene alkylphenylether formaldehyde condensate, polyoxyethylene polyoxypropylene block polymer, alkylpolyoxyethylene polypropylene block polymer ether, polyoxyethylene alkylamine, polyoxyethylene fatty acid amide, polyoxyethylene fatty acid bisphenylether, polyalkylene benzylphenyl ether, polyoxyalkylene styrylphenyl ether, acetylene diol, polyoxyalkylene-added acetylene diol, polyoxyethylene ether silicone, ester silicone, fluorochemical surfactant, polyoxyethylene castor oil and polyoxyethylene hydrogenated castor oil; anionic surfactants such as alkyl sulfate, polyoxyethylene alkylether sulfate, polyoxyethylene alkylphenylether sulfate, polyoxyethylene styrylphenyl ether sulfate, alkyl benzene sulfonate, lignin sulfonate, alkyl sulfosuccinate, naphthalene sulfonate, alkyl naphthalene sulfonate, naphthalenesulfonic acid formaldehyde condensate salt, alkylnaphthalenesulfonic acid formaldehyde condensate salt, fatty acid salt, polycarboxylate, N-methyl-fatty acid sarcosinate, resinate, polyoxyethylene alkylether phosphate, and polyoxyethylene alkylphenylether phosphate; cationic surfactants such as laurylamine hydrochloride, stearylamine hydrochloride, oleylamine hydrochloride, stearylamine acetate, stearylaminopropylamine acetate, alkyltrimethylammonium chloride, and alkyldimethylbenzalkonium chloride; amino acid or betaine type amphoteric surfactants; and the like.

These surfactants may be used alone or in combination of two or more kinds.

Examples of the binder or tackifier may include carboxymethyl cellulose and a salt thereof, dextrin, water-soluble starch, xanthan gum, guar gum, sucrose, polyvinylpyrrolidone, gum arabic, polyvinyl alcohol, polyvinyl acetate, sodium polyacrylate, polyethylene glycol having an average molecular weight of 6,000 to 20,000, polyethylene oxide having an average molecular weight of 100,000 to 5,000,000, natural phospholipids (for instance, cephalic acid, lecithin) and the like.

Examples of the thickener may include water-soluble polymers such as xanthan gum, guar gum, carboxymethyl cellulose, polyvinylpyrrolidone, carboxy vinyl polymer, acrylic polymer, starch derivative and polysaccharide; fine inorganic powders such as high purity bentonite and white carbon; and the like.

Examples of the coloring agent may include inorganic pigments such as iron oxide, titanium oxide and Prussian blue; organic dyes such as alizarin dye, azo dye and metal phthalocyanine dye; and the like.

Examples of the spreader agent may include silicone surfactant, cellulose powder, dextrin, processed starch, polyaminocarboxylic acid chelate compound, crosslinked polyvinylpyrrolidone, maleic acid-styrenes-methacrylic acid copolymer, half ester of polyhydric alcohol polymer with dicarboxylic anhydride, water-soluble salt of polystyrene sulfonate and the like.

Examples of the sticker may include various surfactants such as dialkyl sodium sulfosuccinate, polyoxyethylene alkylether, polyoxyethylene alkylphenylether and polyoxyethylene fatty acid ester, paraffin, terpene, polyamide resin, polyacrylate, polyoxyethylene, wax, polyvinylalkylether, alkylphenol-formaldehyde condensate, synthetic resin emulsion and the like.

Examples of the antifreezing agent may include polyhydric alcohols such as ethylene glycol, diethylene glycol, propylene glycol and glycerin, and the like.

Examples of the anticaking agent may include polysaccharides such as starch, algin acid, mannose and galactose; polyvinylpyrrolidone, white carbon, ester gum, petroleum resin and the like.

Examples of the collapsing agent may include sodium tripolyphosphate, sodium hexametaphosphate, metal stearate, cellulose powder, dextrin, copolymer of methacrylic acid ester, polyvinylpyrrolidone, polyaminocarboxylic chelate compound, sulfonated styrene-isobutylene-maleic anhydride copolymer, starch-polyacrylonitrile graft copolymer and the like.

Examples of the decomposition inhibitor may include desiccants such as zeolite, quicklime and magnesium oxide; antioxidants that are based on phenol, amine, sulfur and phosphoric acid; ultraviolet absorbers that are based on salicylic acid, benzophenone or the like; and the like.

Examples of the antiseptic agent may include potassium sorbate, 1,2-benzthiazolin-3-one and the like.

Examples of the piece of plant may include sawdust, coconut husk, corncob, tobacco stem and the like.

According to the herbicide of the invention, in the case where the additive components described above are included, the content ratio of the carrier (weight base) is generally selected from 5 to 95%, preferably from 20 to 90%, the content ratio of the surfactant is generally selected from 0.1 to 30%, preferably from 0.5 to 10%, and the content ratio of other additives are selected from 0.1 to 30%, preferably from 0.5 to 10%.

The herbicide of the invention can be used in any forms such as liquid formulation, emulsifiable concentrate, wettable powder, dust, oil solution, water dispersible granule, flowable, emulsifiable suspension concentrate, granule, Jumbo formulation, suspoemulsion, and Mametsubu (registered trademark) formulation.

Upon forming into a formulation, a safener, a fertilizer, or at least one kind of pesticides including other herbicide, insecticide, fungicide, plant growth regulator and the like, can be mixed to form into a mixed composition. Alternatively, these may be used in combination upon application.

On the occasion of use, the herbicide can be sprayed after being diluted in an adequate concentration or be used directly.

Known herbicide compounds and plant growth regulators which may be mixed or used in combination are exemplified by:

2,3,6-TBA, 2,4-D, 2,4-DB, DNOC, EPTC, HC-252, MCPA, MCPA-thioethyl, MCPB, S-metolachlor, TCA, ioxynil, aclonifen, azafenidin, acifluorfen, azimsulfuron, asulam, acetochlor, atrazine, anilofos, amicarbazone, amidosulfuron, amitrole, aminopyralid, amiprophos-methyl, ametryn, alachlor, alloxydim, ancymidol, iodosulfulon-methyl-sodium, isouron, isoxachlortole, isoxaflutole, isoxaben, isoproturon, imazaquin, imazapyr, imazamethabenz-methyl, imazapic, imazamox, imazethapyr, imazosulfuron, indanofan, esprocarb, ethametsulfuron-methyl, ethalfluralin, ethidimuron, ethoxysulfuron, ethofumesate, etobenzanid, oxadiazon, oxadiargyl, oxaziclomefone, oxasulfuron, oxyfluorfen, oryzalin, orbencarb, cafenstrole, carfentrazone-ethyl, karbutilate, carbetamide, quizalofop-P, quizalofop-P-ethyl, quizalofop-P-tefuryl, quizalofop-ethyl, quinclorac, quinmerac, cumyluron, glyphosate, glyphosate-trimesium (sulfosate), glufosinate-ammonium, glufosinate-sodium, clethodim, clodinafop-propargyl, clopyralid, clomazone, chlomethoxyfen, clomeprop, cloransulam-methyl, chloramben, chloridazon, chlorimuron-ethyl, chlorsulfuron, chlorthal-dimethyl, chlorthiamid, chlorpropham, chlormequat chloride, chloroxuron, chlorotoluron, chlorobromuron, cyanazine, diuron, dicamba, cycloate, cycloxydim, diclosulam, cyclosulfamuron, dichlobenil, diclofop-methyl, dichlorprop, dichlorprop-P, diquat dibromide, dithiopyr, siduron, dinitramine, cinidon-ethyl, cinosulfuron, dinoseb, dinoterb, cyhalofop-butyl, diphenamid, difenzoquat, diflufenican, diflufenzopyr, diflumetorim, simazine, dimethachlor, dimethametryn, dimethenamid, simetryn, dimepiperate, dimefuron, cinmethylin, sulcotrione, sulfentrazone, sulfosulfuron, sulfometuronmethyl, sethoxydim, terbacil, daimuron, dalapon, thiazopyr, tiocarbazil, thiobencarb, thidiazimin, thidiazuron, thifensulfuron-methyl, desmedipham, desmetryne, thenylchlor, tebutam, tebuthiuron, tepraloxydim, tefuryltrion, terbuthylazine, terbutryn, terbumeton, tembotrione, topramezone, tralkoxydim, triaziflam, triasulfuron, triallate, trietazine, triclopyr, triflusulfuron-methyl, tritosulfuron, trifluralin, trifloxysulfuron-sodium, tribenuron-methyl, naptalam, naproanilide, napropamide, nicosulfuron, neburon, norflurazon, vernolate, paraquat dichloride, haloxyfop, haloxyfop-P, haloxyfop-P-methyl, halosulfuron-methyl, pinoxaden, picloram, picolinafen, bispyribac-sodium, bifenox, piperophos, pyraclonil, pyrasulfotole, pyrazoxyfen, pyrazosulfuron-ethyl, pyrazolynate, bilanafos, pyraflufen-ethyl, pyridafol, pyrithiobac-sodium, pyridate, pyriftalid, pyributicarb, pyribenzoxim, pyrimisulfan, primisulfuron-methyl, pyriminobac-methyl, pyroxysulam, fenuron, fenoxaprop-P-ethyl, fenoxaprop-ethyl, fenclorim, fentrazamide, phenmedipham, foramsulfuron, butachlor, butafenacil, butamifos, butylate, butralin, butroxydim, flazasulfuron, flamprop-M, fluazifop-butyl, fluazifop-P-butyl, fluazolate, fluometuron, fluoroglycofen-ethyl, flucarbazone-sodium, flucetosulfuron, fluthiacet-methyl, flupyrsulfuron-methyl-sodium, flufenacet, flufenpyr-ethyl, flupropanate, flupoxame, flumioxazin, flumiclorac-pentyl, flumetsulam, fluridone, flurtamone, flurprimidol, fluoroxypyr, fluorochloridone, pretilachlor, prodiamine, prosulfuron, prosulfocarb, propaquizafop, propachlor, propazine, propanil, propyzamide, propisochlor, propham, profluazol, propoxycarbazone, propoxycarbazone-sodium, profoxydim, bromacil, prometryn, prometon, bromoxynil, bromofenoxim, bromobutide, florasulam, hexazinone, pethoxamid, benazolin, penoxsulam, beflubutamid, pebulate, bencarbazone, pendimethalin, benzfendizone, bensulide, bensulfuron-methyl, benzobicyclon, benzofenap, bentazone, pentanochlor, pentoxazone, benfluralin, benfuresate, fosamine, fomesafen, forchlorfenuron, maleic hydrazide, mecoprop, mecoprop-P, mesosulfuron-methyl, mesotrione, metazachlor, methabenzthiazuron, metamitron, metamifop, methyl-dimuron, metoxuron, metosulam, metsulfuron-methyl, metobromuron, metobenzuron, metolachlor, metribuzin, mepiquat chloride, mefenacet, monolinuron, molinate, lactofen, linuron, rimsulfuron, lenacil, prohexadione-calcium, trinexapac-ethyl, KIH-485, or an isoxazoline derivative represented by Formula [40]:

[Chemical Formula 31]

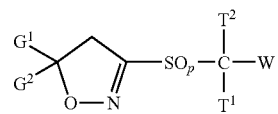

[40]

[wherein p is an integer of 0 to 2; $T^1$ and $T^2$ are each independently a hydrogen atom, a halogen atom, a cyano group, a lower alkoxycarbonyl group or a $C_{1-6}$ alkyl group; $G^1$ and $G^2$ are each independently a hydrogen atom, a $C_{1-6}$ alkyl group or a $C_{1-6}$ haloalkyl group; W is a phenyl group (which is substituted with 1 to 5 of the same or different Vs); V is a hydrogen atom, a $C_{1-6}$ alkyl group {which may be substituted with 1 to 3 of the same or different halogen atoms, a $C_{1-6}$ alkoxy group, a hydroxyl group, a $C_{1-6}$ alkylthio, a $C_{1-6}$ alkylsulfinyl group, a $C_{1-6}$ alkylsulfonyl group, a $C_{1-6}$ alkylamino group, a $C_{1-6}$ dialkylamino group, a cyano group or a (optionally substituted)phenoxy group}, a $C_{1-6}$ alkoxy group (which may be substituted with 1 to 3 of the same or different halogen atoms, a $C_{1-6}$ alkoxy group, a $C_{2-6}$ alkenyl group, a $C_{2-6}$ alkynyl group, a $C_{1-6}$ alkoxycarbonyl group, a $C_{1-6}$ alkylcarbonyl group or a $C_{3-8}$ cycloalkyl group), a $C_{3-8}$ cycloalkyloxy group or a halogen atom].

Known fungicidal compounds which may be mixed and used in combination are exemplified by:

benomyl, carbendazim, fuberidazole, thiabendazole, thiophanate, thiophanate-methyl, chlozolinate, iprodione, procymidone, vinclozolin, azaconazole, bitertanol, bromuconazole, cyproconazole, difenoconazole, diniconazole, epoxiconazole, fenarimol, fenbuconazole, fluquinconazole, flusilazole, flutriafol, hexaconazole, imazalil, imibenconazole, ipconazole, metconazole, myclobutanil, nuarimol, oxpoconazole fumarate, paclobutrazol, pefurazoate, penconazole, prochloraz, propiconazole, prothioconazole, pyrifenox, simeconazole, tebuconazole, tetraconazole, triadimefon, triadimenol, triflumizole, triforine, triticonazole, benalaxyl, furalaxyl, mefenoxam, metalaxyl, metalaxyl-M, ofurace, oxadixyl, aldimorph, dodemorph, fenpropidin, fenpropimorph, piperalin, spiroxamine, tridemorph, edifenphos, iprobenfos, isoprothiolane, pyrazophos, benodanil, boscalid, carboxin, fenfuram, flutolanil, furametpyr, mepronil, oxycarboxin, penthiopyrad, thifluzamide, bupirimate, dimethirimolthirimol, cyprodinil, mepanipyrim, pyrimethanil, diethofencarb, azoxystrobin, dimoxystrobin, enestrobin, famoxadone, fenamidone, fluoxastrobin, kresoxim-methyl, metominostrobin, orysastrobin, picoxystrobin, pyraclostrobin, trifloxystrobin, fenpiclonil, fludioxonil, quinoxyfen, biphenyl, chloroneb, dicloran, etridiazole, quintozene, tecnazene, tolclofos-methyl, fthalide, pyroquilon, tricyclazole, carpropamid, diclocymet, fenoxanil, fenhexamid, pyributicarb, polyoxin, pencycuron, cyazofamid, zoxamide, blasticidin-S, kasugamycin, streptomycin, validamycin, cymoxanil, iodocarb, propamocarb, prothiocarb, binapacryl, dinocap, ferimzone, fluazinam, TPTA(fentin acetate), TPTC(fentin chloride), TPTH(fentin hydroxide), oxolinic acid, hymexazol, octhilinone, fosetyl, phosphonic acid and its salt, tecloftalam, triazoxide, flusulfamide, diclomezine, silthiofam, diflumetorim, benthiavalicarb-isopropyl, dimethomorph, flumorph, iprovalicarb, mandipropamid, oxytetracycline, methasulfocarb, chinomethionat, fluoroimide, milneb, copper hydroxide, copper octanoate, copper oxychloride, copper sulfate, cuprous oxide, mancopper, oxine-copper, sulfur, ferbam, mancozeb, maneb, metiram, propineb, thiram, zineb, ziram, captafol, captan, folpet, chlorothalonil, dichlofluanid, tolylfluanid, anilazine, dodine, guazatine, iminoctadine, dithianon, acibenzolar-S-methyl, probenazole, tiadinil, ethaboxam, cyflufenamid, proquinazid, metrafenone, fluopicolide, dazomet, difenzoquat, amisubrom, Bordeaux mixture, F-991, nabam, phenazine oxide, polycarbamate or pyribencarb.

Known insecticidal and nematocidal compounds which may be mixed or used in combination are exemplified by:

demeton-S-methyl, bioallethrin, bioallethrin S-cyclopentenylisomer, famphur, DDT, DNOC, EPN, XMC, acrinathrin, azadirachtin, azamethiphos, azinphos-ethyl, azinphos-methyl, acequinocyl, acetamiprid, acetoprol, acephate, azocyclotin, abamectin, amitraz, alanycarb, aldicarb, alphacypermethrin, allethrin[(1R)-isomers], d-cis-trans Allethrin, d-trans Allethrin, isocarbophos, isoxathion, isofenphos, isoprocarb, imicyafos, imidacloprid, imiprothrin, indoxacarb, esfenvalerate, ethiofencarb, ethiprole, ethion, ethiprole, etoxazole, etofenprox, ethoprophos, emamectin, endosulfan, Empenthrin, empenthrin[(EZ)-(1R)-isomers], oxamyl, oxydemeton-methyl, omethoate, cadusafos, cartap, carbaryl, carbosulfan, carbofuran, gamma-cyhalothrin, gamma-BCH (Lindane), xylylcarb, quinalphos, kinoprene, quinomethionate, chinomethionat, coumaphos, clothianidin, clofentezine, chromafenozide, chlorethoxyfos, chlordane, chlorpyrifos, chlorpyrifos-methyl, chlorfenapyr, chlorfenvinphos, chlorfluazuron, chlormephos, cyenopyrafen, cyanophos, diafenthiuron, diethofencarb, dienochlor, dicrotophos, dichlofenthion, cycloprothrin, dichlorvos, dicofol, disulfoton, dinotefuran, cyhalothrin, cyphenothrin[(1R)-trans-isomers], cyfluthrin, diflubenzuron, cyflumetofen, cyhexatin, cypermethrin, dimethylvinphos, dimethoate, tartaremetic, silafluofen, cyromazine, spinosad, spirodiclofen, spirotetramat, spiromesifen, sulfotep, zeta-cypermethrin, diazinon, taufluvalinate, thiacloprid, thiamethoxam, thiodicarb, thiocyclam, thiosultap-sodium, thiofanox, thiometon, tetrachlorvinphos, tetradifon, tetramethrin, tetramethrin[(1R)-isomers], depallethrin, tebupirimfos, tebufenozide, tebufenpyrad, tefluthrin, teflubenzuron, temephos, deltamethrin, terbufos, tralomethrin, transfluthrin, triazamate, triazophos, trichlorfon, tribufos, triflumuron, trimethacarb, tolfenpyrad, naled, nicotine, nitenpyram, nemadectin, novaluron, noviflumuron, hydroprene, vamidothion, parathion, parathion-methyl, halfenprox, halofenozide, bioresmethrin, bistrifluoron, pyridaphenthion, hydramethylnon, bifenazate, bifenthrin, piperonyl butoxide, pymetrozine, pyraclofos, pyridafenthion, pyridaben, pyridalyl, pyriproxyfen, pirimicarb, pyrimidifen, pirimiphos-methyl, Pyrethrins(pyrethrum), fipronil, fenazaquin, fenamiphos, fenisobromolate, fenitrothion, fenoxycarb, phenothrin[(1R)-transisomer], fenobucarb, fenthion, phenthoate, fentrifanil, fenvalerate, fenpyroximate, fenbutatin oxide, fenpropathrin, butocarboxim, butoxycarboxim, buprofrzin, furathiocarb, prallethrin, fluacrypyrim, flucycloxuron, flucythrinate, flusulfamide, fluvalinate, flupyrazofos, flufenerim, flufenoxuron, Flubendiamide, flumethrin, flurimfen, prothiofos, flonicamid, propaphos, propargite, profenofos, propetamphos, propoxur, bromopropylate, beta-cyfluthrin, beta-cypermethrin, hexythiazox, hexaflumuron, heptenophos, permethrin, bensultap, benzoximate, bendiocarb, benfuracarb, borax, phoxim, phosalone, fosthiazate, phosphamidon, phosmet, formetanate, phorate, malathion, milbemectin, mecarbam, mesulfenfos, methomyl, metaflumizon, methamidophos, metham-ammonium, metham-sodium, methiocarb, methidathion, methoxychlor, methoxyfenozide, methothrin, methoprene, metolcarb, mevinphos, monocrotophos, lambda-cyhalothrin, rynaxypyr, aluminium phosphide, phosphine, lufenuron, resmethrin, lepmectin, rotenone, *Bacillus sphaericus, Bacillus thuringiensis* subsp. *Aizawai, Bacillus thuringiensis* subsp. *Israelensi, Bacillus thuringiensis* subsp. *Kurstaki, Bacillus thuringiensis* subsp. *tenebrionis*, CL900167, NNI-0101, RU15525, XDE-175 or ZXI8901.

Known fungicidal compounds which may be mixed or used in combination are exemplified by:

benoxacor, furilazole, dichlormid, dicyclonone, DKA-24 ($N^1,N^2$-diallyl-$N^2$-dichloroacetylglycineamide), AD-67 (4-dichloroacetyl-1-oxa-4-azaspiro-[4.5]decane), PPG-1292 (2,2-dichloro-N-(1,3-dioxane-2-ylmethyl)-N-(2-propenyl) acetamide), R-29148(3-dichloroacetyl-2,2,5-trimethyl-1,3-oxazolidine), cloquintcet-mexyl, 1,8-naphthalic Anhydride, mefenpyr-diethyl, mefenpyr, fenchlorazole-ethyl, fenclorim, MG-191(2-dichloromethyl-2-methyl-1,3-dioxane), cyometrinil, flurazole, fluxofenim, isoxandifen-ethyl, mecoprop, MCPA, daimuron, 2,4-D, isoxadifen, MON4660, oxabetrinil or cyprosulfamide.

The blending ratio of active ingredient according to the invention is arbitrarily selected as needed. In the case of dust, granule or the like, the ratio should be arbitrarily selected from 0.01 to 10% (by weight), preferably from 0.05 to 5% (by weight). In the case of emulsifiable concentrate, wettable powder or the like, the ratio should be arbitrarily selected from 1 to 50% (by weight), preferably from 5 to 30% (by weight). In addition, in the case of a flowable or the like, the ratio should be arbitrarily selected from 1 to 40% (by weight), preferably from 5 to 30% (by weight).

The application amount of herbicide according to the invention varies depending on a kind of a compound to be used, target weed, growth pattern, environmental conditions, formulation for use or the like. In the case of a direct use of dust, granule or the like, the amount should be arbitrarily selected from 1 g to 50 kg, preferably from 10 g to 10 kg per hectare as an active ingredient. Further, in the case of using in a liquid form, for example, in the case of emulsifiable concentrate, wettable powder, flowable or the like, the amount should be arbitrarily selected from 0.1 to 50,000 ppm, preferably from 10 to 10,000 ppm.

The herbicide of the invention can be used for foliage application, soil application, submerged application or the like in upland fields, paddy fields, orchards or the like. Moreover, the herbicide of the invention can be used for extermination of general weeds in fallow fields, ridges between rice fields, farm roads, waterways, grass farms, graveyards, parks, roads, playgrounds, vacant lots around buildings, lands under cultivation, neighborhood of railways, forests or the like.

The herbicide of the invention has a beneficial herbicidal effect on various weeds, for example, smartweeds such as *Polygonum lapathifolium* L., *Polygonum longisetum* De Bruyn, and *Rumex japonicus* Houtt.; amaranthus such as *Amaranthus viridis* L., *Amaranthus palmeri* S. Wats., and *Amaranthus retroflexus* L.; forb such as *Solanum carolinense* L., *Solanum nigrum* L., *Chenopodium album* L., *Abutilon theophrasti* medicus, *Sida spinosa* L., *Sesbania exaltata* Cory, *Ambrosia elatior* L., *Papaver rhoeas*, *Ipomoea* spp., *Xanthium strumarium* L., *Stellaria media* Villars, *Matricaria chamomilla* L, *Galium spurium* L. var. *echinospermon* Hayek, *Viola lanceolata* L., *Veronica persica* Poir., *Veronica hederaeforia* L., *Lalium amplexicaule* L., *Vicia angustifolia* L., *Senecio vulgaris* L., and *Capsella Bursa-pastoris* (L.) medik; perennial or anuual cyperaceous weeds such as *Cyperus rotundus* L., *Cyperus esculentus* L., *Cyperus brevifolius* Hassk. var. *leiolepis* T. Koyama, *Cyperus microiria* Steud., and *Cyperus iria*, poaceous weeds such as *Echinochloa esculenta* (A. Braun) H. Scholz, *Digitaria ciliaris* (Retz.) Koel., *Setaria viridis* (L.) P. Beauv., *Poa annua* L., *Alopecurus aequalis* Sobol. var. *amurensis* Ohwi, *Sorghum halepense* Pers., *Alopecurus myosuroides* Huds., *Lolium multiflorum* Lamarck., and *Avena fatua* L., which are caused a problem in a upland field, for a long term of from preemergent to growing season. In addition, annual weeds such as *Echinochloa oryzicola* Vasing, *Echinochloa crus-galli* (L.) P. Beauv. var. *crusgalli*, *Cyperus difformis* L., *Leptochloa chinensis* (L.) Nees, *Monochoria vaginalis* Presl var. *plantaginea* (Roxb.) Solms-Lau., *Lindernia dubia* (L.) Pennel, *Lindernia procumbens* (Krock.) Philcox., *Rotala indica* (Willd.) Koehne var. *uliginosa* (Miq.) Koehne, *Vandellia angustifolia* Benth., *Limnophyla sessiliflora* Blume, *Ammannia multiflora* Roxb., *Elatine triandra* Schk. var. *pedicellata* Krylov., *Ludwigia prostrata* Roxb., *Eclipta prostrata* L., *Bidens* Frondosa L., *Aeschynomene indica* L., and *Murdannia keisak* HandMazz., and perennial weeds such as *Sagittaria pygmaea* Miq., *Sagittaria trifolia* L., *Cyperus serotinus* Rottb., *Eleocharis kuroguwai* Ohwi, *Scirpus juncoides* Roxb., *Alisma canaliculatum* A. Br. et Bouche, *Scirpus nipponicus* Makino, *Scirpus planiculmis* FR. Schmidt, *Potamogeton distinctus* A. Bennet, *Leersia japonica* Makino, *Paspalum distichum* L., *Leersia oryzoides* (L.) Swartz, and *Eleocharis acicularis* Roem. et Schult. var. *longiseta* Svenson can be controlled.

Furthermore, the herbicide of the invention is safe for useful plants and useful crops, for example, cereals such as rice, wheat, barley, oat, rye, foxtail millet, proso millet, corn, and grain sorghum, vegetables such as soybean, cotton, sugar beet, sugarcane, onion, sunflower, rapeseed, peanut, linseed, tobacco plant, coffee, sweet potato, potato, tomato, and other vegetables, and turf.

The useful crops and the useful plants described herein include so-called genetically engineered crops such as corns, soybeans, cotton, rapeseeds, and sugar canes, which are transformed by genetic technology and show resistance to herbicides, pest insects, diseases, or the like; and plants which show resistant to herbicides, pest insects, diseases, or the like by breeding or selection.

Hereinafter, production methods of the compound of Formula [1] according to the compound of the invention, formulation examples, and applications will be described in detail with reference to Examples below. However, the present invention is not limited to these Examples in any way. In the description below, '%' means 'percent by weight' and 'parts' means 'parts by weight'.

EXAMPLES

Example 1

Production of 2-[1,2-dihydro-1-methyl-2-oxo-6-(trifluoromethyl)-pyridine-3-carbonyl]-3-hydroxy-2-cyclohexen-1-one (Inventive Compound No. I-1)

(1) Production of 1,2-dihydro-1-methyl-2-oxo-6-(trifluoromethyl)pyridine-3-carboxylic acid (3-oxo-1-cyclohexan-1-yl) ester 1,2-dihydro-1-methyl-2-oxo-6-(trifluoromethyl)pyridine-3-carboxylic acid (11.2 g, 50.6 mmol) was dissolved in thionyl chloride (70 mL), and the mixture was refluxed for 2 hours. The reaction solution was concentrated under reduced pressure to obtain 1,2-dihydro-1-methyl-2-oxo-6-(trifluoromethyl)pyridine-3-carbonyl chloride. The obtained acid chloride was dissolved in acetonitrile (80 mL), and added dropwise to a mixed solution of 1,3-cyclohexanedione (4.98 g, 44.4 mmol), triethylamine (5.4 g, 53.3 mmol) and acetonitrile (20 mL), under ice cooling. After the stirring for a day at room temperature, the reaction mixture was poured into water and extracted with ethyl acetate. The organic layer was washed with saturated brine, and then dried over anhydrous magnesium sulfate. After separating the inorganic substance by filtration, the solvent was distilled off under reduced pressure, and thus obtained crystal was washed with diisopropylether, to obtain 14.5 g of a subject compound (yield: 90.5%).
$^1$H-NMR Data (CDCl$_3$/TMS δ (ppm)): 2.07-2.15 (2H, m), 2.43-2.48 (2H, m), 2.66-2.70 (2H, m), 3.69 (3H, s), 6.01 (1H, s), 6.75 (1H, d, J=7.5 Hz), 8.18 (1H, d, J=7.5 Hz)

(2) Production of 2-[1,2-dihydro-1-methyl-2-oxo-6-(trifluoromethyl)pyridine-3-carbonyl]-3-hydroxy-2-cyclohexen-1-one Acetonecyanhydrin (0.36 g, 4.5 mmol), triethylamine (5.20 g, 51.4 mmol) and acetonitrile (20 mL) were added to 1,2-dihydro-1-methyl-2-oxo-6-(trifluoromethyl)pyridine-3-carboxylic acid (3-oxo-1-cyclohexan-1-yl) ester (13.5 g, 45.1 mmol) obtained in above-mentioned (1), and the mixture was stirred for a day at room temperature. To a residue obtained by concentrating the mixed solution under reduced pressure, a mixture of aqueous saturated sodium bicarbonate and ethyl acetate was added for extraction and separation. Thus obtained aqueous layer was added with diluted hydrochloric acid to give a pH of 3 to 4, and extracted with chloroform. The obtained organic layer was dried over anhydrous magnesium sulfate, the inorganic substance was separated by filtration, and then the solvent was distilled off under reduced pressure. Thus obtained crystal was washed with a hexane-ether mixed solution (hexane/ether=3/1) to obtain 8.4 g of a subject compound (yield: 62%).

$^1$H-NMR Data (CDCl$_3$/TMS δ (ppm)): 2.02-2.11 (2H, m), 2.46-2.50 (2H, m), 2.71-2.76 (2H, m), 3.61 (3H, s), 6.72 (1H, d, J=7.4 Hz), 7.40 (1H, d, J=7.1 Hz), 16.36 (1H, s)

Example 2

Production of 4-[1,2-dihydro-1-methyl-2-oxo-6-(trifluoromethyl)pyridine-3-carbonyl]-5-hydroxy-1-methyl-1H-pyrazole (Inventive Compound No. IV-1)

(1) Production of 4-[1,2-dihydro-1-methyl-2-oxo-6-(trifluoromethyl)pyridine-3-carbonyl]-5-hydroxy-1-methyl-1H-pyrazole 1,2-dihydro-1-methyl-2-oxo-6-(trifluoromethyl)pyridine-3-carboxylic acid (17.8 g, 80.5 mmol) was dissolved in thionyl chloride (70 mL), and this mixed solution was refluxed for 2 hours. The reaction solution was concentrated under reduced pressure to obtain 1,2-dihydro-1-methyl-2-oxo-6-(trifluoromethyl)pyridine-3-carbonyl chloride. The obtained acid chloride was dissolved in acetonitrile (80 mL), and added dropwise to a mixed solution of 5-hydroxy-1-methyl-1H-pyrazole hydrochloride (10.8 g, 80.3 mmol), triethylamine (20.4 g, 201 mmol) and acetonitrile (20 mL), under ice cooling. After stirring this mixed solution for a day at room temperature, acetonecyanhydrin (0.69 g, 8.05 mmol) and triethylamine (9.8 g, 96.6 mmol) were added thereto, and the mixture was stirred overnight at room temperature. To a residue obtained by concentrating the reaction solution under reduced pressure, a mixture of aqueous saturated sodium bicarbonate and ethyl acetate was added for extraction and separation. Thus obtained aqueous layer was added with diluted hydrochloric acid to give a pH of 3 to 4, and extracted with chloroform. The obtained organic layer was dried over anhydrous magnesium sulfate, and the inorganic substance was separated by filtration. The solvent was distilled off under reduced pressure to obtain 10.4 g of a crude product of a subject compound.

A method of purifying the crude product obtained in (1) is shown in (2) and (3).

(2) To a mixed solution of the 4-[1,2-dihydro-1-methyl-2-oxo-6-(trifluoromethyl)pyridine-3-carbonyl]-5-hydroxy-1-methyl-1H-pyrazole crude product obtained in above (1) (0.70 g), acetyl chloride (0.20 g, 2.6 mmol) and chloroform (20 mL), triethylamine (0.28 g, 2.8 mmol) was added dropwise under ice cooling. After the dropwise addition, the mixture was stirred for 3 hours at room temperature. The reaction solution was poured into water and extracted with chloroform. The organic layer was washed with saturated brine, and then dried over anhydrous magnesium sulfate. After separating the inorganic substance by filtration, the solvent was distilled off under reduced pressure, and thus obtained residue was purified by silica gel column chromatography (elution solvent: ethyl acetate/hexane=1/1.5), to obtain 0.51 g of 5-acetyloxy-4-[1,2-dihydro-1-methyl-2-oxo-6-(trifluoromethyl)pyridine-3-carbonyl]-1-methyl-1H-pyrazole (yield: 64%).

$^1$H-NMR Data (CDCl$_3$/TMS δ (ppm)): 2.41 (3H, s), 3.68 (3H, d), 3.71 (3H, s), 6.74 (1H, d, J=7.3 Hz), 7.62 (1H, d, J=7.3 Hz), 7.73 (1H, s)

(3) 5-acetyloxy-4-[1,2-dihydro-1-methyl-2-oxo-6-(trifluoromethyl)pyridine-3-carbonyl]-1-methyl-1H-pyrazole obtained as above (0.72 g, 2.1 mmol) and lithium hydroxide monohydrate (0.11 g, 2.6 mmol) were dissolved in a mixed solvent of 1,4-dioxane (5 mL) and water (5 mL), and the mixture was stirred for 3 hours at room temperature. To the reaction solution, a mixture of an aqueous sodium bicarbonate solution and ethyl acetate was added for extraction and separation. Thus obtained aqueous layer was added with diluted hydrochloric acid to give a pH of 3 to 4, and extracted with chloroform. The obtained organic layer was dried over anhydrous magnesium sulfate, and the inorganic substance was separated by filtration. The solvent was distilled off under reduced pressure, and thus obtained residue was recrystallized (chloroform/hexane), to obtain 0.37 g of 4-[1,2-dihydro-1-methyl-2-oxo-6-(trifluoromethyl)pyridine-3-carbonyl]-5-hydroxy-1-methyl-1H-pyrazole.

$^1$H-NMR Data (CDCl$_3$/TMS δ (ppm)): 3.68 (3H, s), 3.72 (3H, d), 6.80 (1H, d, J=7.4 Hz), 7.78 (1H, s), 7.87 (1H, d, J=7.4 Hz)

Example 3

Production of 4-[1,2-dihydro-1-methyl-2-oxo-6-(trifluoromethyl)pyridine-3-carbonyl]-1-methyl-5-tosyloxy-1H-pyrazole (Inventive Compound No IV-194)

To a mixed solution of 4-[1,2-dihydro-1-methyl-2-oxo-6-(trifluoromethyl)pyridine-3-carbonyl]-5-hydroxy-1-methyl-1H-pyrazole (0.25 g, 0.80 mmol), pyridine (0.13 g, 1.6 mmol) and chloroform (5 mL), p-toluenesulfonyl chloride (0.23 g, 1.2 mmol) was added little at a time. After the stirring for a day at room temperature, the reaction mixture was poured into water and extracted with chloroform. The organic layer was washed with water, and dried over anhydrous magnesium sulfate. After separating the inorganic substance by filtration, the solvent was distilled off under reduced pressure, and thus obtained residue was purified by silica gel column chromatography (elution solvent: ethyl acetate/hexane=1/1.5), to obtain 0.33 g of a subject compound (yield: 92%).

$^1$H-NMR Data (CDCl$_3$/TMS δ (ppm)): 2.46 (3H, s), 3.62 (3H, s), 6.69 (2H, d, J=7.4 Hz), 7.35 (1H, d, J=8.3 Hz), 7.55 (1H, d, J=7.4 Hz), 7.76 (1H, d, J=8.5 Hz), 7.82 (1H, s)

Example 4

Production of 2-cyano-3-cyclopropyl-1-[1,2-dihydro-1-methyl-2-oxo-6-(trifluoromethyl)pyridin-3-yl]propane-1,3-dione (tautomer of Inventive Compound No. V-9)

1,2-dihydro-1-methyl-2-oxo-6-(trifluoromethyl)pyridine-3-carboxylic acid (1.0 g, 4.5 mmol) was dissolved in thionyl chloride (5 mL), and the mixture was refluxed for 2 hours. The reaction solution was concentrated under reduced pressure to obtain 1,2-dihydro-1-methyl-2-oxo-6-(trifluoromethyl)pyridine-3-carbonyl chloride. The obtained acid chloride was dissolved in acetonitrile (20 mL), and added dropwise to a mixed solution of 3-cyclopropyl-3-oxopropanenitrile (0.49 g, 4.5 mmol), triethylamine (0.55 g, 5.4 mmol) and acetonitrile (10 mL), under ice cooling. After the stirring for a day at room temperature, acetonecyanhydrin (0.04 g, 0.47 mmol) and triethylamine (0.55 g, 5.4 mmol) were further added thereto, and the mixture was stirred for a day at room temperature. The reaction mixture was concentrated under reduced pressure, and thus obtained residue was added with a mixture of aqueous saturated sodium bicarbonate and ethyl acetate for liquid separation. The obtained aqueous layer was added with diluted hydrochloric acid to give a pH of 3 to 4, and extracted with chloroform. The obtained organic layer was dried over anhydrous magnesium sulfate, the solvent was distilled off under reduced pressure, and thus obtained crystal was washed with ether, to obtain 0.29 g of a subject compound (yield: 20%).

$^1$H-NMR Data (CDCl$_3$/TMS δ (ppm)): 1.24-1.31 (2H, m), 1.39-1.44 (2H, m), 2.35-2.43 (1H, m), 3.71 (3H, d), 6.77 (1H, d, J=7.4 Hz), 7.72 (1H, d, J=7.4 Hz), 17.2 (1H, s)

Example 5

Production of 2-[1,2-dihydro-2-oxo-1-phenyl-6-(trifluoromethyl)pyridine-3-carbonyl]-3-hydroxy-2-cyclohexen-1-one (Inventive Compound No. I-72)

Toluene (20 mL), thionyl chloride (1.3 g, 10.7 mmol) and a catalytic amount of N,N'-dimethylformamide were added to 1,2-dihydro-2-oxo-1-phenylmethyl-6-(trifluoromethyl)pyridine-3-carboxylic acid (2.0 g, 7.2 mmol), and the mixture was refluxed for 2 hours. The reaction mixture was concentrated under reduced pressure to obtain 1,2-dihydro-2-oxo-1-phenylmethyl-6-(trifluoromethyl)pyridine-3-carbonyl chloride. The obtained acid chloride was dissolved in acetonitrile (30 mL), and 1,3-cyclohexanedione (0.9 g, 7.9 mmol) and sodium cyanide (0.8 g, 15.8 mmol) were added thereto. This mixture was stirred for a day at room temperature. The reaction mixture was poured into water, and extracted with ethyl acetate. The organic layer was washed with saturated brine, and then dried over anhydrous magnesium sulfate. After separating the inorganic substance by filtration, the solvent was distilled off under reduced pressure and thus obtained concentrated solution was purified by column chromatography, to obtain 1.5 g of a desired product (yield: 68%).

$^1$H-NMR Data (CDCl$_3$/TMS δ (ppm)): 1.99-2.08 (2H, m), 2.42-2.47 (2H, m), 2.68-2.72 (2H, m), 5.33 (1H, s), 6.80 (1H, d, J=7.3 Hz), 7.11-7.32 (6H, m), 7.48 (1H, d, J=7.3 Hz), 16.21 (1H, s)

Example 6

Production of 2-[1,2-dihydro-1-methyl-6-methylthio-2-oxo-pyridine-3-carbonyl]-3-hydroxy-2-cyclohexen-1-one (Inventive Compound No. I-240)

1,2-dihydro-1-methyl-6-methylthio-2-oxopyridine-3-carboxylic acid (3-oxo-1-cyclohexen-1-yl) ester (1.18 g, 4.0 mmol), 0.03 g of acetonecyanhydrin (0.4 mmol) and 0.49 g of triethylamine (4.8 mmol) were dissolved in acetonitrile, and the mixture was stirred for a day at room temperature. To a residue obtained by concentrating the mixed solution under reduced pressure, a mixture of aqueous saturated sodium bicarbonate and ethyl acetate was added for extraction and separation. Thus obtained aqueous layer was added with diluted hydrochloric acid to give a pH of 3 to 4, and extracted with chloroform. The obtained organic layer was dried over anhydrous magnesium sulfate, the inorganic substance was separated by filtration, and then the solvent was distilled off under reduced pressure. Thus obtained crystal was recrystallized from a hexane-ether mixed solution to obtain 0.44 g of a subject compound (yield: 37%).

$^1$H-NMR Data (CDCl$_3$/TMS δ (ppm)): 2.02-2.10 (2H, m), 2.49-2.54 (2H, m), 2.54 (3H, s), 2.63-2.70 (2H, m), 3.57 (3H, s), 6.02 (1H, d, J=7.3 Hz), 7.57 (1H, d, J=7.3 Hz), 16.30 (1H, s)

Example 7

Production of 2-[1,2-dihydro-1-methyl-6-methylsulfinyl-2-oxopyridine-3-carbonyl]-3-hydroxy-2-cyclohexen-1-one and 2-[1,2-dihydro-1-methyl-6-methylsulfonyl-2-oxopyridine-3-carbonyl]-3-hydroxy-2-cyclohexen-1-one (Inventive Compounds Nos. I-241, I-242)

2-[1,2-dihydro-1-methyl-6-methylthio-2-oxopyridine-3-carbonyl]-3-hydroxy-2-cyclohexen-1-one (1.2 g, 4.1 mmol), sodium tungstate (0.13 g, 0.4 mmol) and aqueous 35% hydrogen peroxide (0.48 g, 5.4 mmol) were dissolved in methanol (2 mL), and the mixture was stirred for 5 hours at room temperature. The mixed solution was poured into a sodium hydrogensulfite solution, and extracted with chloroform. The obtained organic layer was dried over anhydrous magnesium sulfate, the inorganic substance was separated by filtration, and then the solvent was distilled off under reduced pressure. Thus obtained residue was purified by column chromatography to obtain 0.36 g of 2-[1,2-dihydro-1-methyl-6-methylsulfinyl-2-oxopyridine-3-carbonyl]-3-hydroxy-2-cyclohexen-1-one (1.2 mmol, yield: 29%) and 0.16 g of 2-[1,2-dihydro-1-methyl-6-methylsulfonyl-2-oxopyridine-3-carbonyl]-3-hydroxy-2-cyclohexen-1-one (0.49 mmol, yield: 12%).

$^1$H-NMR Data of former compound (CDCl$_3$/TMS δ (ppm)): 2.05-2.11 (2H, m), 2.46-2.49 (2H, m), 2.75 (3H, s), 2.71-2.75 (2H, m), 3.48 (3H, s), 6.97 (1H, d, J=7.3 Hz), 7.61 (1H, d, J=7.3 Hz), 16.46 (1H, s)

$^1$H-NMR Data of latter compound (CDCl$_3$/TMS δ (ppm)): 2.05-2.08 (2H, m), 2.46-2.49 (2H, m), 3.24 (3H, s), 2.73-2.76 (2H, m), 3.85 (3H, s), 7.19 (1H, d, J=7.3 Hz), 7.44 (1H, d, J=7.3 Hz), 16.33 (1H, s)

Structural formulae and physical properties of the compound [1] of the present application synthesized according to above-mentioned Examples are shown in Tables 22 to 31 including above-mentioned Examples. Herein, symbols in the tables have the same meanings as defined above. The compound numbers are referred to in the following descriptions.

TABLE 22

| Compound No. | M.P. (° C.) OR R.I. ($n_D^{20}$) | |
|---|---|---|
| I-1 | M.P. | 76-77 |
| I-2 | R.I. | 1.5507 |
| I-3 | M.P. | 71-73 |
| I-4 | R.I. | 1.5251 |
| I-5 | R.I. | 1.5361 |
| I-6 | M.P. | 100-102 |
| I-7 | R.I. | 1.5380 |
| I-9 | R.I. | 1.5263 |
| I-10 | R.I. | 1.5012 |
| I-11 | | UNMEASURABLE |
| I-12 | M.P. | 116-118 |
| I-13 | R.I. | 1.5439 |
| I-14 | M.P. | 130-131 |
| I-16 | M.P. | 90-93 |
| I-18 | R.I. | 1.5512 |

TABLE 22-continued

| Compound No. | M.P. (° C.) OR R.I. ($n_D^{20}$) | |
|---|---|---|
| I-20 | R.I. | 1.5518 |
| I-26 | R.I. | 1.5639 |
| I-27 | R.I. | 1.5265 |
| I-28 | R.I. | 1.5220 |
| I-30 | R.I. | 1.5379 |
| I-31 | R.I. | 1.5322 |
| I-32 | R.I. | 1.5410 |
| I-33 | R.I. | 1.5312 |
| I-34 | R.I. | 1.5292 |
| I-42 | R.I. | 1.5362 |
| I-43 | R.I. | 1.5543 |
| I-44 | R.I. | 1.5461 |
| I-46 | R.I. | 1.5727 |
| I-47 | R.I. | 146-148 |
| I-48 | R.I. | 1.5510 |
| I-49 | R.I. | 169-171 |
| I-50 | R.I. | 1.5558 |
| I-51 | M.P. | 137-140 |
| I-52 | R.I. | 1.5699 |
| I-53 | M.P. | 125-128 |
| I-54 | M.P. | 77-79 |
| I-55 | R.I. | 1.5533 |
| I-56 | M.P. | 83-85 |
| I-57 | R.I. | 1.5645 |
| I-58 | | UNMEASURABLE |
| I-59 | | UNMEASURABLE |
| I-60 | M.P. | 102-104 |
| I-61 | R.I. | 1.5386 |
| I-62 | R.I. | 152-154 |
| I-63 | R.I. | 1.5614 |
| I-64 | | UNMEASURABLE |

M.P.: Melting Point
R.I.: Refractive Index

TABLE 23

| Compound No. | M.P. (° C.) OR R.I. ($n_D^{20}$) | |
|---|---|---|
| I-66 | R.I. | 1.5642 |
| I-67 | M.P. | 64-67 |
| I-69 | R.I. | 1.5653 |
| I-70 | | UNMEASURABLE |
| I-71 | R.I. | 1.5470 |
| I-72 | M.P. | 143-144 |
| I-73 | M.P. | 169-171 |
| I-74 | M.P. | 148-149 |
| I-75 | R.I. | 1.5658 |
| I-76 | M.P. | 157-159 |
| I-77 | R.I. | 1.5659 |
| I-78 | M.P. | 139-141 |
| I-79 | M.P. | 106-108 |
| I-80 | M.P. | 137-139 |
| I-81 | | UNMEASURABLE |
| I-82 | R.I. | 1.5713 |
| I-83 | M.P. | 177-179 |
| I-85 | M.P. | 111-113 |
| I-86 | M.P. | 144-146 |
| I-87 | M.P. | 81-83 |
| I-88 | M.P. | 87-90 |
| I-89 | M.P. | 148-149 |
| I-90 | M.P. | 154-156 |
| I-91 | M.P. | 172-174 |
| I-92 | M.P. | 165-167 |
| I-93 | M.P. | 177-178 |
| I-94 | M.P. | 69-71 |
| I-95 | M.P. | 187-189 |
| I-96 | M.P. | 198-200 |
| I-97 | M.P. | 262-265 |
| I-98 | M.P. | 149-151 |
| I-99 | M.P. | 180-182 |
| I-100 | M.P. | 150-153 |
| I-101 | M.P. | 158-159 |
| I-102 | M.P. | 134-136 |
| I-103 | M.P. | 150-151 |
| I-104 | M.P. | 190-191 |

TABLE 23-continued

| Compound No. | M.P. (° C.) OR R.I. ($n_D^{20}$) | |
|---|---|---|
| I-105 | M.P. | 145-146 |
| I-106 | M.P. | 170-171 |
| I-107 | M.P. | 132-135 |
| I-108 | M.P. | 114-116 |
| I-109 | M.P. | 162-164 |
| I-110 | M.P. | 165-167 |
| I-111 | R.I. | 1.5618 |
| I-112 | R.I. | 1.5729 |

M.P.: Melting Point
R.I.: Refractive Index

TABLE 24

| Compound No. | M.P. (° C.) OR R.I. ($n_D^{20}$) | |
|---|---|---|
| I-113 | M.P. | 184-187 |
| I-114 | M.P. | 109-111 |
| I-115 | M.P. | 64-66 |
| I-116 | M.P. | 53-55 |
| I-117 | M.P. | 86-88 |
| I-118 | M.P. | 66-68 |
| I-119 | M.P. | 48-50 |
| I-120 | M.P. | 60-63 |
| I-121 | | UNMEASURABLE |
| I-122 | | UNMEASURABLE |
| I-123 | M.P. | 83-86 |
| I-124 | M.P. | 70-72 |
| I-126 | M.P. | 108-109 |
| I-127 | M.P. | 113-114 |
| I-128 | R.I. | 1.5530 |
| I-129 | R.I. | 1.5613 |
| I-133 | R.I. | 1.5412 |
| I-137 | R.I. | 1.5313 |
| I-138 | R.I. | 1.5470 |
| I-140 | M.P. | 225-228 |
| I-142 | M.P. | 152-155 |
| I-147 | | UNMEASURABLE |
| I-148 | M.P. | 163-165 |
| I-149 | M.P. | 77-79 |
| I-150 | M.P. | 134-136 |
| I-151 | M.P. | 116-118 |
| I-153 | R.I. | 1.5422 |
| I-154 | R.I. | UNMEASURABLE |
| I-156 | M.P. | 154-156 |
| I-157 | M.P. | 109-111 |
| I-158 | R.I. | 1.5505 |
| I-159 | R.I. | 1.5419 |
| I-160 | R.I. | 1.5302 |
| I-161 | M.P. | 82-83 |
| I-162 | M.P. | 102-103 |
| I-163 | M.P. | 102-103 |
| I-164 | R.I. | 1.5432 |
| I-165 | R.I. | 1.5359 |
| I-166 | R.I. | 1.5227 |
| I-167 | R.I. | 1.5501 |
| I-168 | M.P. | 70-72 |
| I-169 | R.I. | 1.544 |
| I-170 | R.I. | 1.5471 |
| I-171 | R.I. | 1.5361 |
| I-172 | R.I. | 1.5356 |

M.P.: Melting Point
R.I.: Refractive Index

TABLE 25

| Compound No. | M.P. (° C.) OR R.I. ($n_D^{20}$) | |
|---|---|---|
| I-173 | R.I. | 1.5288 |
| I-174 | R.I. | 1.5219 |
| I-175 | R.I. | 1.5399 |
| I-176 | M.P. | 101-102 |
| I-177 | R.I. | 1.5495 |
| I-178 | M.P. | 147-149 |

TABLE 25-continued

| Compound No. | M.P. (° C.) OR R.I. ($n_D^{20}$) | |
|---|---|---|
| I-179 | M.P. | 193-195 |
| I-180 | M.P. | 236-238 |
| I-182 | M.P. | 70-72 |
| I-186 | M.P. | 164-166 |
| I-189 | M.P. | 137-139 |
| I-190 | M.P. | 103-106 |
| I-191 | M.P. | 130-133 |
| I-192 | | UNMEASURABLE |
| I-193 | M.P. | 100-103 |
| I-194 | M.P. | 144-146 |
| I-195 | M.P. | 97-99 |
| I-196 | M.P. | 86-88 |
| I-197 | R.I. | 1.5519 |
| I-202 | M.P. | 120-122 |
| I-215 | R.I. | 1.5462 |
| I-221 | | UNMEASURABLE |
| I-222 | M.P. | 136-139 |
| I-223 | M.P. | 113-116 |
| I-224 | M.P. | 116-119 |
| I-225 | R.I. | 1.5708 |
| I-226 | R.I. | 1.5691 |
| I-227 | R.I. | 1.5306 |
| I-229 | M.P. | 163-165 |
| I-230 | M.P. | 145-147 |
| I-231 | M.P. | 175-177 |
| I-232 | M.P. | 234-235 |
| I-233 | M.P. | 161-163 |
| I-234 | M.P. | 165-167 |
| I-235 | M.P. | 144-146 |
| I-236 | M.P. | 156-158 |
| I-237 | M.P. | 102-104 |
| I-238 | M.P. | 126-129 |
| I-239 | M.P. | 120-122 |
| I-240 | M.P. | 147-150 |
| I-241 | M.P. | 140-142 |
| I-242 | | UNMEASURABLE |
| I-243 | M.P. | 166-168 |
| I-244 | M.P. | 149-151 |

M.P.: Melting Point
R.I.: Refractive Index

TABLE 26

| Compound No. | M.P. (° C.) OR R.I. ($n_D^{20}$) | |
|---|---|---|
| II-1 | R.I. | 1.5491 |
| II-2 | R.I. | 1.5402 |
| II-3 | M.P. | 120-121 |
| II-5 | R.I. | 1.5403 |
| II-7 | R.I. | 1.5436 |
| II-8 | M.P. | 57-60 |
| II-9 | M.P. | 60-63 |
| II-10 | M.P. | 68-70 |
| II-11 | M.P. | 190-192 |
| II-12 | | UNMEASURABLE |
| II-13 | M.P. | 183-186 |
| II-14 | M.P. | 159-162 |
| II-15 | M.P. | 70-72 |
| II-16 | M.P. | 196-197 |
| II-17 | M.P. | 168-171 |
| II-19 | | UNMEASURABLE |
| II-22 | M.P. | 141-143 |
| II-25 | R.I. | 1.5509 |
| II-27 | R.I. | 1.5201 |
| II-29 | R.I. | 1.5355 |
| II-30 | | UNMEASURABLE |
| II-31 | R.I. | 1.5223 |
| II-32 | R.I. | 1.5464 |
| II-33 | M.P. | 115-116 |
| II-34 | M.P. | 118-120 |
| II-35 | | UNMEASURABLE |
| II-40 | R.I. | 1.5337 |
| II-41 | M.P. | 54-56 |
| II-42 | M.P. | 87-88 |

TABLE 26-continued

| Compound No. | M.P. (° C.) OR R.I. ($n_D^{20}$) | |
|---|---|---|
| II-43 | M.P. | 128-131 |
| II-44 | M.P. | 168-170 |

M.P.: Melting Point
R.I.: Refractive Index

TABLE 27

| Compound No. | M.P. (° C.) OR R.I. ($n_D^{20}$) | |
|---|---|---|
| III-1 | M.P. | 97-99 |
| III-2 | R.I. | 1.5511 |
| III-3 | R.I. | 1.5479 |
| III-5 | M.P. | 138-140 |
| III-6 | R.I. | 1.5444 |
| III-8 | R.I. | 1.5395 |
| III-10 | R.I. | 1.5383 |
| III-11 | R.I. | 1.5500 |
| III-14 | | UNMEASURABLE |
| III-15 | R.I. | 1.6017 |
| III-18 | R.I. | 1.5519 |
| III-19 | R.I. | 1.5503 |
| III-20 | R.I. | 1.5433 |
| III-21 | R.I. | 1.5354 |
| III-22 | R.I. | 1.5467 |
| III-23 | R.I. | 1.5359 |
| III-24 | R.I. | 1.5355 |
| III-25 | R.I. | 1.5348 |
| III-26 | R.I. | 1.5562 |
| III-27 | R.I. | 80-83 |
| III-28 | R.I. | UNMEASURABLE |
| III-29 | R.I. | 1.5485 |
| III-30 | R.I. | 88-89 |
| III-31 | R.I. | 1.5683 |
| III-32 | R.I. | 1.5495 |
| III-33 | M.P. | 66-69 |
| III-34 | M.P. | 130-132 |
| III-35 | M.P. | 79-82 |
| III-36 | M.P. | 255-257 |
| III-37 | M.P. | 90-92 |
| III-38 | R.I. | 1.549 |
| III-39 | M.P. | 172-174 |
| III-41 | M.P. | 67-70 |
| III-42 | R.I. | 1.5702 |
| III-43 | | UNMEASURABLE |
| III-44 | R.I. | 1.5381 |

M.P.: Melting Point
R.I.: Refractive Index

TABLE 28

| Compound No. | M.P. (° C.) OR R.I. ($n_D^{20}$) | |
|---|---|---|
| IV-1 | M.P. | 182-185 |
| IV-2 | M.P. | 192-193 |
| IV-3 | M.P. | 151-153 |
| IV-4 | M.P. | 133-136 |
| IV-6 | M.P. | 137-139 |
| IV-8 | M.P. | 105-107 |
| IV-10 | M.P. | 110-112 |
| IV-11 | M.P. | 164-166 |
| IV-12 | R.I. | 1.5301 |
| IV-13 | M.P. | 177-179 |
| IV-15 | R.I. | 1.5373 |
| IV-18 | M.P. | 218-220 |
| IV-19 | M.P. | 149-151 |
| IV-21 | M.P. | 155-157 |
| IV-30 | R.I. | 1.5682 |
| IV-31 | R.I. | 1.5460 |
| IV-32 | M.P. | 122-124 |
| IV-33 | M.P. | 58-60 |
| IV-34 | | UNMEASURABLE |
| IV-35 | M.P. | 93-96 |
| IV-36 | M.P. | 81-83 |
| IV-37 | M.P. | 87-90 |

TABLE 28-continued

| Compound No. | M.P. (° C.) OR R.I. ($n_D^{20}$) | |
|---|---|---|
| IV-38 | M.P. | 108-110 |
| IV-39 | R.I. | 1.517 |
| IV-47 | | UNMEASURABLE |
| IV-48 | R.I. | 1.5250 |
| IV-49 | | UNMEASURABLE |
| IV-52 | R.I. | 1.5475 |
| IV-53 | M.P. | 135-138 |
| IV-54 | M.P. | 148-150 |
| IV-55 | | UNMEASURABLE |
| IV-56 | R.I. | 1.5647 |
| IV-57 | R.I. | 1.5444 |
| IV-58 | R.I. | 1.5558 |
| IV-59 | R.I. | 1.5309 |
| IV-60 | R.I. | 1.5543 |
| IV-61 | M.P. | 93-96 |
| IV-62 | M.P. | 214-217 |
| IV-63 | M.P. | 244-247 |
| IV-64 | M.P. | 135-137 |
| IV-66 | M.P. | 152-155 |
| IV-67 | M.P. | 203-206 |
| IV-68 | M.P. | 148-150 |
| IV-72 | M.P. | 163-165 |
| IV-73 | | UNMEASURABLE |

M.P.: Melting Point
R.I.: Refractive Index

TABLE 29

| Compound No. | M.P. (° C.) OR R.I. ($n_D^{20}$) | |
|---|---|---|
| IV-74 | M.P. | 204-205 |
| IV-75 | M.P. | 135-137 |
| IV-76 | M.P. | 130-132 |
| IV-77 | M.P. | 211-213 |
| IV-78 | M.P. | 190-192 |
| IV-79 | M.P. | 117-120 |
| IV-80 | M.P. | 169-171 |
| IV-81 | M.P. | 217-220 |
| IV-82 | M.P. | 176-178 |
| IV-83 | M.P. | 200-203 |
| IV-84 | M.P. | 169-171 |
| IV-85 | M.P. | 142-144 |
| IV-86 | M.P. | 212-215 |
| IV-87 | M.P. | 170-173 |
| IV-88 | M.P. | 172-174 |
| IV-89 | | UNMEASURABLE |
| IV-90 | M.P. | 186-188 |
| IV-91 | M.P. | 182-183 |
| IV-92 | M.P. | 108-110 |
| IV-93 | M.P. | 143-145 |
| IV-94 | M.P. | 155-157 |
| IV-95 | M.P. | 129-130 |
| IV-96 | M.P. | 168-171 |
| IV-97 | M.P. | 249-252 |
| IV-98 | M.P. | 153-155 |
| IV-99 | M.P. | 150-153 |
| IV-100 | R.I. | 1.5366 |
| IV-101 | M.P. | 152-155 |
| IV-103 | M.P. | 95-97 |
| IV-104 | | UNMEASURABLE |
| IV-106 | M.P. | 111-112 |
| IV-107 | M.P. | 143-144 |
| IV-108 | M.P. | 116-118 |
| IV-118 | R.I. | 1.5151 |
| IV-119 | | UNMEASURABLE |
| IV-129 | M.P. | 59-61 |
| IV-130 | R.I. | 1.5172 |
| IV-131 | R.I. | 1.5578 |
| IV-132 | R.I. | 1.5417 |
| IV-133 | M.P. | 144-146 |
| IV-134 | M.P. | 120-122 |
| IV-135 | R.I. | 1.5522 |

TABLE 29-continued

| Compound No. | M.P. (° C.) OR R.I. ($n_D^{20}$) | |
|---|---|---|
| IV-136 | R.I. | 1.5424 |
| IV-137 | R.I. | 1.5281 |
| IV-138 | | UNMEASURABLE |

M.P.: Melting Point
R.I.: Refractive Index

TABLE 30

| Compound No. | M.P. (° C.) OR R.I. ($n_D^{20}$) | |
|---|---|---|
| IV-139 | R.I. | 1.5622 |
| IV-140 | R.I. | 1.5328 |
| IV-141 | R.I. | 1.5553 |
| IV-142 | | UNMEASURABLE |
| IV-143 | | UNMEASURABLE |
| IV-146 | M.P. | 157-160 |
| IV-148 | M.P. | 103-105 |
| IV-174 | M.P. | 143-144 |
| IV-180 | R.I. | 1.5302 |
| IV-189 | M.P. | 102-104 |
| IV-190 | R.I. | 1.5698 |
| IV-191 | R.I. | 1.5679 |
| IV-192 | M.P. | 133-136 |
| IV-193 | | UNMEASURABLE |
| IV-194 | | UNMEASURABLE |
| IV-195 | R.I. | 1.5287 |
| IV-196 | M.P. | 65-68 |
| IV-197 | M.P. | 134-136 |
| IV-198 | M.P. | 69-72 |
| IV-199 | R.I. | 1.5465 |
| IV-200 | R.I. | 1.5668 |
| IV-202 | R.I. | 1.5191 |
| IV-203 | | UNMEASURABLE |
| IV-204 | R.I. | 1.5191 |
| IV-205 | | UNMEASURABLE |
| IV-206 | | UNMEASURABLE |
| IV-207 | R.I. | 1.5277 |
| IV-208 | M.P. | 49-51 |
| IV-213 | M.P. | 114-115 |
| IV-219 | M.P. | 65-67 |
| IV-220 | M.P. | 100-102 |
| IV-225 | M.P. | 134-136 |
| IV-228 | R.I. | 1.5688 |
| IV-231 | M.P. | 194-195 |
| IV-236 | M.P. | 127-128 |
| IV-237 | M.P. | 166-169 |
| IV-238 | | UNMEASURABLE |
| IV-239 | R.I. | 1.5288 |
| IV-240 | | UNMEASURABLE |
| IV-241 | M.P. | 95-97 |
| IV-242 | M.P. | 163-165 |
| IV-243 | M.P. | 189-191 |

M.P.: Melting Point
R.I.: Refractive Index

TABLE 31

| Compound No | M.P. (° C.) OR R.I. ($n_D^{20}$) | |
|---|---|---|
| V-9 | M.P. | 158-159 |
| V-21 | M.P. | 119-120 |
| V-22 | M.P. | 131-133 |
| V-23 | M.P. | 172-174 |
| V-24 | M.P. | 99-102 |
| V-25 | M.P. | 111-113 |
| V-26 | M.P. | 105-106 |
| IV-247 | M.P. | 186-188 |
| IV-248 | M.P. | 195-198 |
| IV-250 | R.I. | 1.5440 |
| IV-251 | R.I. | 1.5521 |
| IV-252 | R.I. | 1.5542 |
| IV-253 | M.P. | 76-79 |

TABLE 31-continued

| Compound No | M.P. (° C.) OR R.I. ($n_o^{20}$) | |
|---|---|---|
| IV-254 | M.P. | 97-99 |
| IV-255 | M.P. | 178-180 |
| IV-256 | M.P. | 142-144 |
| IV-257 | M.P. | 168-170 |
| IV-258 | M.P. | 172-174 |
| IV-259 | M.P. | 168-169 |
| IV-260 | M.P. | 186-188 |
| IV-105 | M.P. | 84-86 |

M.P.: Melting Point
R.I.: Refractive Index

In regard to compounds Nos. I-11, I-58, I-59, I-64, I-70, I-81, I-121, I-122, I-147, I-154, 1-192, I-221, I-242, II-12, II-19, II-30, II-35, III-14, III-28, III-43, IV-34, IV-47, IV-49, IV-55, IV-73, IV-89, IV-104, IV-119, IV-138, IV-142, IV-143, IV-193, IV-194, IV-203, IV-205, IV-206, IV-238, and IV-240, $^1$H-NMR data (CDCl$_3$/TMS δ (ppm) value) are shown below.

Compound No. I-11: 2.02-2.10 (2H, m), 2.44-2.49 (2H, m), 2.70-2.74 (2H, m), 4.67 (2H, d, J=5.5 Hz), 5.15-5.23 (2H, m), 5.81-5.94 (1H, s), 6.73 (1H, d, J=7.1 Hz), 7.41 (1H, d, J=7.4 Hz), 16.36 (1H, br)

Compound No. I-58: 0.54 (2H, m), 0.73 (2H, m), 1.28 (2H, m), 2.06 (2H, m), 2.44 (2H, m), 2.74 (2H, m), 3.22 (2H, d, J=7.3 Hz), 5.37 (2H, bs), 6.84 (1H, d, J=7.3 Hz), 7.44 (1H, d, J=7.3 Hz), 16.4 (1H, s)

Compound No. I-59: 1.4-1.8 (8H, m), 2.07 (2H, m), 2.46 (2H, m), 2.74 (2H, m), 3.64 (1H, m), 5.22 (2H, bs), 6.73 (1H, d, J=7.3 Hz), 7.35 (1H, d, J=7.0 Hz), 16.4 (1H, s).

Compound No. I-64: 2.07 (2H, m), 2.46 (2H, m), 2.76 (2H, m), 4.25 (2H, m), 5.50 (2H, bs), 6.87 (1H, d, J=7.1 Hz), 7.47 (1H, d, J=7.1 Hz), 16.4 (1H, s)

Compound No. I-70: 2.06 (m, 2H), 2.15 (2H, m), 2.45 (2H, m), 2.59 (3H, s), 2.76 (2H, m), 4.26 (2H, q, J=7.1 Hz), 6.73 (1H, d, J=7.4 Hz), 7.37 (1H, s), 7.51 (1H, d, J=6.9 Hz), 16.2 (1H, s)

Compound No. I-81: 2.06 (m, 2H), 2.44 (2H, m), 2.6-2.8 (5H, m), 6.83 (1H, d, J=6.8 Hz), 7.4-7.8 (5H, m), 16.2 (1H, s)

Compound No. I-121: 2.03 (2H, m), 2.44 (2H, m), 2.70 (2H, m), 3.78 (3H, s), 5.43 (2H, bs), 6.6-6.8 (4H, m), 7.1-7.2 (1H, m), 7.47 (1H, d, J=7.1 Hz), 16.2 (1H, s)

Compound No. I-122: 2.04 (2H, m), 2.45 (2H, m), 2.70 (2H, m), 3.76 (3H, s), 5.26 (2H, bs), 6.6-6.8 (3H, m), 7.09 (2H, d, J=8.5 Hz), 7.45 (1H, d, J=7.1 Hz), 16.2 (1H, s)

Compound No. I-147: 2.01 (2H, m), 2.43 (2H, m), 2.69 (2H, m), 6.81 (1H, d, J=7.4 Hz), 7.02-7.05 (2H, m), 7.42-7.48 (2H, m), 16.2 (1H, s)

Compound No. I-154: 1.6-2.1 (5H, m), 2.4-2.8 (4H, m), 3.5-4.2 (6H, m), 6.79 (1H, d, J=7.3 Hz), 7.41 (1H, d, J=7.1 Hz)

Compound No. I-192: 1.31 (3H, t, J=7.4 Hz), 2.04 (m, 2H), 2.40 (2H, m), 2.76 (2H, m), 2.82 (2H, m), 4.22 (t, 2H d, J=7.7 Hz), 6.75 (1H, m), 7.40 (1H, d, J=7.4 Hz), 16.4 (1H, s)

Compound No. I-221: 2.02-2.11 (2H, m), 2.30-2.50 (2H, m), 2.71-2.75 (2H, m), 3.59 (3H, s), 6.35-6.70 (1H, t, J=53 Hz), 6.46 (1H, d, J=7.1 Hz), 7.42 (1H, d, J=7.1 Hz), 16.41 (1H, br)

Compound No. I-242: 2.07 (2H, m), 2.47 (2H, m), 2.75 (2H, m), 3.23 (3H, s), 3.85 (3H, s), 7.19 (1H, d, J=7.3 Hz), 7.44 (1H, d, J=7.3 Hz), 16.33 (1H, s)

Compound No. II-12: 2.02-2.08 (2H, m), 2.42-2.55 (4H, m), 3.61 (3H, s), 6.77 (1H, d, J=7.4 Hz), 7.26-7.43 (3H, m), 7.54 (1H, s), 7.99 (1H, d, J=7.4 Hz)

Compound No. II-19: 1.07 (3H, s), 1.15 (3H, s), 2.35-2.69 (4H, m), 3.40 (3H, s), 6.30 (1H, d, J=7.3 Hz), 6.69 (1H, d, J=7.1 Hz), 7.13-7.31 (5H, m)

Compound No. II-30: 1.92-2.03 (2H, m), 2.38-2.51 (4H, m), 3.34 (3H, s), 3.48 (2H, t, J=6.0 Hz), 4.12 (2H, t, J=7.7 Hz), 6.77 (1H, d, J=7.4 Hz), 7.36-7.56 (5H, m), 7.94 (1H, d, J=7.4 Hz)

Compound No. II-35: 1.13 (3H, d, J=6.8 Hz), 1.72-1.84 (1H, m), 2.07-2.16 (1H, m), 2.45-2.52 (1H, m), 2.70-2.74 (2H, m), 3.64 (3H, s), 3.80 (3H, s), 6.74 (1H, d, J=7.3 Hz), 8.02 (1H, d, J=7.5 Hz)

Compound No. III-14: 2.05-2.20 (6H, m), 2.92 (1H, br), 3.18 (1H, br), 3.40 (3H, s), 6.28-6.32 (1H, m), 6.58-6.72 (1H, dd), 7.12-7.31 (5H, m)

Compound No. III-28: 1.6-2.2 (6H, m), 2.21 (3H, 3), 2.76 (2H, t, J=7.9 Hz), 2.92 (1H, m), 3.10 (1H, m), 4.22 (2H, t, J=7.9 Hz), 6.71 (1H, d, J=7.4 Hz), 7.36 (1H, d, J=7.1 Hz), 16.4 (1H, s)

Compound No. III-43: 1.2-2.1 (4H, m), 2.5-2.7 (2H, m), 3.35 (1H, m), 3.37 (1H, m), 3.7-3.9 (3H, m), 4.3-4.5 (2H, m), 6.3-6.4 (2H, m), 6.7 (1H, d, J=7.3 Hz), 7.37 (1H, d, J=7.1), 16.6 (1H, s)

Compound No. III-46: 1.6-2.1 (4H, m), 2.5-2.7 (2H, m), 3.4 (1H, m), 3.5 (1H, m), 3.7-3.9 (3H, m), 4.3-4.4 (2H, m), 6.3-6.4 (2H, m), 7.26-7.43 (3H, m), 6.70 (1H, d, J=7.3 Hz), 7.38 (1H, d, J=7.1 Hz), 16.6 (1H, s)

Compound No. IV-34: 1.18 (3H, t, J=6.8), 3.53 (2H, q, J=6.8 Hz), 3.67 (3H, s), 3.73 (2H, t, J=6.6 Hz), 4.36 (2H, t, J=6.9 Hz), 6.80 (1H, d, J=7.4 Hz), 7.77 (1H, s), 7.88 (1H, d, J=7.4 Hz)

Compound No. IV-47: 2.0-2.1 (2H, m), 3.35 (3H, s), 3.54 (2H, t, J=5.8 Hz), 3.67 (3H, s), 4.23 (2H, t, J=8.0 Hz), 6.80 (1H, d, J=7.4 Hz), 7.78 (1H, s), 7.88 (1H, d, J=7.4 Hz)

Compound No. IV-49: 1.19 (3H, t, J=7.4 Hz), 1.25 (3H, d, J=6.0 Hz), 2.08 (2H, m), 3.73 (2H, m), 3.85 (3H, s), 4.0-4.6 (5H, m), 6.75 (1H, d, J=7.4 Hz), 7.11-7.45 (5H, m), 7.45 (1H, s), 7.64 (1H, d, J=7.4 Hz)

Compound No. IV-55: 1.17 (3H, t, J=7.4 Hz), 2.09 (m, 2H), 3.11 (s, 3H), 3.45 (m, 2H), 3.74 (2H, m), 3.88 (3H, s), 4.50 (2H, m), 6.85 (1H, d, J=7.1 Hz), 7.65 (1H, s), 7.71 (1H, d, J=7.4 Hz)

Compound No. IV-73: 1.16 (3H, t, J=7.4 Hz), 2.10 (2H, m), 2.75 (3H, s), 3.71 (3H, m), 3.85 (3H, s), 6.88 (1H, d, J=7.4 Hz), 7.4-7.8 (5H, m), 7.79 (1H, d, J=7.1 Hz)

Compound No. IV-89: 2.43 (3H, s), 3.70 (3H, s), 6.92 (1H, d, J=7.4 Hz), 7.44 (1H, t, J=9.1 Hz), 7.74 (1H, s), 7.81 (1H, d, J=7.1 Hz), 8.29 (1H, m), 8.45 (1H, m)

Compound No. IV-104: 1.15 (3H, t, J=7.4 Hz), 2.09 (m, 2H), 3.71 (m, 2H), 3.77 (3H, s), 3.84 (3H, s), 5.34 (2H, bs), 6.6-6.9 (4H, m), 7.21 (1H, d, J=7.7 Hz), 7.57 (1H, s), 7.73 (1H, d, J=7.4 Hz)

Compound No. IV-119: 3.67 (3H, s), 3.8-4.1 (4H, m), 4.32 (2H, d, J=5 Hz), 5.45 (1H, t, J=5 Hz), 6.80 (1H, d, J=7.4 Hz), 7.78 (1H, s), 7.87 (1H, d, J=7.1 Hz)

Compound No. IV-138: 1.7-2.1 (4H, m), 2.56 (3H, s), 3.64 (3H, s), 3.73-4.45 (5H, m), 5.54 (2H, s), 6.74 (1H, d, J=7.1 Hz), 7.12 (1H, d, J=7.7 Hz), 7.29 (1H, d, J=7.7 Hz), 7.59-7.63 (3H, m)

Compound No. IV-142: 1.58-2.17 (4H, m), 3.73-3.88 (2H, m), 3.92 (3H, s), 4.02-4.23 (2H, m), 4.39 (1H, br), 6.66 (1H, d, J=7.1 Hz), 7.40 (1H, d, J=7.4 Hz), 7.69 (1H, s), 8.22 (2H, d, J=8.5 Hz), 8.36 (2H, d, J=8.5 Hz)

Compound No. IV-143: 1.75-2.1 (3H, m), 3.53-4.30 (6H, m), 3.64 (3H, s), 6.82 (1H, d, J=7.4 Hz), 7.74 (1H, s), 7.88 (1H, d, J=7.4 Hz)

Compound No. IV-193: 3.52 (3H, s), 3.67 (3H, s), 3.83 (3H, s), 5.48 (2H, s), 6.71 (1H, d, J=7.1 Hz), 6.87-6.95 (2H, m), 7.30-7.37 (2H, m), 7.55-7.57 (2H, m)

Compound No. IV-194: 2.46 (3H, s), 3.62 (6H, s), 6.68 (1H, d, J=7.4 Hz), 7.34 (2H, d, J=8.3 Hz), 7.53 (1H, d, J=7.4 Hz), 7.75 (2H, d, J=8.3 Hz), 7.82 (1H, s)

Compound No. IV-203: 1.42 (3H, t, J=8.3 Hz), 3.36 (3H, s), 3.53 (2H, t, J=4.4 Hz), 3.66 (2H, t, J=4.5 Hz), 3.79 (2H, t, J=6.6 Hz), 4.04 (2H, q, J=7.2 Hz), 4.38 (2H, t, J=6.8 Hz), 6.80 (1H, d, J=7.4 Hz), 7.75 (1H, s), 7.87 (1H, d, J=7.4 Hz)

Compound No. IV-205: 1.42 (3H, t, J=7.1 Hz), 1.64-2.16 (4H, m), 3.71-4.46 (7H, m), 6.79 (1H, d, J=7.4 Hz), 7.77 (1H, s), 7.85 (1H, d, J=7.4 Hz)

Compound No. IV-206: 1.47 (3H, t, J=7.1 Hz), 1.61-2.16 (4H, m), 3.7-4.4 (7H, m), 6.74 (1H, d, J=7.4 Hz), 7.46 (2H, s), 7.69 (1H, d, J=7.4 Hz), 7.83 (1H, s)

Compound No. IV-238: 1.62-2.16 (4H, m), 2.10 (3H, s), 3.60 (3H, s), 3.7-3.9 (2H, m), 4.0-4.5 (3H, m), 6.80 (1H, d, J=7.1 Hz), 7.50 (1H, d, J=7.1 Hz)

Compound No. IV-240: 1.58-2.10 (4H, m), 2.41 (3H, s), 2.47 (3H, s), 3.7-4.4 (5H, m), 6.59 (1H, d, J=7.3 Hz), 7.30 (2H, d, J=8.0 Hz), 7.41 (1H, d, J=7.3 Hz), 7.64 (2H, d, J=8.6 Hz)

Reference Example 1

(Production Intermediate) Production of 1,2-dihydro-1-methyl-2-oxo-6-(trifluoromethyl)-pyridine-3-carboxylic acid (Production Intermediate VI-1) (Synthesis Method 1)

(1) Production of 1,2-dihydro-2-oxo-6-(trifluoromethyl)pyridine-3-carboxamide

Sodium methoxide (74 g, 1.37 mol) was dissolved in methanol (1,000 mL), and malon diamide (100 g, 0.979 mol) was added to this solution at room temperature. To this mixture, 4-ethoxy-1,1,1-trifluoro-3-buten-2-one (191 g, 1.14 mol) was added dropwise at a temperature between 25 and 30° C., and the resultant mixture was refluxed under heating for 2 hours. After cooling to 45° C., concentrated hydrochloric acid was added to the mixed solution to give a pH of 3 to 4, and 500 mL of methanol was distilled off at normal pressure. To the residue, water (500 mL) was added, and the mixture was stirred for a day at room temperature. The resultant product was precipitated while cooling with ice. Thus obtained crystal was collected by filtration, washed with water, and then dried under reduced pressure, to obtain 167 g of a subject compound (yield: 83%).

(2) Production of 1,2-dihydro-1-methyl-2-oxo-6-(trifluoromethyl)pyridine-3-carboxamide 1,2-dihydro-2-oxo-6-(trifluoromethyl)pyridine-3-carboxamide (22 g, 0.11 mol) obtained as above was dissolved in a mixed solvent of dimethoxyethane (200 mL) and DMF (50 mL). To this mixture, under nitrogen atmosphere, sodium hydride (purity: 60%, 4.5 g, 0.11 mol) was added little at a time, and then lithium bromide (18.6 g, 0.21 mol) was added thereto. After the stirring at room temperature for 15 minutes, the solution temperature was raised to be between 65 and 70° C., and methyl iodide (30.4 g, 0.21 mol) was added dropwise thereto. After the stirring for 10 hours, the solution was cooled back to room temperature, and precipitated crystals were removed by filtration. The obtained mixture was poured into saturated brine, and extracted with ethyl acetate. The organic layer was dried over anhydrous magnesium sulfate. The solvent was distilled off under reduced pressure, and thus obtained crystal was washed with diisopropylether to obtain 16.4 g of a subject compound (yield: 70%).

$^1$H-NMR Data (CDCl$_3$/TMS δ (ppm)): 3.72 (3H, s), 6.20 (1H, br), 6.88 (1H, d, J=7.4 Hz), 8.55 (1H, d, J=7.6 Hz), 9.32 (1H, br)

(3) Production of 1,2-dihydro-1-methyl-2-oxo-6-(trifluoromethyl)pyridine-3-carboxylic acid To 1,2-dihydro-1-methyl-2-oxo-6-(trifluoromethyl)pyridine-3-carboxyamide (16.4 g, 74.5 mmol) obtained as above, concentrated hydrochloric acid (50 mL) was added, and the mixture was stirred for 4 hours at 90 to 100° C. After cooling the reaction mixture to room temperature, it was poured into ice water, extracted with chloroform, and washed with saturated brine. The obtained organic layer was dried over anhydrous magnesium sulfate. The solvent was distilled off under reduced pressure, and thus obtained crystal was washed with n-hexane, to obtain 15.9 g of a subject compound (yield: 96%).

$^1$H-NMR Data (CDCl$_3$/TMS δ (ppm)): 3.81 (3H, s), 7.03 (1H, s, J=7.4 Hz), 8.57 (1H, d, J=7.4 Hz), 13.91 (1H, s)

Reference Example 2

(Production Intermediate) Production of 1,2-dihydro-1-methyl-2-oxo-6-(trifluoromethyl)pyridine-3-caroxylic acid (Production Intermediate VI-1) (Synthesis Method 2)

(1) Synthesis of N,N'-dimethylmalondiamide

To diethyl malonate (25 g, 0.16 mol), a 40% aqueous solution of methylamine (60 g, 0.75 mol) was added at room temperature, and the mixture was allowed to react overnight. The solvent was distilled off to obtain N,N'-dimethylmalondiamide.

(2) Production of 1,2-dihydro-N,1-dimethyl-2-oxo-6-(trifluoromethyl)pyridine-3-carboxylic acid amide N,N'-dimethylmalondiamide (20.3 g, 0.16 mol) obtained in above (1) was dissolved in ethanol (200 mL), and a 20% ethanolic solution of sodium ethylate (59 g, 0.17 mol) was added thereto at room temperature. The mixture was stirred for 10 minutes. Thereto, 4-ethoxy-1,1,1-trifluoro-3-buten-2-one (29 g, 0.17 mol) was added dropwise at room temperature, and the mixture was allowed to react for 5 hours at 80° C. After cooling, citric acid and brine were added thereto, and extraction with ethyl acetate was subjected. The organic layer was washed with an aqueous sodium bicarbonate solution and water in the this order, dried, and concentrated, and thus obtained oily product was purified by column chromatography (elution solvent: hexane/ethyl acetate=4/1 to 2/3), to obtain 7.1 g of a desired product (yield: 19%).

$^1$H-NMR Data (CDCl$_3$/TMS δ (ppm)): 3.00 (3H, d, J=4.9 Hz), 3.71 (3H, s), 6.88 (1H, s, J=7.7 Hz), 8.55 (1H, d, J=7.4 Hz), 9.55 (1H, br)

(3) Production of 1,2-dihydro-1-methyl-2-oxo-6-(trifluoromethyl)pyridine-3-carboxylic acid To 1,2-dihydro-N,1-dimethyl-2-oxo-6-(trifluoromethyl)-pyridine-3-carboxamide (1.2 g, 5.1 mmol) obtained as above, concentrated hydrochloric acid (20 mL) was added, and the mixture was stirred for 10 hours at 120° C. After cooling to room temperature, the reaction mixture was poured into ice water, and extracted with ethyl acetate. The organic layer was extracted with sodium bicarbonate, acidified by adding citric acid, and extracted with ethyl acetate. The organic layer was washed with water, dried, and concentrated, and thus obtained crystal was washed with n-hexane, to obtain 1.08 g of a desired product (yield: 98%).

Reference Example 3

(Production Intermediate) Production of 1,2-dihydro-1-methyl-2-oxo-6-(trifluoromethyl)pyridine-3-carboxylic acid (Production Intermediate VI-1) (Synthesis Method 3)

(1) Production of 2-oxo-6-(trifluoromethyl)-2H-pyrane-3-carboxylic acid ethyl ester Diethyl malonate (33.7 g, 0.2 mol) was dissolved in acetonitrile (200 mL), and magnesium chloride (21.4 g, 0.22 mol) was slowly added thereto at 0 to 5° C. After 10 minutes, triethylamine (44.5 g, 0.44 mol) was added dropwise thereto at 0 to 5° C., and the mixture was allowed to react for 1 hour at room temperature. To the reaction mixture, 4-ethoxy-1,1,1-trifluoro-3-butene-2-one (37.0 g, 0.22 mol) was added dropwise at 0 to 5° C., and the mixture was allowed to react for 1 hour at room temperature. The reaction mixture was poured into diluted hydrochloric acid, and extracted with ethyl acetate. The organic layer was washed with water, dried, and concentrated. Thus obtained oily product was dissolved in toluene (100 mL), p-toluenesulfonic acid (5 g) was added thereto, and the mixture was allowed to react for 3 hours under heating. After cooling, the solvent was distilled off, and thus obtained crystal was recrystallized from ethyl acetate, to obtain 31.8 g of a desired product (yield: 67%).

$^1$H-NMR Data (CDCl$_3$/TMS δ (ppm)): 1.36 (3H, t, J=7.1 Hz), 4.36 (2H, q, J=7.1 Hz), 6.75 (1H, d, J=7.1 Hz), 8.19 (1H, d, J=6.9 Hz)

(2) Production of 1,2-dihydro-1-methyl-2-oxo-6-(trifluoromethyl)pyridine-3-carboxylic acid 2-oxo-6-(trifluoromethyl)-2H-pyrane-3-carboxylic acid ethyl ester produced as above (8.0 g, 34 mmol) was dissolved in diethylether (50 mL), and a 30% ethanolic solution of methylamine (4.2 g, 41 mmol) was added dropwise thereto under ice cooling. The mixture was stirred overnight at room temperature. The precipitated sold was separated by filtration, and washed with diethylether. This solid was dissolved in ethanol (70 mL), and a 20% ethanolic solution of sodium ethylate (10.3 g, 30 mmol) was added thereto at room temperature. The mixture was stirred for 6 hours under heating. After cooling, the reaction mixture was poured into an aqueous solution of citric acid, and extracted with ethyl acetate. The organic layer was extracted with sodium bicarbonate, acidified by adding citric acid, and extracted with ethyl acetate. The organic layer was washed with water, dried, and concentrated, and thus obtained crystal was washed with n-hexane, to obtain 2.26 g of a desired product (yield: 30%).

Reference Example 4

(Production Intermediate) Production of 1,2-dihydro-2-oxo-1-phenyl-6-(trifluoromethyl)pyridine-3-carboxylic acid (Production Intermediate VI-56)

(1) Production of 2-phenylcarbamoylacetic acid ethyl ester

Ethyl malonyl chloride (15.1 g, 0.10 mol) was added to a mixed solution of aniline (9.3 g, 0.10 mol), triethylamine (11.1 g, 0.11 mol), N,N-dimethylaminopyridine (1.5 g, 0.012 mol) and dichloromethane (300 mL), at 10° C. or below. This mixture was stirred for 3 hours at room temperature, and then poured into water. The organic layer was washed with diluted hydrochloric acid, aqueous saturated sodium bicarbonate and saturated brine, in this order. The obtained organic layer was dried over anhydrous magnesium sulfate, and the solvent was distilled off under reduced pressure, to obtain 19.5 g of a subject compound (yield: 94%).

(2) Production of 1,2-dihydro-2-oxo-1-phenyl-6-(trifluoromethyl)pyridine-3-carboxylic acid ethyl ester To a mixed solution obtained by dissolving 2-phenylcarbamoylacetic acid ethyl ester produced as above (8.3 g, 40 mmol) and 6.7 g of 4-ethoxy-1,1,1-trifluoro-3-buten-2-one (40 mmol) in THF (100 mL), DBU (6.4 g, 42 mmol) was added dropwise at room temperature. After the 5 hour stirring, the mixture was poured into water, extracted with ethyl acetate, and washed with diluted hydrochloric acid and saturated brine in this order. The obtained organic layer was dried over anhydrous magnesium sulfate, and an inorganic substance was separated by filtration. The solvent was distilled off under reduced pressure. To a residue thus obtained, a catalytic amount of p-toluenesulfonic acid monohydrate and toluene (300 mL) were added, and the mixture was refluxed for 30 minutes under heating while removing water with a Dean-Stark apparatus. After cooling to room temperature, the obtained mixture was washed with water, aqueous saturated sodium bicarbonate, and water in this order. The organic layer was dried over anhydrous magnesium sulfate, the solvent was distilled off under reduced pressure, and thus obtained crystal was purified by recrystallization (ethanol/hexane), to obtain 3.5 g of a subject compound. Alternatively, the residue was purified by silica gel column chromatography (elution solvent: ethyl acetate/hexane=3/7), to obtain 2.3 g of a subject compound (yield: 46%).

$^1$H-NMR Data (CDCl$_3$/TMS δ (ppm)): 1.36 (3H, s, J=7.1 Hz), 4.37 (2H, q, J=7.2 Hz), 6.79 (1H, s, J=7.6 Hz), 7.22-7.24 (2H, m), 7.48-7.52 (3H, m), 8.19 (1H, d, J=7.4 Hz)

(3) Production of 1,2-dihydro-2-oxo-1-phenyl-6-(trifluoromethyl)pyridine-3-carboxylic acid 1,2-dihydro-2-oxo-1-phenyl-6-(trifluoromethyl)pyridine-3-carboxylic acid ethyl ester (5.1 g, 16 mmol) produced as above and lithium hydroxide monohydrate (1.4 g, 33 mmol) were dissolved in a mixed solvent of 1,4-dioxane (60 mL) and water (60 mL), and the mixture was stirred for 3 hours at room temperature. After concentrating the reaction mixture to half the amount, water was added to a residue, and washed with ethyl acetate. The obtained aqueous layer was acidified by adding diluted hydrochloric acid, and extracted with ethyl acetate. The organic layer was dried over anhydrous magnesium sulfate, and the solvent was distilled off under reduced pressure, to obtain 3.1 g of a subject compound (yield: 67%).

$^1$H-NMR Data (CDCl$_3$/TMS δ (ppm)): 7.13 (1H, s, J=7.6 Hz), 7.26-7.30 (2H, m), 7.56-7.61 (3H, m), 8.68 (1H, d, J=7.2 Hz), 13.55 (1H, s)

Reference Example 5

(Production Intermediate) Production of 1,2-dihydro-1-(dimethylamino)-2-oxo-6-(trifluoromethyl)-pyridine-3-carboxylic acid (Production Intermediate VI-19)

(1) Production of 2-(dimethylamino)carbamoylacetic acid ethyl ester

Ethyl malonyl chloride (5.0 g, 33 mmol) was added to a mixed solution of N,N-dimethylhydrazine (4.0 g, 67 mmol), triethylamine (6.7 g, 66 mmol) and acetonitrile (30 mL) at 10° C. or below. The mixture was stirred overnight at room temperature. The reaction mixture was added with an aqueous solution of citric acid, and extracted with chloroform. The organic layer was washed with water, dried, and concentrated, to obtain 4.6 g of a desired product (yield: 79%).

(2) Production of 1,2-dihydro-1-(dimethylamino)-2-oxo-6-(trifluoromethyl)pyridine-3-carboxylic acid ethyl ester To a mixed solution of 2-(dimethylamino)carbamoylacetic acid ethyl ester produced as above (4.6 g, 26 mmol), 4.4 g of 4-ethoxy-1,1,1-trifluoro-3-buten-2-one (26 mmol) and THF (50 mL), DBU (4.0 g, 26 mmol) was added dropwise at room temperature, and the mixture was stirred for 5 hours under heating at 70° C. Thereto, an aqueous solution of citric acid was added, and extraction with ethyl acetate was subjected. The organic layer was washed with an aqueous sodium bicarbonate solution and water, dried, and concentrated, and thus obtained oily product was purified by column chromatography (elution solvent: hexane/ethyl acetate=4/1 to 2/3), to obtain 2.0 g of a desired product (yield: 22%).
$^1$H-NMR Data (CDCl$_3$/TMS δ (ppm)): 1.31 (3H, t, J=7.1 Hz), 3.04 (6H, s), 4.36 (2H, q, J=7.2 Hz), 6.57 (1H, d, J=7.6 Hz), 8.04 (1H, d, J=7.4 Hz)

(3) Production of 1,2-dihydro-1-(dimethylamino)-2-oxo-6-(trifluoromethyl)pyridine-3-carboxylic acid 1,2-dihydro-1-(dimethylamino)-2-oxo-6-(trifluoromethyl)pyridine-3-carboxylic acid ethyl ester produced as above (2.0 g, 7.2 mmol) and lithium hydroxide monohydrate (0.6 g, 14 mmol) were dissolved in a mixed solvent of 1,4-dioxane (10 mL) and water (3 mL), and the mixture was stirred overnight at room temperature. Thereto, a sodium bicarbonate solution was added, and extraction with ethyl acetate was subjected. The aqueous layer was acidified with citric acid, and then extracted with ethyl acetate. The organic layer was washed with water, dried, and concentrated, to obtain 1.50 g of a desired product (yield: 83%).
$^1$H-NMR Data (CDCl$_3$/TMS δ (ppm)): 3.08 (6H, s), 6.91 (1H, d, J=7.6 Hz), 8.51 (1H, d, J=7.4 Hz), 13.62 (1H, br)

Reference Example 6

(Production Intermediate) Production of 1,2-dihydro-1-(2-methyl-2-propen-1-yl)-2-oxo-6-(trifluoromethyl)pyridine-3-carboxylic acid (Production Intermediate VI-7)

(1) Production of 1,2-dihydro-1-(2-methyl-2-propen-1-yl)-2-oxo-6-(trifluoromethyl)pyridine-3-carboxylic acid methyl ester Sodium hydride (60% in mineral oil, 2.2 g, 55 mmol) washed with hexane was suspended in N,N-dimethylformamide (70 mL), and 1,2-dihydro-2-oxo-6-(trifluoromethyl)pyridine-3-carboxylic acid methyl ester (10.0 g, 45 mmol) was slowly added thereto under ice cooling. Thereafter, the mixture was stirred for 20 minutes at room temperature. Thereto, 3-bromo-2-methylpropene (7.9 g, 59 mmol) was added, and the mixture was stirred for 6 hours at 60° C. After cooling, water was added thereto, and extraction with ethyl acetate was subjected. The organic layer was washed with an aqueous solution of citric acid and water, dried, and concentrated, to obtain a mixture of 2-(2-methyl-2-propen-1-yloxy)-6-(trifluoromethyl)pyridine-3-carboxylic acid methyl ester and 1,2-dihydro-1-(2-methyl-2-propen-1-yl)-2-oxo-6-(trifluoromethyl)pyridine-3-carboxylic acid methyl ester. This mixture was dissolved in chloroform (50 mL), and dichlorobis(benzonitrile)palladium (II) (1.7 g, 4.4 mmol) was added thereto under a nitrogen atmosphere. The mixture was allowed to react overnight at room temperature. A sodium bicarbonate solution was added thereto, and the organic layer was washed with an aqueous solution of citric acid and water, dried, and concentrated. Thus obtained oily product was purified by column chromatography (elution solvent: hexane/ethyl acetate=4/1 to 2/3) to obtain 7.5 g of a desired product.
$^1$H-NMR Data (CDCl$_3$/TMS δ (ppm)): 1.82 (3H, s), 3.93 (3H, s), 4.27 (1H, s), 4.63 (2H, s), 4.83 (1H, s), 6.74 (1H, d, J=7.6 Hz), 8.10 (1H, d, J=7.6 Hz)

(2) Production of 1,2-dihydro-1-(2-methyl-2-propen-1-yl)-2-oxo-6-(trifluoromethyl)pyridine-3-carboxylic acid 1,2-dihydro-2-oxo-6-(trifluoromethyl)pyridine-3-carboxylic acid methyl ester (1.54 g, 5.6 mmol) obtained as above was added to a mixed solvent of 1,4-dioxane (30 mL) and water (10 mL), and lithium hydroxide monohydrate (0.5 g, 12 mmol) was added thereto. The mixture was allowed to react overnight at room temperature. Thereto, a sodium bicarbonate solution was added, and extraction with ethyl acetate was subjected. The aqueous layer was acidified with citric acid, and then extracted with ethyl acetate. The organic layer was washed with water, dried, and concentrated to obtain 1.36 g of a desired product.
$^1$H-NMR Data (CDCl$_3$/TMS δ (ppm)): 1.87 (3H, s), 4.23 (1H, s), 4.75 (2H, s), 4.90 (1H, s), 7.06 (1H, d, J=7.6 Hz), 8.60 (1H, d, J=7.6 Hz), 13.80 (1H, br)

Reference Example 7

(Production Intermediate) Production of 1,2-dihydro-1-ethylsulfonylmethyl-2-oxo-6-(trifluoromethyl)pyridine-3-carboxylic acid (Production Intermediate VI-45)

(1) Production of 1,2-dihydro-1-methyl-2-oxo-6-(trifluoromethyl)pyridine-3-carboxylic acid methyl ester 1,2-dihydro-1-methyl-2-oxo-6-(trifluoromethyl)pyridine-3-carboxylic acid (114.0 g, 0.52 mol) was dissolved in dichloromethane (500 mL), and oxalyl chloride (99 g, 0.78 mol) was added thereto at room temperature. Thereto, N,N'-dimethylformamide (1 mL) was added, and the mixture was refluxed for 2 hours under heating. The solvent was distilled off, acetonitrile (500 mL) was added, and a mixture of methanol (33 g, 1.03 mol) and triethylamine (104 g, 1.03 mol) was added dropwise under ice cooling. After the 2 hours reaction at room temperature, the solvent was distilled off, an aqueous sodium bicarbonate solution was added, and extraction with chloroform was subjected. The organic layer was washed with an aqueous solution of citric acid and water, dried, and concentrated. Thus obtained oily product was purified by column chromatography (elution solvent: hexane/ethyl acetate=4/1 to 1/1) to obtain 113.5 g of a desired product (yield: 94%).

$^1$H-NMR Data (CDCl$_3$/TMS δ (ppm)): 3.67 (3H, s), 3.93 (3H, s), 6.70 (1H, d, J=7.3 Hz), 8.08 (1H, d, J=7.3 Hz)

(2) Production of 1-bromomethyl-1,2-dihydro-2-oxo-6-(trifluoromethyl)pyridine-3-carboxylic acid methyl ester 1,2-dihydro-1-methyl-2-oxo-6-(trifluoromethyl)pyridine-3-carboxylic acid methyl ester (30.0 g, 0.128 mol) obtained as above was added to 400 mL of carbon tetrachloride. Thereto, N-bromosuccinimide (68.3 g, 0.384 mol) and 0.2 g of 2,2'-azobisisobutylonitrile were added. The mixture was refluxed for 16 hours while irradiating with a 500-W tungsten lamp. After cooling, the solid was separated by filtration, and an oily product obtained by concentration was purified by column chromatography (elution solvent: hexane/ethyl acetate=4/1 to 3/2), to obtain 24.0 g of a desired product (yield: 60%).

$^1$H-NMR Data (CDCl$_3$/TMS δ (ppm)): 3.94 (3H, s), 5.38 (1H, br), 6.21 (1H, br), 6.80 (1H, d, J=7.3 Hz), 8.13 (1H, d, J=7.3 Hz)

(3) Production of 1,2-dihydro-1-ethylthiomethyl-2-oxo-6-(trifluoromethyl)pyridine-3-carboxylic acid methyl ester Ethyl mercaptan (3.0 g, 48 mmol) and potassium carbonate (6.6 g, 48 mmol) were suspended in N,N'-dimethylformamide (50 mL), and to this suspension, 30 mL of an N,N'-dimethylformamide solution of 1-bromomethyl-1,2-dihydro-2-oxo-6-(trifluoromethyl)pyridine-3-carboxylic acid methyl ester (10.0 g, 32 mol) obtained as above was added dropwise at room temperature. After the 2 hour stirring at room temperature, water was added, and extraction with ethyl acetate was subjected. The organic layer was washed with an aqueous solution of citric acid and water, dried, and concentrated. Thus obtained oily product was purified by column chromatography (elution solvent: hexane/ethyl acetate=4/1 to 3/2) to obtain 6.79 g of a desired product (yield: 72%).

$^1$H-NMR Data (CDCl$_3$/TMS δ (ppm)): 1.26 (3H, t), 2.94 (2H, q), 3.93 (3H, s), 5.25 (2H, br), 6.71 (1H, d, J=7.4 Hz), 8.08 (1H, d, J=7.4 Hz)

(4) Production of 1,2-dihydro-1-ethylsulfonylmethyl-2-oxo-6-(trifluoromethyl)pyridine-3-carboxylic acid methyl ester 1,2-dihydro-1-ethylthiomethyl-2-oxo-6-(trifluoromethyl) pyridine-3-carboxylic acid methyl ester (6.79 g, 23 mmol) obtained as above was dissolved in 100 mL of chloroform, and 70% m-chloroperbenzoic acid (12.5 g, 51 mmol) was added little at a time under ice cooling. Thereafter, the mixture was stirred overnight at room temperature. The solid was separated by filtration, and the organic layer was washed with an aqueous solution of sodium thiosulfate, an aqueous sodium bicarbonate solution, and water, dried, and concentrated, to obtain 7.36 g of a desired product (yield: 98%).

$^1$H-NMR Data (CDCl$_3$/TMS δ (ppm)): 1.48 (3H, t), 3.39 (2H, q), 3.93 (3H, s), 5.39 (2H, br), 6.85 (1H, d, J=7.7 Hz), 8.20 (1H, d, J=7.7 Hz)

(5) Production of 1,2-dihydro-1-ethylsulfonylmethyl-2-oxo-6-(trifluoromethyl)pyridine-3-carboxylic acid 1,2-dihydro-1-ethylsulfonylmethyl-2-oxo-6-(trifluoromethyl)pyridine-3-carboxylic acid methyl ester (7.36 g, 22 mmol) obtained as above was dissolved in 1,4-dioxane (50 mL), 6N hydrochloric acid (45 mL) was added thereto, and the mixture was stirred overnight at 50° C. The reaction mixture was poured into water, and extracted with ethyl acetate. To the organic layer, an aqueous sodium bicarbonate solution was added for liquid separation. The aqueous layer was acidified by adding citric acid. Water layer was extracted with ethyl acetate. The organic layer was washed with water, dried, and concentrated, and thus obtained crystal was washed with diisopropylether to obtain 5.76 g of a desired product (yield: 82%).

$^1$H-NMR Data (CDCl$_3$/TMS δ (ppm)): 1.52 (3H, t), 3.38 (2H, q), 5.46 (2H, br), 7.15 (1H, d, J=7.7 Hz), 8.65 (1H, d, J=7.7 Hz)

Reference Example 8

(Production Intermediate) Production of 6-cyano-1,2-dihydro-2-oxo-1-phenylpyridine-3-carboxylic acid (Production Intermediate VI-64)

(1) Production of 1,2-dihydro-6-methyl-2-oxo-1-phenylpyridine-3-carboxylic acid

Ethyl 3-oxo-3-(phenylamino)propionate (56.8 g, 0.27 mol) and 4-methoxy-3-buten-2-one (30.2 g, 0.30 mol) were dissolved in methanol (300 mL), and 20% sodium ethoxide. (112 g, 0.33 mol) was added dropwise thereto at room temperature. After the dropwise addition, the mixture was refluxed for 8 hours under heating. The reaction mixture was cooled and then concentrated under reduced pressure, and thus obtained residue was dissolved in a mixed solution of 1,4-dioxane (200 mL) and water (200 mL). To the resultant solution, lithium hydroxide monohydrate (23.0 g, 0.55 mol) was added, and the mixture was stirred overnight at room temperature. The reaction mixture was poured into water, and washed with ethyl acetate. The aqueous layer was acidified by adding citric acid, and then extracted with chloroform. The organic layer was washed with water, dried, and concentrated, and thus obtained crystal was washed with ethyl acetate, to obtain 43.4 g of a desired product (yield: 69%).

$^1$H-NMR Data (CDCl$_3$/TMS δ (ppm)): 2.15 (3H, s), 6.53 (1H, d, J=7.4 Hz), 7.22 (2H, m), 7.54 (3H, m), 8.48 (1H, d, J=7.3 Hz), 13.98 (1H, s)

(2) Production of 1,2-dihydro-6-methyl-2-oxo-1-phenylpyridine-3-carboxylic acid ethyl ester 33.4 g (0.146 mol) of 1,2-dihydro-6-methyl-2-oxo-1-phenylpyridine-3-carboxylic acid obtained as above was dissolved in dichloromethane (150 mL). Thereto, oxalyl chloride (37.1 g, 0.29 mol) was added at room temperature, and five drops of N,N'-dimethylformamide were added. The mixture was refluxed for 2 hours under heating. The solvent was distilled off, acetonitrile (250 mL) was added, and a mixture of ethanol (13.4 g, 0.29 mol) and triethylamine (29.5 g, 0.29 mol) was added dropwise to the mixture under ice cooling. After carrying out the 2 hour reaction at room temperature, the solvent was distilled off, an aqueous solution of citric acid was added, and extraction with chloroform was subjected. The organic layer was washed with water, dried, and concentrated, and thus obtained solid was washed with a mixed solvent of hexane/ethyl acetate=1/1, to obtain 33.1 g of a desired product (yield: 88%).

$^1$H-NMR Data (CDCl$_3$/TMS δ (ppm)): 1.33 (3H, s), 2.03 (3H, s), 4.31 (2H, q), 6.19 (1H, d, J=7.4 Hz), 7.16 (2H, m), 7.43 (3H, m), 8.17 (1H, d, J=7.4 Hz)

(3) Production of 5-bromo-6-bromomethyl-1,2-dihydro-2-oxo-1-phenylpyridine-3-carboxylic acid ethyl ester 1,2-dihydro-6-methyl-2-oxo-1-phenylpyridine-3-carboxylic acid ethyl ester (33.1 g, 0.129 mol) obtained as above was added to carbon tetrachloride (400 mL), and N-bromosuccinimide (57.0 g, 0.32 mol) and 0.2 g of 2,2'-azobisisobutylonitrile were added thereto. The mixture was refluxed for 5 hours while irradiating with a 500-W tungsten lamp. After cooling the reaction mixture, the solid was separated by filtration, and a solid obtained by concentrating the filtrate was washed with a mixed solvent of hexane/ethyl acetate=1/1, to obtain 45.3 g of a desired product (yield: 85%).

$^1$H-NMR Data (CDCl$_3$/TMS δ (ppm)): 1.34 (3H, t), 2.04 (3H, s), 4.1 (2H, s), 4.33 (2H, q), 7.30 (2H, m), 7.50 (3H, m), 8.30 (1H, s)

(4) Production of 5-bromo-1,2-dihydro-6-hydroxymethyl-2-oxo-1-phenylpyridine-3-carboxylic acid ethyl ester 5-bromo-6-bromomethyl-1,2-dihydro-2-oxo-1-phenylpyridine-3-carboxylic acid ethyl ester (25.9 g, 62 mmol) obtained as above was suspended in 1,4-dioxane (100 mL) and water (50 mL), sodium bicarbonate (15.7 g, 0.187 mol) was added to this suspension, and the mixture was allowed to react for 3 hours at 60° C. After the cooling the reaction mixture, it was poured into water, and extracted with chloroform. The organic layer was washed with an aqueous solution of citric acid and water, dried, and concentrated. The obtained solid was washed with a mixed solvent of hexane/ethyl acetate=1/1 to obtain 16.1 g of a desired product (yield: 73%).

$^1$H-NMR Data (CDCl3/TMS δ (ppm)): 1.34 (3H, t), 2.04 (1H, s), 4.32 (4H, m), 7.24 (2H, m), 7.49 (3H, m), 8.33 (1H, s)

(5) Production of 1,2-dihydro-6-hydroxymethyl-2-oxo-1-phenylpyridine-3-carboxylic acid ethyl ester 5-bromo-1,2-dihydro-6-hydroxymethyl-2-oxo-1-phenylpyridine-3-carboxylic acid ethyl ester (16.1 g, 46 mmol) obtained as above was suspended in 200 mL of ethyl acetate, and ammonium formate (8.6 g, 0.136 mol) and 10% palladium carbon (1.6 g) were added to the suspension under a nitrogen atmosphere. The mixture was allowed to react for 8 hours at 65° C. The reaction mixture was cooled, the insolubles were filtered and concentrated, and thus obtained solid was washed with a mixed solvent of hexane/ethyl acetate=1/1, to obtain 8.4 g of a desired product (yield: 67%).

$^1$H-NMR Data (CDCl$_3$/TMS δ (ppm)): 1.32 (3H, t), 2.95 (1H, t), 4.05 (2H, d), 4.29 (2H, q), 6.55 (1H, d, J=7.7 Hz), 7.07 (2H, m), 7.45 (3H, m), 8.24 (1H, d, J=7.7 Hz)

(6) Production of 1,2-dihydro-6-(hydroxyimino)methyl-2-oxo-1-phenylpyridine-3-carboxylic acid ethyl ester 1,2-dihydro-6-hydroxymethyl-2-oxo-1-phenylpyridine-3-carboxylic acid ethyl ester (5.0 g, 18 mmol) obtained as above was dissolved in dichloromethane (50 mL), and a DMP reagent (1,1,1-triacetoxy-1,1-dihydro-1,2-benziodoxol-3 (1H)-one) (9.3 g, 22 mol) was added thereto at room temperature. The mixture was allowed to react overnight. The reaction mixture was poured into an aqueous sodium bicarbonate solution, and extracted with chloroform. The organic layer was washed with water, dried, and concentrated, to obtain crude 6-formyl-1-phenyl-1,2-dihydro-2-oxopyridine-3-carboxylic acid ethyl ester. This crude product was dissolved in ethanol (100 mL), and hydroxylamine hydrochloride (2.5 g, 36 mmol) and potassium acetate (3.5 g, 36 mmol) were added thereto. The mixture was allowed to react for 8 hours at 50° C. The reaction mixture was concentrated, an aqueous sodium bicarbonate was added thereto, and extraction with warm chloroform was subjected. The organic layer was washed with warm water, dried, and concentrated, and thus obtained solid was washed with isopropylether to obtain 4.57 g of a desired product (yield: 89%, two stages).

$^1$H-NMR Data (CDCl$_3$/TMS δ (ppm)): 1.33 (3H, t), 4.32 (2H, q), 6.86 (1H, d, J=7.4 Hz), 7.15 (2H, m), 7.47 (3H, m), 8.23 (1H, d, J=7.7 Hz), 8.82 (1H, s)

(7) Production of 6-cyano-1,2-dihydro-2-oxo-1-phenylpyridine-3-carboxylic acid ethyl ester 1,2-dihydro-6-(hydroxyimino)methyl-2-oxo-1-phenylpyridine-3-carboxylic acid ethyl ester (4.57 g, 16 mmol) obtained as above was dissolved in dichloromethane (150 mL), and WSC(N-(3-dimethylaminopropyl)-N'-ethylcarbodiimide) (3.7 g, 19 mmol) and 4-dimethylaminopyridine (2.3 g, 19 mmol) were added thereto at room temperature. The mixture was allowed to react for 5 hours at 50° C. The reaction mixture was poured into an aqueous solution of citric acid, and a liquid separation was subjected. The organic layer was washed with water, dried, and concentrated. Thus obtained solid was washed with isopropylether to obtain 4.0 g of a desired product (yield: 93%).

$^1$H-NMR Data (CDCl$_3$/TMS δ (ppm)): 1.35 (3H, t), 4.35 (2H, q), 6.83 (1H, d, J=7.1 Hz), 7.26 (2H, m), 7.52 (3H, m), 8.12 (1H, d, J=7.1 Hz)

(8) Production of 6-cyano-1,2-dihydro-2-oxo-1-phenylpyridine-3-carboxylic acid 6-cyano-1,2-dihydro-2-oxo-1-phenylpyridine-3-carboxylic acid ethyl ester (2.0 g, 16 mmol) obtained as above was dissolved in a mixed solvent of 1,4-dioxane (20 mL) and water (5 mL), and lithium hydroxide monohydrate (0.38 g, 9.1 mmol) was added thereto at room temperature. The mixture was allowed to react overnight. The reaction mixture was added with water, and washed with ethyl acetate. The aqueous layer was acidified with citric acid, and extracted with chloroform. The organic layer was washed with water, dried, and concentrated, and thus obtained solid was washed with isopropylether, to obtain 1.20 g of a desired product (yield: 67%).

$^1$H-NMR Data (CDCl$_3$/TMS δ (ppm)): 7.15 (1H, d, J=7.4 Hz), 7.37 (2H, m), 7.64 (3H, m), 8.62 (1H, d, J=7.1 Hz)

Reference Example 9

(Production Intermediate) Production of 6-difluoromethyl-1,2-dihydro-2-oxo-1-phenylpyridine-3-carboxylic acid (Production Intermediate VI-65)

(1) Production of 6-difluoromethyl-1,2-dihydro-2-oxo-1-phenylpyridine-3-carboxylic acid ethyl ester 1,2-dihydro-6-hydroxymethyl-2-oxo-1-phenylpyridine-3-carboxylic acid ethyl ester (5.0 g, 18 mmol) was dissolved in dichloromethane (50 mL), and a DMP reagent (1,1,1-triacetoxy-1,1-dihydro-1,2-benziodoxol-3(1H)-one) (8.5 g, 20 mol) was added thereto at room temperature. The mixture was allowed to react for 4 hours. The reaction mixture was poured into an aqueous sodium bicarbonate solution, and extracted with chloroform. The organic layer was washed with water, dried, and concentrated, to obtain crude 6-formyl-1-phenyl-1,2-dihydro-2-oxopyridine-3-carboxylic acid ethyl ester. This crude product was dissolved in dichloromethane (50 mL), and a DAST reagent (diethylamino sulfur trifluoride) (4.8 g, 30 mmol) was added to this solution at 5° C. under a nitrogen atmosphere. The mixture was allowed to react overnight at room temperature. The reaction mixture was poured into water, and the organic layer was washed with an aqueous sodium bicarbonate solution and water, dried, and concentrated. Thus obtained residue was purified by column chromatography (elution solvent: hexane/ethyl acetate: 4/1 to 3/2), and thus obtained solid was washed with a mixed solution of hexane/ethyl acetate=1/1, to obtain 2.29 g of a desired product (yield: 57%, two stages).

$^1$H-NMR Data (CDCl$_3$/TMS δ (ppm)): 1.34 (3H, t), 4.34 (2H, q), 6.04 (1H, J=53 Hz), 6.70 (1H, d, J=7.4 Hz), 7.24 (2H, m), 7.50 (3H, m), 8.25 (1H, d, J=7.7 Hz)

(2) Production of 6-difluoromethyl-1,2-dihydro-2-oxo-1-phenylpyridine-3-carboxylic acid 6-difluoromethyl-1,2-dihydro-2-oxo-1-phenylpyridine-3-carboxylic acid ethyl ester (1.52 g, 5.2 mmol) obtained as above was dissolved in a mixed solvent of 1,4-dioxane (20 mL) and water (5 mL), and lithium hydroxide monohydrate (0.43 g, 10.2 mmol) was added thereto at room temperature. The mixture was allowed to react overnight. The reaction mixture was added with water, and extracted with ethyl acetate. The aqueous layer was acidified by adding citric acid, and extracted with ethyl acetate. The organic layer was washed with water, dried, and concentrated, and thus obtained solid was washed with isopropylether, to obtain 1.22 g of a desired product (yield: 89%).

$^1$H-NMR Data (CDCl$_3$/TMS δ (ppm)): 6.13 (1H, J=53 Hz), 7.03 (1H, d, J=7.4 Hz), 7.26 (2H, m), 7.63 (3H, m), 8.691 (1H, d, J=7.7 Hz)

Reference Example 10

(Production Intermediate) Production of 1,2-dihydro-2-oxo-1-phenyl-6-(n-propylsulfonylmethyl)pyridine-3-carboxylic acid (Production Intermediate IV-66)

(1) Production of 1,2-dihydro-2-oxo-1-phenyl-6-(n-propylthiomethyl)pyridine-3-carboxylic acid ethyl ester 1,2-dihydro-6-hydroxymethyl-2-oxo-1-phenylpyridine-3-carboxylic acid ethyl ester (5.0 g, 18 mmol) was dissolved in dichloromethane (100 mL), and phosphorus tribromide (1.95 g, 7.2 mol) was added to this solution at −20° C. under a nitrogen atmosphere. The mixture was allowed to react for 4 hours. The reaction mixture was poured into water and a liquid separation was subjected. The organic layer was washed with an aqueous sodium bicarbonate solution and water, dried, and concentrated to obtain 3.30 g of a crude desired product. This crude product was dissolved in N,N'-dimethylformamide (30 mL), and potassium carbonate (2.0 g, 14 mmol) and propyl mercaptan (1.1 g, 14 mmol) were added thereto. The mixture was allowed to react for 2 hours at room temperature. The reaction mixture was poured into water, and extracted with ethyl acetate. The organic layer was washed with an aqueous solution of citric acid and water, dried, and concentrated. Thus obtained oily product was purified by column chromatography (elution solvent: hexane/ethyl acetate=3/2) to obtain 1.17 g of a desired product (yield: 20%, two stages).

$^1$H-NMR Data (CDCl$_3$/TMS δ (ppm)): 0.89 (3H, t), 1.33 (3H, t), 1.41 (2H, m), 2.34 (2H, t), 3.25 (2H, s), 4.31 (2H, q), 6.33 (1H, d, J=7.4 Hz), 7.23 (2H, m), 7.44 (3H, m), 8.19 (1H, d, J=7.7 Hz)

(2) Production of 1,2-dihydro-2-oxo-1-phenyl-6-(n-propylsulfonylmethyl)pyridine-3-carboxylic acid ethyl ester 1,2-dihydro-2-oxo-1-phenyl-6-(n-propylthiomethyl)pyridine-3-carboxylic acid ethyl ester (1.95 g, 5.9 mmol) obtained as above was dissolved in chloroform (50 mL), and 65% m-chloroperbenzoic acid (3.4 g, 12.8 mmol) was added little at a time under ice cooling. Thereafter, the mixture was stirred overnight at room temperature. A solid of the reaction mixture was separated by filtration, and an organic layer of the filtrate was washed with an aqueous solution of sodium thiosulfate, an aqueous sodium bicarbonate solution and water, dried, and concentrated, to obtain 2.03 g of a desired product (yield: 95%).

$^1$H-NMR Data (CDCl$_3$/TMS δ (ppm)): 0.96 (3H, t), 1.33 (3H, t), 1.58 (2H, m), 2.77 (2H, t), 3.98 (2H, s), 4.32 (2H, q), 6.61 (1H, d, J=7.4 Hz), 7.26 (2H, m), 7.50 (3H, m), 8.20 (1H, d, J=7.7 Hz)

(3) Production of 1,2-dihydro-2-oxo-1-phenyl-6-(n-propylsulfonylmethyl)pyridine-3-carboxylic acid 1,2-dihydro-2-oxo-1-phenyl-6-(n-propylsulfonylmethyl)pyridine-3-carboxylic acid ethyl ester (2.03 g, 5.6 mmol) obtained as above was dissolved in 1,4-dioxane (10 mL), and 6N hydrochloric acid (10 mL) was added thereto. Thereafter, the mixture was stirred for 1 hour at 50° C. The reaction mixture was poured into water and extracted with ethyl acetate. To the organic layer, sodium bicarbonate was added, and extraction was subjected. The aqueous layer was acidified by adding citric acid, extracted with chloroform, washed with water, dried, and concentrated. Thus obtained crystal was washed with diisopropylether to obtain 1.84 g of a desired product (yield: 98%).

$^1$H-NMR Data (CDCl$_3$/TMS δ (ppm)): 0.98 (3H, t), 1.60 (2H, m), 2.85 (2H, m), 4.08 (2H, s), 6.91 (1H, d, J=7.4 Hz), 7.34 (2H, m), 7.62 (3H, m), 8.58 (1H, d, J=7.7 Hz)

Reference Example 11

(Production Intermediate) Production of 1,2-dihydro-1-methyl-6-methylthio-2-oxopyridine-3-carboxylic acid (Production Intermediate IV-67)

(1) Production of methyl 2-hydroxy-6-methylthiopyridine-3-carboxylate

To a mixture of N,N-dimethylformamide (DMF) (70 mL) and 8.6 g of methyl mercaptan sodium (0.12 mol), a DMF solution (40 mL) of 7.69 g of methyl 2-hydroxy-6-chloropyridine-3-carboxylate (41.0 mmol) was added dropwise at 40° C. This mixture was stirred for 1 hour, and then poured into water and extracted with ethyl acetate. The organic layer was dried, and the solvent was distilled off under reduced pressure. Thus obtained residue was purified by column chromatography to obtain 4.91 g of a desired product (yield: 60%).

(2) Production of methyl 1,2-dihydro-1-methyl-6-methylthio-2-oxopyridine-3-carboxylate To a suspension of sodium hydride (60% dispersion, 0.40 g, 10 mmol) and dimethoxyethane (24 mL), a DMF solution (6 mL) of methyl 2-hydroxy-6-methylthiopyridine-3-carboxylate (2.0 g, 10 mmol) was added dropwise under ice cooling. The mixture was stirred for 15 minutes at room temperature, and then lithium bromide (1.7 g, 20 mmol) was added thereto. The mixture was stirred for 15 minutes. The reaction mixture was heated to 60° C., methyl iodide (2.8 g, 20 mmol) was added dropwise thereto, and then further stirred for 3 hours. After cooling to room temperature, the reaction mixture was poured into water and extracted with ethyl acetate. The organic layer was dried, and then the solvent was distilled off under reduced pressure. Thus obtained residue was purified by column chromatography to obtain 2.1 g of a desired product (yield: 98%).

(3) Production of 1,2-dihydro-1-methyl-6-methylthio-2-oxopyridine-3-carboxylic acid Methyl 1,2-dihydro-1-methyl-6-methylthio-2-oxopyridine-3-carboxylate (2.1 g, 9.8 mmol) and lithium hydroxide monohydrate (0.50 g, 12 mmol) were dissolved in a mixed solvent of THF (30 mL) and water (2 mL), and stirred for a day at room temperature. The reaction mixture was concentrated under reduced pressure. To thus obtained residue, a mixed solution of aqueous saturated sodium bicarbonate and ethyl acetate was added, and then liquid separation and extraction were subjected. The obtained liquid layer was added with diluted hydrochloric acid to give a pH of 3 to 4, and extracted with chloroform. The organic layer was dried over anhydrous magnesium sulfate, and the solvent was distilled off under reduced pressure, to obtain 1.6 g of a desired product (yield: 82%).

$^1$H-NMR Data (CDCl$_3$/TMS δ (ppm)): 2.64 (3H, s), 3.72 (3H, s), 6.30 (1H, d, J=8.0 Hz), 8.35 (1H, d, J=8.2 Hz), 14.1 (1H, s)

Structural formulae and physical properties of the compounds synthesized according to above-mentioned Reference Examples are shown in Tables 32 and 33 including above-mentioned Reference Examples. Herein, symbols in the tables have the same meanings as defined above. The compound numbers are referred to in the following descriptions.

TABLE 32

| Compound No | R$^1$ | R$^2$ | R$^3$ | M.P. (°C.) or R.I. (n$_p^{20}$) | |
|---|---|---|---|---|---|
| VI-1 | Me | CF$_3$ | H | M.P. | 98-99 |
| VI-2 | Et | CF$_3$ | H | M.P. | 79-74 |
| VI-3 | Pr-n | CF$_3$ | H | M.P. | 66-67 |
| VI-4 | Pr-i | CF$_3$ | H | | |
| VI-5 | Pr-c | CF$_3$ | H | M.P. | 136-137 |
| VI-6 | CH$_2$CH=CH$_2$ | CF$_3$ | H | | |
| VI-7 | CH$_2$C(Me)=CH$_2$ | CF$_3$ | H | | |
| VI-8 | CH$_2$C≡CH | CF$_3$ | H | | |
| VI-9 | Bu-n | CF$_3$ | H | | |
| VI-10 | Bu-i | CF$_3$ | H | | |
| VI-11 | Bu-s | CF$_3$ | H | M.P. | 48-50 |
| VI-12 | Bu-t | CF$_3$ | H | | |
| VI-13 | Pen-c | CF$_3$ | H | M.P. | 59-62 |
| VI-14 | CH$_2$CF$_3$ | CF$_3$ | H | M.P. | 77-79 |
| VI-15 | CH$_2$Br | CF$_3$ | H | M.P. | 88-90 |
| VI-16 | CH$_2$CH$_2$CH=CMe$_2$ | CF$_3$ | H | M.P. | 75-76 |
| VI-17 | CH$_2$CH$_2$CH$_2$CH$_2$C(Me)=CF$_3$ | CF$_3$ | H | M.P. | 72-74 |
| VI-18 | CH$_2$CH$_2$CH=CCl$_2$ | CF$_3$ | H | M.P. | 111-119 |
| VI-19 | NH$_2$ | CF$_3$ | H | | |
| VI-20 | NMe$_2$ | CF$_3$ | H | M.P. | 99-100 |
| VI-21 | (N-linked thiomorpholine) | CF$_3$ | H | M.P. | 189-191 |
| VI-22 | (N-linked thiomorpholine-1,1-dioxide, SO$_2$) | CF$_3$ | H | M.P. | 292-295 |
| VI-23 | NHC(=O)OMe | CF$_3$ | H | M.P. | 155-157 |
| VI-24 | NHC(=O)OEt | CF$_3$ | H | M.P. | 125-126 |
| VI-25 | N(Me)C(=O)OMe | CF$_3$ | H | M.P. | 109-110 |
| VI-26 | N(Et)C(=O)OMe | CF$_3$ | H | M.P. | 86-88 |
| VI-27 | N(Me)C(=O)OBu-t | CF$_3$ | H | M.P. | 104-105 |
| VI-28 | N(Et)C(=O)OBu-t | CF$_3$ | H | M.P. | 82-83 |
| VI-29 | N(Me)C(=O)OBn | CF$_3$ | H | M.P. | 128-129 |
| VI-30 | CH$_2$CH$_2$OMe | CF$_3$ | H | M.P. | 39-42 |
| VI-31 | CH(Me)CH$_2$OMe | CF$_3$ | H | R.I. | 1.4843 |
| VI-32 | CH$_2$CH$_2$OCH$_2$CH$_2$OMe | CF$_3$ | H | R.I. | 1.4929 |
| VI-33 | CH$_2$CH$_2$CH$_2$OMe | CF$_3$ | H | M.P. | 54-55 |
| VI-34 | CH$_2$CH(OMe)$_2$ | CF$_3$ | H | R.I. | 1.4027 |

M.P.: Melting Point
R.I.: Refractive Index

TABLE 33

| Compound No | R$^1$ | R$^2$ | R$^3$ | M.P. (°C.) or R.I. (n$_p^{20}$) | |
|---|---|---|---|---|---|
| VI-35 | (1,3-dioxolan-2-ylmethyl) | CF$_3$ | H | R.I. | 1.5127 |
| VI-36 | (tetrahydrofuran-2-ylmethyl) | CF$_3$ | H | M.P. | 92-94 |
| VI-37 | (tetrahydrofuran-3-ylmethyl) | CF$_3$ | H | R.I | 1.5141 |
| VI-38 | CH$_2$SCN | CF$_3$ | H | M.P. | 114-116 |
| VI-39 | CH$_2$SPr-c | CF$_3$ | H | M.P. | 65-66 |
| VI-40 | CH$_2$SBu-t | CF$_3$ | H | M.P. | 73-74 |
| VI-41 | CH$_2$SCH$_2$Pr-c | CF$_3$ | H | M.P. | 1.5364 |
| VI-42 | CH$_2$SPen-c | CF$_3$ | H | M.P. | 76-78 |
| VI-43 | CH$_2$SHex-c | CF$_3$ | H | M.P. | 101-102 |
| VI-44 | CH$_2$SO$_2$Me | CF$_3$ | H | M.P. | 137-139 |
| VI-45 | CH$_2$SO$_2$Et | CF$_3$ | H | M.P. | 159-161 |

TABLE 33-continued

| Compound No | R¹ | R² | R³ | M.P. (°C.) or R.I. ($n_p^{20}$) |
|---|---|---|---|---|
| VI-46 | $CH_2SO_2Pr$-i | $CF_3$ | H | M.P. 109-111 |
| VI-47 | $CH_2SO_2Pr$-c | $CF_3$ | H | M.P. 196-198 |
| VI-48 | $CH_2SO_2Bu$-t | $CF_3$ | H | M.P. 149-150 |
| VI-49 | $CH_2SO_2CH_2Pr$-c | $CF_3$ | H | M.P. 118-120 |
| VI-50 | $CH_2SO_2Pen$-c | $CF_3$ | H | M.P. 132-133 |
| VI-51 | $CH_2SO_2Hex$-c | $CF_3$ | H | M.P. 181-182 |
| VI-52 | $CH_2SO_2CF_3$ | $CF_3$ | H | M.P. 94-96 |
| VI-53 | $CH_2SO_2CH_2CF_3$ | $CF_3$ | H | M.P. 165-166 |
| VI-54 | $CH_2CH_2CH_2SO_2Me$ | $CF_3$ | H | M.P. 110-112 |
| VI-55 | $CH_2CH_2SO_2Me$ | $CF_3$ | H | M.P. 94-96 |
| VI-56 | Ph | $CF_3$ | H | M.P. 108-111 |
| VI-57 | Ph(3-SMe) | $CF_3$ | H | M.P. 145-147 |
| VI-58 | Ph(3,4-di-Cl) | $CF_3$ | H | M.P. 172-174 |
| VI-59 | Ph(2,6-di-F) | $CF_3$ | H | M.P. 141-143 |
| VI-60 | 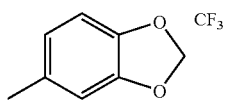 | $CF_3$ | H | M.P. 134-136 |
| VI-61 | OMe | $CF_3$ | H | M.P. 89-90 |
| VI-62 | 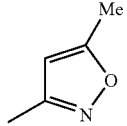 | $CF_3$ | H | M.P. 108-110 |
| VI-63 | 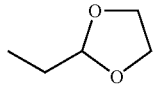 | $CF_3$ | H | R.I. 1.5127 |
| VI-64 | Ph | CN | H | M.P. 172-173 |
| VI-65 | Ph | $CHF_2$ | H | M.P. 160-163 |
| VI-66 | Ph | $CH_2SO_2Pr$-n | H | M.P. 170-171 |
| VI-67 | Me | SMe | H | |
| VI-68 | Ph | Me | H | M.P. 210-211 |

M.P.: Melting Point
R.I.: Refractive Index

Next, a formulation preparing method will be described in detail with reference to representative Formulation Examples. The type and blending ratio of the compound and additive are not limited thereto and they can be changed in a wide range. In the description below, 'parts' means 'parts by weight'.

<Formulation Example 1> Wettable Powder

| | |
|---|---|
| Compound of Compound No. I-1 | 10 parts |
| Polyoxyethyleneoctylphenyl ether | 0.5 parts |
| Sodium salt of β-naphthalene sulfonic acid formalin condensate | 0.5 parts |
| Diatomite | 20 parts |
| Clay | 69 parts |

Above materials were mixed and crushed to obtain wettable powder. Also, instead of Compound No. I-1, other compounds mentioned in Tables 1 to 21 may be used to obtain wettable powders in the same manner.

<Formulation Example 2> Flowable

| | |
|---|---|
| Compound of Compound No. IV-140 | 20 parts |
| Water | 69 parts |
| Polyoxyethylene styrenated phenyl ether sulfate | 4 parts |
| Ethylene glycol | 7 parts |

To above materials, silicone AF-118N (produced by Asahi Chemical Industry Co., Ltd.) was added by 200 ppm with respect to the total amount, and mixed for 30 minutes with a high-speed stirrer. Thereafter, the mixture was crushed using a wet pulverizer to obtain a flowable. Also, instead of Compound No. IV-144, other compounds mentioned in Tables 1 to 21 may be used to obtain flowables in the same manner.

<Formulation Example 3> Emulsifiable concentrate

| | |
|---|---|
| Compound of Compound No. I-72 | 30 parts |
| Mixture of equal parts of xylene and isophorone | 60 parts |
| Polyoxyethylene sorbitan alkylate | 4 parts |
| Polyoxyethylene polyalkylaryl ether | 4 parts |
| Alkylaryl sulfonate | 2 parts |

Above materials were homogeneously dissolved to obtain an emulsifiable concentrate. Also, instead of Compound No. I-72, other compounds mentioned in Tables 1 to 21 may be used to obtain emulsifiable concentrate in the same manner.

<Formulation Example 4> Granule

| | |
|---|---|
| Compound of Compound No. III-33 | 10 parts |
| Mixture of talc and bentonite (1:3) | 80 parts |
| White Carbon | 5 parts |
| Polyoxyethylene sorbitan alkylate | 2 parts |
| Polyoxyethylene polyalkylaryl ether | 2 parts |
| Alkylaryl sulfonate | 1 part |

Above materials were homogeneously mixed and crushed. To this mixture, 10 parts equivalent amount of water was added for kneading. With the use of an extrusion-type granulator, the kneaded product was pushed out of a sieve having a diameter of 0.7 mm, it was then dried and cut in a length of 0.5 to 1 mm, to obtain a granule. Also, instead of Compound No. 111-33, other compounds mentioned in Tables 1 to 21 may be used to obtain granules in the same manner.

In addition, with the compounds mentioned in Tables 1 to 21, it was possible to produce various formulations as above according to Formulation Examples 1 to 4.

Next, effects exhibited by the compound of the invention will be described with reference to Test Examples.

Test Example 1

Test on Herbicidal Effect by Soil Application to Paddy Field

In a 100 cm2 plastic pot, paddy field soil was filled. After puddling and leveling, seeds of early watergrass (*Echinochloa oryzicola* Vasing), heartshape false pickerelweed (*Monochoria vaginalis* (Burm.f.) C.Presl) and Japanese bulrush (*Scirpus juncoides* Roxb.) were sown, and water was filled to be flooded to a water depth of 3 cm. On the following day, the wettable powder prepared according to Formulation Example 1 was diluted in water and added dropwise to a water surface. The amount of application was set for an active ingredient to be 1,000 g equivalent per 1 hectare. Then, on the 21st day after the application to the plants grew in a greenhouse, the herbicidal effect was examined in accordance with a standard shown in Table 34. The results are shown in Tables 34 to 44.

TABLE 34

| Index | Herbicidal Effect (degree of suppressing growth) and crop phytotoxicity |
|---|---|
| 5 | 90% or more of herbicidal effect and crop phytotoxicity |
| 4 | 70 to less than 90% of herbicidal effect and crop phytotoxicity |
| 3 | 50 to less than 70% of herbicidal effect and crop phytotoxicity |
| 2 | 30 to less than 50% of herbicidal effect and crop phytotoxicity |
| 1 | 10 to less than 30% of herbicidal effect and crop phytotoxicity |
| 0 | 0 to less than 10% of herbicidal effect and crop phytotoxicity |

TABLE 35

| Compound No. | Echinochloa oryzicola Vasing | Monochoria vaginalis (Burm. f.) C. Presl | Scirpus juncoides Roxb. |
|---|---|---|---|
| I-1 | 5 | 5 | 5 |
| I-2 | 5 | 5 | 5 |
| I-3 | 5 | 5 | 5 |
| I-4 | 5 | 5 | 5 |
| I-5 | 5 | 5 | 5 |
| I-6 | 5 | 5 | 5 |
| I-7 | 5 | 5 | 5 |
| I-9 | 5 | 5 | 5 |
| I-10 | 5 | 5 | 5 |
| I-11 | 5 | 5 | 5 |
| I-12 | 5 | 5 | 5 |
| I-13 | 5 | 5 | 5 |
| I-14 | 5 | 5 | 5 |
| I-16 | 5 | 5 | 5 |
| I-18 | 5 | 5 | 5 |
| I-20 | 5 | 5 | 5 |
| I-26 | 5 | 5 | 5 |
| I-27 | 5 | 5 | 5 |
| I-28 | 5 | 5 | 4 |
| I-30 | 3 | 5 | 3 |
| I-31 | 5 | 5 | 5 |
| I-32 | 5 | 5 | 5 |
| I-33 | 5 | 5 | 5 |
| I-34 | 5 | 5 | 5 |
| I-42 | 5 | 5 | 5 |
| I-43 | 5 | 4 | 5 |
| I-44 | 5 | 5 | 5 |
| I-46 | 5 | 5 | 5 |
| I-47 | 5 | 5 | 5 |
| I-48 | 5 | 5 | 5 |
| I-49 | 5 | 5 | 5 |
| I-50 | 5 | 5 | 5 |
| I-51 | 5 | 5 | 5 |
| I-52 | 5 | 5 | 5 |
| I-53 | 5 | 5 | 5 |
| I-54 | 5 | 5 | 5 |
| I-55 | 5 | 5 | 5 |
| I-56 | 5 | 5 | 5 |
| I-57 | 5 | 5 | 5 |
| I-58 | 5 | 5 | 5 |
| I-59 | 5 | 5 | 5 |
| I-60 | 5 | 5 | 5 |
| I-61 | 5 | 5 | 4 |

TABLE 36

| Compound No. | Echinochloa oryzicola Vasing | Monochoria vaginalis (Burm. f.) C. Presl | Scirpus juncoides Roxb. |
|---|---|---|---|
| I-62 | 5 | 5 | 4 |
| I-63 | 5 | 5 | 5 |
| I-64 | 4 | 5 | 5 |
| I-66 | 5 | 5 | 5 |
| I-67 | 5 | 5 | 5 |
| I-69 | 5 | 5 | 5 |
| I-70 | 5 | 5 | 5 |
| I-71 | 5 | 5 | 5 |
| I-72 | 5 | 5 | 5 |
| I-73 | 5 | 5 | 5 |
| I-74 | 5 | 5 | 5 |
| I-75 | 5 | 5 | 5 |
| I-76 | 5 | 5 | 5 |
| I-77 | 5 | 5 | 5 |
| I-78 | 5 | 5 | 5 |
| I-79 | 5 | 5 | 5 |
| I-80 | 5 | 5 | 5 |
| I-81 | 5 | 5 | 5 |
| I-82 | 5 | 5 | 5 |
| I-83 | 5 | 5 | 5 |
| I-85 | 5 | 5 | 5 |
| I-86 | 5 | 5 | 5 |
| I-87 | 5 | 5 | 5 |
| I-88 | 5 | 5 | 5 |
| I-89 | 5 | 5 | 5 |
| I-90 | 5 | 5 | 5 |
| I-91 | 5 | 5 | 5 |
| I-92 | 5 | 5 | 5 |
| I-93 | 5 | 5 | 5 |
| I-94 | 5 | 5 | 5 |
| I-95 | 5 | 5 | 5 |
| I-96 | 5 | 5 | 5 |
| I-97 | 4 | 5 | 4 |
| I-98 | 5 | 5 | 5 |
| I-99 | 5 | 5 | 5 |
| I-100 | 5 | 5 | 5 |
| I-101 | 5 | 5 | 5 |
| I-102 | 5 | 5 | 5 |
| I-103 | 5 | 5 | 5 |
| I-104 | 5 | 5 | 5 |
| I-105 | 5 | 5 | 5 |
| I-106 | 5 | 5 | 5 |
| I-107 | 5 | 5 | 5 |

TABLE 37

| Compound No. | Echinochloa oryzicola Vasing | Monochoria vaginalis (Burm. f.) C. Presl | Scirpus juncoides Roxb. |
|---|---|---|---|
| I-108 | 5 | 5 | 5 |
| I-109 | 4 | 5 | 5 |
| I-110 | 5 | 5 | 5 |
| I-111 | 5 | 5 | 5 |
| I-112 | 5 | 5 | 5 |
| I-113 | 5 | 5 | 5 |
| I-114 | 5 | 5 | 5 |
| I-115 | 5 | 5 | 5 |
| I-116 | 5 | 5 | 5 |
| I-117 | 5 | 5 | 5 |
| I-118 | 5 | 5 | 5 |
| I-119 | 5 | 5 | 5 |
| I-120 | 5 | 5 | 5 |
| I-121 | 5 | 5 | 5 |
| I-122 | 5 | 5 | 5 |
| I-123 | 5 | 5 | 5 |
| I-124 | 5 | 5 | 5 |
| I-126 | 5 | 5 | 5 |
| I-127 | 4 | 4 | 3 |
| I-128 | 5 | 5 | 5 |
| I-129 | 5 | 4 | 5 |

TABLE 37-continued

| Compound No. | Echinochloa oryzicola Vasing | Monochoria vaginalis (Burm. f.) C. Presl | Scirpus juncoides Roxb. |
|---|---|---|---|
| I-133 | 5 | 5 | 5 |
| I-137 | 5 | 5 | 5 |
| I-138 | 5 | 5 | 5 |
| I-140 | 5 | 5 | 5 |
| I-142 | 5 | 5 | 5 |
| I-147 | 5 | 5 | 5 |
| I-148 | 5 | 5 | 5 |
| I-149 | 5 | 5 | 5 |
| I-150 | 5 | 5 | 5 |
| I-151 | 5 | 5 | 5 |
| I-153 | 5 | 5 | 5 |
| I-154 | 5 | 5 | 5 |
| I-156 | 5 | 5 | 5 |
| I-157 | 5 | 5 | 5 |
| I-158 | 5 | 5 | 5 |
| I-159 | 5 | 5 | 5 |
| I-160 | 5 | 5 | 5 |
| I-161 | 5 | 5 | 5 |
| I-162 | 5 | 5 | 5 |
| I-163 | 5 | 5 | 5 |
| I-164 | 5 | 5 | 5 |
| I-165 | 5 | 5 | 5 |

TABLE 38

| Compound No. | Echinochloa oryzicola Vasing | Monochoria vaginalis (Burm. f.) C. Presl | Scirpus juncoides Roxb. |
|---|---|---|---|
| I-166 | 5 | 5 | 5 |
| I-167 | 5 | 5 | 5 |
| I-168 | 5 | 5 | 5 |
| I-169 | 5 | 5 | 5 |
| I-170 | 5 | 5 | 5 |
| I-171 | 5 | 5 | 5 |
| I-172 | 5 | 5 | 5 |
| I-173 | 5 | 5 | 5 |
| I-174 | 5 | 5 | 5 |
| I-175 | 5 | 5 | 5 |
| I-176 | 5 | 5 | 5 |
| I-177 | 5 | 5 | 5 |
| I-178 | 5 | 5 | 5 |
| I-179 | 5 | 5 | 5 |
| I-180 | 5 | 5 | 5 |
| I-182 | 5 | 5 | 5 |
| I-186 | 5 | 5 | 5 |
| I-189 | 5 | 5 | 5 |
| I-190 | 5 | 5 | 5 |
| I-191 | 5 | 5 | 5 |
| I-192 | 5 | 5 | 5 |
| I-193 | 5 | 5 | 5 |
| I-194 | 5 | 5 | 5 |
| I-195 | 5 | 5 | 5 |
| I-196 | 5 | 5 | 4 |
| I-197 | 5 | 5 | 5 |
| I-202 | 5 | 5 | 5 |
| I-215 | 5 | 5 | 5 |
| I-221 | 5 | 5 | 5 |
| I-222 | 5 | 5 | 5 |
| I-223 | 5 | 5 | 5 |
| I-224 | 5 | 5 | 5 |
| I-225 | 5 | 5 | 5 |
| I-226 | 5 | 5 | 5 |
| I-227 | 5 | 5 | 5 |
| I-229 | 4 | 5 | 4 |
| I-230 | 5 | 5 | 5 |
| I-231 | 5 | 5 | 5 |
| I-232 | 5 | 5 | 5 |
| I-233 | 5 | 5 | 5 |
| I-235 | 5 | 5 | 5 |
| I-236 | 5 | 5 | 5 |

TABLE 38-continued

| Compound No. | Echinochloa oryzicola Vasing | Monochoria vaginalis (Burm. f.) C. Presl | Scirpus juncoides Roxb. |
|---|---|---|---|
| I-238 | 5 | 5 | 5 |
| I-243 | 5 | 5 | 5 |

TABLE 39

| Compound No. | Echinochloa oryzicola Vasing | Monochoria vaginalis (Burm. f.) C. Presl | Scirpus juncoides Roxb. |
|---|---|---|---|
| II-1 | 5 | 5 | 5 |
| II-2 | 5 | 5 | 5 |
| II-3 | 5 | 5 | 5 |
| II-5 | 5 | 5 | 5 |
| II-7 | 5 | 5 | 5 |
| II-8 | 5 | 5 | 5 |
| II-9 | 5 | 5 | 5 |
| II-11 | 5 | 5 | 5 |
| II-12 | 5 | 5 | 5 |
| II-13 | 5 | 5 | 5 |
| II-14 | 5 | 5 | 5 |
| II-15 | 5 | 5 | 5 |
| II-16 | 5 | 5 | 5 |
| II-17 | 5 | 5 | 5 |
| II-19 | 5 | 5 | 5 |
| II-22 | 5 | 5 | 5 |
| II-25 | 5 | 5 | 5 |
| II-27 | 5 | 5 | 5 |
| II-29 | 5 | 5 | 5 |
| II-30 | 5 | 5 | 5 |
| II-31 | 5 | 5 | 5 |
| II-32 | 5 | 5 | 5 |
| II-33 | 5 | 5 | 5 |
| II-34 | 5 | 5 | 5 |
| II-35 | 5 | 5 | 5 |
| II-40 | 5 | 5 | 5 |
| II-41 | 5 | 5 | 4 |
| II-44 | 5 | 5 | 5 |

TABLE 40

| Compound No. | Echinochloa oryzicola Vasing | Monochoria vaginalis (Burm. f.) C. Presl | Scirpus juncoides Roxb. |
|---|---|---|---|
| III-1 | 5 | 5 | 5 |
| III-2 | 5 | 5 | 5 |
| III-3 | 5 | 5 | 5 |
| III-5 | 5 | 5 | 5 |
| III-6 | 5 | 5 | 5 |
| III-8 | 5 | 5 | 5 |
| III-10 | 5 | 5 | 5 |
| III-11 | 5 | 5 | 5 |
| III-14 | 5 | 5 | 5 |
| III-15 | 5 | 5 | 5 |
| III-18 | 5 | 5 | 5 |
| III-19 | 5 | 5 | 5 |
| III-20 | 5 | 5 | 5 |
| III-21 | 5 | 5 | 5 |
| III-22 | 5 | 5 | 5 |
| III-23 | 5 | 5 | 5 |
| III-24 | 5 | 5 | 5 |
| III-25 | 5 | 5 | 5 |
| III-28 | 5 | 5 | 5 |
| III-29 | 5 | 5 | 5 |
| III-31 | 5 | 5 | 5 |
| III-32 | 5 | 5 | 5 |
| III-33 | 5 | 5 | 5 |
| III-34 | 5 | 5 | 5 |

TABLE 40-continued

| Compound No. | Echinochloa oryzicola Vasing | Monochoria vaginalis (Burm. f.) C. Presl | Scirpus juncoides Roxb. |
|---|---|---|---|
| III-35 | 5 | 5 | 5 |
| III-37 | 5 | 5 | 4 |
| III-38 | 5 | 5 | 5 |
| III-42 | 5 | 5 | 5 |
| III-43 | 5 | 5 | 5 |
| III-44 | 5 | 5 | 5 |

TABLE 41

| Compound No. | Echinochloa oryzicola Vasing | Monochoria vaginalis (Burm. f.) C. Presl | Scirpus juncoides Roxb. |
|---|---|---|---|
| IV-1 | 5 | 5 | 5 |
| IV-2 | 5 | 5 | 5 |
| IV-3 | 5 | 5 | 5 |
| IV-4 | 5 | 5 | 5 |
| IV-6 | 5 | 5 | 5 |
| IV-8 | 5 | 5 | 5 |
| IV-10 | 5 | 5 | 5 |
| IV-11 | 5 | 5 | 5 |
| IV-12 | 5 | 5 | 5 |
| IV-13 | 5 | 5 | 5 |
| IV-15 | 5 | 5 | 5 |
| IV-18 | 5 | 5 | 5 |
| IV-19 | 5 | 5 | 5 |
| IV-21 | 5 | 5 | 5 |
| IV-30 | 5 | 5 | 5 |
| IV-32 | 5 | 5 | 5 |
| IV-33 | 5 | 5 | 5 |
| IV-34 | 5 | 5 | 5 |
| IV-35 | 5 | 5 | 5 |
| IV-36 | 5 | 5 | 5 |
| IV-37 | 5 | 5 | 5 |
| IV-38 | 5 | 5 | 5 |
| IV-39 | 5 | 5 | 5 |
| IV-47 | 5 | 5 | 5 |
| IV-48 | 5 | 5 | 5 |
| IV-49 | 5 | 5 | 3 |
| IV-52 | 4 | 4 | 4 |
| IV-53 | 4 | 4 | 4 |
| IV-54 | 5 | 4 | 4 |
| IV-55 | 4 | 5 | 4 |
| IV-56 | 5 | 5 | 5 |
| IV-57 | 5 | 5 | 2 |
| IV-58 | 5 | 4 | 4 |
| IV-59 | 4 | 4 | 3 |
| IV-60 | 5 | 5 | 5 |
| IV-61 | 5 | 5 | 5 |
| IV-62 | 5 | 5 | 5 |
| IV-63 | 5 | 5 | 5 |
| IV-64 | 5 | 5 | 5 |
| IV-66 | 5 | 5 | 5 |
| IV-67 | 5 | 5 | 5 |
| IV-68 | 4 | 5 | 4 |
| IV-73 | 4 | 3 | 4 |
| IV-74 | 4 | 4 | 5 |
| IV-75 | 5 | 5 | 5 |

TABLE 42

| Compound No. | Echinochloa oryzicola Vasing | Monochoria vaginalis (Burm. f.) C. Presl | Scirpus juncoides Roxb. |
|---|---|---|---|
| IV-76 | 4 | 5 | 5 |
| IV-77 | 5 | 5 | 5 |
| IV-80 | 5 | 5 | 5 |
| IV-81 | 5 | 5 | 3 |
| IV-82 | 5 | 5 | 3 |
| IV-83 | 5 | 5 | 5 |
| IV-84 | 5 | 5 | 5 |
| IV-85 | 5 | 5 | 5 |
| IV-86 | 5 | 5 | 4 |
| IV-87 | 5 | 5 | 5 |
| IV-88 | 5 | 5 | 4 |
| IV-89 | 4 | 5 | 4 |
| IV-90 | 5 | 5 | 5 |
| IV-91 | 4 | 4 | 5 |
| IV-92 | 5 | 5 | 5 |
| IV-93 | 5 | 5 | 5 |
| IV-94 | 5 | 5 | 5 |
| IV-95 | 5 | 5 | 5 |
| IV-96 | 5 | 5 | 4 |
| IV-97 | 5 | 5 | 5 |
| IV-98 | 5 | 5 | 5 |
| IV-99 | 5 | 5 | 5 |
| IV-100 | 5 | 5 | 5 |
| IV-101 | 5 | 5 | 5 |
| IV-103 | 4 | 5 | 4 |
| IV-104 | 5 | 5 | 4 |
| IV-106 | 5 | 5 | 5 |
| IV-107 | 5 | 5 | 5 |
| IV-108 | 5 | 4 | 5 |
| IV-118 | 5 | 5 | 5 |
| IV-119 | 5 | 5 | 5 |
| IV-129 | 5 | 5 | 5 |
| IV-130 | 5 | 5 | 5 |
| IV-131 | 5 | 5 | 5 |
| IV-132 | 5 | 5 | 5 |
| IV-133 | 5 | 5 | 5 |
| IV-134 | 5 | 5 | 5 |
| IV-135 | 5 | 5 | 5 |
| IV-136 | 5 | 5 | 5 |
| IV-137 | 4 | 4 | 3 |
| IV-138 | 5 | 5 | 5 |
| IV-139 | 5 | 5 | 5 |
| IV-140 | 5 | 5 | 5 |
| IV-141 | 5 | 5 | 5 |
| IV-142 | 5 | 5 | 5 |
| IV-143 | 5 | 5 | 5 |

TABLE 43

| Compound No. | Echinochloa oryzicola Vasing | Monochoria vaginalis (Burm. f.) C. Presl | Scirpus juncoides Roxb. |
|---|---|---|---|
| IV-146 | 5 | 5 | 5 |
| IV-148 | 5 | 5 | 5 |
| IV-174 | 5 | 5 | 5 |
| IV-180 | 5 | 5 | 5 |
| IV-189 | 5 | 5 | 5 |
| IV-190 | 5 | 5 | 5 |
| IV-191 | 5 | 5 | 5 |
| IV-192 | 5 | 5 | 5 |
| IV-193 | 5 | 5 | 5 |
| IV-194 | 5 | 5 | 5 |
| IV-196 | 5 | 5 | 5 |
| IV-197 | 5 | 5 | 5 |
| IV-198 | 5 | 5 | 5 |
| IV-199 | 5 | 5 | 5 |
| IV-200 | 5 | 5 | 5 |
| IV-202 | 5 | 5 | 5 |
| IV-203 | 5 | 5 | 5 |
| IV-204 | 5 | 5 | 5 |
| IV-205 | 5 | 5 | 5 |
| IV-206 | 5 | 5 | 5 |
| IV-207 | 5 | 5 | 5 |

TABLE 43-continued

| Compound No. | Echinochloa oryzicola Vasing | Monochoria vaginalis (Burm. f.) C. Presl | Scirpus juncoides Roxb. |
|---|---|---|---|
| IV-208 | 5 | 5 | 5 |
| IV-213 | 5 | 5 | 5 |
| IV-219 | 5 | 5 | 5 |
| IV-220 | 5 | 5 | 5 |
| IV-225 | 5 | 5 | 5 |
| IV-228 | 5 | 5 | 5 |
| IV-231 | 5 | 5 | 5 |
| IV-236 | 5 | 5 | 5 |
| IV-237 | 5 | 5 | 5 |
| IV-238 | 4 | 5 | 5 |
| IV-239 | 5 | 5 | 5 |
| IV-240 | 5 | 5 | 5 |
| IV-241 | 5 | 5 | 5 |
| IV-242 | 5 | 4 | 5 |
| IV-243 | 5 | 5 | 5 |

TABLE 44

| Compound No. | Echinochloa oryzicola Vasing | Monochoria vaginalis (Burm.f.) C.Presl | Scirpus juncoides Roxb. |
|---|---|---|---|
| V-9 | 5 | 5 | 5 |
| V-21 | 5 | 5 | 5 |
| V-23 | 5 | 5 | 5 |
| V-24 | 5 | 5 | 5 |
| V-25 | 5 | 5 | 5 |
| V-26 | 5 | 5 | 4 |
| Comp. Compound 1 | 1 | 0 | 0 |
| Comp. Compound 2 | 0 | 0 | 0 |

Herein, Comparative Compound 1 and Comparative Compound 2 in the table are Compound No. 70 and Compound No. 34 disclosed in EP No. 283261, respectively. Their structural formulae are shown below.

[Chemical Formula 32]

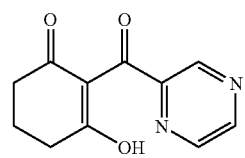

Comparative Compound 1

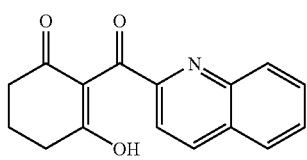

Comparative Compound 2

Test Example 2

Test on Herbicidal Effect by Soil Application to Upland field

In a 80 cm2 plastic pot, field soil was filled. Seeds of barnyardgrass (*Echinochloa crus-galli* (L.) *P. Beauv.* var. *crus-galli*), green foxtail (*Setaria viridis* (L.) *P. Beauv.*), velvetleaf (*Abutilon theophrasti* medicus), and slender amaranth (*Amaranthus viridis* L.) were sown and covered with soils. The wettable powder prepared according to Formulation Example 1 was diluted in water and a 1,000 liter equivalent amount per 1 hectare so that the active ingredient becomes 1,000 g per 1 hectare was uniformly sprayed on a soil surface using a small sprayer. Then, on the 21st day after the application to the plants grew in a greenhouse, the herbicidal effect was examined in accordance with a standard shown in Table 34. The results are shown in Tables 45 to 50.

TABLE 45

| Compound No. | Barnyardgrass | Green Foxtail | Velvetleaf | Slender Amaranth |
|---|---|---|---|---|
| I-1 | 5 | 4 | 5 | 5 |
| I-3 | 5 | 5 | 5 | 5 |
| I-4 | 5 | 4 | 5 | 5 |
| I-5 | 5 | 5 | 5 | 5 |
| I-6 | 5 | 5 | 5 | 5 |
| I-7 | 5 | 5 | 5 | 5 |
| I-9 | 4 | 4 | 5 | 5 |
| I-10 | 5 | 3 | 5 | 3 |
| I-11 | 5 | 4 | 5 | 5 |
| I-16 | 5 | 5 | 5 | 5 |
| I-18 | 5 | 5 | 5 | 5 |
| I-20 | 5 | 5 | 5 | 5 |
| I-26 | 5 | 5 | 5 | 5 |
| I-31 | 5 | 5 | 5 | 5 |
| I-32 | 5 | 5 | 5 | 5 |
| I-33 | 5 | 3 | 5 | 5 |
| I-34 | 5 | 5 | 5 | 5 |
| I-44 | 5 | 5 | 5 | 5 |
| I-46 | 5 | 3 | 5 | 5 |
| I-48 | 5 | 4 | 5 | 5 |
| I-49 | 5 | 4 | 5 | 5 |
| I-50 | 5 | 5 | 5 | 5 |
| I-51 | 5 | 5 | 5 | 5 |
| I-52 | 5 | 5 | 5 | 5 |
| I-53 | 5 | 5 | 5 | 5 |
| I-54 | 5 | 4 | 5 | 5 |
| I-55 | 5 | 5 | 5 | 5 |
| I-56 | 4 | 5 | 5 | 5 |
| I-57 | 5 | 5 | 5 | 5 |
| I-58 | 5 | 5 | 5 | 5 |
| I-59 | 5 | 4 | 5 | 5 |
| I-60 | 5 | 5 | 5 | 5 |
| I-63 | 5 | 4 | 5 | 5 |
| I-66 | 5 | 5 | 5 | 5 |
| I-67 | 5 | 5 | 5 | 5 |
| I-70 | 5 | 5 | 5 | 5 |
| I-71 | 5 | 5 | 5 | 5 |
| I-72 | 5 | 5 | 5 | 5 |
| I-73 | 5 | 5 | 5 | 5 |
| I-74 | 5 | 5 | 5 | 5 |
| I-75 | 5 | 5 | 5 | 5 |
| I-76 | 5 | 5 | 5 | 5 |

TABLE 46

| Compound No. | Barnyardgrass | Green Foxtail | Velvetleaf | Slender Amaranth |
|---|---|---|---|---|
| I-79 | 5 | 5 | 5 | 5 |
| I-80 | 5 | 5 | 5 | 5 |
| I-81 | 5 | 5 | 5 | 5 |
| I-82 | 5 | 5 | 5 | 5 |
| I-83 | 5 | 5 | 5 | 5 |
| I-85 | 5 | 5 | 5 | 5 |
| I-86 | 5 | 5 | 5 | 5 |
| I-87 | 5 | 5 | 5 | 5 |
| I-88 | 5 | 5 | 5 | 5 |
| I-89 | 5 | 5 | 5 | 5 |
| I-90 | 5 | 5 | 5 | 5 |
| I-91 | 5 | 5 | 5 | 5 |
| I-92 | 5 | 5 | 5 | 5 |
| I-93 | 5 | 5 | 5 | 5 |
| I-94 | 5 | 5 | 5 | 5 |

TABLE 46-continued

| Compound No. | Barnyardgrass | Green Foxtail | Velvetleaf | Slender Amaranth |
|---|---|---|---|---|
| I-95 | 5 | 5 | 5 | 5 |
| I-96 | 5 | 5 | 5 | 3 |
| I-98 | 5 | 5 | 5 | 5 |
| I-99 | 5 | 4 | 5 | 5 |
| I-100 | 5 | 4 | 5 | 5 |
| I-101 | 5 | 5 | 5 | 5 |
| I-102 | 5 | 5 | 5 | 5 |
| I-103 | 5 | 5 | 5 | 5 |
| I-105 | 5 | 5 | 5 | 5 |
| I-106 | 5 | 5 | 5 | 5 |
| I-107 | 5 | 5 | 5 | 5 |
| I-108 | 5 | 4 | 5 | 5 |
| I-109 | 5 | 5 | 5 | 5 |
| I-110 | 5 | 4 | 5 | 5 |
| I-111 | 5 | 5 | 5 | 5 |
| I-112 | 5 | 5 | 5 | 5 |
| I-113 | 5 | 5 | 5 | 5 |
| I-114 | 5 | 4 | 5 | 5 |
| I-118 | 5 | 4 | 5 | 5 |
| I-119 | 5 | 5 | 5 | 5 |
| I-124 | 5 | 5 | 5 | 5 |
| I-126 | 5 | 5 | 5 | 5 |
| I-128 | 5 | 4 | 5 | 5 |
| I-129 | 5 | 4 | 5 | 5 |
| I-133 | 5 | 4 | 5 | 5 |
| I-137 | 5 | 5 | 5 | 5 |

TABLE 47

| Compound No. | Barnyardgrass | Green Foxtail | Velvetleaf | Slender Amaranth |
|---|---|---|---|---|
| I-140 | 5 | 4 | 5 | 5 |
| I-142 | 5 | 5 | 5 | 5 |
| I-147 | 5 | 4 | 5 | 5 |
| I-148 | 5 | 5 | 5 | 5 |
| I-149 | 5 | 5 | 5 | 5 |
| I-150 | 5 | 5 | 5 | 5 |
| I-151 | 5 | 5 | 5 | 5 |
| I-153 | 5 | 5 | 5 | 5 |
| I-154 | 4 | 3 | 5 | 5 |
| I-156 | 5 | 4 | 5 | 5 |
| I-158 | 5 | 5 | 5 | 5 |
| I-159 | 5 | 5 | 5 | 5 |
| I-161 | 5 | 5 | 5 | 5 |
| I-162 | 5 | 5 | 5 | 4 |
| I-164 | 5 | 5 | 5 | 5 |
| I-165 | 5 | 3 | 5 | 5 |
| I-167 | 5 | 5 | 5 | 5 |
| I-168 | 5 | 5 | 5 | 5 |
| I-169 | 5 | 5 | 5 | 5 |
| I-170 | 5 | 5 | 5 | 5 |
| I-171 | 5 | 4 | 5 | 5 |
| I-175 | 5 | 5 | 5 | 5 |
| I-177 | 5 | 5 | 5 | 5 |
| I-178 | 5 | 5 | 5 | 5 |
| I-179 | 5 | 5 | 5 | 5 |
| I-180 | 5 | 5 | 5 | 5 |
| I-182 | 5 | 4 | 5 | 5 |
| I-186 | 5 | 5 | 5 | 5 |
| I-190 | 5 | 4 | 5 | 5 |
| I-191 | 5 | 5 | 5 | 5 |
| I-202 | 5 | 5 | 5 | 5 |
| I-215 | 5 | 5 | 5 | 5 |
| I-221 | 5 | 3 | 5 | 5 |
| I-223 | 5 | 5 | 5 | 5 |
| I-224 | 5 | 5 | 5 | 5 |
| I-226 | 4 | 3 | 5 | 5 |
| I-227 | 4 | 5 | 5 | 5 |
| I-230 | 4 | 5 | 5 | 5 |
| I-238 | 5 | 4 | 5 | 5 |
| I-243 | 5 | 5 | 5 | 5 |
| I-233 | 4 | 3 | 5 | 5 |

TABLE 48

| Compound No. | Barnyardgrass | Green Foxtail | Velvetleaf | Slender Amaranth |
|---|---|---|---|---|
| II-5 | 5 | 5 | 5 | 5 |
| II-14 | 4 | 3 | 5 | 5 |
| II-22 | 4 | 4 | 5 | 5 |
| II-25 | 5 | 5 | 5 | 5 |
| II-29 | 5 | 5 | 5 | 5 |
| II-31 | 5 | 5 | 5 | 5 |
| II-32 | 5 | 5 | 5 | 5 |
| II-33 | 5 | 5 | 5 | 5 |
| II-34 | 5 | 5 | 5 | 5 |
| II-40 | 5 | 5 | 5 | 5 |
| II-41 | 4 | 5 | 5 | 5 |
| II-42 | 5 | 3 | 5 | 5 |
| II-44 | 5 | 5 | 5 | 5 |
| III-1 | 5 | 5 | 5 | 5 |
| III-3 | 5 | 5 | 5 | 5 |
| III-5 | 5 | 5 | 5 | 5 |
| III-6 | 5 | 5 | 5 | 5 |
| III-10 | 5 | 5 | 5 | 5 |
| III-11 | 4 | 4 | 5 | 5 |
| III-14 | 4 | 4 | 5 | 5 |
| III-15 | 5 | 5 | 5 | 5 |
| III-18 | 5 | 3 | 5 | 5 |
| III-19 | 5 | 5 | 5 | 5 |
| III-20 | 5 | 5 | 5 | 5 |
| III-21 | 5 | 5 | 5 | 5 |
| III-22 | 5 | 5 | 5 | 5 |
| III-23 | 5 | 5 | 5 | 5 |
| III-24 | 5 | 5 | 5 | 5 |
| III-25 | 5 | 5 | 5 | 5 |
| III-28 | 5 | 5 | 5 | 5 |
| III-29 | 5 | 5 | 5 | 5 |
| III-30 | 5 | 5 | 5 | 5 |
| III-32 | 5 | 5 | 5 | 5 |
| III-33 | 4 | 5 | 5 | 5 |
| III-34 | 5 | 5 | 5 | 5 |
| III-35 | 5 | 5 | 5 | 5 |
| III-37 | 4 | 4 | 5 | 4 |
| III-38 | 5 | 3 | 5 | 5 |
| III-42 | 4 | 3 | 5 | 5 |

TABLE 49

| Compound No. | Barnyardgrass | Green Foxtail | Velvetleaf | Slender Amaranth |
|---|---|---|---|---|
| IV-1 | 5 | 4 | 5 | 5 |
| IV-2 | 5 | 5 | 5 | 5 |
| IV-3 | 5 | 5 | 5 | 5 |
| IV-4 | 5 | 5 | 5 | 5 |
| IV-6 | 5 | 5 | 5 | 5 |
| IV-8 | 5 | 5 | 5 | 5 |
| IV-10 | 5 | 5 | 5 | 5 |
| IV-11 | 5 | 4 | 5 | 5 |
| IV-18 | 5 | 5 | 5 | 5 |
| IV-19 | 5 | 5 | 5 | 5 |
| IV-21 | 3 | 5 | 5 | 5 |
| IV-30 | 5 | 3 | 5 | 5 |
| IV-31 | 4 | 3 | 4 | 5 |
| IV-32 | 4 | 3 | 5 | 5 |
| IV-33 | 5 | 5 | 5 | 5 |
| IV-34 | 5 | 5 | 5 | 5 |
| IV-35 | 5 | 5 | 5 | 5 |
| IV-36 | 5 | 3 | 5 | 5 |
| IV-37 | 5 | 5 | 5 | 5 |
| IV-38 | 5 | 4 | 5 | 5 |
| IV-39 | 5 | 3 | 4 | 4 |
| IV-47 | 4 | 5 | 5 | 5 |
| IV-48 | 4 | 5 | 5 | 5 |
| IV-54 | 5 | 5 | 5 | 5 |
| IV-55 | 5 | 5 | 4 | 5 |
| IV-62 | 5 | 5 | 5 | 5 |
| IV-68 | 4 | 4 | 5 | 5 |
| IV-80 | 5 | 5 | 5 | 5 |
| IV-81 | 5 | 5 | 5 | 5 |

TABLE 49-continued

| Compound No. | Barnyardgrass | Green Foxtail | Velvetleaf | Slender Amaranth |
|---|---|---|---|---|
| IV-82 | 5 | 4 | 5 | 4 |
| IV-83 | 5 | 5 | 5 | 5 |
| IV-84 | 5 | 5 | 5 | 5 |
| IV-85 | 5 | 5 | 5 | 5 |
| IV-86 | 5 | 5 | 5 | 5 |
| IV-87 | 5 | 5 | 5 | 5 |
| IV-88 | 5 | 5 | 5 | 5 |
| IV-89 | 5 | 4 | 5 | 4 |
| IV-90 | 5 | 3 | 5 | 5 |
| IV-92 | 5 | 5 | 5 | 5 |
| IV-93 | 5 | 4 | 5 | 5 |
| IV-94 | 5 | 4 | 5 | 5 |
| IV-95 | 5 | 5 | 5 | 5 |

TABLE 50

| Compound No. | Barnyardgrass | Green Foxtail | Velvetleaf | Slender Amaranth |
|---|---|---|---|---|
| IV-96 | 4 | 3 | 5 | 4 |
| IV-97 | 5 | 4 | 5 | 5 |
| IV-98 | 3 | 5 | 5 | 5 |
| IV-99 | 5 | 3 | 4 | 4 |
| IV-101 | 5 | 4 | 4 | 5 |
| IV-106 | 5 | 5 | 5 | 5 |
| IV-107 | 5 | 5 | 5 | 5 |
| IV-118 | 5 | 5 | 5 | 5 |
| IV-119 | 5 | 5 | 5 | 5 |
| IV-129 | 4 | 3 | 5 | 5 |
| IV-130 | 4 | 4 | 5 | 5 |
| IV-131 | 4 | 3 | 4 | 5 |
| IV-133 | 5 | 3 | 4 | 5 |
| IV-140 | 5 | 5 | 5 | 5 |
| IV-143 | 5 | 5 | 5 | 5 |
| IV-146 | 5 | 5 | 5 | 5 |
| IV-148 | 5 | 5 | 5 | 5 |
| IV-174 | 5 | 5 | 5 | 5 |
| IV-189 | 5 | 4 | 4 | 5 |
| IV-190 | 5 | 5 | 5 | 5 |
| IV-196 | 5 | 4 | 5 | 5 |
| IV-197 | 4 | 4 | 5 | 5 |
| IV-198 | 3 | 3 | 4 | 5 |
| IV-199 | 5 | 4 | 5 | 5 |
| IV-200 | 5 | 4 | 5 | 5 |
| IV-202 | 5 | 5 | 5 | 5 |
| IV-203 | 5 | 5 | 5 | 5 |
| IV-204 | 5 | 5 | 5 | 5 |
| IV-205 | 5 | 5 | 5 | 5 |
| IV-207 | 5 | 5 | 5 | 5 |
| IV-219 | 5 | 3 | 5 | 5 |
| IV-237 | 4 | 4 | 4 | 5 |
| IV-241 | 4 | 3 | 5 | 5 |
| IV-243 | 5 | 3 | 5 | 5 |
| V-21 | 5 | 5 | 5 | 5 |
| V-22 | 4 | 4 | 5 | 5 |
| V-23 | 5 | 5 | 5 | 5 |
| V-25 | 5 | 5 | 5 | 5 |
| Comp. Compound 1 | 1 | 1 | 1 | 0 |
| Comp. Compound 2 | 3 | 0 | 2 | 2 |

Herein, Comparative Compound 1 and Comparative Compound 2 in the table are Compound No. 70 and Compound No. 34 disclosed in EP No. 283261, respectively.

Test Example 3

Test on Herbicidal Effect by Application to Upland Field

In a 80 cm2 plastic pot, field soil was filled. Seeds of barnyardgrass (*Echinochloa crus-galli* (L.) *P. Beauv.* var. crus-galli), green foxtail (*Setaria viridis* (L.) *P. Beauv.*), velvetleaf (*Abutilon theophrasti* medicus), and slender amaranth (*Amaranthus viridis* L.) were sown and allowed to grow for two weeks in a greenhouse. Thereafter, the wettable powder prepared according to Formulation Example 1 was diluted in water and a 1,000 liter equivalent amount per 1 hectare so that the active ingredient becomes 1,000 g per 1 hectare was sprayed using a small sprayer from a top of the plants through its entire body for foliage treatment. Then, on the 14th day after the application to the plants grew in a greenhouse, the herbicidal effect was examined in accordance with a standard shown in Table 34. The results are shown in Tables 51 to 58.

TABLE 51

| Compound No. | Barnyardgrass | Green Foxtail | Velvetleaf | Slender Amaranth |
|---|---|---|---|---|
| I-1 | 4 | 3 | 5 | 5 |
| I-2 | 5 | 5 | 5 | 5 |
| I-3 | 5 | 5 | 5 | 5 |
| I-4 | 5 | 3 | 5 | 5 |
| I-5 | 5 | 5 | 5 | 5 |
| I-6 | 5 | 5 | 5 | 5 |
| I-7 | 5 | 5 | 5 | 5 |
| I-9 | 5 | 4 | 5 | 5 |
| I-10 | 5 | 4 | 5 | 5 |
| I-11 | 5 | 5 | 5 | 5 |
| I-12 | 5 | 5 | 5 | 5 |
| I-13 | 5 | 5 | 5 | 5 |
| I-14 | 5 | 5 | 5 | 5 |
| I-16 | 5 | 5 | 5 | 5 |
| I-18 | 5 | 5 | 5 | 5 |
| I-20 | 5 | 5 | 5 | 5 |
| I-26 | 4 | 4 | 5 | 5 |
| I-27 | 4 | 3 | 5 | 5 |
| I-28 | 5 | 5 | 5 | 5 |
| I-31 | 5 | 5 | 5 | 5 |
| I-32 | 5 | 5 | 5 | 5 |
| I-33 | 5 | 4 | 5 | 5 |
| I-34 | 5 | 5 | 5 | 5 |
| I-42 | 5 | 5 | 5 | 5 |
| I-43 | 5 | 4 | 5 | 5 |
| I-44 | 5 | 5 | 5 | 5 |
| I-46 | 5 | 3 | 5 | 5 |
| I-47 | 5 | 4 | 5 | 5 |
| I-48 | 5 | 5 | 5 | 5 |
| I-49 | 5 | 5 | 5 | 5 |
| I-50 | 5 | 3 | 5 | 5 |
| I-51 | 5 | 5 | 5 | 5 |
| I-52 | 5 | 5 | 5 | 5 |
| I-53 | 5 | 5 | 5 | 5 |
| I-54 | 5 | 5 | 5 | 5 |
| I-55 | 5 | 5 | 5 | 5 |
| I-56 | 5 | 5 | 5 | 5 |
| I-57 | 5 | 5 | 5 | 5 |
| I-58 | 5 | 5 | 5 | 5 |
| I-59 | 5 | 5 | 5 | 5 |

TABLE 52

| Compound No. | Barnyardgrass | Green Foxtail | Velvetleaf | Slender Amaranth |
|---|---|---|---|---|
| I-60 | 5 | 5 | 5 | 5 |
| I-61 | 5 | 4 | 5 | 5 |
| I-63 | 5 | 5 | 5 | 5 |
| I-66 | 5 | 5 | 5 | 5 |
| I-67 | 5 | 5 | 5 | 5 |
| I-69 | 5 | 5 | 5 | 5 |
| I-70 | 5 | 5 | 5 | 5 |
| I-71 | 5 | 5 | 5 | 5 |
| I-72 | 5 | 5 | 5 | 5 |
| I-73 | 5 | 4 | 5 | 5 |
| I-74 | 5 | 5 | 5 | 5 |
| I-75 | 5 | 5 | 5 | 5 |

TABLE 52-continued

| Compound No. | Barnyardgrass | Green Foxtail | Velvetleaf | Slender Amaranth |
|---|---|---|---|---|
| I-76 | 5 | 3 | 5 | 5 |
| I-78 | 5 | 5 | 5 | 5 |
| I-79 | 5 | 5 | 5 | 5 |
| I-80 | 5 | 5 | 5 | 5 |
| I-81 | 5 | 5 | 5 | 5 |
| I-82 | 5 | 5 | 5 | 5 |
| I-83 | 5 | 5 | 5 | 5 |
| I-85 | 5 | 5 | 5 | 5 |
| I-86 | 5 | 5 | 5 | 5 |
| I-87 | 5 | 5 | 5 | 5 |
| I-88 | 5 | 5 | 5 | 5 |
| I-89 | 5 | 5 | 5 | 5 |
| I-90 | 5 | 5 | 5 | 5 |
| I-91 | 5 | 4 | 5 | 5 |
| I-92 | 5 | 5 | 5 | 5 |
| I-93 | 5 | 5 | 5 | 5 |
| I-94 | 5 | 5 | 5 | 5 |
| I-95 | 5 | 5 | 5 | 5 |
| I-98 | 5 | 5 | 5 | 5 |
| I-99 | 5 | 4 | 5 | 5 |
| I-100 | 5 | 4 | 5 | 5 |
| I-101 | 5 | 5 | 5 | 5 |
| I-102 | 5 | 5 | 5 | 5 |
| I-103 | 5 | 5 | 5 | 5 |
| I-104 | 5 | 4 | 5 | 5 |
| I-105 | 5 | 5 | 5 | 5 |
| I-106 | 5 | 5 | 5 | 5 |
| I-107 | 5 | 3 | 5 | 5 |
| I-108 | 5 | 5 | 5 | 5 |

TABLE 53

| Compound No. | Barnyardgrass | Green Foxtail | Velvetleaf | Slender Amaranth |
|---|---|---|---|---|
| I-109 | 5 | 4 | 5 | 5 |
| I-110 | 5 | 3 | 4 | 5 |
| I-111 | 5 | 5 | 5 | 5 |
| I-112 | 5 | 5 | 5 | 5 |
| I-113 | 5 | 5 | 4 | 5 |
| I-114 | 5 | 4 | 5 | 5 |
| I-116 | 5 | 3 | 5 | 5 |
| I-118 | 5 | 5 | 5 | 5 |
| I-119 | 5 | 5 | 5 | 5 |
| I-126 | 5 | 5 | 5 | 5 |
| I-127 | 5 | 5 | 5 | 5 |
| I-128 | 5 | 4 | 5 | 5 |
| I-129 | 5 | 5 | 5 | 5 |
| I-133 | 5 | 4 | 5 | 5 |
| I-137 | 5 | 4 | 5 | 5 |
| I-138 | 5 | 4 | 5 | 5 |
| I-140 | 5 | 5 | 5 | 5 |
| I-142 | 5 | 5 | 5 | 5 |
| I-147 | 5 | 5 | 5 | 5 |
| I-148 | 5 | 5 | 5 | 5 |
| I-149 | 5 | 5 | 5 | 5 |
| I-150 | 5 | 5 | 5 | 5 |
| I-151 | 5 | 5 | 5 | 5 |
| I-153 | 5 | 5 | 5 | 5 |
| I-154 | 4 | 5 | 5 | 5 |
| I-156 | 5 | 4 | 5 | 5 |
| I-157 | 5 | 5 | 5 | 5 |
| I-158 | 5 | 5 | 5 | 5 |
| I-159 | 5 | 5 | 5 | 5 |
| I-160 | 4 | 3 | 5 | 5 |
| I-161 | 5 | 5 | 5 | 5 |
| I-162 | 5 | 5 | 5 | 5 |
| I-163 | 5 | 5 | 5 | 5 |
| I-164 | 5 | 5 | 5 | 5 |
| I-168 | 5 | 5 | 5 | 5 |
| I-169 | 5 | 5 | 5 | 5 |
| I-170 | 5 | 4 | 5 | 5 |
| I-171 | 5 | 4 | 5 | 5 |
| I-172 | 5 | 5 | 5 | 5 |

TABLE 53-continued

| Compound No. | Barnyardgrass | Green Foxtail | Velvetleaf | Slender Amaranth |
|---|---|---|---|---|
| I-173 | 4 | 5 | 5 | 4 |
| I-175 | 5 | 4 | 5 | 5 |

TABLE 54

| Compound No. | Barnyardgrass | Green Foxtail | Velvetleaf | Slender Amaranth |
|---|---|---|---|---|
| I-176 | 5 | 5 | 5 | 5 |
| I-177 | 5 | 4 | 5 | 5 |
| I-178 | 5 | 5 | 5 | 5 |
| I-179 | 5 | 5 | 5 | 5 |
| I-180 | 5 | 5 | 5 | 5 |
| I-186 | 5 | 5 | 5 | 5 |
| I-189 | 4 | 4 | 5 | 5 |
| I-190 | 5 | 5 | 5 | 5 |
| I-191 | 5 | 5 | 5 | 5 |
| I-195 | 5 | 4 | 5 | 3 |
| I-215 | 5 | 5 | 5 | 5 |
| I-221 | 5 | 4 | 5 | 5 |
| I-222 | 5 | 4 | 5 | 5 |
| I-223 | 5 | 5 | 5 | 5 |
| I-224 | 5 | 5 | 5 | 5 |
| I-227 | 3 | 5 | 5 | 5 |
| I-229 | 4 | 4 | 5 | 5 |
| I-230 | 5 | 4 | 5 | 5 |
| I-231 | 4 | 3 | 4 | 4 |
| I-237 | 5 | 4 | 5 | 5 |
| I-238 | 5 | 4 | 5 | 5 |
| I-243 | 5 | 5 | 5 | 5 |

TABLE 55

| Compound No. | Barnyardgrass | Green Foxtail | Velvetleaf | Slender Amaranth |
|---|---|---|---|---|
| II-3 | 3 | 4 | 5 | 5 |
| II-5 | 4 | 3 | 5 | 4 |
| II-7 | 4 | 4 | 5 | 5 |
| II-25 | 5 | 5 | 5 | 5 |
| II-29 | 5 | 5 | 5 | 5 |
| II-31 | 5 | 5 | 5 | 5 |
| II-32 | 5 | 5 | 5 | 5 |
| II-33 | 5 | 5 | 5 | 5 |
| II-34 | 5 | 5 | 5 | 5 |
| II-40 | 5 | 4 | 5 | 5 |
| II-41 | 5 | 5 | 5 | 4 |
| II-42 | 5 | 3 | 5 | 5 |
| II-43 | 5 | 4 | 5 | 5 |
| II-44 | 5 | 5 | 5 | 5 |

TABLE 56

| Compound No. | Barnyardgrass | Green Foxtail | Velvetleaf | Slender Amaranth |
|---|---|---|---|---|
| III-1 | 4 | 5 | 5 | 5 |
| III-2 | 5 | 5 | 5 | 5 |
| III-3 | 5 | 5 | 5 | 5 |
| III-5 | 5 | 5 | 5 | 5 |
| III-6 | 5 | 5 | 5 | 5 |
| III-8 | 5 | 5 | 5 | 3 |
| III-10 | 5 | 5 | 5 | 4 |
| III-11 | 5 | 5 | 5 | 5 |
| III-14 | 5 | 5 | 5 | 5 |
| III-15 | 5 | 5 | 5 | 5 |
| III-18 | 5 | 5 | 5 | 5 |
| III-19 | 5 | 5 | 5 | 5 |
| III-20 | 5 | 5 | 5 | 5 |
| III-21 | 5 | 5 | 5 | 5 |

TABLE 56-continued

| Compound No. | Barnyardgrass | Green Foxtail | Velvetleaf | Slender Amaranth |
|---|---|---|---|---|
| III-22 | 5 | 5 | 5 | 5 |
| III-23 | 5 | 5 | 5 | 5 |
| III-24 | 5 | 5 | 5 | 5 |
| III-25 | 5 | 5 | 5 | 5 |
| III-26 | 5 | 5 | 5 | 5 |
| III-27 | 5 | 5 | 5 | 5 |
| III-28 | 5 | 5 | 5 | 5 |
| III-29 | 5 | 5 | 5 | 5 |
| III-30 | 5 | 5 | 5 | 5 |
| III-31 | 5 | 5 | 5 | 5 |
| III-32 | 5 | 5 | 5 | 5 |
| III-33 | 5 | 5 | 5 | 5 |
| III-34 | 5 | 5 | 5 | 5 |
| III-35 | 5 | 5 | 5 | 5 |
| III-38 | 5 | 4 | 5 | 5 |
| III-43 | 5 | 3 | 5 | 5 |
| III-44 | 4 | 5 | 5 | 5 |

TABLE 57

| Compound No. | Barnyardgrass | Green Foxtail | Velvetleaf | Slender Amaranth |
|---|---|---|---|---|
| IV-1 | 4 | 4 | 5 | 5 |
| IV-2 | 5 | 5 | 5 | 5 |
| IV-3 | 5 | 5 | 5 | 5 |
| IV-4 | 5 | 4 | 5 | 5 |
| IV-6 | 5 | 5 | 5 | 5 |
| IV-8 | 5 | 4 | 5 | 5 |
| IV-10 | 5 | 4 | 4 | 5 |
| IV-11 | 5 | 5 | 5 | 5 |
| IV-12 | 5 | 4 | 5 | 5 |
| IV-13 | 5 | 5 | 5 | 5 |
| IV-15 | 4 | 5 | 5 | 5 |
| IV-18 | 5 | 5 | 5 | 5 |
| IV-19 | 5 | 5 | 5 | 5 |
| IV-21 | 5 | 4 | 5 | 5 |
| IV-30 | 5 | 5 | 5 | 5 |
| IV-33 | 5 | 5 | 5 | 5 |
| IV-34 | 5 | 5 | 5 | 5 |
| IV-35 | 5 | 5 | 5 | 5 |
| IV-36 | 5 | 5 | 5 | 5 |
| IV-37 | 5 | 3 | 5 | 5 |
| IV-38 | 5 | 5 | 5 | 5 |
| IV-39 | 5 | 3 | 5 | 5 |
| IV-47 | 4 | 5 | 5 | 5 |
| IV-48 | 5 | 4 | 5 | 5 |
| IV-54 | 5 | 5 | 5 | 5 |
| IV-58 | 5 | 4 | 4 | 5 |
| IV-62 | 5 | 5 | 5 | 5 |
| IV-63 | 4 | 4 | 5 | 5 |
| IV-67 | 4 | 4 | 5 | 5 |
| IV-74 | 4 | 4 | 5 | 5 |
| IV-77 | 5 | 3 | 5 | 5 |
| IV-80 | 5 | 5 | 5 | 5 |
| IV-81 | 4 | 4 | 5 | 5 |
| IV-83 | 5 | 5 | 5 | 5 |
| IV-84 | 4 | 3 | 5 | 4 |
| IV-85 | 5 | 5 | 5 | 5 |
| IV-86 | 5 | 4 | 5 | 5 |
| IV-90 | 5 | 5 | 5 | 5 |
| IV-92 | 4 | 4 | 4 | 5 |
| IV-93 | 4 | 4 | 4 | 5 |
| IV-95 | 5 | 5 | 5 | 5 |
| IV-96 | 3 | 5 | 5 | 4 |

TABLE 58

| Compound No. | Barnyardgrass | Green Foxtail | Velvetleaf | Slender Amaranth |
|---|---|---|---|---|
| IV-97 | 5 | 5 | 5 | 5 |
| IV-98 | 5 | 4 | 5 | 5 |

TABLE 58-continued

| Compound No. | Barnyardgrass | Green Foxtail | Velvetleaf | Slender Amaranth |
|---|---|---|---|---|
| IV-99 | 5 | 5 | 5 | 5 |
| IV-100 | 5 | 5 | 5 | 4 |
| IV-101 | 5 | 3 | 4 | 4 |
| IV-106 | 5 | 5 | 5 | 5 |
| IV-107 | 5 | 5 | 5 | 5 |
| IV-108 | 4 | 4 | 5 | 4 |
| IV-118 | 5 | 5 | 5 | 5 |
| IV-119 | 5 | 4 | 4 | 5 |
| IV-129 | 5 | 4 | 5 | 5 |
| IV-130 | 5 | 4 | 4 | 5 |
| IV-136 | 4 | 4 | 4 | 5 |
| IV-139 | 5 | 4 | 5 | 5 |
| IV-140 | 5 | 3 | 5 | 5 |
| IV-142 | 5 | 5 | 5 | 5 |
| IV-143 | 5 | 5 | 5 | 5 |
| IV-146 | 5 | 5 | 5 | 5 |
| IV-148 | 5 | 5 | 5 | 5 |
| IV-174 | 5 | 5 | 5 | 5 |
| IV-180 | 5 | 4 | 5 | 5 |
| IV-190 | 5 | 4 | 5 | 5 |
| IV-193 | 3 | 4 | 5 | 5 |
| IV-196 | 4 | 3 | 5 | 5 |
| IV-197 | 4 | 4 | 5 | 5 |
| IV-198 | 4 | 3 | 5 | 5 |
| IV-199 | 4 | 3 | 5 | 5 |
| IV-200 | 4 | 3 | 5 | 5 |
| IV-202 | 5 | 5 | 5 | 5 |
| IV-203 | 5 | 5 | 5 | 5 |
| IV-204 | 5 | 5 | 5 | 5 |
| IV-205 | 5 | 5 | 5 | 5 |
| IV-208 | 5 | 4 | 5 | 5 |
| IV-219 | 5 | 3 | 5 | 5 |
| IV-220 | 4 | 3 | 5 | 5 |
| IV-231 | 3 | 5 | 5 | 5 |
| IV-243 | 5 | 4 | 5 | 5 |
| Comp. Compound 1 | 0 | 0 | 2 | 1 |
| Comp. Compound 2 | 0 | 0 | 5 | 1 |

Herein, Comparative Compound 1 and Comparative Compound 2 in the table are Compound No. 70 and Compound No. 34 disclosed in EP No. 283261, respectively.

The invention claimed is:
1. A pyridone derivative of Formula [1]:

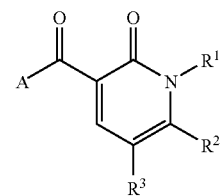

wherein $R^1$ is:
  a $C_{1-6}$ alkyl group,
  a $C_{2-6}$ alkenyl group,
  a $C_{2-6}$ alkynyl group,
  a $C_{3-8}$ cycloalkyl group,
  a $C_{3-8}$ cycloalkyl $C_{1-6}$ alkyl group,
  a $C_{1-6}$ haloalkyl group,
  a $C_{2-6}$ haloalkenyl group,
  a $C_{2-6}$ haloalkynyl group,
  a $C_{1-6}$ alkylamino $C_{1-6}$ alkyl group,
  a di($C_{1-6}$ alkyl)amino $C_{1-6}$ alkyl group,
  a $C_{1-6}$ alkylthio $C_{1-6}$ alkyl group,
  a $C_{1-6}$ alkylsulfinyl $C_{1-6}$ alkyl group, a $C_{1-6}$ alkylsulfonyl $C_{1-6}$ alkyl group,
a $C_{3-8}$ cycloalkylthio $C_{1-6}$ alkyl group,
a $C_{3-8}$ cycloalkylsulfinyl $C_{1-6}$ alkyl group,
a $C_{3-8}$ cycloalkylsulfonyl $C_{1-6}$ alkyl group,
a $C_{3-8}$ cycloalkyl $C_{1-6}$ alkylthio $C_{1-6}$ alkyl group,
a $C_{3-8}$ cycloalkyl $C_{1-6}$ alkylsulfinyl $C_{1-6}$ alkyl group,
a $C_{3-8}$ cycloalkyl $C_{1-6}$ alkylsulfonyl $C_{1-6}$ alkyl group,
a $C_{2-6}$ alkenylthio $C_{1-6}$ alkyl group,
a $C_{2-6}$ alkenylsulfinyl $C_{1-6}$ alkyl group,
a $C_{2-6}$ alkenylsulfonyl $C_{1-6}$ alkyl group,
a $C_{2-6}$ alkynylthio $C_{1-6}$ alkyl group,
a $C_{2-6}$ alkynylsulfinyl $C_{1-6}$ alkyl group,
a $C_{2-6}$ alkynylsulfonyl $C_{1-6}$ alkyl group,
a $C_{1-6}$ haloalkylthio $C_{1-6}$ alkyl group,
a $C_{1-6}$ haloalkylsulfinyl $C_{1-6}$ alkyl group,
a $C_{1-6}$ haloalkylsulfonyl $C_{1-6}$ alkyl group,
a $C_{1-6}$ alkoxy $C_{1-6}$ alkyl group,
a $C_{1-6}$ alkoxy $C_{1-6}$ alkoxy $C_{1-6}$ alkyl group,
a $C_{3-8}$ cycloalkyloxy $C_{1-6}$ alkyl group,
a benzyloxy $C_{1-6}$ alkyl group which may be substituted with one or more substituents selected from Substituent Group α,
a cyano $C_{1-6}$ alkyl group,
a $C_{1-6}$ haloalkoxy $C_{1-6}$ alkyl group,
a phenyl group which may be substituted with one or more substituents selected from Substituent Group α,
a benzyl group which may be substituted with one or more substituents selected from Substituent Group α,
a phenyl $C_{1-6}$ alkyl group which may be substituted with one or more substituents selected from Substituent Group α,
a phenyl $C_{2-6}$ alkenyl group which may be substituted with one or more substituents selected from Substituent Group α,
a phenyl $C_{2-6}$ alkynyl group which may be substituted with one or more substituents selected from Substituent Group α,
a $C_{1-6}$ alkoxyimino $C_{1-6}$ alkyl group,
a phenoxyimino $C_{1-6}$ alkyl group which may be substituted with one or more substituents selected from Substituent Group α,
a di($C_{1-6}$ alkoxy)$C_{1-6}$ alkyl group,
a formyl $C_{1-6}$ alkyl group,
a $C_{2-6}$ alkylideneamino group,
a di($C_{1-10}$ alkyl)amino $C_{1-6}$ alkylideneamino group,
a $NR^{31}R^{32}$ group,
a $C_{1-6}$ alkoxy group,
a $C_{2-6}$ alkenyloxy group,
a $C_{2-6}$ alkynyloxy group,
a $C_{3-8}$ cycloalkyloxy group,
a $C_{3-8}$ cycloalkyl $C_{1-3}$ alkyloxy group,
a $C_{1-6}$ haloalkoxy group,
a $C_{2-10}$ heterocyclic group having one or more of the same or different hetero atoms selected from the group consisting of an oxygen atom, a sulfur atom and a nitrogen atom (wherein the heterocyclic group is optionally substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano group),
a $C_{1-6}$ alkyl group substituted with a $C_{2-10}$ heterocyclic ring having one or more of the same or different hetero atoms selected from the group consisting of an oxygen atom, a sulfur atom and a nitrogen atom and wherein the $C_{2-10}$ heterocyclic ring, substituted on the $C_{1-6}$ alkyl group, is optionally substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups
a $C_{1-6}$ alkylamino group substituted with a $C_{2-10}$ heterocyclic ring having one or more of the same or different hetero atoms selected from the group consisting of an oxygen atom, a sulfur atom and a nitrogen atom and wherein the $C_{2-10}$ heterocyclic ring, substituted on the $C_{1-6}$ alkylamino group, is optionally substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups), or
a $C_{1-6}$ alkoxy $C_{1-6}$ alkyl group substituted with a $C_{2-10}$ heterocyclic ring having one or more of the same or different hetero atoms selected from the group consisting of an oxygen atom, a sulfur atom and a nitrogen atom and wherein the $C_{2-10}$ heterocyclic ring, substituted on the $C_{1-6}$ alkoxy $C_{1-6}$ alkyl group, is optionally substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups;

wherein $R^2$ and $R^3$ are each independently:
a hydrogen atom,
a nitro group,
a cyano group,
a $C_{1-6}$ alkyl group,
a $C_{2-6}$ alkenyl group,
a $C_{2-6}$ alkynyl group,
a $C_{3-8}$ cycloalkyl group,
a $C_{1-6}$ haloalkyl group,
a $C_{2-6}$ haloalkenyl group,
a $C_{2-6}$ haloalkynyl group,
a $C_{1-6}$ alkoxy group,
a $C_{1-6}$ haloalkoxy group,
a $C_{1-6}$ alkylthio group,
a $C_{1-6}$ alkylsulfinyl group,
a $C_{1-6}$ alkylsulfonyl group,
a $C_{1-6}$ alkylsulfonyl $C_{1-6}$ alkyl group,
a $C_{1-6}$ haloalkylthio group,
a $C_{1-6}$ haloalkylsulfinyl group,
a $C_{1-6}$ haloalkylsulfonyl group,
a $C_{1-6}$ alkoxy $C_{1-6}$ alkyl group,
a $C_{3-8}$ cycloalkyloxy $C_{1-4}$ alkyl group,
a di($C_{1-6}$ alkoxy) $C_{1-6}$ alkyl group,
a phenyl group which may be substituted with one or more substituents selected from Substituent Group α,
a benzyl group which may be substituted with one or more substituents selected from Substituent Group α,
a phenyl $C_{1-6}$ alkyl group which may be substituted with one or more substituents selected from Substituent Group α,
a phenyl $C_{2-6}$ alkenyl group which may be substituted with one or more substituents selected from Substituent Group α,
a phenyl $C_{2-6}$ alkynyl group which may be substituted with one or more substituents selected from Substituent Group α, or
a halogen atom; and
wherein A is selected from the group consisting of Formula A-1, Formula A-2, Formula A-3, Formula A-4, and Formula A-5:

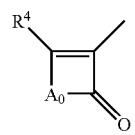

A-1

-continued

[A-2 structure: thiazine ring with R14, R15, R16, R17, R18, R4, S]

[A-3 structure: pyrazole with R21, R4, R20]

[A-4 structure: isoxazole with R23, R24]

[A-5 structure: HO-C(R24)=C(R25)-CH3]

wherein $R^4$ is:
a hydroxyl group,
$O^-M^+$ (where $M^+$ represents an alkali metal cation or an ammonium cation),
a halogen atom,
a cyano group,
an isothiocyanate group,
an isocyanate group,
a hydroxycarbonyloxy group,
a $C_{1-6}$ alkoxycarbonyloxy group,
a benzyloxy carbonyloxy group which may be substituted with one or more substituents selected from Substituent Group α,
a $C_{1-12}$ alkoxy group,
a $C_{2-6}$ alkenyloxy group,
a $C_{2-6}$ alknyloxy group,
a $C_{3-6}$ cycloalkyloxy group,
a cyanomethyleneoxy group,
a $C_{3-8}$ cycloalkyl $C_{1-3}$ alkyloxy group,
a $C_{1-8}$ alkylcarbonyloxy group,
a $C_{1-6}$ haloalkylcarbonyloxy group,
a $C_{2-6}$ alkenylcarbonyloxy group,
a $C_{2-6}$ haloalkenylcarbonyloxy group,
a $C_{2-6}$ alkynylcarbonyloxy group,
a $C_{2-6}$ haloalkynylcarbonyloxy group,
a $C_{1-6}$ alkoxycarbonyl $C_{1-6}$ alkoxy group,
a phenyloxy group which may be substituted with one or more substituents selected from Substituent Group α,
a benzyloxy group which may be substituted with one or more substituents selected from Substituent Group α,
a phenylcarbonyloxy group which may be substituted with one or more substituents selected from Substituent Group α,
a benzylcarbonyloxy group which may be substituted with one or more substituents selected from Substituent Group α,
a phenylcarbonyl $C_{1-6}$ alkyloxy group which may be substituted with one or more substituents selected from Substituent Group α,
a $C_{1-3}$ alkylsulfonyloxy group,
a phenylsulfonyloxy group which may be substituted with one or more substituents selected from Substituent Group α,
a benzylsulfonyloxy group which may be substituted with one or more substituents selected from Substituent Group α,
a $C_{1-10}$ alkylthio group, a $C_{1-10}$ alkylsulfinyl group,
a $C_{1-10}$ alkylsulfonyl group, a phenylthio group which may be substituted with one or more substituents selected from Substituent Group α,
a benzylthio group which may be substituted with one or more substituents selected from Substituent Group α,
a phenylsulfinyl group which may be substituted with one or more substituents selected from Substituent Group α,
a benzylsulfinyl group which may be substituted with one or more substituents selected from Substituent Group α,
a phenylsulfonyl group which may be substituted with one or more substituents selected from Substituent Group α,
a benzylsulfonyl group which may be substituted with one or more substituents selected from Substituent Group α,
a $C_{1-10}$ alkylamino group,
a di($C_{1-10}$ alkyl)amino group,
a $C_{1-6}$ alkoxycarbonylamino group,
a $C_{1-6}$ alkyloxy group substituted with a $C_{2-10}$ heterocyclic ring having one or more of the same or different hetero atoms selected from the group consisting of an oxygen atom, a sulfur atom and a nitrogen atom, and wherein the $C_{2-10}$ heterocyclic ring, substituted on the $C_{1-6}$ alkyloxy group, is optionally substituted with 1 to 5 halogen atoms, oxo groups, $C_{1-6}$ alkyl groups, $C_{1-6}$ haloalkyl groups, $C_{1-6}$ alkoxy groups or cyano groups, or
a $C_{2-10}$ heterocyclic group having one or more of the same or different hetero atoms selected from the group consisting of an oxygen atom, a sulfur atom and a nitrogen atom, wherein the $C_{2-10}$ heterocyclic group is optionally substituted with 1 to 5 halogen atoms, oxo groups, $C_{1-6}$ alkyl groups, $C_{1-8}$ haloalkyl groups, $C_{1-6}$ alkoxy groups or cyano group);
wherein $A_0$ is selected from the group consisting of Formula $X_{10}$ and Formula $X_{11}$:

$$-\underset{R^5}{C}=\underset{R^6}{C}-O- \quad [X_{10}]$$

$$-A_1-A_2-A_3- \quad [X_{11}]$$

wherein $A_1$ is selected from the group consisting of Formula $X_1$ and Formula $X_2$:

$$-\underset{R^5}{\overset{R^6}{C}}- \quad [X_1]$$

$$-\underset{R^7}{N}- \quad [X_2]$$

wherein $A_2$ is selected from the group consisting of Formula $X_3$, Formula $X_4$, Formula $X_5$, Formula $X_6$, and Formula $X_7$:

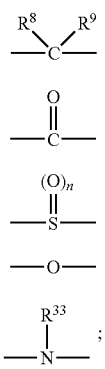

[X₃]

[X₄]

[X₅]

[X₆]

[X₇]

wherein $A_3$ is selected from the group consisting of Formula $X_8$ and Formula $X_9$:

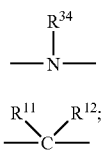

[X₈]

[X₉]

wherein:
  n is 0, 1 or 2;
  $R^5$, $R^6$, $R^8$, $R^9$, $R^{11}$ and $R^{12}$ are each independently a hydrogen atom or a $C_{1-6}$ alkyl group,
  $R^5$ and $R^8$ may form a ring by bonding with a $C_{1-5}$ alkylene chain or a $C_{2-5}$ alkenylene chain, or $R^5$ and $R^{11}$ may form a ring by bonding with a $C_{2-5}$ alkylene chain or a $C_{2-5}$ alkenylene chain;
  $R^7$, $R^{33}$, and $R^{34}$ are each independently a hydrogen atom, a $C_{1-6}$ alkyl group, a $C_{1-6}$ haloalkyl group, a $C_{2-6}$ alkenyl group, a $C_{2-6}$ alkynyl group or a $C_{1-6}$ alkoxy group;
  $R^{14}$, $R^{15}$, $R^{16}$, and $R^{17}$ are each independently a hydrogen atom, a $C_{1-6}$ alkyl group, a $C_{1-6}$ alkoxy group or a benzyl group which may be substituted with one or more substituents selected from Substituent Group α;
  $R^{18}$ is a hydrogen atom, a $C_{1-6}$ alkyl group, a $C_{2-6}$ alkenyl group, a $C_{2-6}$ alkynyl group, a cyanomethyl group or a benzyl group which may be substituted with one or more substituents selected from Substituent Group α;
  $R^{20}$ is a $C_{1-6}$ alkyl group, a $C_{2-6}$ alkenyl group, a $C_{2-6}$ alkynyl group, a $C_{3-8}$ cycloalkyl group or a $C_{3-5}$ cycloalkyl $C_{1-6}$ alkyl group;
  $R^{21}$ is a hydrogen atom, a $C_{1-6}$ alkyl group or a halogen atom;
  $R^{23}$ is:
    a $C_{1-6}$ alkyl group,
    a $C_{1-6}$ haloalkyl group,
    a $C_{3-8}$ cycloalkyl group,
    a $C_{1-10}$ alkylthio group,
    a $C_{1-10}$ alkylsulfinyl group,
    a $C_{1-10}$ alkylsulfonyl group,
    a phenylthio group which may be substituted with one or more substituents selected from Substituent Group α,
    a benzylthio group which may be substituted with one or more substituents selected from Substituent Group α,
    a phenylsulfinyl group which may be substituted with one or more substituents selected from Substituent Group α,
    a benzylsulfinyl group which may be substituted with one or more substituents selected from Substituent Group α,
    a phenylsulfonyl group which may be substituted with one or more substituents selected from Substituent Group α, or
    a benzylsulfonyl group which may be substituted with one or more substituents selected from Substituent Group α;
  $R^{24}$ is a hydrogen atom, a halogen atom, a cyano group, a $C_{1-6}$ alkyl group, a $C_{3-8}$ cycloalkyl group, or a $C_{1-6}$ alkoxycarbonylamino group; and
  $R^{25}$ is a $C_{1-6}$ alkoxycarbonyl group, a cyano group or a nitro group, and
  $R^{31}$ and $R^{32}$ are each independently:
    a hydrogen atom,
    a $C_{1-6}$ alkyl group, a phenyl group which may be substituted with one or more substituents selected from Substituent Group α,
    a benzyl group which may be substituted with one or more substituents selected from Substituent Group α,
    a $C_{1-6}$ alkoxy $C_{1-6}$ alkyl group,
    a $C_{1-6}$ alkylcarbonyl group,
    a $C_{1-6}$ alkoxycarbonyl group,
    a benzyloxycarbonyl group which may be substituted with one or more substituents selected from Substituent Group α,
    a $C_{1-6}$ haloalkyl group,
    a $C_{3-8}$ cycloalkyl group,
    a $C_{3-8}$ cycloalkyl $C_{1-6}$ alkyl group,
    a $C_{1-6}$ alkylsulfonyl group,
    a phenylsulfonyl group which may be substituted with one or more substituents selected from Substituent Group α,
    a benzylsulfonyl group which may be substituted with one or more substituents selected from Substituent Group α,
    a $C_{2-10}$ heterocyclic group having one or more of the same or different hetero atoms selected from the group consisting of an oxygen atom, a sulfur atom and a nitrogen atom and wherein the $C_{2-10}$ heterocyclic group of $R^{31}$ and $R^{32}$ may be substituted with 1 to 5 halogen atoms, oxo groups, $C_{1-6}$ alkyl groups, $C_{1-6}$ haloalkyl groups, $C_{1-6}$ alkoxy groups or cyano groups, or
    a $C_{1-6}$ alkyl group substituted with a $C_{2-10}$ heterocyclic ring having one or more of the same or different hetero atoms selected from the group consisting of an oxygen atom, a sulfur atom and a nitrogen atom and wherein the $C_{2-10}$ heterocyclic ring of the $C_{1-6}$ alkyl group may be substituted with 1 to 5 halogen atoms, oxo groups, alkyl groups, $C_{1-6}$ haloalkyl groups, $C_{1-6}$ alkoxy groups or cyano groups, and
  wherein Substituent Group α is a halogen atom, a $C_{1-6}$ alkyl group, a $C_{1-6}$ haloalkyl group, a $C_{1-6}$ alkoxy group, a $C_{1-6}$ haloalkoxy group, a $C_{1-4}$ alkylenedioxy group, a nitro group, a cyano group, a $C_{1-6}$ alkylthio group, a $C_{1-6}$ alkylsulfinyl group, a $C_{1-6}$ alkylsulfonyl group, a $C_{1-6}$ alkoxy $C_{1-6}$ alkyl group and a $C_{1-6}$ haloalkylsulfonylamino group, or an agriculturally acceptable salt thereof.

2. The pyridone derivative or an agriculturally acceptable salt thereof according to claim 1,
  wherein,
  A is selected from the group consisting of Formula A-1, Formula A-2, Formula A-3, Formula A-4 and Formula A-5; and $A_0$ in A-1 is selected from the group consisting of Formula $X_{10}$, Formula $X_{11}$-a and Formula $X_{11}$-b:

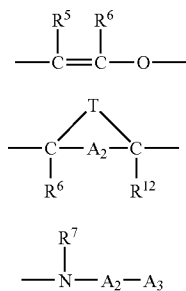

[$X_{10}$]

[$X_{11}$-a]

[$X_{11}$-b]

where $A_2$ is selected from the group consisting of Formula $X_3$, Formula $X_4$, Formula $X_5$, Formula $X_6$, and Formula $X_7$:

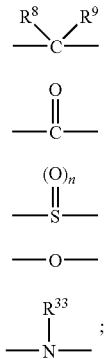

[$X_3$]

[$X_4$]

[$X_5$]

[$X_6$]

[$X_7$]

$A_3$ is selected from the group consisting of Formula $X_8$ and Formula $X_9$:

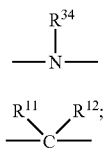

[$X_8$]

[$X_9$]

n is 0, 1 or 2;
$R^5$, $R^6$, $R^8$, $R^9$, $R^{11}$ and $R^{12}$ are each independently a hydrogen atom or a $C_{1-6}$ alkyl group;
$R^7$, $R^{33}$, and $R^{34}$ are each independently a hydrogen atom, a $C_{1-6}$ alkyl group, a $C_{1-6}$ haloalkyl group, a $C_{2-6}$ alkenyl group, a $C_{2-6}$ alkynyl group or a $C_{1-6}$ alkoxy group; and
T is a $C_{2-5}$ alkylene chain or a $C_{2-5}$ alkenylene chain.

3. The pyridone derivative or an agriculturally acceptable salt thereof according to claim 1,
wherein, $R^1$ is:
a $C_{3-8}$ cycloalkyl $C_{1-6}$ alkyl group,
a $C_{2-6}$ haloalkenyl group,
a $C_{2-6}$ haloalkynyl group,
a $C_{1-6}$ alkylamino $C_{1-6}$ alkyl group,
a di($C_{1-6}$ alkyl)amino $C_{1-6}$ alkyl group,
a $C_{1-6}$ alkylthio $C_{1-6}$ alkyl group,
a $C_{1-6}$ alkylsulfinyl $C_{1-6}$ alkyl group,
a $C_{1-6}$ alkylsulfonyl $C_{1-6}$ alkyl group,
a $C_{3-8}$ cycloalkylthio $C_{1-6}$ alkyl group,
a $C_{3-8}$ cycloalkylsulfinyl $C_{1-6}$ alkyl group,
a $C_{3-8}$ cycloalkylsunfonyl $C_{1-6}$ alkyl group,
a $C_{3-8}$ cycloalkyl $C_{1-6}$ alkylthio $C_{1-6}$ alkyl group,
a $C_{3-8}$ cycloalkyl $C_{1-6}$ alkylsulfinyl $C_{1-6}$ alkyl group,
a $C_{3-6}$ cycloalkyl $C_{1-6}$ alkylsulfonyl $C_{1-6}$ alkyl group,
a $C_{2-6}$ alkenylthio $C_{1-6}$ alkyl group,
a $C_{2-6}$ alkenylsulfinyl $C_{1-6}$ alkyl group,
a $C_{2-6}$ alkenylsulfonyl $C_{1-6}$ alkyl group,
a $C_{2-6}$ alkynylthio $C_{1-6}$ alkyl group,
a $C_{2-6}$ alkynylsulfinyl $C_{1-6}$ alkyl group,
a $C_{2-6}$ alkynylsulfonyl $C_{1-6}$ alkyl group,
a $C_{1-6}$ haloalkylthio $C_{1-6}$ alkyl group,
a $C_{1-6}$ haloalkylsulfinyl $C_{1-6}$ alkyl group,
a $C_{1-6}$ haloalkylsulfonyl $C_{1-6}$ alkyl group,
a $C_{1-6}$ alkoxy $C_{1-6}$ alkyl group,
a $C_{1-6}$ alkoxy $C_{1-6}$ alkoxy $C_{1-6}$ alkyl group,
a $C_{3-8}$ cycloalkyloxy $C_{1-6}$ alkyl group,
a benzyloxy $C_{1-6}$ alkyl group which may be substituted with one or more substituents selected from Substituent Group α,
a cyano $C_{1-6}$ alkyl group,
a $C_{1-6}$ haloalkoxy $C_{1-6}$ alkyl group,
a phenyl group which is substituted with one or more substituents selected from Substituent Group α',
a benzyl group which is optionally substituted with one or more substituents selected from the Substituent Group α,
a phenyl $C_{1-6}$ alkyl group which may be substituted with one or more substituents selected from the Substituent Group α,
a phenyl $C_{2-6}$ alkenyl group which may be substituted with one or more substituents selected from the Substituent Group α,
a phenyl $C_{2-6}$ alkynyl group which may be substituted with one or more substituents selected from the Substituent Group α,
a $C_{1-6}$ alkoxyimino $C_{1-6}$ alkyl group, a phenoxyimino $C_{1-6}$ alkyl group which may be substituted with one or more substituents selected from the Substituent Group α,
a di($C_{1-6}$ alkoxy)$C_{1-6}$ alkyl group, a formyl $C_{1-6}$ alkyl group,
a $C_{2-6}$ alkylideneamino group,
a di($C_{1-10}$ alkyl)amino $C_{1-6}$ alkylideneamino group,
a $NR^{31}R^{32}$ group, a $C_{2-6}$ alkenyloxy group,
a $C_{2-6}$ alkynyloxy group,
a $C_{3-8}$ cycloalkyloxy group,
a $C_{3-8}$ cycloalkyl $C_{1-3}$ alkyloxy group,
a $C_{2-10}$ heterocyclic group having one or more of the same or different hetero atoms selected from the group consisting of an oxygen atom, a sulfur atom and a nitrogen atom and wherein the $C_{2-10}$ heterocyclic group is substituted with one or more substituents selected from the group consisting of a halogen atom, an oxo group, a $C_{1-6}$ alkyl group, a $C_{1-6}$ haloalkyl group, a $C_{1-6}$ alkoxy group, a $C_{1-6}$ haloalkoxy group and a cyano group),
a $C_{1-6}$ alkyl group substituted with a $C_{2-10}$ heterocyclic ring having one or more of the same or different hetero atoms selected from the group consisting of an oxygen atom, a sulfur atom and a nitrogen atom and wherein the $C_{2-10}$ heterocyclic ring of the $C_{1-6}$ alkyl group is optionally substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups),
a $C_{1-6}$ alkylamino group substituted with a $C_{2-10}$ heterocyclic ring having one or more of the same or different hetero atoms selected from the group consisting of an oxygen atom, a sulfur atom and a nitrogen atom and (wherein the heterocyclic ring of the group is optionally substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups, or a $C_{1-6}$ alkoxy $C_{1-6}$ alkyl group substituted with a $C_{2-10}$ heterocyclic ring having one or more of the same or different hetero atoms selected from the group consisting of an oxygen atom, a sulfur atom and a nitrogen atom and wherein the heterocyclic ring of the $C_{1-6}$ alkylamino group is optionally substituted with 1 to 5 halogen atoms, oxo groups, $C_{1-6}$ alkyl groups, $C_{1-6}$ haloalkyl groups, $C_{1-6}$ alkoxy groups, $C_{1-6}$ haloalkoxy groups or cyano groups, wherein $R^{31}$ is:
  a hydrogen atom,
  a $C_{1-6}$ alkyl group,
  a phenyl group which may be substituted with one or more substituents selected from the Substituent Group α,
  a benzyl group which may be substituted with one or more substituents selected from the Substituent Group α,
  a $C_{1-6}$ alkoxy $C_{1-6}$ alkyl group,
  a $C_{1-6}$ alkoxycarbonyl group,
  a benzyloxycarbonyl group which may be substituted with one or more substituents selected from Substituent Group α,
  a $C_{1-6}$ haloalkyl group,
  a $C_{3-8}$ a cycloalkyl group,
  a $C_{3-8}$ cycloalkyl $C_{1-6}$ alkyl group,
  a $C_{1-6}$ alkylsulfonyl group, a phenylsulfonyl group which may be substituted with one or more substituents selected from the Substituent Group α,
  a benzylsulfonyl group which may be substituted with one or more substituents selected from the Substituent Group α,
  a $C_{2-10}$ heterocyclic group having one or more of the same or different hetero atoms selected from the group consisting of an oxygen atom, a sulfur atom and a nitrogen atom and wherein the heterocyclic group may be substituted with 1 to 5 halogen atoms, oxo groups, $C_{1-6}$ alkyl groups, $C_{1-6}$ haloalkyl groups, $C_{1-6}$ alkoxy groups or cyano groups, or
  a $C_{1-6}$ alkyl group substituted with a $C_{2-10}$ heterocyclic ring having one or more of the same or different hetero atoms selected from the group consisting of an oxygen atom, a sulfur atom and a nitrogen atom and wherein the heterocyclic ring of the $C_{1-6}$ alkyl group is optionally substituted with 1 to 5 halogen atoms, oxo groups, $C_{1-6}$ alkyl groups, $C_{1-6}$ haloalkyl groups, $C_{1-6}$ alkoxy groups or cyano groups); and wherein $R^{32}$ is:
  a phenyl group which may be substituted with one or more substituents selected from the Substituent Group α,
  a benzyl group which may be substituted with one or more substituents selected from the Substituent Group α,
  a $C_{1-6}$ alkoxy $C_{1-6}$ alkyl group,
  a $C_{1-6}$ alkoxycarbonyl group, a benzyloxycarbonyl group which may be substituted with one or more substituents selected from Substituent Group α,
  a $C_{1-6}$ haloalkyl group,
  a $C_{3-8}$ cycloalkyl group,
  a $C_{3-8}$ cycloalkyl $C_{1-6}$ alkyl group,
  a $C_{1-6}$ alkylsulfonyl group, a phenylsulfonyl group which may be substituted with one or more substituents selected from the Substituent Group α,
  a benzylsulfonyl group which may be substituted with one or more substituents selected from the Substituent Group α,
  a $C_{2-10}$ heterocyclic group having one or more of the same or different hetero atoms selected from the group consisting of an oxygen atom, a sulfur atom and a nitrogen atom and wherein the $C_{2-10}$ heterocyclic group is optionally substituted with 1 to 5 halogen atoms, oxo groups, $C_{1-6}$ alkyl groups, $C_{1-6}$ haloalkyl groups, $C_{1-6}$ alkoxy groups or cyano groups), or
  a $C_{1-6}$ alkyl group substituted with a $C_{2-10}$ heterocyclic ring having one or more of the same or different hetero atoms selected from the group consisting of an oxygen atom, a sulfur atom and a nitrogen atom and wherein the heterocyclic ring of the $C_{1-6}$ alkyl group is optionally substituted with 1 to 5 halogen atoms, oxo groups, $C_{1-6}$ alkyl groups, $C_{1-6}$ haloalkyl groups, $C_{1-6}$ alkoxy groups or cyano groups, and wherein Substituent Group α' is a $C_{1-6}$ haloalkyl group, a $C_{1-6}$ haloalkoxy group, a methylenedioxy group, a nitro group, a cyano group, a $C_{1-6}$ alkylthio group, a $C_{1-6}$ alkylsulfinyl group, a $C_{1-6}$ alkylsulfonyl group, a $C_{1-6}$ alkoxy $C_{1-6}$ alkyl group or a $C_{1-6}$ haloalkylsulfonylamino group.

4. A herbicide containing the pyridone derivative or an agriculturally acceptable salt thereof according to claim 3, as the active ingredient.

5. A herbicide containing the pyridone derivative or an agriculturally acceptable salt thereof according to claim 1, as the active ingredient.

6. A herbicide containing the pyridone derivative or an agriculturally acceptable salt thereof according to claim 2, as the active ingredient.

* * * * *

UNITED STATES PATENT AND TRADEMARK OFFICE
CERTIFICATE OF CORRECTION

PATENT NO. : 8,076,487 B2
APPLICATION NO. : 12/087892
DATED : December 13, 2011
INVENTOR(S) : Fumiaki Takabe et al.

It is certified that error appears in the above-identified patent and that said Letters Patent is hereby corrected as shown below:

Column 129, line 59, claim 1, change "group" to --groups--.
Column 129, line 67, claim 1, insert a --,-- after "groups", third occurrence.
Column 132, line 41, claim 1, change "$C_{1-8}$" to --$C_{1-6}$--.
Column 132, line 42, claim 1, change "group" to --groups--.
Column 132, line 42, claim 1, remove the ")" after "group".
Column 133, line 50, claim 1, change "$C_{3-5}$" to --$C_{3-8}$--.
Column 136, line 65, claim 3, remove the ")" after "groups".
Column 137, line 3, claim 3, remove the "(" before "wherein".
Column 137, line 50, claim 3, remove the ")" after "groups".
Column 138, line 25, claim 3, remove the ")" after "groups", second occurrence.

Signed and Sealed this
Twenty-eighth Day of August, 2012

David J. Kappos
*Director of the United States Patent and Trademark Office*